United States Patent
Al-Ali et al.

(10) Patent No.: US 11,926,613 B2
(45) Date of Patent: Mar. 12, 2024

(54) KINASE INHIBITORS FOR THE TREATMENT OF CENTRAL AND PERIPHERAL NERVOUS SYSTEM DISORDERS

(71) Applicant: UNIVERSITY OF MIAMI, Miami, FL (US)

(72) Inventors: Hassan Al-Ali, Miami, FL (US); Vance Lemmon, Miami, FL (US); John Bixby, Miami, FL (US)

(73) Assignee: UNIVERSITY OF MIAMI, Miami, FL (US)

(*) Notice: Subject to any disclaimer, the term of this patent is extended or adjusted under 35 U.S.C. 154(b) by 0 days.

(21) Appl. No.: 16/760,365

(22) PCT Filed: Oct. 31, 2018

(86) PCT No.: PCT/US2018/058411
§ 371 (c)(1),
(2) Date: Apr. 29, 2020

(87) PCT Pub. No.: WO2019/089729
PCT Pub. Date: May 9, 2019

(65) Prior Publication Data
US 2021/0163444 A1 Jun. 3, 2021

Related U.S. Application Data

(60) Provisional application No. 62/579,368, filed on Oct. 31, 2017.

(51) Int. Cl.
| | |
|---|---|
| C07D 401/12 | (2006.01) |
| A61P 25/28 | (2006.01) |
| C07D 213/81 | (2006.01) |
| C07D 401/14 | (2006.01) |
| C07D 403/12 | (2006.01) |
| C07D 471/04 | (2006.01) |

(52) U.S. Cl.
CPC .......... C07D 401/12 (2013.01); A61P 25/28 (2018.01); C07D 213/81 (2013.01); C07D 401/14 (2013.01); C07D 403/12 (2013.01); C07D 471/04 (2013.01)

(58) Field of Classification Search
CPC ............................ C07D 401/12; C07D 403/12
See application file for complete search history.

(56) References Cited

U.S. PATENT DOCUMENTS

| | | | |
|---|---|---|---|
| 5,466,468 A | 11/1995 | Schneider et al. | |
| 5,583,222 A * | 12/1996 | Barbier | C07D 223/12 540/602 |
| 2008/0176920 A1 | 7/2008 | Ambron et al. | |
| 2017/0147743 A1 | 5/2017 | Bixby et al. | |

FOREIGN PATENT DOCUMENTS

| | | |
|---|---|---|
| EP | 0663393 A1 | 7/1995 |
| EP | 3067351 A1 | 9/2016 |
| WO | 94/20062 A2 | 9/1994 |
| WO | 2003/76429 A2 | 9/2003 |
| WO | 2007/095586 A2 | 8/2007 |
| WO | 2014/210167 A1 | 12/2014 |

OTHER PUBLICATIONS

Breitenlechner et al.J. Med. Chem. 2004, 47, 1375-1390.*
Al-Ali et al., Chemical Interrogation of the Neuronal Kinome Using a Primary Cell-Based Screening Assay, ACS Chem. Biol.,8:1027-1036 (2013).
Al-Ali et al., Rational polypharmacology: systematically identifying and engaging multiple drug targets to promote axon growth, ACS Chem. Biol., 10(8):1939-512015 (2015).
ASHP Handbook on Injectable Drugs, Toissel, 4th ed., 622-630 (1986).
Barnett et al., The Akt/PKB Family of Protein Kinases: A Review of Small Molecule Inhibitors and Progress Towards Target Validation, Curr. Top. Med. Chem., 5(2):109-125 (2005).
Berge et al., Pharmaceutical salts, J. Pharm. Sci., 66:1-19 (1977).
Breitenlechner et al., Structure-Based Optimization of Novel Azepane Derivatives as PKB Inhibitors, Journal of Medicinal Chemistry, 47(6):1375-1390 (2004).
Chalmers et al., Pharmaceutics and pharmacy practice, J. B. Lippincott Co., Philadelphia. Pa., 238-250 (1982).
Di et al., Solution Stability-Plasma, Gastrointestinal, Bioassay, Curr. Drug Metab., 9(9):860-868 (2008).
International Application No. PCT/US2018/058411, International Preliminary Report on Patentability, dated May 14, 2020.
International Application No. PCT/US2018/058411, International Search Report and Written Opinion, dated Jan. 15, 2019, 16 pages.
Pande et al., The Protein Kinase Inhibitor Balanol: Structure-Activity Relationships and Structure-Based Computational Studies, Anticancer Agents Med Chem., 8(6):638-645 (2008).
Rice et al., Pyrazolopyrimidines as dual Akt/p70S6K inhibitors, Bioorganic & Medicinal Chemistry Letters, 22(8):2693-2697 (2012).

(Continued)

*Primary Examiner* — Brian E McDowell
(74) *Attorney, Agent, or Firm* — MARSHALL, GERSTEIN & BORUN LLP

(57) ABSTRACT

Provided herein are compounds of the general Formula (I) which act as kinase inhibitors, e.g. ROCK, S6K, and/or PKC inhibitors, and are useful in neurite growth and axonal growth.

(I)

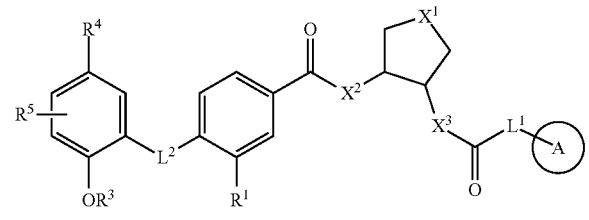

15 Claims, 2 Drawing Sheets

(56) References Cited

OTHER PUBLICATIONS

Sung et al., A novel inhibitor of active protein kinase G attenuates chronic inflammatory and osteoarthritic pain, Pain, 158(5):822-832 (2017).
Tandon et al., A Targeted Library Screen Reveals a New Inhibitor Scaffold for Protein Kinase D, Plos One, 7(9):e44653 (2012).

* cited by examiner

KINASE INHIBITORS FOR THE TREATMENT OF CENTRAL AND PERIPHERAL NERVOUS SYSTEM DISORDERS

BACKGROUND

Recovery from spinal cord injury (SCI) is limited by the inability of central nervous system (CNS) neurons to regenerate their damaged axons. Developing drugs to treat SCI is complicated by the existence of two mechanisms that inhibit axon growth: 1) a loss of the intrinsic regenerative capacity of CNS neurons, and 2) the inhibitory CNS microenvironment confronting damaged axons. It is hypothesized that effective cures may be based upon simultaneously treat both sources of regeneration failure in order to induce clinically meaningful axon regrowth after injury.

SUMMARY

Provided herein are compounds of Formula (I), or pharmaceutically acceptable salts thereof:

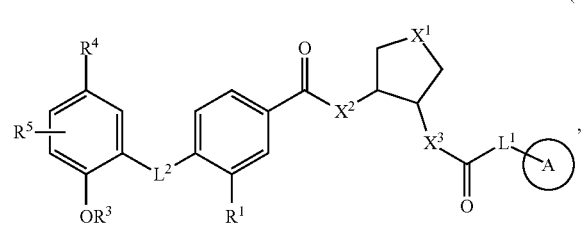

(I)

wherein ring A comprises a 5-6-membered monocyclic heteroaryl ring or a 8-11-membered bicyclic heteroaryl ring having 1, 2, or 3 nitrogen ring atoms; $L^1$ is null or $C_{1-2}$alkylene; $X^1$ is —NH—, —CH$_2$NH—, —NHCH$_2$—, —CH$_2$CH$_2$NH—, or —NHCH$_2$CH$_2$—; $X^2$ is $NR^2$ or O; $X^3$ is $NR^2$ or O; $L^2$ is C(O), O, CH$_2$, or CHOH; $R^1$ is H or halo; each $R^2$ is independently H or $C_{1-3}$alkyl; $R^3$ is H, $C_{1-3}$alky, $C_{3-6}$cycloalkyl, aryl, C(O)$C_{1-3}$alkyl, C(O)$C_{3-6}$cycloalkyl, or C(O)aryl; $R^4$ is H, OH, halo, $C_{1-4}$alkyl, $C_{1-4}$alkoxy, C(O)$C_{1-4}$alkoxy, $C_{3-6}$cycloalkyl, aryl, —O$C_{3-6}$cycloalkyl, $C_{1-4}$alkoxy-aryl, C(O)O$C_{3-6}$cycloalkyl, or C(O)Oaryl; and $R^5$ is H, halo, $C_{1-4}$alkyl, or $C_{1-4}$alkoxy.

Further provided are methods of using compounds as disclosed herein or salts thereof to inhibit Rho kinasae (ROCK) or ribosomal protein S6 kinase (S6K) or PKC. Also provided are methods of inhibiting each of ROCK and S6K with a compound as disclosed herein or salt thereof.

Also provided are methods of inducing neurite growth by contacting neurites with a compound as disclosed herein or salt thereof. Further provided are methods of treating a CNS disorder associated with neuronal and/or axonal damage in a subject by administering a compound as disclosed herein or salt thereof in an amount effective to repair neuronal and/or axonal damage and thereby treat the CNS disorder. In some cases, the CNS disorder is paralysis, spinal cord injury, optic nerve injury, glaucoma, multiple sclerosis, traumatic brain injury, diffuse axonal injury, stroke, or a degenerative disease (such as Parkinson's disease).

Further provided are methods of treating a peripheral nervous system (PNS) disorder associated with neuronal and/or axonal damage in a subject by administering a compound as disclosed herein or salt thereof in an amount effective to repair neuronal and/or axonal damage and thereby treat the PNS disorder. In some cases, the PNS disorder is peripheral nerve trauma, repetitive stress, amyotrophic lateral sclerosis (ALS), erectile dysfunction, a disorder associated with an organ transplant, neurofibromatosis, blood vessel disease, diabetes, an autoimmune disorder, a disorder associated with chemical toxicity, or kidney disease.

Also provided are methods of treating nerve degeneration in a subject undergoing cancer therapy, comprising administering a compound as disclosed herein or a salt thereof in an amount effective to treat the nerve degeneration.

DETAILED DESCRIPTION

Figure 1:
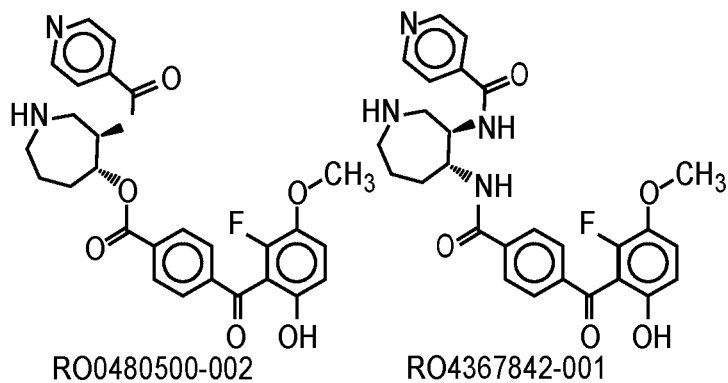
FIG. 1 shows the structure of RO480500-002 and its amide derivative, RO4367842-001, and a graph showing that both compounds promote neurite outgrowth in primary CNS neurons.
Figure 1:
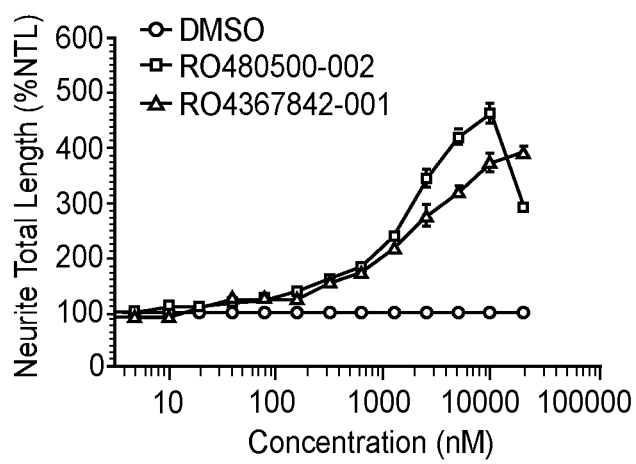
Figure 2:
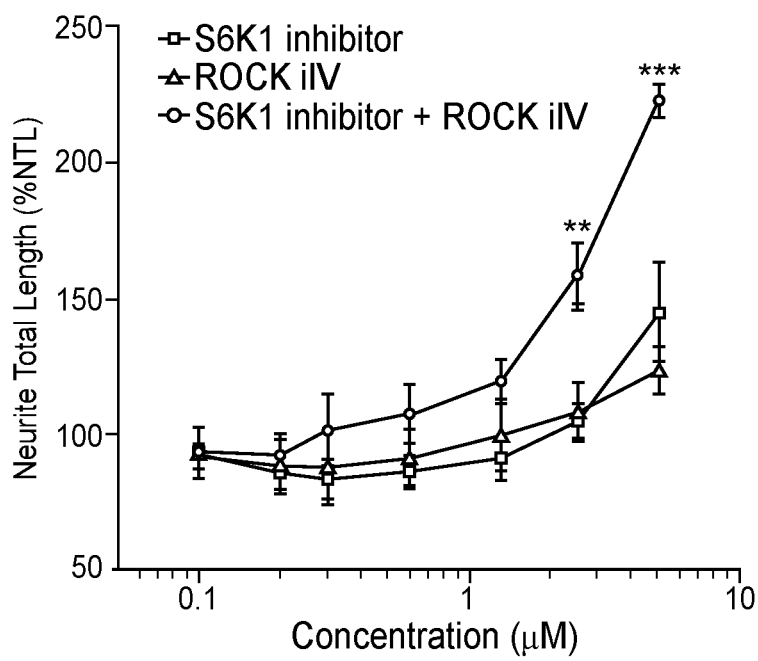
FIG. 2 shows the effect of a selective ROCK inhibitor (H-1152) and a selective S6K inhibitor (PF-4708761) on neurite outgrowth in primary CNS neurons. Combining the inhibitors of ROCK and S6K synergistically promotes neurite outgrowth.

Provided herein are compounds, or pharmaceutically acceptable salts thereof, having a structure of Formula (I):

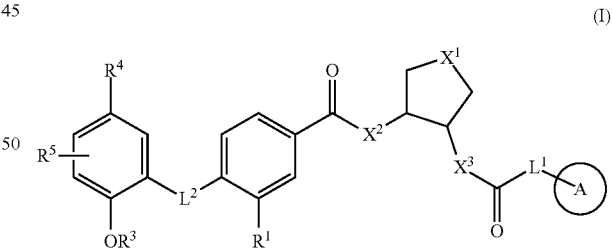

(I)

wherein ring A comprises a 5-6-membered monocyclic heteroaryl ring or a 8-11-membered bicyclic heteroaryl ring having 1, 2, or 3 nitrogen ring atoms; $L^1$ is null or $C_{1-2}$alkylene; $X^1$ is —NH—, —CH$_2$NH—, —NHCH$_2$—, —CH$_2$CH$_2$NH—, or —NHCH$_2$CH$_2$—; $X^2$ is $NR^2$ or O; $X^3$ is $NR^2$ or O; $L^2$ is C(O), O, or CHOH; $R^1$ is H or halo; each $R^2$ is independently H or $C_{1-3}$alkyl; $R^3$ is H, $C_{1-3}$alky, $C_{3-6}$cycloalkyl, aryl, C(O)$C_{1-3}$alkyl, C(O)$C_{3-6}$cycloalkyl, or C(O)aryl; $R^4$ is H, OH, halo, $C_{1-4}$alkyl, $C_{1-4}$alkoxy, C(O)$C_{1-4}$alkoxy, $C_{3-6}$cycloalkyl, aryl, —O$C_{3-6}$cycloalkyl, —Oaryl, $C_{1-4}$alkoxy-aryl, C(O)O$C_{3-6}$cycloalkyl, or C(O)Oaryl; and $R^5$ is H, halo, $C_{1-4}$alkyl, or $C_{1-4}$alkoxy.

Kinases known to mediate extrinsic inhibition of axon growth, such as Rho Kinase (ROCK) and protein kinase C (PKC). These kinases suppress axon growth in the presence of inhibitory molecules within the CNS microenvironment. Kinases known to mediate intrinsic inhibition of axon growth, such as ribosomal protein S6 kinase (S6K). These kinases suppress the intrinsic regenerative state of neurons. Treating cultured primary neurons with selective inhibitors of ROCK and/or S6K induced neurite outgrowth. Further, co-treating the cultured primary neurons with inhibitors of both kinases had a strong synergistic effect on neurite outgrowth. Treating cultured neurons with a dual inhibitor of ROCK and S6K induces an increase in neurite outgrowth (400% relative to controls). In a mouse model of SCI, dual inhibition of ROCK and S6K, via a single cortical injection, was sufficient to induce robust axon regeneration following injury (dorsal hemisection). This regeneration was accompanied by significant recovery of sensorimotor functions. RO48 (A92) was tested in a second model of spinal cord regeneration (pyramidatomy), and it was found that delivering RO48 to the CSF of injured animals enhanced compensatory sprouting from spared axons. A preliminary experiment using a third model of CNS injury (optic nerve crush) was performed, and it was found found that injecting RO40 into the eye of animals enhanced regeneration of optic nerve axons.

Based upon these results, a medicinal chemistry program was initiated, and derivatives were prepared. Several derivatives showed a strong effect on neurite outgrowth promotion in culture (some approaching 700% of controls).

Note: In addition to inhibiting ROCK, PKC, and S6K, the disclosed compounds can also inhibit 2 other kinases that were determined by to be potential targets for promoting neurite outgrowth. These are PKG and PKX.

The compounds disclosed herein can inhibit one or more kinases, e.g., Rho kinase (ROCK), ribosomal protein S6 kinase (S6K), and/or protein kinase C. inhibition of one or more of these kinases can promote neurite outgrowth and/or axon growth in the central nervous system (CNS).

Compounds of Formula (I)

Disclosed herein are compounds, or pharmaceutically acceptable salts thereof, having a structure of Formula (I):

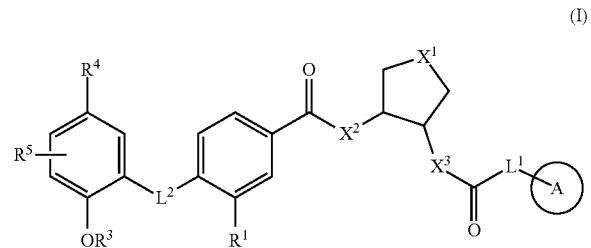

(I)

wherein ring A comprises a 5-6-membered monocyclic heteroaryl ring or a 8-11-membered bicyclic heteroaryl ring having 1, 2, or 3 nitrogen ring atoms; $L^1$ is null or $C_{1-2}$alkylene; $X^1$ is —NH—, —CH$_2$NH—, —NHCH$_2$—, —CH$_2$CH$_2$NH—, or —NHCH$_2$CH$_2$—; $X^2$ is NR$^2$ or O; $X^3$ is NR$^2$ or O; $L^2$ is C(O), O, or CHOH; R$^1$ is H or halo; each R$^2$ is independently H or $C_{1-3}$alkyl; R$^3$ is H, $C_{1-3}$alky, $C_{3-6}$cycloalkyl, aryl, C(O)$C_{1-3}$alkyl, C(O)$C_{3-6}$cycloalkyl, or C(O)aryl; R$^4$ is H, OH, halo, $C_{1-4}$alkyl, $C_{1-4}$alkoxy, C(O) $C_{1-4}$alkoxy, $C_{3-6}$cycloalkyl, aryl, —O$C_{3-6}$cycloalkyl, —Oaryl, $C_{1-4}$alkoxy-aryl, C(O)O$C_{3-6}$cycloalkyl, or C(O) Oaryl; and R$^5$ is H, halo, $C_{1-4}$alkyl, or $C_{1-4}$alkoxy. In some embodiments, $X^1$ is —NH—, —CH$_2$NH—, or —NHCH$_2$—. In some embodiments, R$^4$ is H, OH, halo, $C_{1-4}$alkyl, $C_{1-4}$alkoxy, C(O)$C_{1-4}$alkoxy, $C_{3-6}$cycloalkyl, aryl, —O$C_{3-6}$cycloalkyl, —Oaryl, C(O)O$C_{3-6}$cycloalkyl, C(O) Oaryl; and R$^5$ is H, halo, $C_{1-4}$alkyl, or $C_{1-4}$alkoxy.

As used herein, the term "alkyl" refers to straight chained and branched saturated hydrocarbon groups. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. Non-limiting examples of substituted alkyl groups include haloalkyl groups (i.e., alkyl groups substituted with one or more halo groups), hydroxyalkyl groups (i.e., alkyl groups substituted with one or more hydroxy groups), and the like.

The term "alkylene" used herein refers to an alkyl group having a substituent. For example, the term "alkylenearyl" refers to an alkyl group substituted with an aryl group. For example, an alkylene group can be —CH$_2$CH$_2$— or —CH$_2$—. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

The term "alkoxy" refer to an alkyl group substituted with an oxygen, e.g., alkyl-O—.

As used herein, the term "cycloalkyl" refers to an aliphatic cyclic hydrocarbon group. The term $C_n$ means the cycloalkyl group has "n" carbon atoms. For example, $C_5$ cycloalkyl refers to a cycloalkyl group that has 5 carbon atoms in the ring. $C_3$-$C_6$ cycloalkyl refers to cycloalkyl groups having a number of carbon atoms encompassing the entire range (i.e., 3 to 6 carbon atoms), as well as all subgroups (e.g., 3-5, 4-6, 5-6, 3, 4, 5, and 6 carbon atoms). Nonlimiting examples of cycloalkyl groups include cyclopropyl, cyclobutyl, cyclopentyl, and cyclohexyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group.

As used herein, the term "aryl" refers to a monocyclic or polycyclic aromatic group, preferably a monocyclic or bicyclic aromatic group having 6 to 10 carbon ring atoms, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Aryl groups can be isolated or fused to another aryl group, a cycloalkyl group, a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, "heteroaryl" refers to a 5-6 membered monocyclic aromatic ring having 1, 2, or 3 heteroatoms selected from N, S, and O, or a 8-11 membered bicyclic aromatic ring having 1, 2, 3, or 4 heteroatoms selected from N, S, and O. In some embodiments, the heteroaryl ring comprises at least 1 ring nitrogen, or 1, 2, or 3 ring nitrogens. Examples of contemplated heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. In some cases, the heteroaryl can be pyrrolyl, pyrazolyl, imidazolyl, triazolyl, pyridyl, pyrazinyl, pyrimidinyl, indolyl, indazolyl, benzotriazolyl, benzoimidazolyl, pyrrolopyridinyl, or imidazopyrindinyl. In various cases, the heteroaryl can be pyridyl, pyrimidinyl, pyrrolopyridinyl, indazolyl, or imidazopyrindinyl.

The term "halo" refers to fluoro, chloro, bromo, and iodo.

Specifically contemplated compounds of the disclosure include those in the below Table.

| Cpd ID | IUPAC Name | Structure |
|---|---|---|
| A1 | N-{4-[4-(2-fluoro-3,6-dimethoxybenzoyl)benzamido]pyridin-3-yl}pyridine-4-carboxamide | 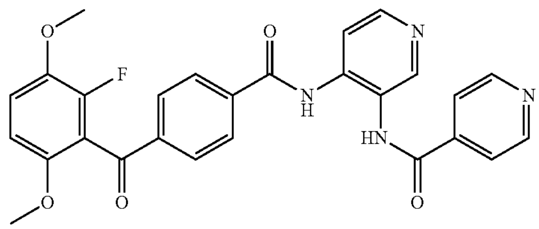 [SMILES: COc1ccc(OC)c(C(=O)c2ccc(C(=O)Nc3ccncc3NC(=O)c3ccncc3)cc2)c1F] |
| A2 | N-{4-[4-(2-fluoro-6-hydroxy-3-methoxybenzoyl)benzamido]pyridin-3-yl}pyridine-4-carboxamide | 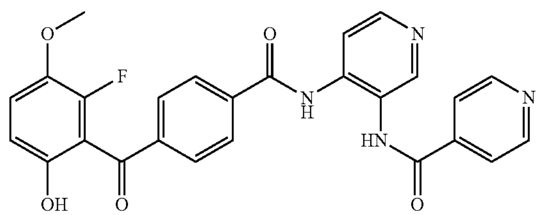 [SMILES: COc1ccc(O)c(C(=O)c2ccc(C(=O)Nc3ccncc3NC(=O)c3ccncc3)cc2)c1F] |
| A3 | N-[4-(4-benzoylbenzamido)pyridin-3-yl]pyridine-4-carboxamide | 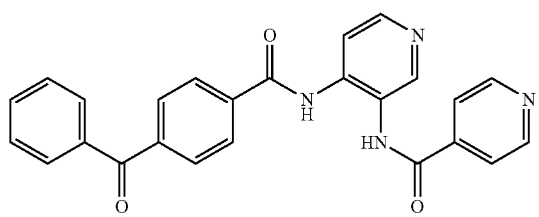 [SMILES: O=C(Nc1ccncc1NC(=O)c1ccncc1)c1ccc(C(=O)c2ccccc2)cc1] |
| A4 | N-{2-[4-(2-fluoro-3,6-dimethoxybenzoyl)benzamido]phenyl}pyridine-4-carboxamide | 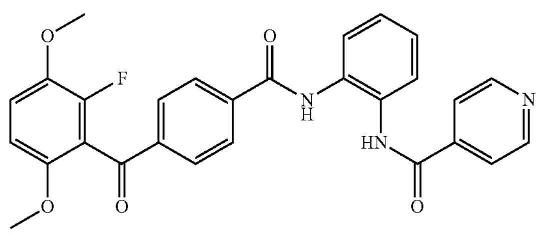 [SMILES: COc1ccc(OC)c(C(=O)c2ccc(C(=O)Nc3ccccc3NC(=O)c3ccncc3)cc2)c1F] |
| A5 | N-{2-[4-(2-fluoro-6-hydroxy-3-methoxybenzoyl)benzamido]phenyl}pyridine-4-carboxamide | 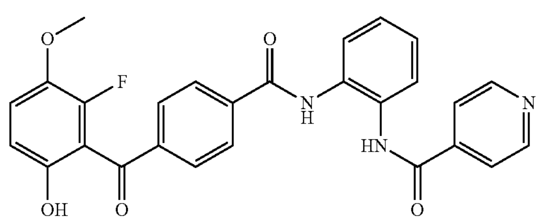 [SMILES: COc1ccc(O)c(C(=O)c2ccc(C(=O)Nc3ccccc3NC(=O)c3ccncc3)cc2)c1F] |
| A6 | N-[2-(4-benzoylbenzamido)phenyl]pyridine-4-carboxamide | 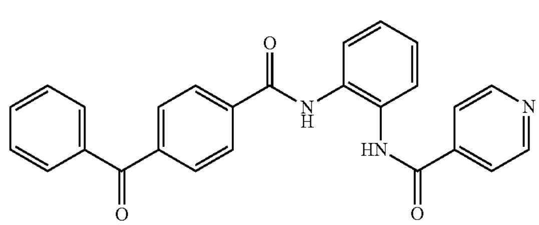 [SMILES: O=C(Nc1ccccc1NC(=O)c1ccc(C(=O)c2ccccc2)cc1)c1ccncc1] |

-continued

| Cpd ID | IUPAC Name | Structure |
| --- | --- | --- |
| A7 | 1-(4-benzoylbenzoyl)-4-(pyridine-4-carbonyl)piperazine | 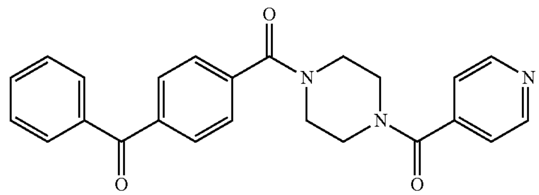 [SMILES: O=C(c1ccccc1)c1ccc(C(=O)N2CCN(C(=O)c3ccncc3)CC2)cc1] |
| A8 | 1-[4-(2-fluoro-3,6-dimethoxybenzoyl)benzoyl]-4-(pyridine-4-carbonyl)piperazine | 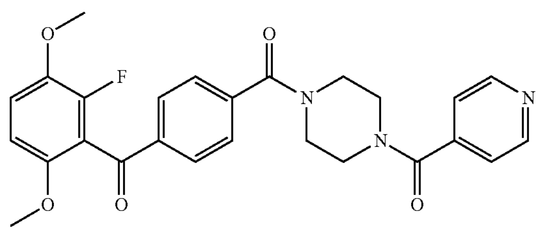 [SMILES: COc1ccc(OC)c(C(=O)c2ccc(C(=O)N3CCN(C(=O)c4ccncc4)CC3)cc2)c1F] |
| A9 | 3-fluoro-4-methoxy-2-{4-[4-(pyridine-4-carbonyl)piperazine-1-carbonyl]benzoyl}phenol | 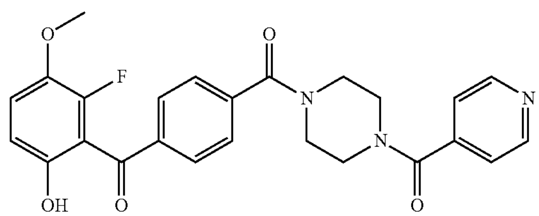 [SMILES: COc1ccc(O)c(C(=O)c2ccc(C(=O)N3CCN(C(=O)c4ccncc4)CC3)cc2)c1F] |
| A10 | N-[(3R,4R)-4-(pyridine-4-amido)pyrrolidin-3-yl]pyridine-4-carboxamide | 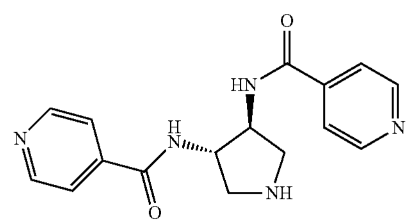 [SMILES: O=C(N[C@H]1CNC[C@@H]1NC(=O)c1ccncc1)c1ccncc1] |
| A11 | N-[(1R,2R)-1-(4-benzoylbenzamido)-2,3-dihydro-1H-inden-2-yl]pyridine-4-carboxamide | 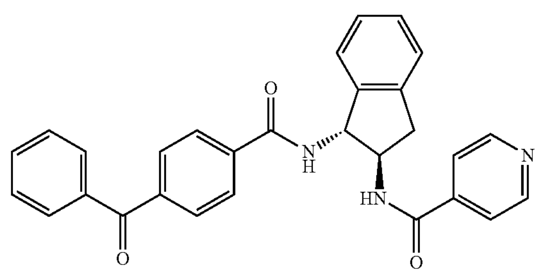 [SMILES: O=C(N[C@@H]1c2ccccc2C[C@H]1NC(=O)c1ccncc1)c1ccc(C(=O)c2ccccc2)cc1] |
| A12 | N-[(1R,2R)-1-[4-(2-fluoro-3,6-dimethoxybenzamido)benzamido]-2,3-dihydro-1H-inden-2-yl]pyridine-4-carboxamide | 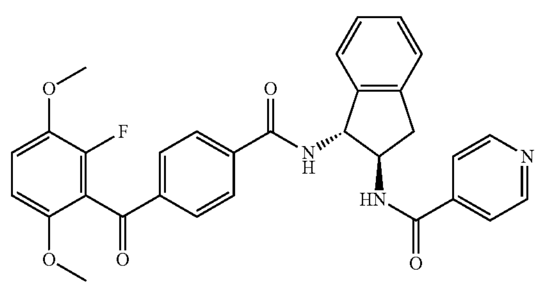 [SMILES: COc1ccc(OC)c(C(=O)c2ccc(C(=O)N[C@@H]3c4ccccc4C[C@H]3NC(=O)c3ccncc3)cc2)c1F] |

| Cpd ID | IUPAC Name | Structure |
|---|---|---|
| A13 | N-[(3R,4R)-4-(4-benzoylbenzamido)pyrrolidin-3-yl]pyridine-4-carboxamide | 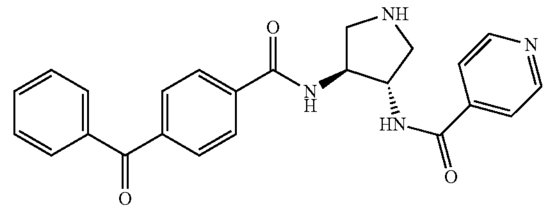 [SMILES: O=C(N[C@H]1CNC[C@@H]1NC(=O)c1ccc(C(=O)c2ccccc2)cc1)c1ccncc1] |
| A14 | N-[(1R,2R)-1-[4-(2-fluoro-6-hydroxy-3-methoxybenzoyl)benzamido]-2,3-dihydro-1H-inden-2-yl]pyridine-4-carboxamide | 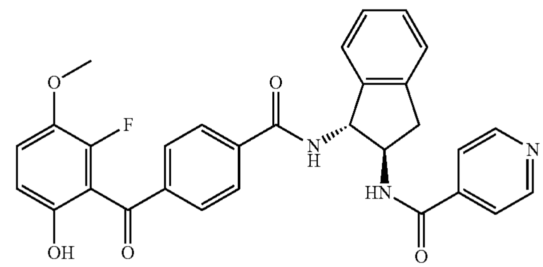 [SMILES: COc1ccc(O)c(C(=O)c2ccc(C(=O)N[C@@H]3c4ccccc4C[C@H]3NC(=O)c3ccncc3)cc2)c1F] |
| A15 | N-[(1R,2R)-2-(4-benzoylbenzamido)cyclopentyl]pyridine-4-carboxamide | 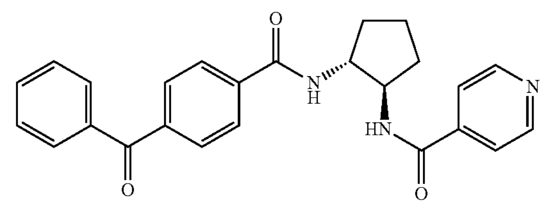 [SMILES: O=C(N[C@@H]1CCC[C@H]1NC(=O)c1ccc(C(=O)c2ccccc2)cc1)c1ccncc1] |
| A16 | N-[(3R,4R)-4-[4-(2-fluoro-6-hydroxy-3-methoxybenzoyl)benzamido]pyrrolidin-3-yl]pyridine-4-carboxamide | 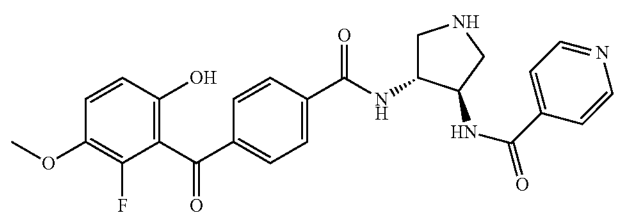 [SMILES: COc1ccc(O)c(C(=O)c2ccc(C(=O)N[C@@H]3CNC[C@H]3NC(=O)c3ccncc3)cc2)c1F] |
| A17 | N-[(1R,2R)-2-[4-(2-fluoro-3,6-dimethoxybenzoyl)benzamido]cyclopentyl]pyridine-4-carboxamide | 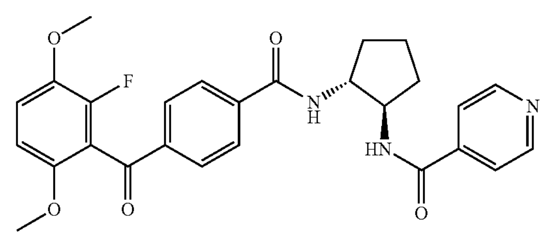 [SMILES: COc1ccc(OC)c(C(=O)c2ccc(C(=O)N[C@@H]3CCC[C@H]3NC(=O)c3ccncc3)cc2)c1F] |
| A18 | N-[(1R,2R)-2-[4-(2-fluoro-6-hydroxy-3-methoxybenzoyl)benzamido]cyclopentyl]pyridine-4-carboxamide | 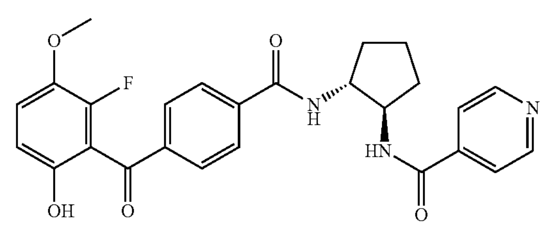 [SMILES: COc1ccc(O)c(C(=O)c2ccc(C(=O)N[C@@H]3CCC[C@H]3NC(=O)c3ccncc3)cc2)c1F] |
| A19 | N-[(1R,2R)-2-(4-benzoylbenzamido)cyclohexyl]pyridine-4-carboxamide | 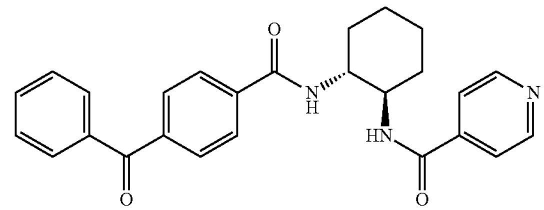 [SMILES: O=C(N[C@@H]1CCCC[C@H]1NC(=O)c1ccc(C(=O)c2ccccc2)cc1)c1ccncc1] |

-continued

| Cpd ID | IUPAC Name | Structure |
|---|---|---|
| A20 | N-[(3R,4R)-4-benzamidopyrrolidin-3-yl]pyridine-4-carboxamide | 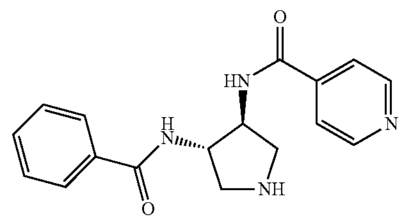 [SMILES: O=C(N[C@H]1CNC[C@@H]1NC(=O)c1ccncc1)c1ccccc1] |
| A21 | N-[(1R,2R)-2-[4-(2-fluoro-3,6-dimethoxybenzoyl)benzamido]cyclohexyl]pyridine-4-carboxamide | 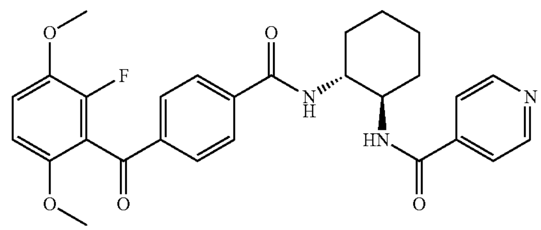 [SMILES: COc1ccc(OC)c(C(=O)c2ccc(C(=O)N[C@@H]3CCCC[C@H]3NC(=O)c3ccncc3)cc2)c1F] |
| A22 | N-[(1R,2R)-2-[4-(2-fluoro-6-hydroxy-3-methoxybenzoyl)benzamido]cyclohexyl]pyridine-4-carboxamide | 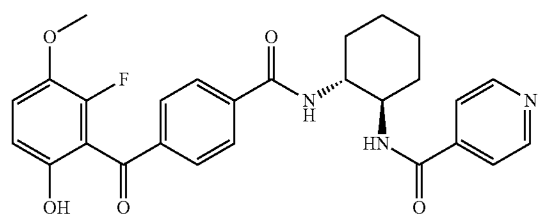 [SMILES: COc1ccc(O)c(C(=O)c2ccc(C(=O)N[C@@H]3CCCC[C@H]3NC(=O)c3ccncc3)cc2)c1F] |
| A23 | N-[(1R,2R)-2-(4-benzoylbenzamido)cycloheptyl]pyridine-4-carboxamide | 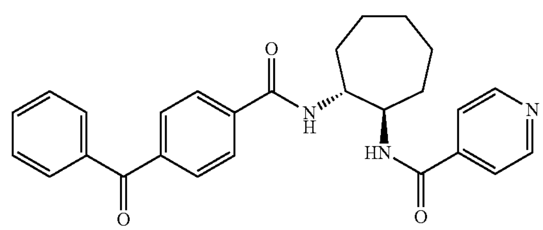 [SMILES: O=C(N[C@@H]1CCCCC[C@H]1NC(=O)c1ccc(C(=O)c2ccccc2)cc1)c1ccncc1] |
| A24 | N-[(1R,2R)-2-[4-(2-fluoro-3,6-dimethoxybenzoyl)benzamido]cycloheptyl]pyridine-4-carboxamide | 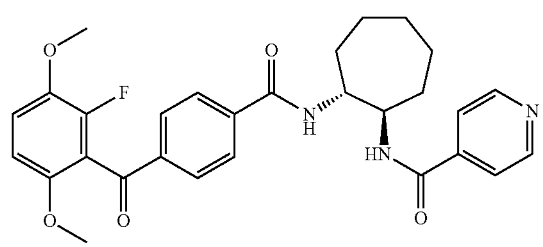 [SMILES: COc1ccc(OC)c(C(=O)c2ccc(C(=O)N[C@@H]3CCCCC[C@H]3NC(=O)c3ccncc3)cc2)c1F] |
| A25 | N-[(1R,2R)-2-[4-(2-fluoro-6-hydroxy-3-methoxybenzoyl)benzamido]cycloheptyl]pyridine-4-carboxamide | 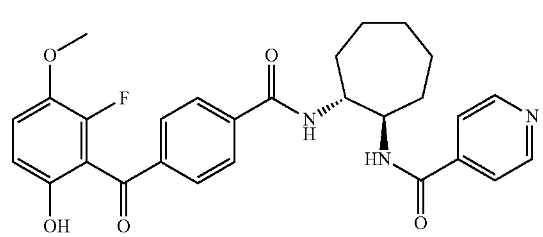 [SMILES: COc1ccc(O)c(C(=O)c2ccc(C(=O)N[C@@H]3CCCCC[C@H]3NC(=O)c3ccncc3)cc2)c1F] |

-continued

| Cpd ID | IUPAC Name | Structure |
|---|---|---|
| A26 | 4-(2-fluoro-3,6-dimethoxybenzoyl)-N-{2-[(pyridin-4-yl)formamido]ethyl}benzamide | 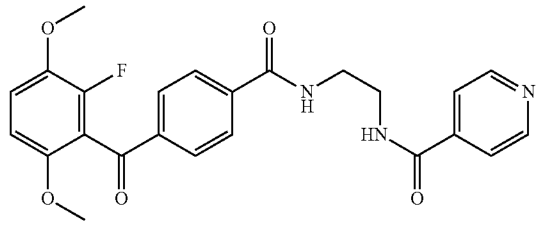 [SMILES: COc1ccc(OC)c(C(=O)c2ccc(C(=O)NCCNC(=O)c3ccncc3)cc2)c1F] |
| A27 | 4-(2-fluoro-6-hydroxy-3-methoxybenzoyl)-N-{2-[(pyridin-4-yl)formamido]ethyl}benzamide | 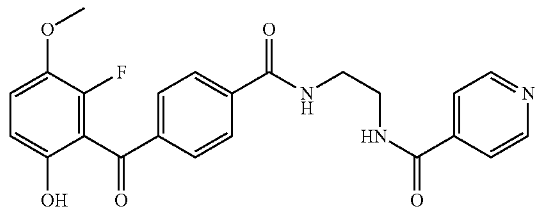 [SMILES: COc1ccc(O)c(C(=O)c2ccc(C(=O)NCCNC(=O)c3ccncc3)cc2)c1F] |
| A28 | (3R,4R)-1-methyl-4-(pyridine-4-amido)pyrrolidin-3-yl 4-(2-fluoro-3,6-dimethoxybenzoyl)benzoate | 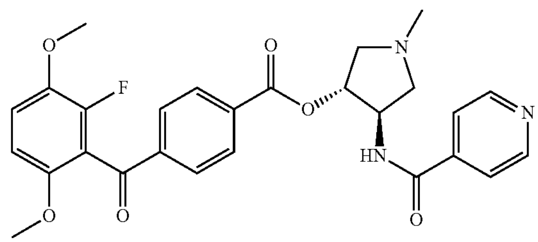 [SMILES: COc1ccc(OC)c(C(=O)c2ccc(C(=O)O[C@@H]3CN(C)C[C@H]3NC(=O)c3ccncc3)cc2)c1F] |
| A29 | (3R,4R)-4-(pyridine-4-amido)pyrrolidin-3-yl 4-(2-fluoro-6-hydroxy-3-methoxybenzoyl)benzoate | 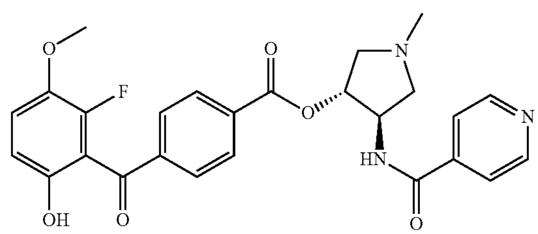 [SMILES: COc1ccc(O)c(C(=O)c2ccc(C(=O)O[C@@H]3CN(C)C[C@H]3NC(=O)c3ccncc3)cc2)c1F] |
| A30 | (3R,4R)-1-methyl-3-(pyridine-4-amido)piperidin-4-yl 4-(2-fluoro-3,6-dimethoxybenzoyl)benzoate | 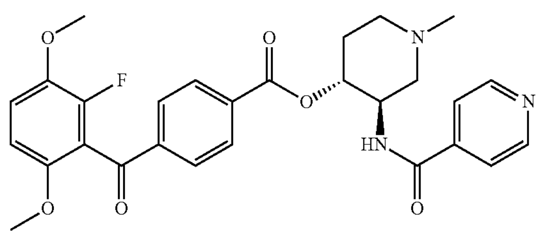 [SMILES: COc1ccc(OC)c(C(=O)c2ccc(C(=O)O[C@@H]3CCN(C)C[C@H]3NC(=O)c3ccncc3)cc2)c1F] |
| A31 | (3R,4R)-3-(pyridine-4-amido)piperidin-4-yl 4-(2-fluoro-6-hydroxy-3-methoxybenzoyl)benzoate | 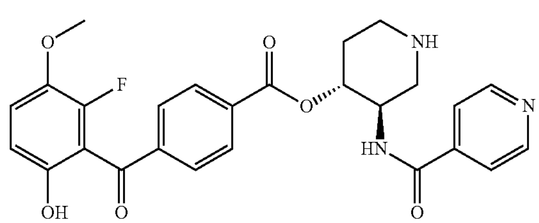 [SMILES: COc1ccc(O)c(C(=O)c2ccc(C(=O)O[C@@H]3CCNC[C@H]3NC(=O)c3ccncc3)cc2)c1F] |

-continued

| Cpd ID | IUPAC Name | Structure |
|---|---|---|
| A32 | N-[(3R,4S)-4-[4-(2-fluoro-6-hydroxy-3-methoxybenzoyl)benzamido]pyrrolidin-3-yl]pyridine-4-carboxamide | 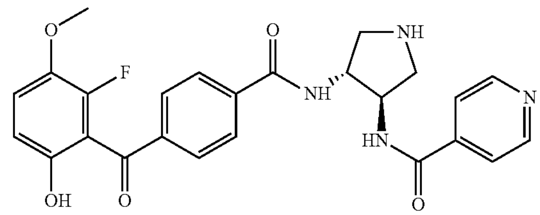 [SMILES: COc1ccc(O)c(C(=O)c2ccc(C(=O)N[C@@H]3CNC[C@H]3NC(=O)c3ccncc3)cc2)c1F] |
| A33 | N-[(3R,4R)-4-[4-(2-fluoro-3,6-dimethoxybenzoyl)benzamido]-1-methylpyrrolidin-3-yl]pyridine-4-carboxamide | 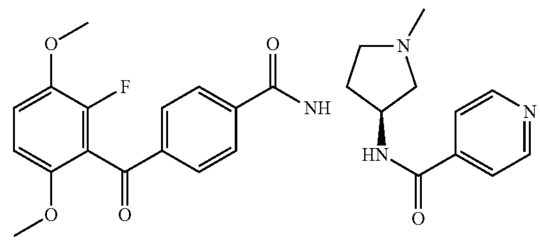 |
| A34 | N-[(3S,4S)-4-[4-(2-fluoro-6-hydroxy-3-methoxybenzoyl)benzamido]pyrrolidin-3-yl]pyridine-4-carboxamide | 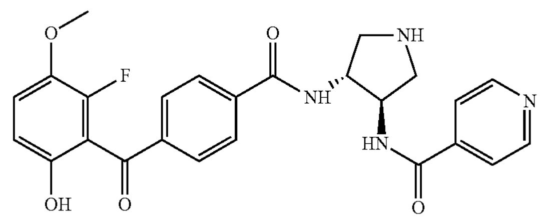 [SMILES: COc1ccc(O)c(C(=O)c2ccc(C(=O)N[C@@H]3CNC[C@H]3NC(=O)c3ccncc3)cc2)c1F] |
| A35 | N-[(3R,4R)-4-[4-(2-fluoro-6-hydroxy-3-methoxybenzoyl)benzamido]pyrrolidin-3-yl]-2-oxo-2,3-dihydro-1H-indole-5-carboxamide | 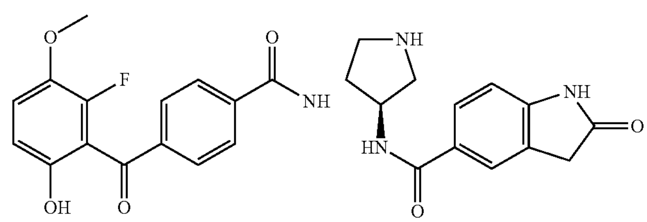 |
| A36 | 2-amino-N-[(3R,4R)-4-[4-(2-fluoro-6-hydroxy-3-methoxybenzoyl)benzamido]pyrrolidin-3-yl]pyrimidine-4-carboxamide | 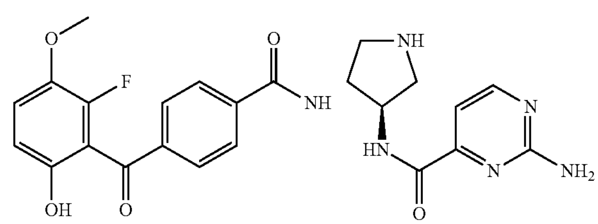 |
| A37 | N-[(3R,4R)-4-[4-(2-fluoro-6-hydroxy-3-methoxybenzoyl)benzamido]pyrrolidin-3-yl]-4-hydroxybenzamide | 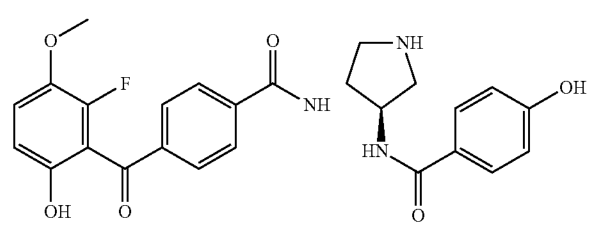 |
| A38 | N-[(3R,4R)-4-[4-(2-fluoro-6-hydroxy-3-methoxybenzoyl)benzamido]pyrrolidin-3-yl]pyridine-3-carboxamide | 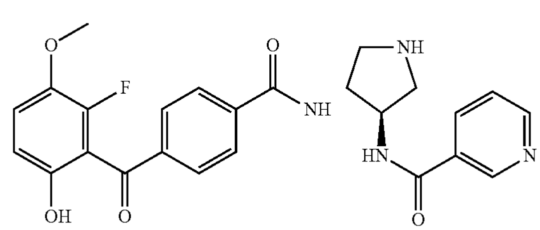 |

-continued

| Cpd ID | IUPAC Name | Structure |
|---|---|---|
| A39 | N-[(3R,4R)-4-[4-(2-fluoro-6-hydroxy-3-methoxybenzoyl)benzamido]pyrrolidin-3-yl]-6-hydroxypyridine-3-carboxamide | 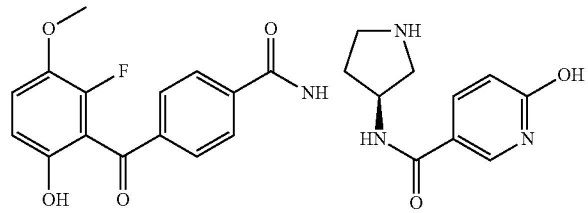 |
| A40 | N-[(3R,4R)-4-[4-(2-fluoro-6-hydroxy-3-methoxybenzoyl)benzamido]pyrrolidin-3-yl]-2-hydroxypyridine-4-carboxamide | 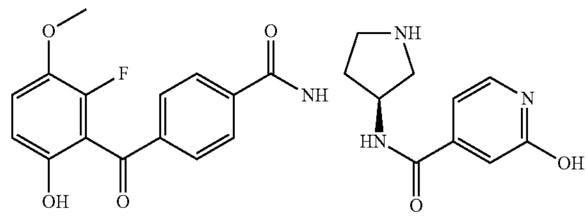 |
| A41 | N-[(3R,4R)-4-[4-(2-fluoro-6-hydroxy-3-methoxybenzoyl)benzamido]pyrrolidin-3-yl]pyrimidine-4-carboxamide | 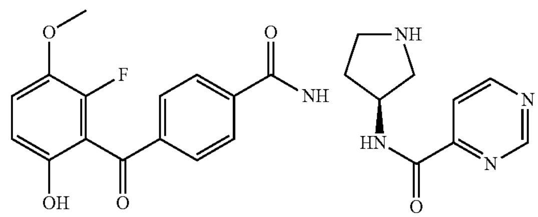 |
| A42 | N-[(3R,4R)-4-[4-(2-fluoro-6-hydroxy-3-methoxybenzoyl)benzamido]pyrrolidin-3-yl]-1H-indazole-5-carboxamide | 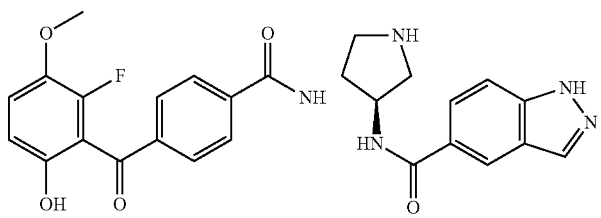 |
| A43 | N-[(3R,4R)-4-[4-(2-fluoro-6-hydroxy-3-methoxybenzoyl)benzamido]pyrrolidin-3-yl]-1H-pyrazole-4-carboxamide | 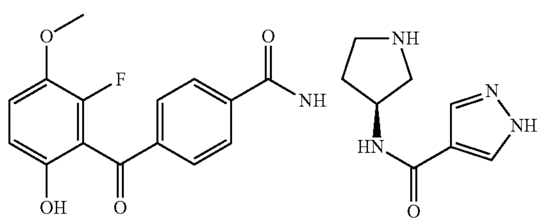 |
| A44 | 2-amino-N-[(3R,4R)-4-{4-[(2-fluoro-6-hydroxy-3-methoxyphenyl)(hydroxy)methyl]benzamido}pyrrolidin-3-yl]pyrimidine-4-carboxamide | 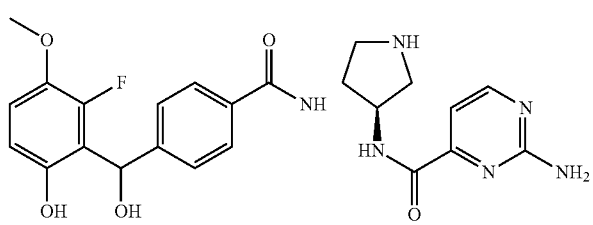 |
| A45 | 2-amino-N-[(3R,4R)-4-{4-[(2-fluoro-6-hydroxy-3-methoxyphenyl)methyl]benzamido}pyrrolidin-3-yl]pyrimidine-4-carboxamide | 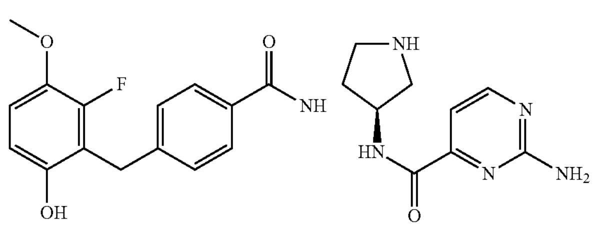 |

-continued

| Cpd ID | IUPAC Name | Structure |
|---|---|---|
| A46 | 4-(2-fluoro-6-hydroxy-3-methoxybenzoyl)-N-[(3R,4R)-4-[2-(pyridin-3-yl)acetamido]pyrrolidin-3-yl]benzamide | 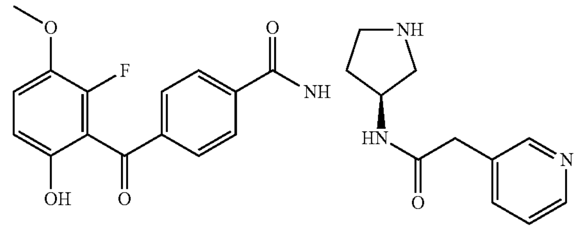 |
| A47 | 4-(2-fluoro-6-hydroxy-3-methoxybenzoyl)-N-[(3R,4R)-4-[2-(1H-pyrazol-4-yl)acetamido]pyrrolidin-3-yl]benzamide | 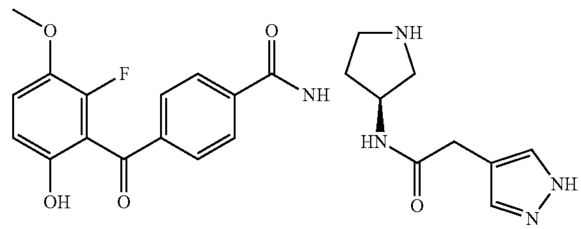 |
| A48 | N-[(3R,4R)-4-[4-(2-fluoro-6-hydroxy-3-methoxybenzoyl)benzamido]pyrrolidin-3-yl]-3H-imidazo[4,5-b]pyridine-7-carboxamide | 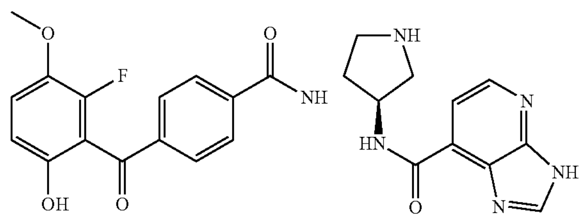 |
| A49 | N-[(3R,4R)-4-[4-(2-fluoro-6-hydroxybenzoyl)benzamido]pyrrolidin-3-yl]-1H-indazole-5-carboxamide | 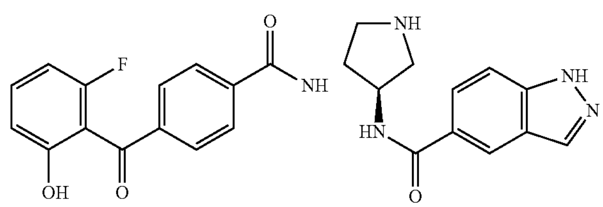 |
| A50 | 2-amino-N-[(3R,4R)-4-[4-(2-fluoro-6-hydroxybenzoyl)benzamido]pyrrolidin-3-yl]pyrimidine-4-carboxamide | 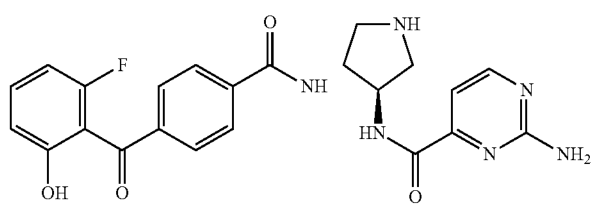 |
| A51 | N-[(3R,4R)-4-[4-(2-fluoro-6-hydroxybenzoyl)benzamido]pyrrolidin-3-yl]pyridine-4-carboxamide | 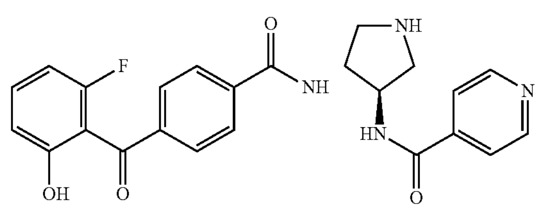 |
| A52 | N-[(3R,4R)-4-[4-(2-fluoro-6-hydroxy-3-methoxybenzoyl)benzamido]pyrrolidin-3-yl]-1H-1,3-benzodiazole-5-carboxamide | 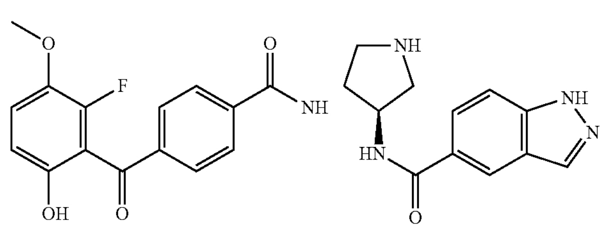 |

-continued

| Cpd ID | IUPAC Name | Structure |
|---|---|---|
| A53 | N-[(3R,4R)-4-[4-(2-fluoro-6-hydroxy-3-methoxybenzoyl)benzamido]pyrrolidin-3-yl]-1-methyl-1H-indazole-5-carboxamide | 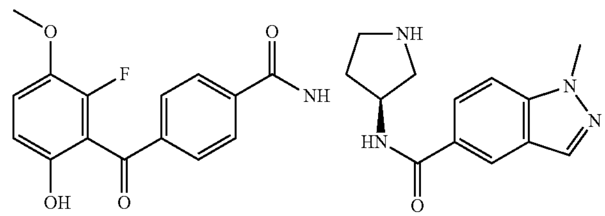 |
| A54 | 2-amino-N-[(3R,4R)-4-[4-(2-fluoro-6-hydroxy-3-methoxybenzoyl)benzamido]pyrrolidin-3-yl]pyridine-4-carboxamide | 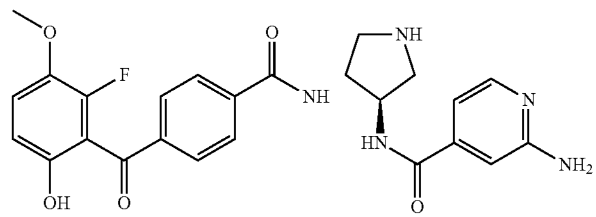 |
| A55 | N[(3R,4R)-4-{4-[(2-fluoro-6-hydroxy-3-methoxyphenyl)methyl]benzamido}pyrrolidin-3-yl]pyridine-4-carboxamide | 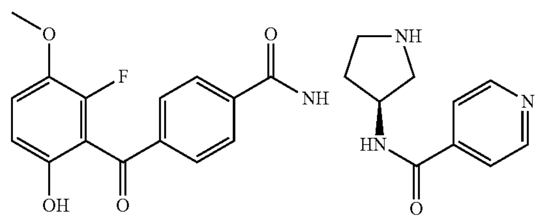 |
| A56 | N-[(3R,4R)-4-[4-(2-fluoro-6-hydroxy-3-methoxybenzoyl)benzamido]pyrrolidin-3-yl]-1H-pyrrolo[2,3-b]pyridine-4-carboxamide | 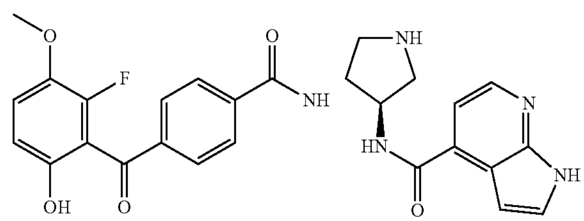 |
| A57 | N-[(3R,4R)-4-[4-(2-fluoro-6-hydroxy-3-methoxybenzoyl)benzamido]pyrrolidin-3-yl]-1H-indazole-6-carboxamide | 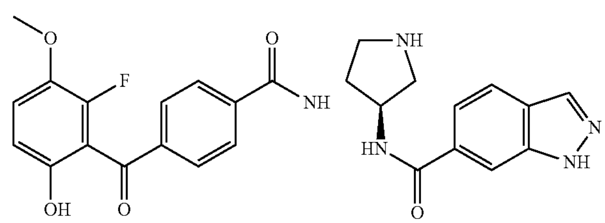 |
| A58 | N-[(3R,4R)-4-[4-(2-fluoro-6-hydroxy-3-methoxybenzoyl)benzamido]pyrrolidin-3-yl]-1H-1,2,3-benzotriazole-5-carboxamide | 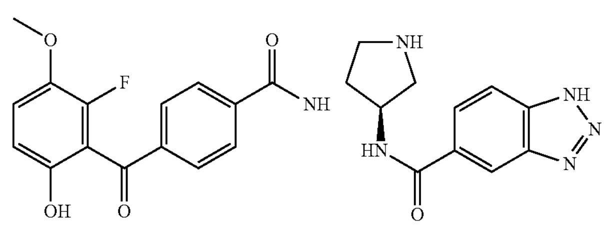 |
| A59 | N-[(3R,4R)-4-{4-[(2-fluoro-6-hydroxy-3-methoxyphenyl)(hydroxy)methyl]benzamido}pyrrolidin-3-yl]pyridine-4-carboxamide | 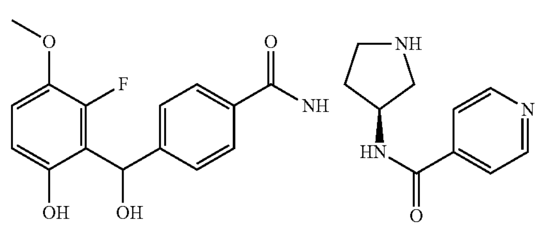 |

-continued

| Cpd ID | IUPAC Name | Structure |
|---|---|---|
| A60 | 2-amino-N-[(3R,4R)-4-[4-(2-methoxyphenoxy)benzamido]pyrrolidin-3-yl]pyrimidine-4-carboxamide | 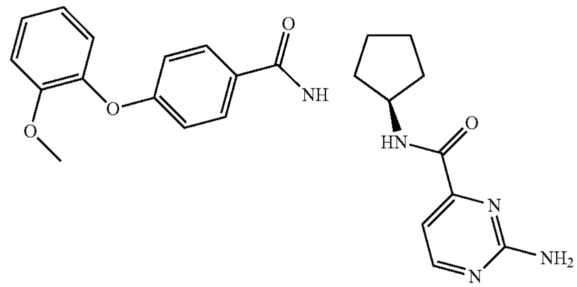 |
| A61 | N-[(3R,4R)-4-[4-(2-methoxyphenoxy)benzamido]pyrrolidin-3-yl]pyridine-4-carboxamide | 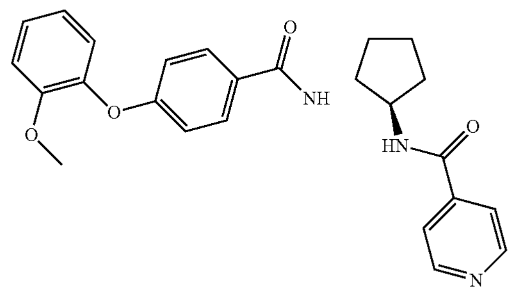 |
| A62 | 2-amino-N-[(3R,4R)-4-[1-(2-hydroxy-5-methoxybenzoyl)piperidine-4-amido]pyrrolidin-3-yl]pyrimidine-4-carboxamide | 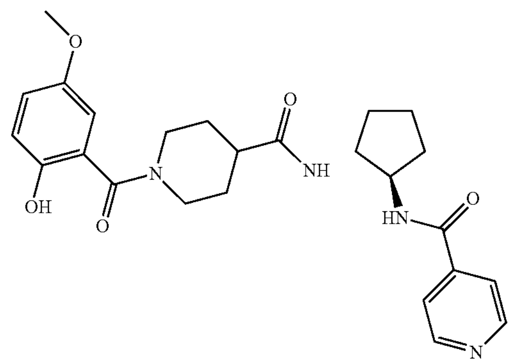 |
| A63 | N-[(3R,4R)-4-[1-(2-hydroxy-5-methoxybenzoyl)piperidine-4-amido]pyrrolidin-3-yl]pyridine-4-carboxamide | 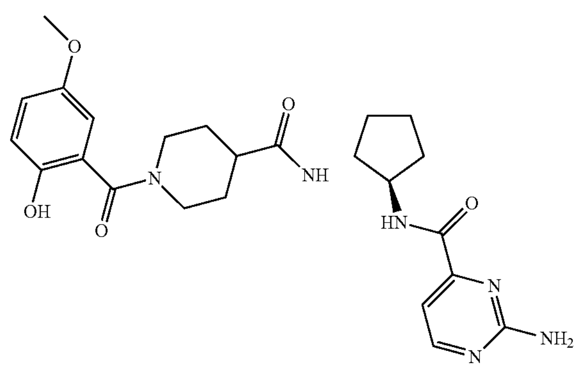 |
| A64 | N-[(3R,4R)-4-[4-(2-hydroxybenzoyl)-3-methylbenzamido]pyrrolidin-3-yl]pyridine-4-carboxamide | 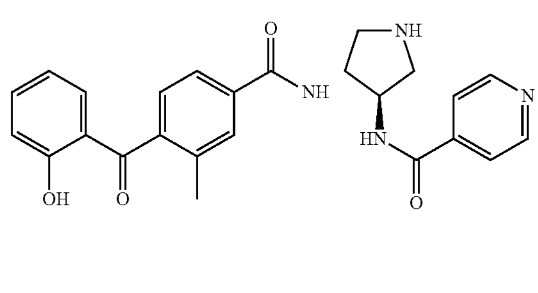 |

-continued

| Cpd ID | IUPAC Name | Structure |
|---|---|---|
| A65 | N-[(3R,4R)-4-[2-chloro-4-(2-hydroxybenzoyl)benzamido]pyrrolidin-3-yl]pyridine-4-carboxamide | 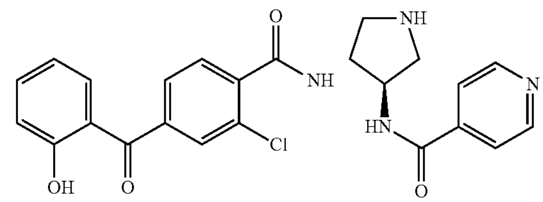 |
| A66 | 2-amino-N-[(3R,4R)-4-[3-chloro-4-(2-hydroxybenzoyl)benzamido]pyrrolidin-3-yl]pyrimidine-4-carboxamide | 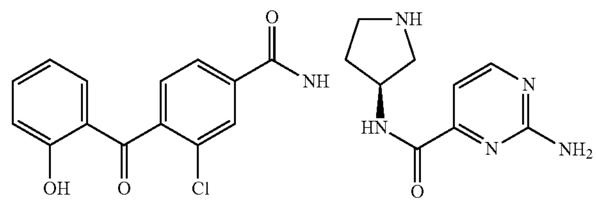 |
| A67 | N-[(3R,4R)-4-[3-chloro-4-(2-hydroxybenzoyl)benzamido]pyrrolidin-3-yl]pyridine-4-carboxamide | 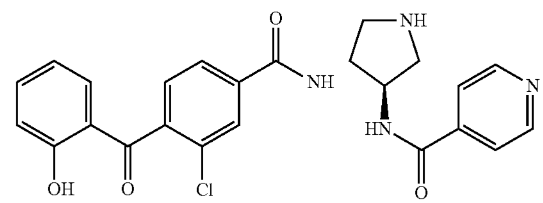 |
| A68 | 2-amino-N-[(3R,4R)-4-[4-(2-hydroxybenzoyl)-2-methoxybenzamido]pyrrolidin-3-yl]pyrimidine-4-carboxamide | 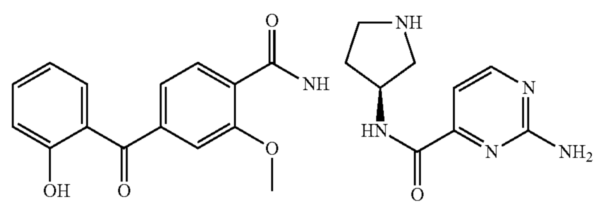 |
| A69 | N-[(3R,4R)-4-[4-(2-hydroxybenzoyl)-2-methoxybenzamido]pyrrolidin-3-yl]pyridine-4-carboxamide | 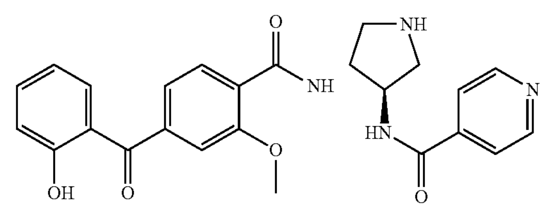 |
| A70 | 2-amino-N-[(3R,4R)-4-[4-(3-chloro-2-hydroxybenzoyl)benzamido]pyrrolidin-3-yl]pyrimidine-4-carboxamide | 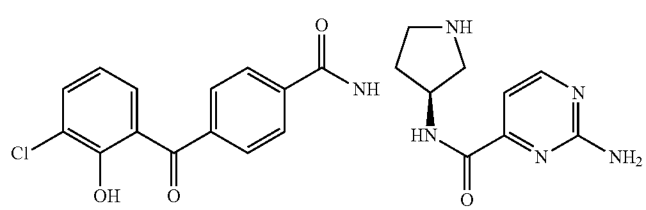 |
| A71 | N-[(3R,4R)-4-[4-(3-chloro-2-hydroxybenzoyl)benzamido]pyrrolidin-3-yl]pyridine-4-carboxamide | 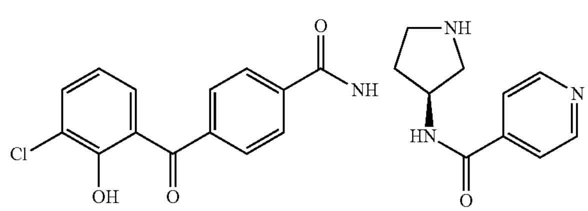 |

-continued

| Cpd ID | IUPAC Name | Structure |
| --- | --- | --- |
| A72 | 2-amino-N-[(3R,4R)-4-[4-(2-hydroxy-3-methoxybenzoyl)benzamido]pyrrolidin-3-yl]pyrimidine-4-carboxamide | 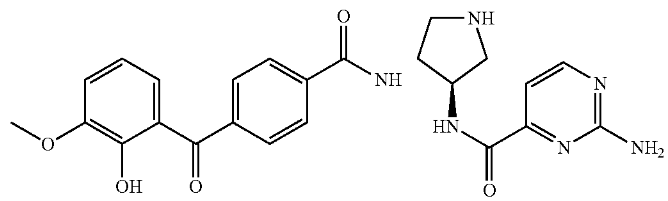 |
| A73 | N-[(3R,4R)-4-[4-(2-hydroxy-3-methoxybenzoyl)benzamido]pyrrolidin-3-yl]pyridine-4-carboxamide | 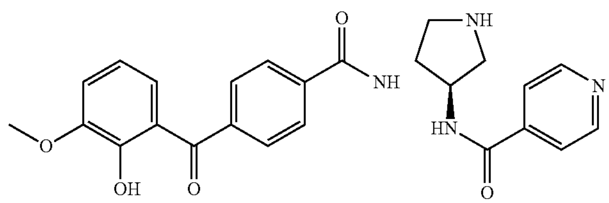 |
| A74 | 2-amino-N-[(3R,4R)-4-[4-(2-hydroxy-3-methylbenzoyl)benzamido]pyrrolidin-3-yl]pyrimidine-4-carboxamide | 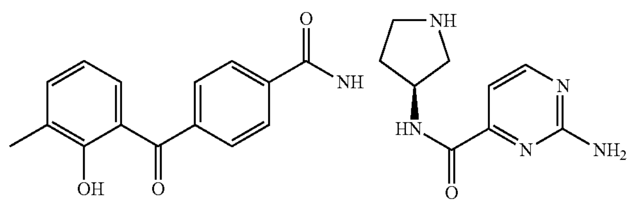 |
| A75 | N-[(3R,4R)-4-[4-(2-hydroxy-3-methylbenzoyl)benzamido]pyrrolidin-3-yl]pyridine-4-carboxamide | 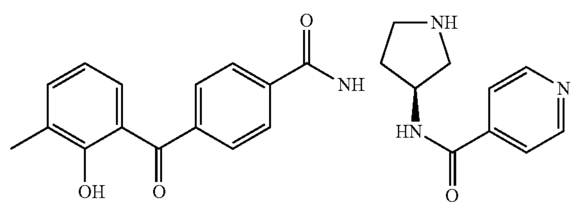 |
| A76 | 2-amino-N-[(3R,4R)-4-[4-(2-hydroxy-5-methoxybenzoyl)benzamido]pyrrolidin-3-yl]pyrimidine-4-carboxamide | 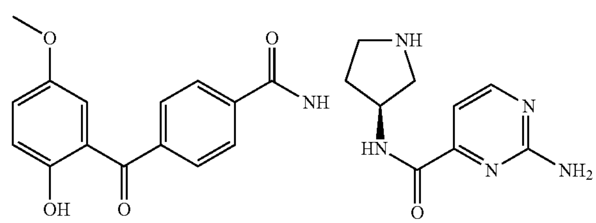 |
| A77 | N-[(3R,4R)-4-[4-(2-hydroxy-5-methoxybenzoyl)benzamido]pyrrolidin-3-yl]pyridine-4-carboxamide | 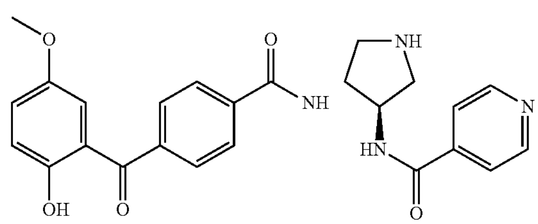 |
| A78 | N-[(3R,4R)-4-[4-(2-hydroxy-5-methylbenzoyl)benzamido]pyrrolidin-3-yl]pyridine-4-carboxamide | 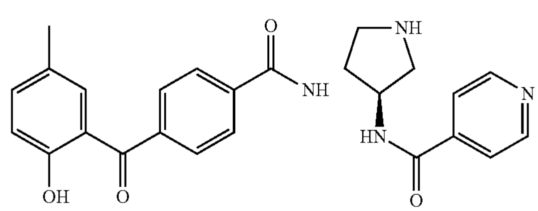 |

-continued

| Cpd ID | IUPAC Name | Structure |
| --- | --- | --- |
| A79 | N-[(3R,4R)-4-[4-(4-chloro-2-hydroxybenzoyl)benzamido]pyrrolidin-3-yl]pyridine-4-carboxamide | 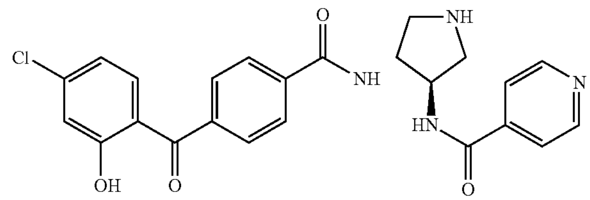 |
| A80 | 2-amino-N-[(3R,4R)-4-[4-(2-hydroxy-4-methylbenzoyl)benzamido]pyrrolidin-3-yl]pyrimidine-4-carboxamide | 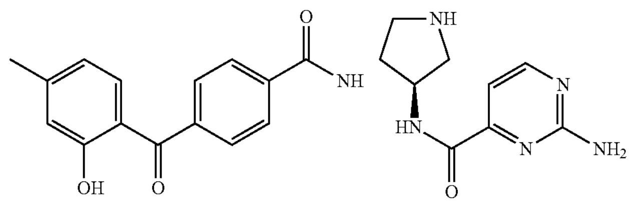 |
| A81 | N-[(3R,4R)-4-[4-(2-hydroxy-4-methylbenzoyl)benzamido]pyrrolidin-3-yl]pyridine-4-carboxamide | 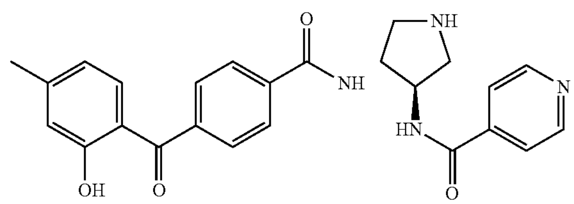 |
| A82 | 2-amino-N-[(3R,4R)-4-[4-(2-hydroxy-4-methoxybenzoyl)benzamido]pyrrolidin-3-yl]pyrimidine-4-carboxamide | 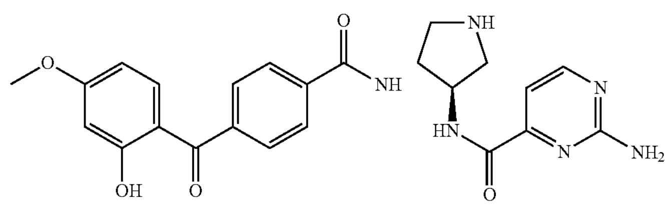 |
| A83 | N-[(3R,4R)-4-[4-(2-hydroxy-4-methoxybenzoyl)benzamido]pyrrolidin-3-yl]pyridine-4-carboxamide | 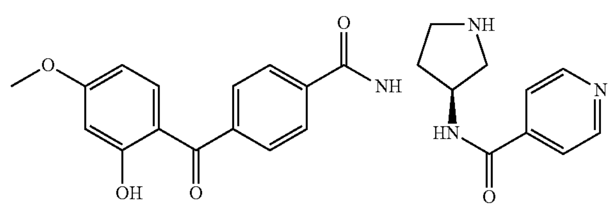 |
| A84 | 2-amino-N-[(3R,4R)-4-[4-(5-chloro-2-hydroxybenzoyl)benzamido]pyrrolidin-3-yl]pyrimidine-4-carboxamide | 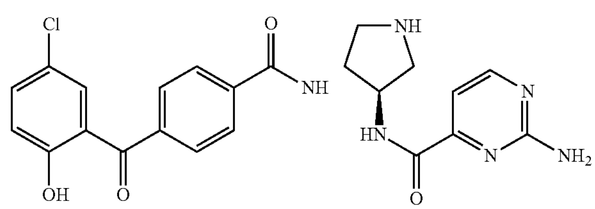 |
| A85 | N-[(3R,4R)-4-[4-(5-chloro-2-hydroxybenzoyl)benzamido]pyrrolidin-3-yl]pyridine-4-carboxamide | 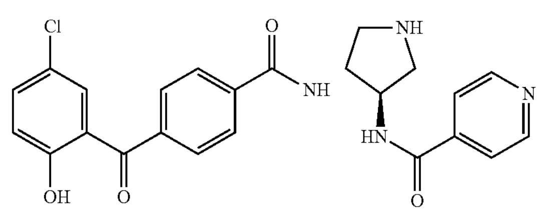 |

| Cpd ID | IUPAC Name | Structure |
|---|---|---|
| A86 | N-[(3R,4R)-4-[4-(2-hydroxybenzoyl)benzamido]pyrrolidin-3-yl]pyridine-4-carboxamide | 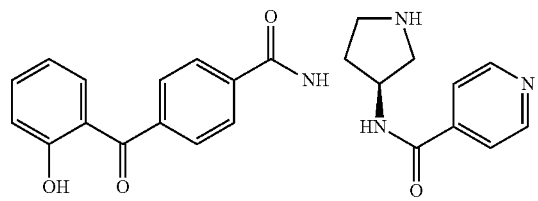 |
| A87 | 2-(4-(((3R,4R)-4-(isonicotinamido)pyrrolidin-3-yl)carbamoyl)benzoyl)-4-methoxyphenyl benzoate | |
| A88 | N-((3R,4R)-4-(4-(5-bromo-2-hydroxybenzoyl)benzamido)pyrrolidin-3-yl)isonicotinamide | |
| A89 | 2-(4-(((3R,4R)-4-(isonicotinamido)pyrrolidin-3-yl)carbamoyl)benzoyl)-4-methoxyphenyl acetate | |
| A90 | N-((3R,4R)-4-(4-(5-ethoxy-2-hydroxybenzoyl)benzamido)pyrrolidin-3-yl)isonicotinamide | 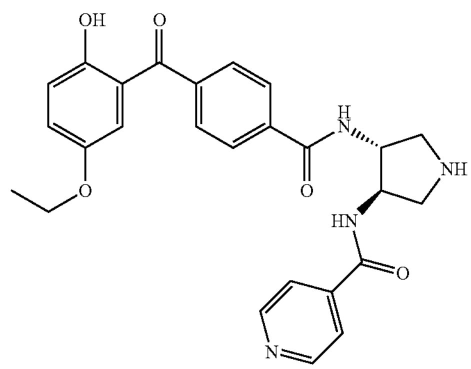 [SMILES: CCOc1ccc(O)c(C(=O)c2ccc(C(=O)N[C@@H]3CNC[C@H]3NC(=O)c3ccncc3)cc2)c1] |
| A91 | N-((3R,4R)-4-(4-(5-fluoro-2-hydroxybenzoyl)benzamido)pyrrolidin-3-yl)isonicotinamide | 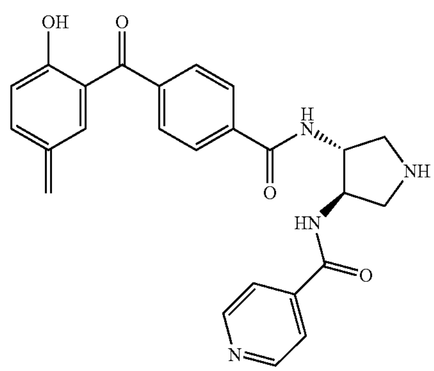 |
| A92 | (3R,4R)-3-(isonicotinamido)azepan-4-yl 4-(2-fluoro-6-hydroxy-3-methoxybenzoyl)benzoate | 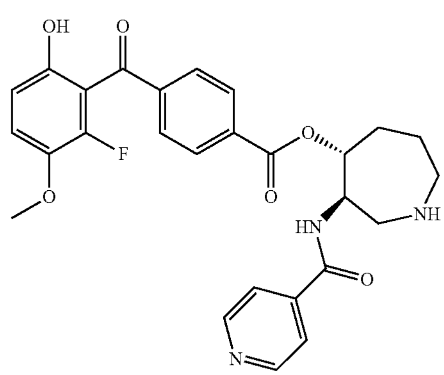 [SMILES: COc1ccc(O)c(C(=O)c2ccc(C(=O)O[C@@H]3CCCNC[C@H]3NC(=O)c3ccncc3)cc2)c1F] |

-continued

| Cpd ID | IUPAC Name | Structure |
|---|---|---|
| A93 | N-((3R,4R)-4-(4-(4-hydroxy-[1,1'-biphenyl]-3-carbonyl)benzamido)pyrrolidin-3-yl)isonicotinamide | 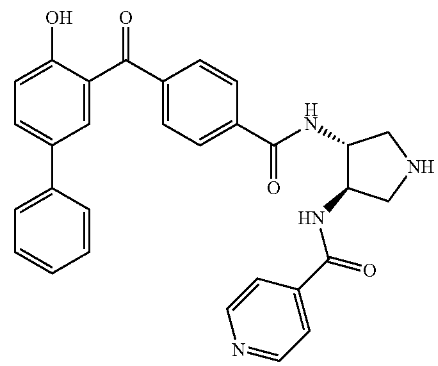 [SMILES: O=C(N[C@@H]1CNC[C@H]1NC(=O)c1ccc(C(=O)c2cc(-c3ccccc3)ccc2O)cc1)c1ccncc1] |
| A94 | N-((3R,4R)-4-(4-(2-fluoro-6-hydroxy-3-methoxybenzoyl)benzamido)azepan-3-yl)isonicotinamide | 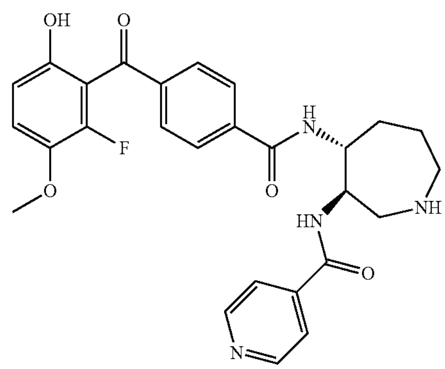 [SMILES: COc1ccc(O)c(C(=O)c2ccc(C(=O)N[C@@H]3CCCNC[C@H]3NC(=O)c3ccncc3)cc2)c1F] |
| A95 | N-((3R,4R)-4-(4-(5-ethyl-2-hydroxybenzoyl)benzamido)pyrrolidin-3-yl)isonicotinamide | 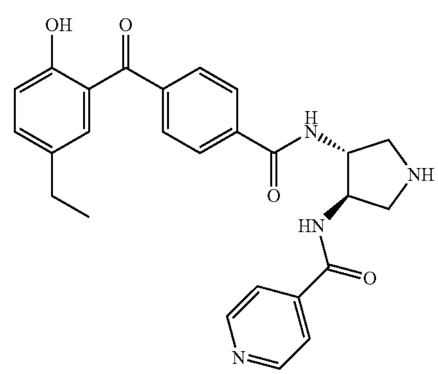 [SMILES: CCc1ccc(O)c(C(=O)c2ccc(C(=O)N[C@@H]3CNC[C@H]3NC(=O)c3ccncc3)cc2)c1] |
| A96 | N-((3R,4R)-4-(4-(2-hydroxy-5-(trifluoromethoxy)benzoyl)benzamido)pyrrolidin-3-yl)isonicotinamide | 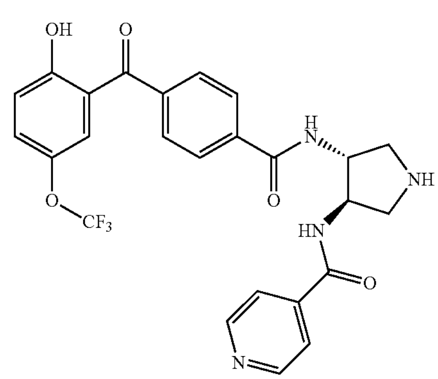 [SMILES: O=C(N[C@@H]1CNC[C@H]1NC(=O)c1ccc(C(=O)c2cc(OC(F)(F)F)ccc2O)cc1)c1ccncc1] |

| Cpd ID | IUPAC Name | Structure |
| --- | --- | --- |
| A97 | N-((3R,4R)-4-(4-(5-(benzyloxy)-2-hydroxybenzoyl)benzamido)pyrrolidin-3-yl)isonicotinamide | 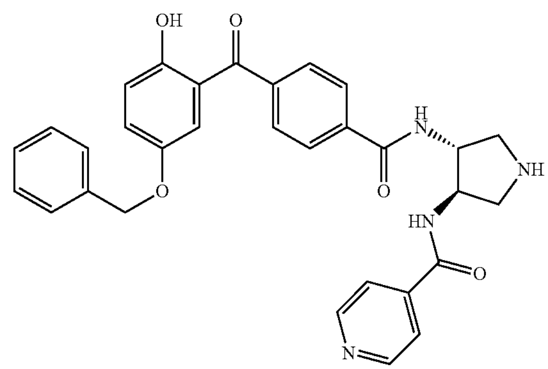 [SMILES: O=C(N[C@@H]1CNC[C@H]1NC(=O)c1ccc(C(=O)c2cc(OCc3ccccc3)ccc2O)cc1)c1ccncc1] |
| A98 | N-((3R,4R)-4-(4-(5-(tert-butoxy)-2-hydroxybenzoyl)benzamido)pyrrolidin-3-yl)isonicotinamide | 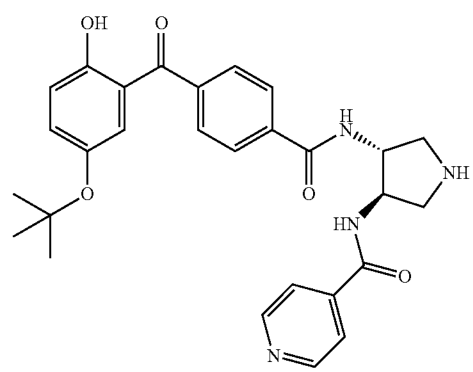 [SMILES: CC(C)(C)Oc1ccc(O)c(C(=O)c2ccc(C(=O)N[C@@H]3CNC[C@H]3NC(=O)c3ccncc3)cc2)c1] |
| A99 | N-((3R,4R)-4-(4-(2-hydroxy-5-(trifluoromethyl)benzoyl)benzamido)pyrrolidin-3-yl)isonicotinamide | 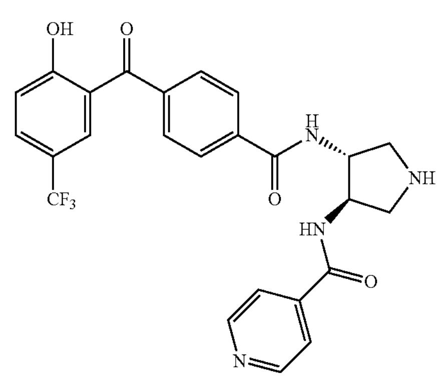 [SMILES: O=C(N[C@@H]1CNC[C@H]1NC(=O)c1ccc(C(=O)c2cc(C(F)(F)F)ccc2O)cc1)c1ccncc1] |

In some cases, the compound is a compound or salt selected from A1-A86.
In some cases, the compounds of the disclosure include those listed in Table A, or a pharmaceutically acceptable salt thereof:
TABLE A
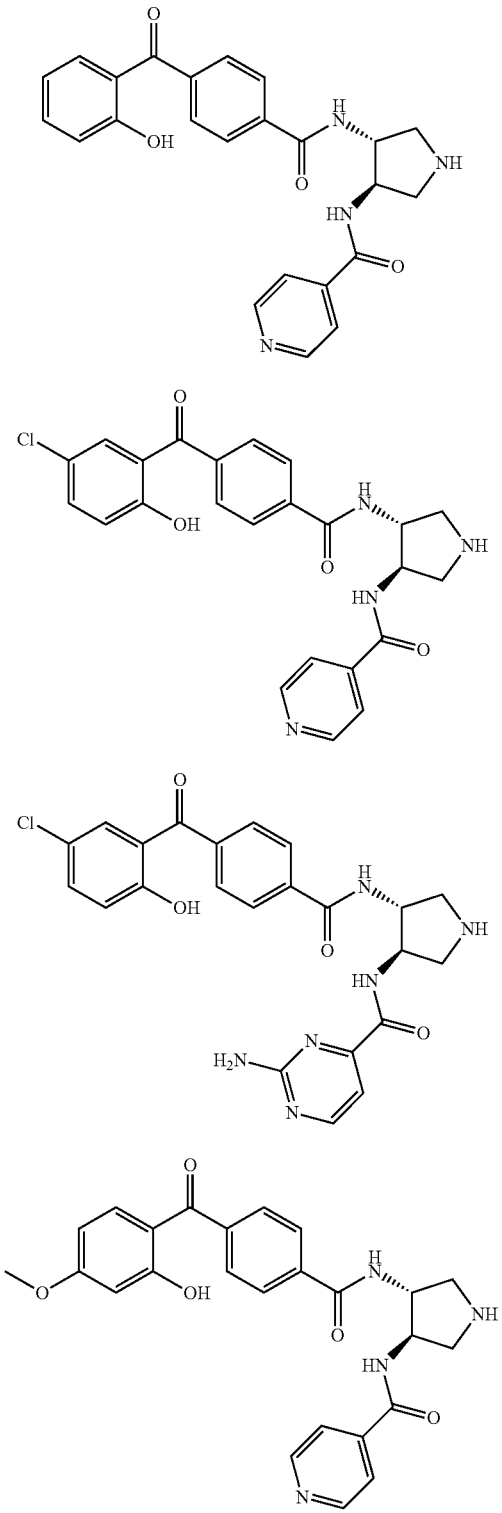
TABLE A-continued
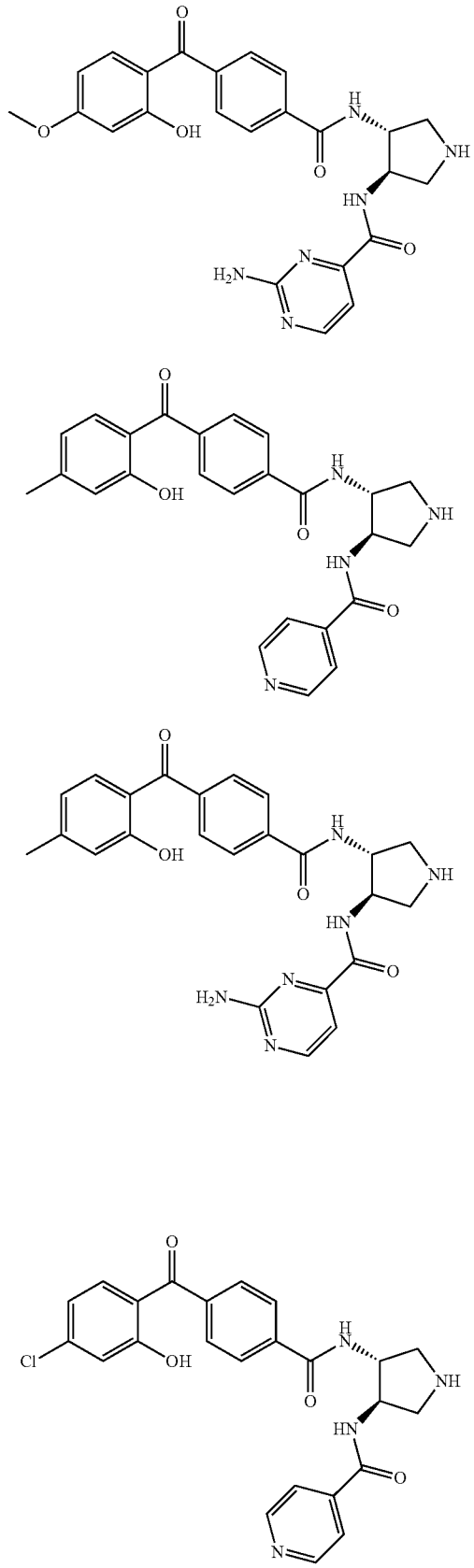

TABLE A-continued
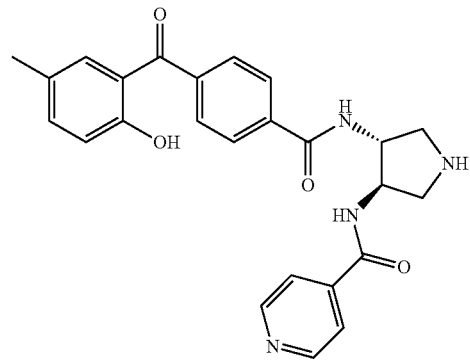 [SMILES: Cc1ccc(O)c(C(=O)c2ccc(C(=O)N[C@@H]3CNC[C@H]3NC(=O)c3ccncc3)cc2)c1]
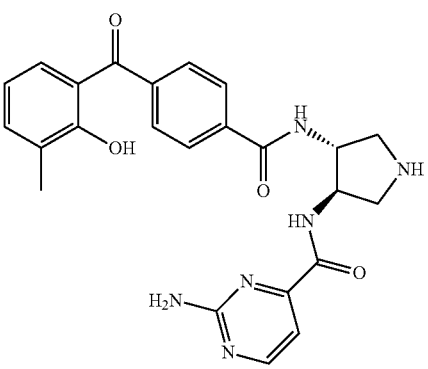
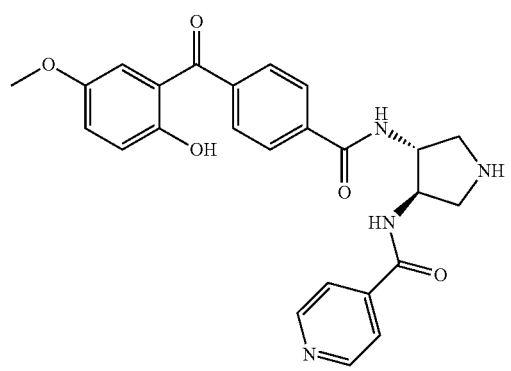 [SMILES: COc1ccc(O)c(C(=O)c2ccc(C(=O)N[C@@H]3CNC[C@H]3NC(=O)c3ccncc3)cc2)c1]
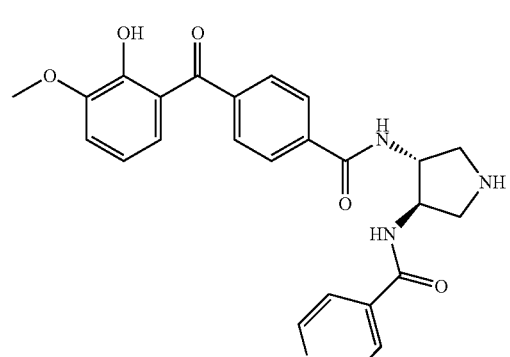
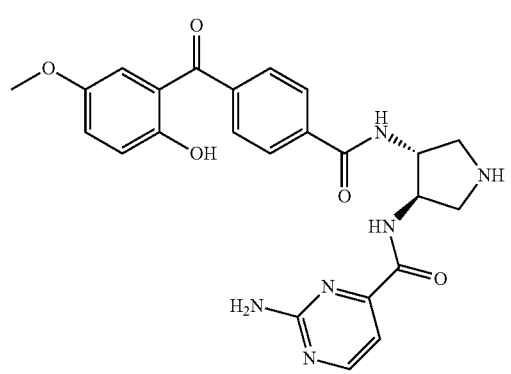 [SMILES: COc1ccc(O)c(C(=O)c2ccc(C(=O)N[C@@H]3CNC[C@H]3NC(=O)c3ccnc(N)n3)cc2)c1]
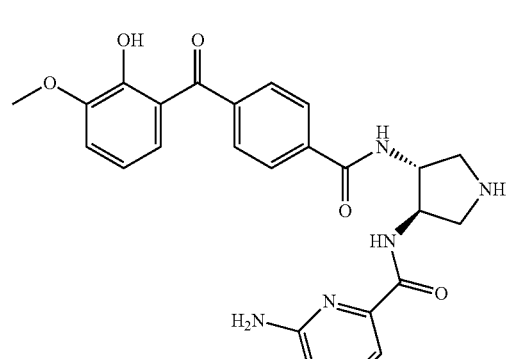
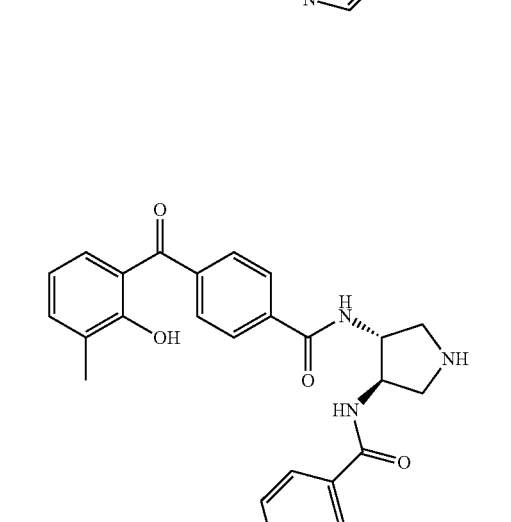
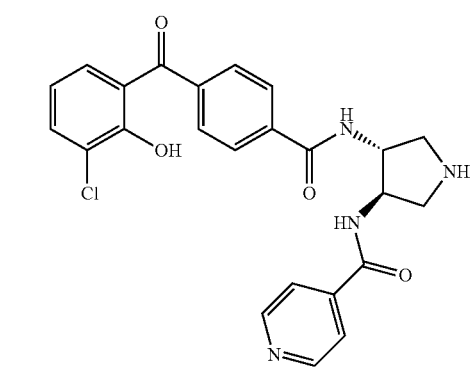 [SMILES: O=C(N[C@@H]1CNC[C@H]1NC(=O)c1ccc(C(=O)c2cccc(Cl)c2O)cc1)c1ccncc1]

TABLE A-continued
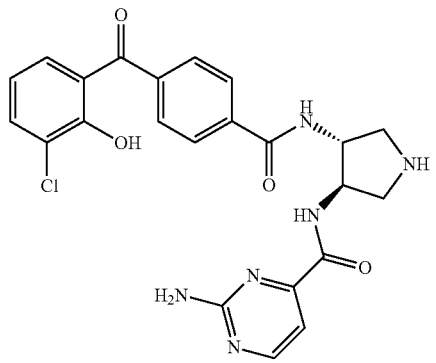 [SMILES: Nc1nccc(C(=O)N[C@@H]2CNC[C@H]2NC(=O)c2ccc(C(=O)c3cccc(Cl)c3O)cc2)n1]
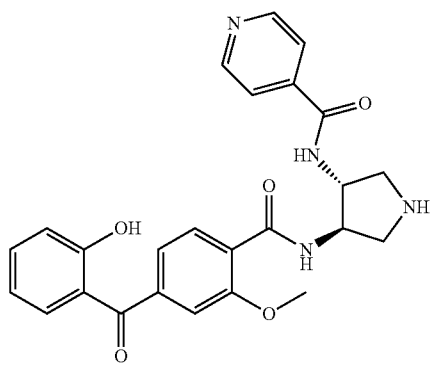 [SMILES: COc1cc(C(=O)c2ccccc2O)ccc1C(=O)N[C@@H]1CNC[C@H]1NC(=O)c1ccncc1]
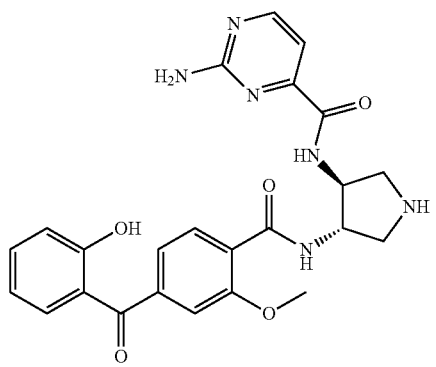 [SMILES: COc1cc(C(=O)c2ccccc2O)ccc1C(=O)N[C@H]1CNC[C@@H]1NC(=O)c1ccnc(N)n1]
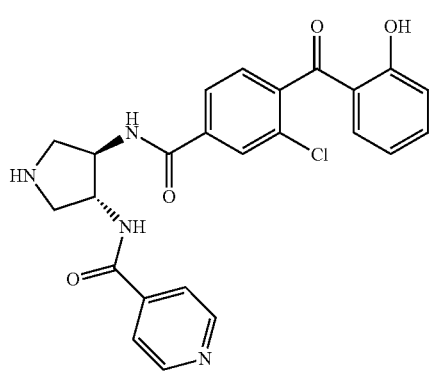 [SMILES: O=C(N[C@@H]1CNC[C@H]1NC(=O)c1ccc(C(=O)c2ccccc2O)c(Cl)c1)c1ccncc1]
TABLE A-continued
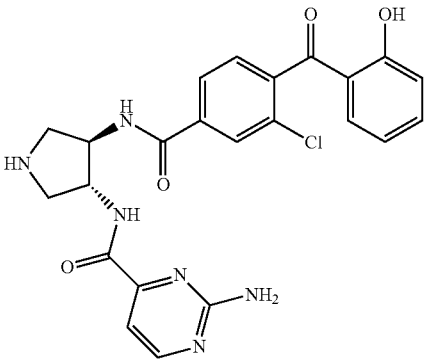 [SMILES: Nc1nccc(C(=O)N[C@@H]2CNC[C@H]2NC(=O)c2ccc(C(=O)c3ccccc3O)c(Cl)c2)n1]
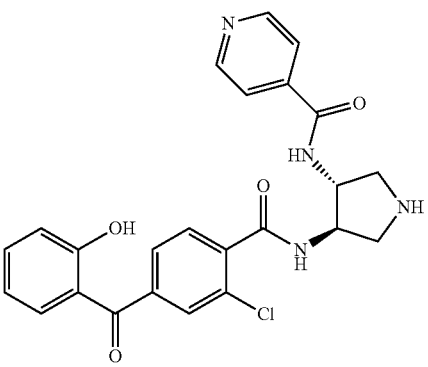 [SMILES: O=C(N[C@@H]1CNC[C@H]1NC(=O)c1ccc(C(=O)c2ccccc2O)cc1Cl)c1ccncc1]
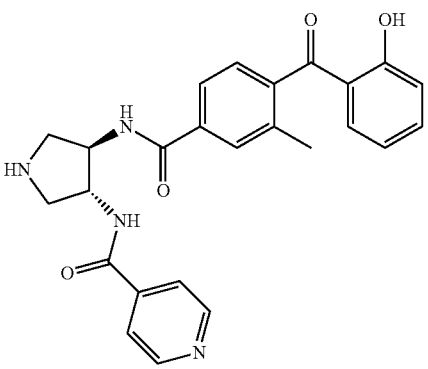 [SMILES: Cc1cc(C(=O)N[C@@H]2CNC[C@H]2NC(=O)c2ccncc2)ccc1C(=O)c1ccccc1O]
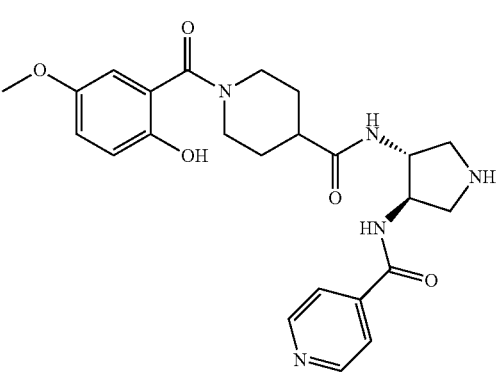 [SMILES: COc1ccc(O)c(C(=O)N2CCC(C(=O)N[C@@H]3CNC[C@H]3NC(=O)c3ccncc3)CC2)c1]

TABLE A-continued
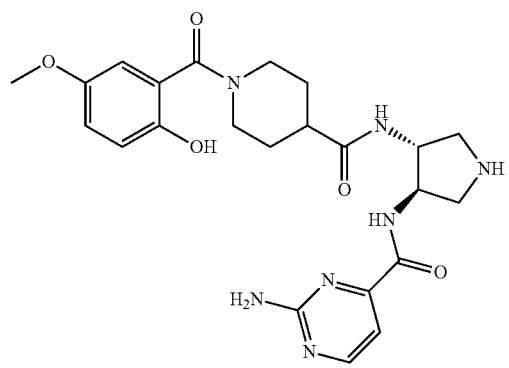 [SMILES: COc1ccc(O)c(C(=O)N2CCC(C(=O)N[C@@H]3CNC[C@H]3NC(=O)c3ccnc(N)n3)CC2)c1]
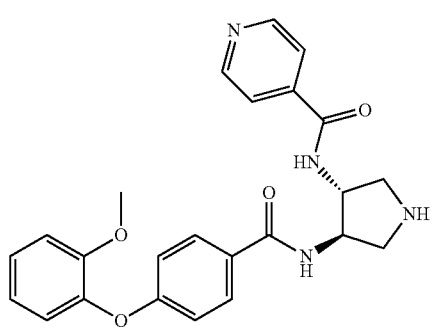 [SMILES: COc1ccccc1Oc1ccc(C(=O)N[C@@H]2CNC[C@H]2NC(=O)c2ccncc2)cc1]
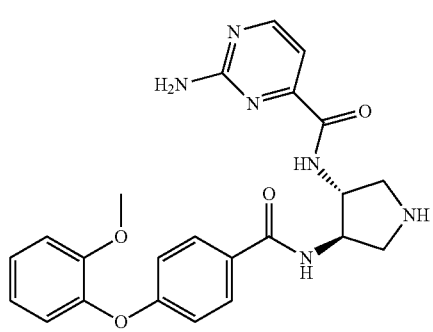 [SMILES: COc1ccccc1Oc1ccc(C(=O)N[C@@H]2CNC[C@H]2NC(=O)c2ccnc(N)n2)cc1]
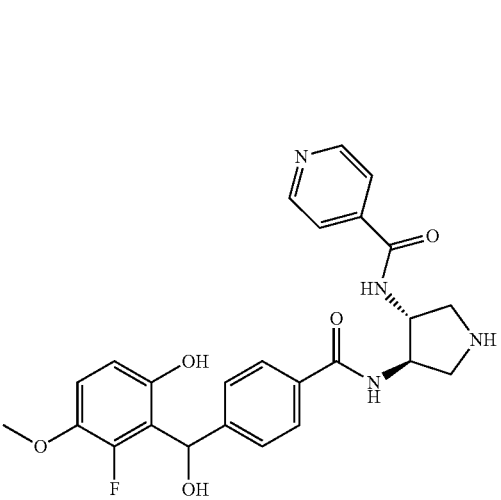 [SMILES: COc1ccc(O)c(C(O)c2ccc(C(=O)N[C@@H]3CNC[C@H]3NC(=O)c3ccncc3)cc2)c1F]
TABLE A-continued
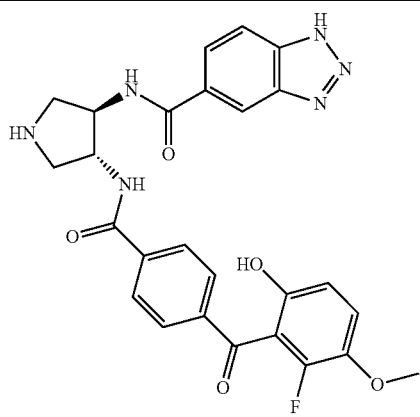
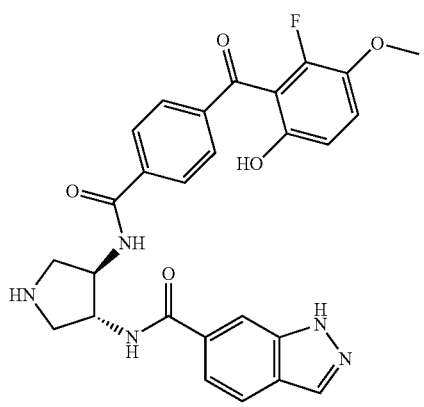 [SMILES: COc1ccc(O)c(C(=O)c2ccc(C(=O)N[C@@H]3CNC[C@H]3NC(=O)c3ccc4cn[nH]c4c3)cc2)c1F]
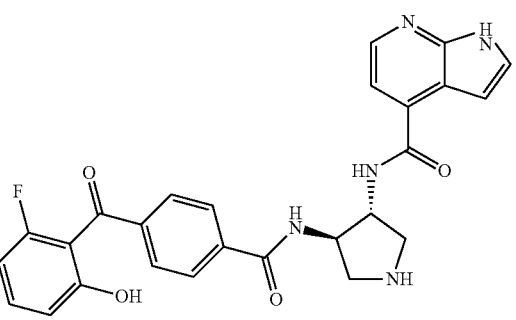
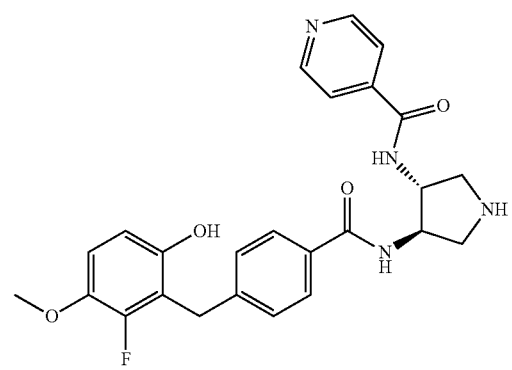 [SMILES: COc1ccc(O)c(Cc2ccc(C(=O)N[C@@H]3CNC[C@H]3NC(=O)c3ccncc3)cc2)c1F]

TABLE A-continued
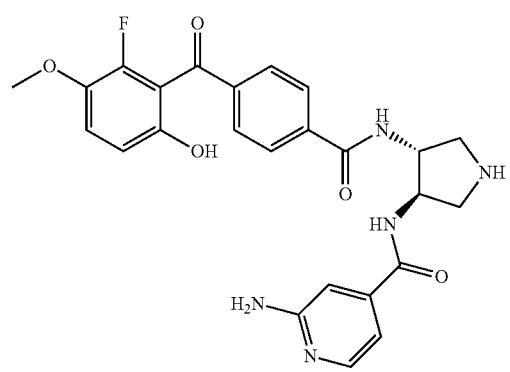 [SMILES: COc1ccc(O)c(C(=O)c2ccc(C(=O)N[C@@H]3CNC[C@H]3NC(=O)c3ccnc(N)c3)cc2)c1F]
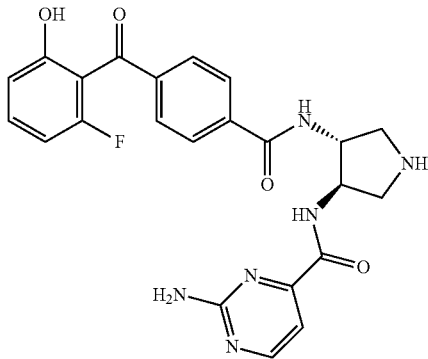
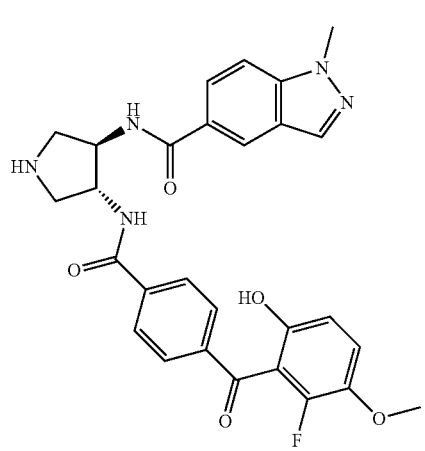 [SMILES: COc1ccc(O)c(C(=O)c2ccc(C(=O)N[C@@H]3CNC[C@H]3NC(=O)c3ccc4c(cnn4C)c3)cc2)c1F]
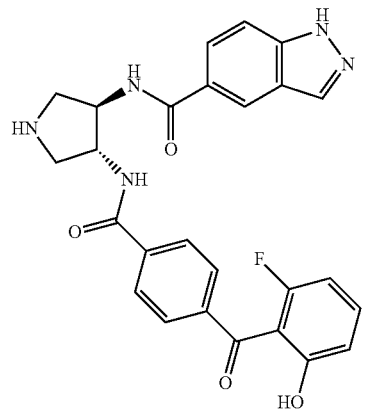 [SMILES: O=C(N[C@@H]1CNC[C@H]1NC(=O)c1ccc2[nH]ncc2c1)c1ccc(C(=O)c2c(O)cccc2F)cc1]
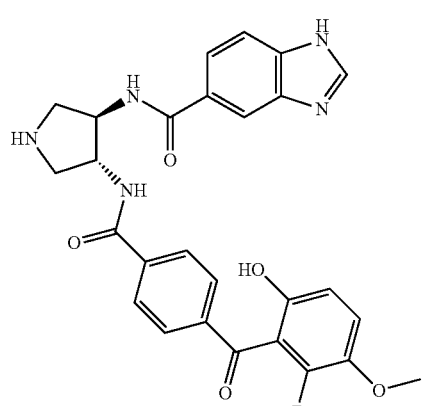
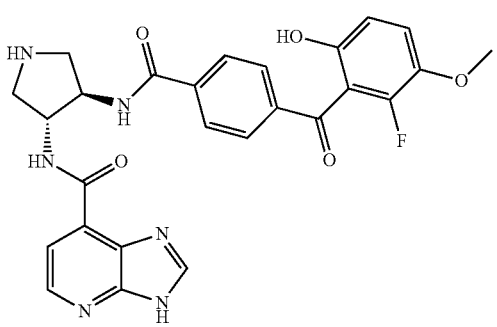 [SMILES: COc1ccc(O)c(C(=O)c2ccc(C(=O)N[C@@H]3CNC[C@H]3NC(=O)c3ccnc4[nH]cnc34)cc2)c1F]
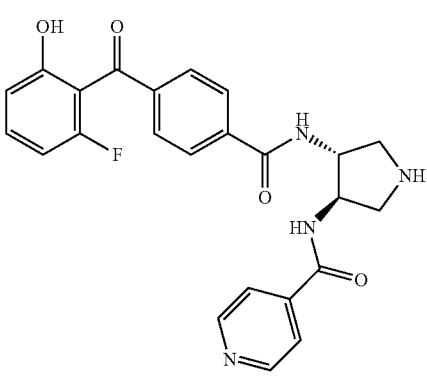
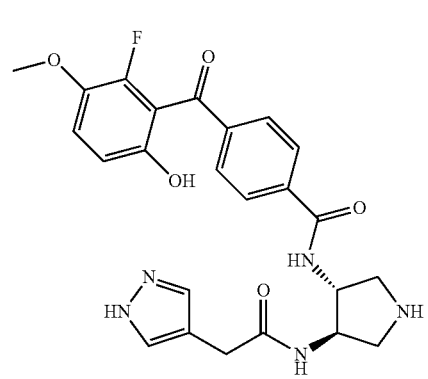 [SMILES: COc1ccc(O)c(C(=O)c2ccc(C(=O)N[C@@H]3CNC[C@H]3NC(=O)Cc3cn[nH]c3)cc2)c1F]

TABLE A-continued
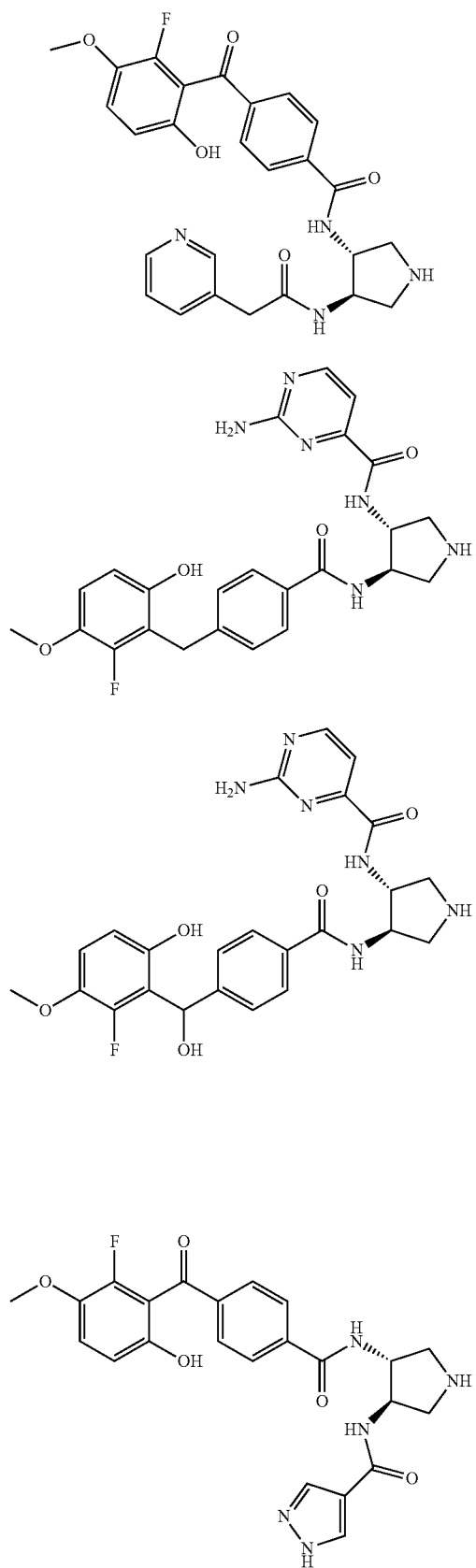
TABLE A-continued
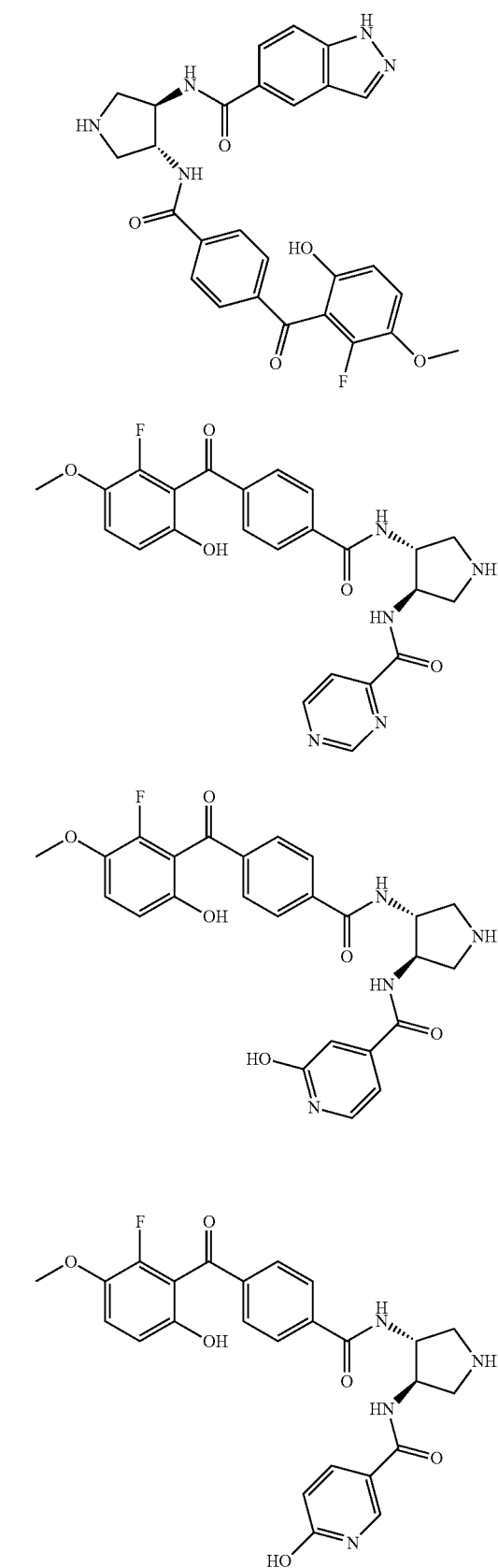

TABLE A-continued
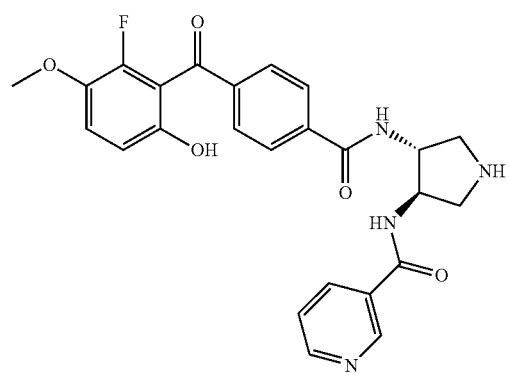 [SMILES: COc1ccc(O)c(C(=O)c2ccc(C(=O)N[C@@H]3CNC[C@H]3NC(=O)c3cccnc3)cc2)c1F]
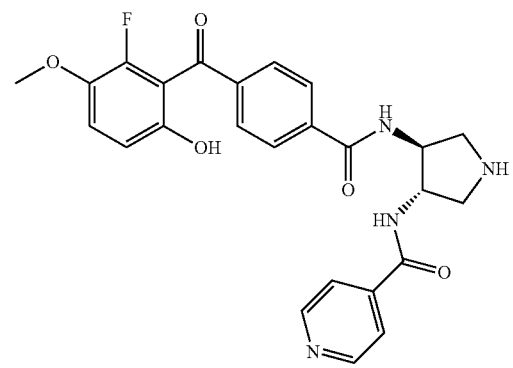
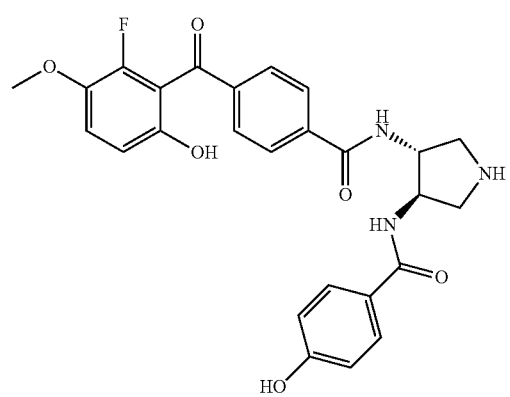 [SMILES: COc1ccc(O)c(C(=O)c2ccc(C(=O)N[C@@H]3CNC[C@H]3NC(=O)c3ccc(O)cc3)cc2)c1F]
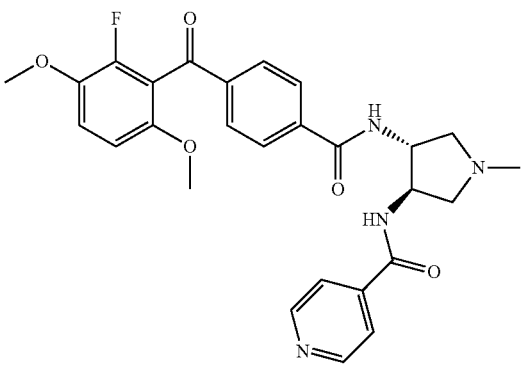
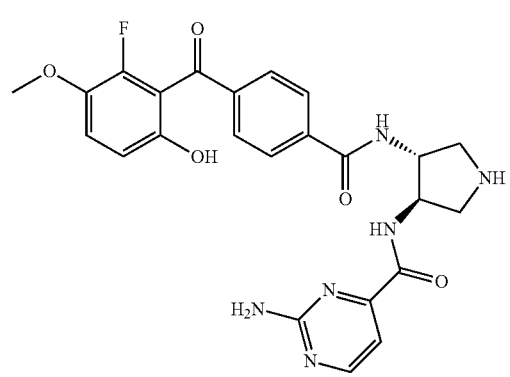
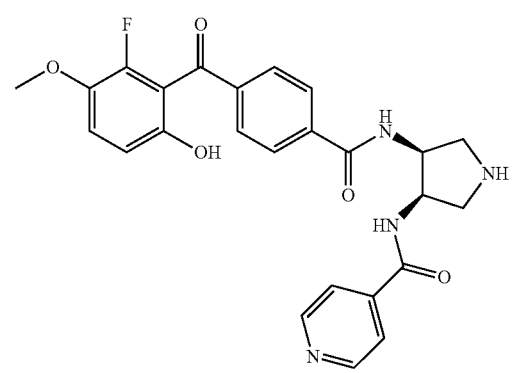 [SMILES: COc1ccc(O)c(C(=O)c2ccc(C(=O)N[C@H]3CNC[C@H]3NC(=O)c3ccncc3)cc2)c1F]
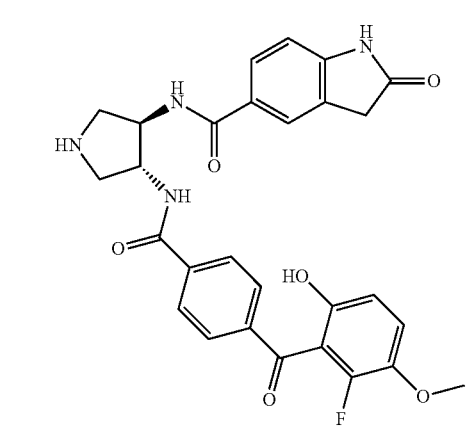
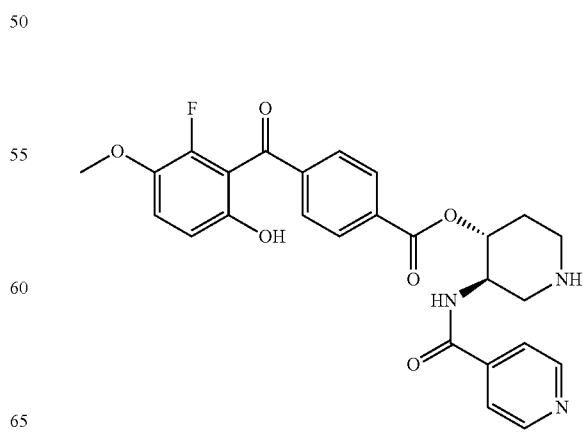

TABLE A-continued
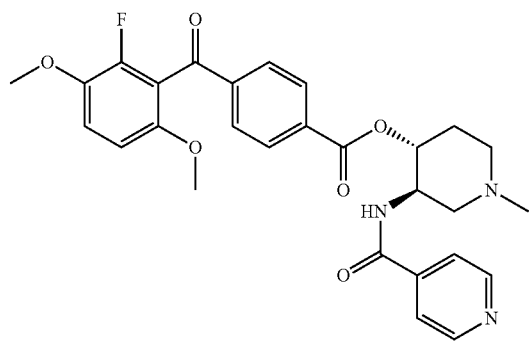
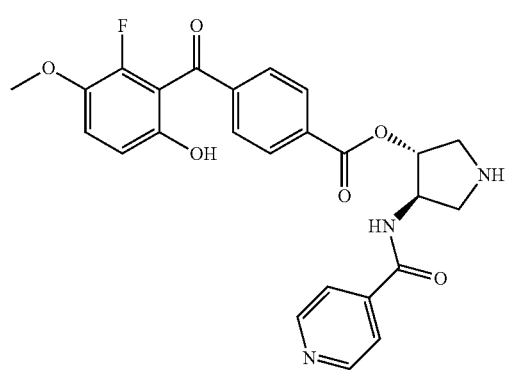 [SMILES: COc1ccc(O)c(C(=O)c2ccc(C(=O)O[C@@H]3CNC[C@H]3NC(=O)c3ccncc3)cc2)c1F]
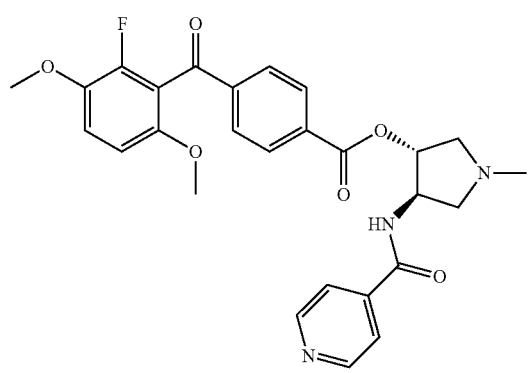
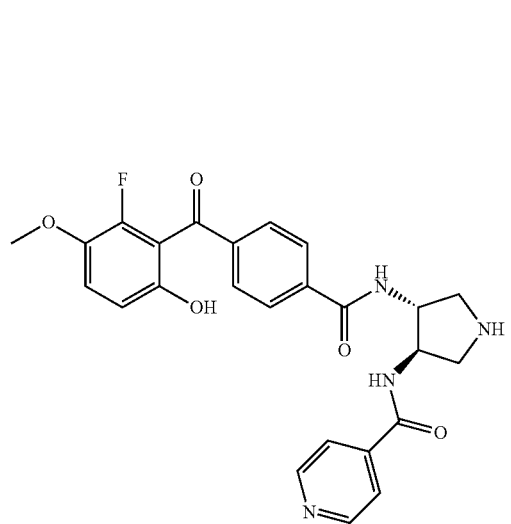 [SMILES: COc1ccc(O)c(C(=O)c2ccc(C(=O)N[C@@H]3CNC[C@H]3NC(=O)c3ccncc3)cc2)c1F]
In some cases, the compound is one as listed in Table B, or a pharmaceutically acceptable salt thereof:
TABLE B
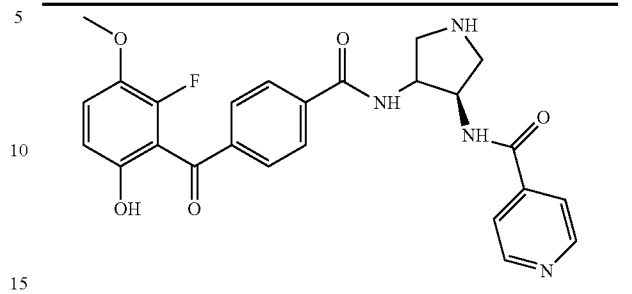
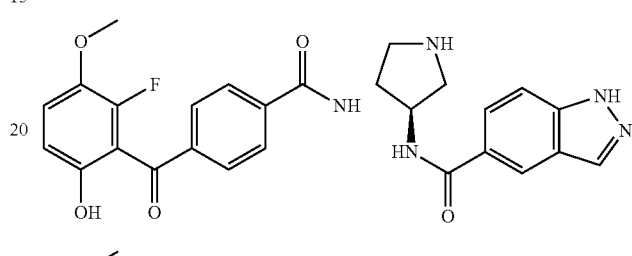
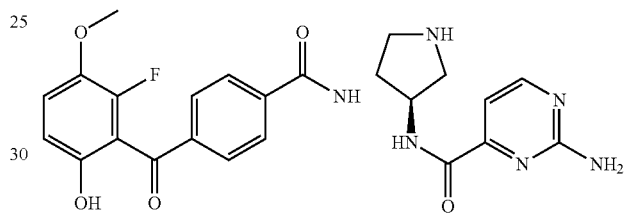
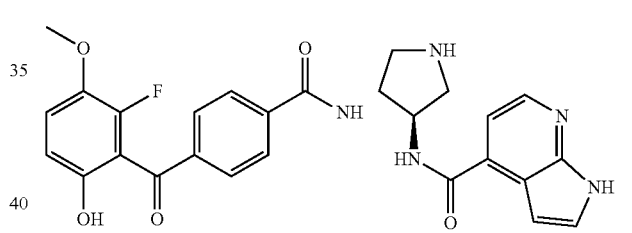
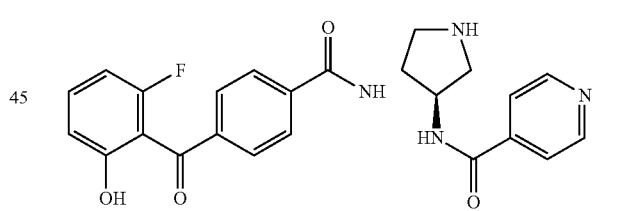
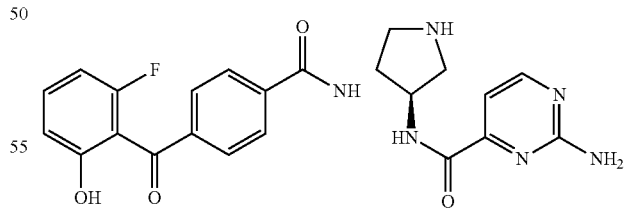
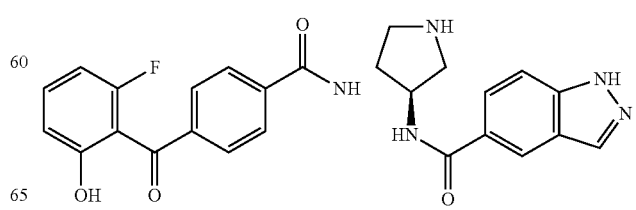

TABLE B-continued
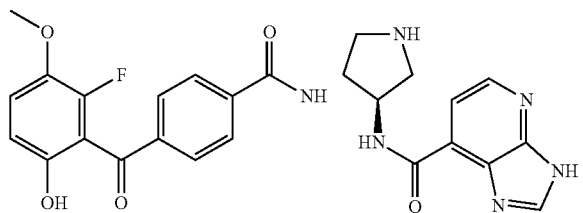
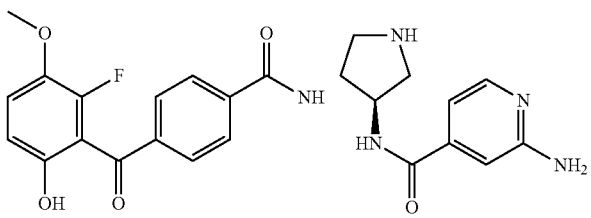
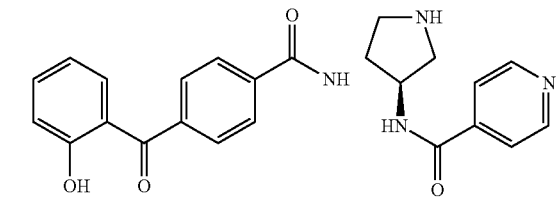
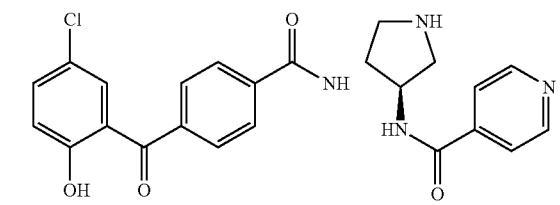
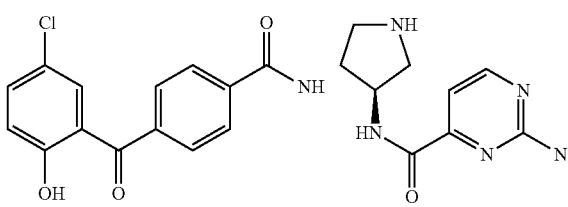
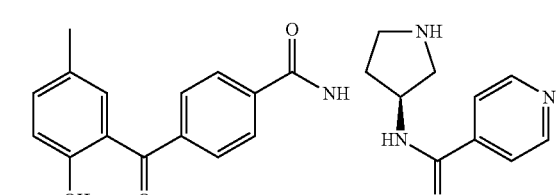
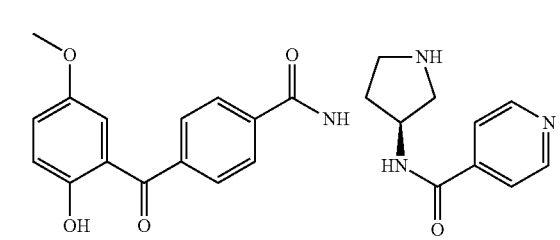
TABLE B-continued
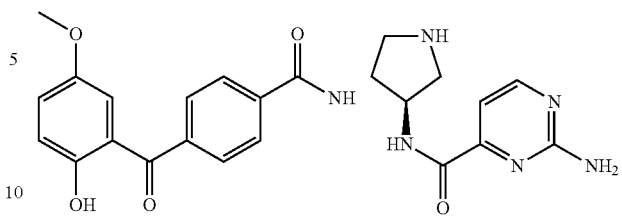
In some cases, the compound is one as listed in Table C, or a pharmaceutically acceptable salt thereof:
TABLE C
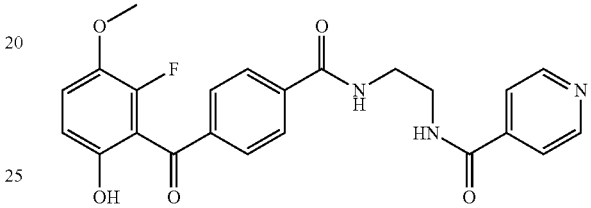
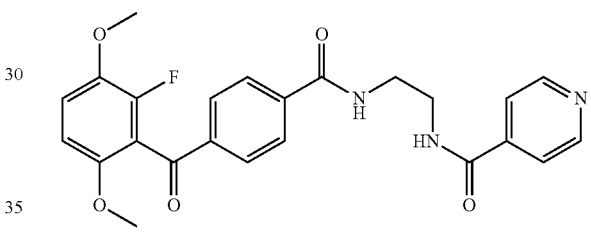
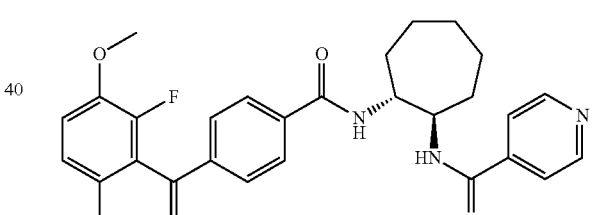
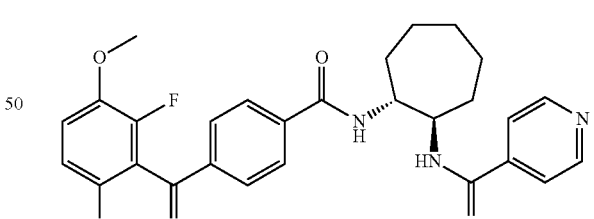
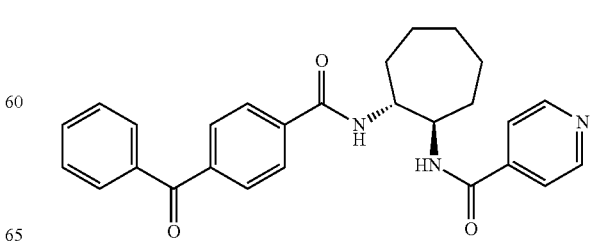

TABLE C-continued
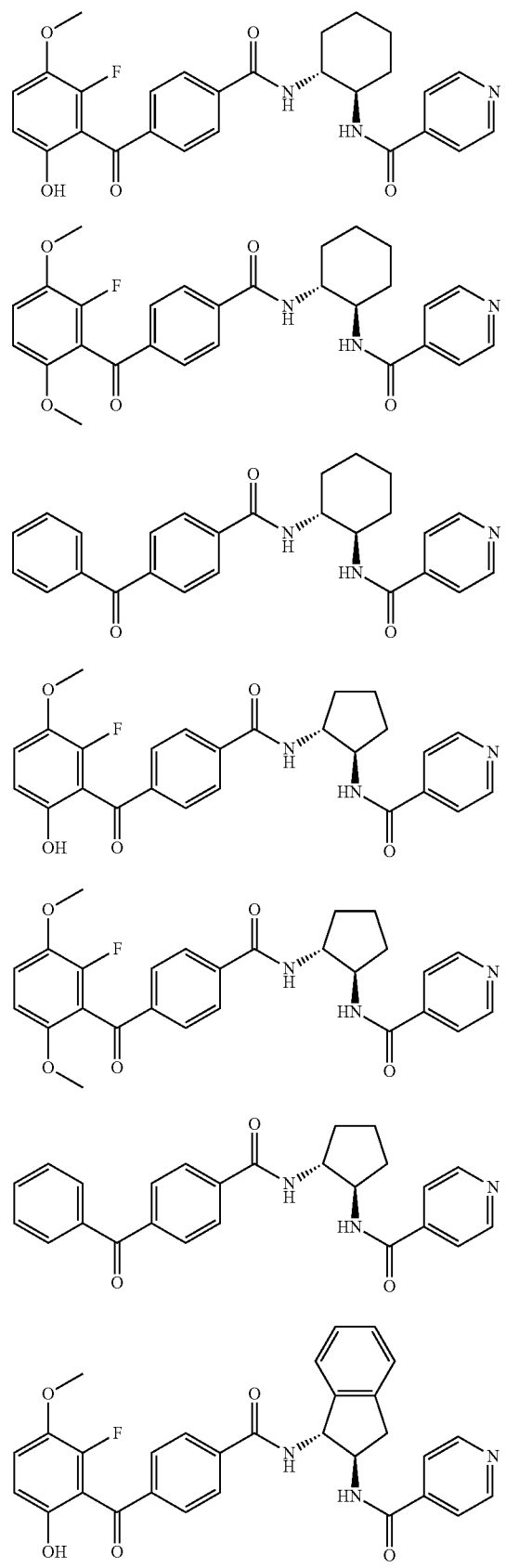
TABLE C-continued
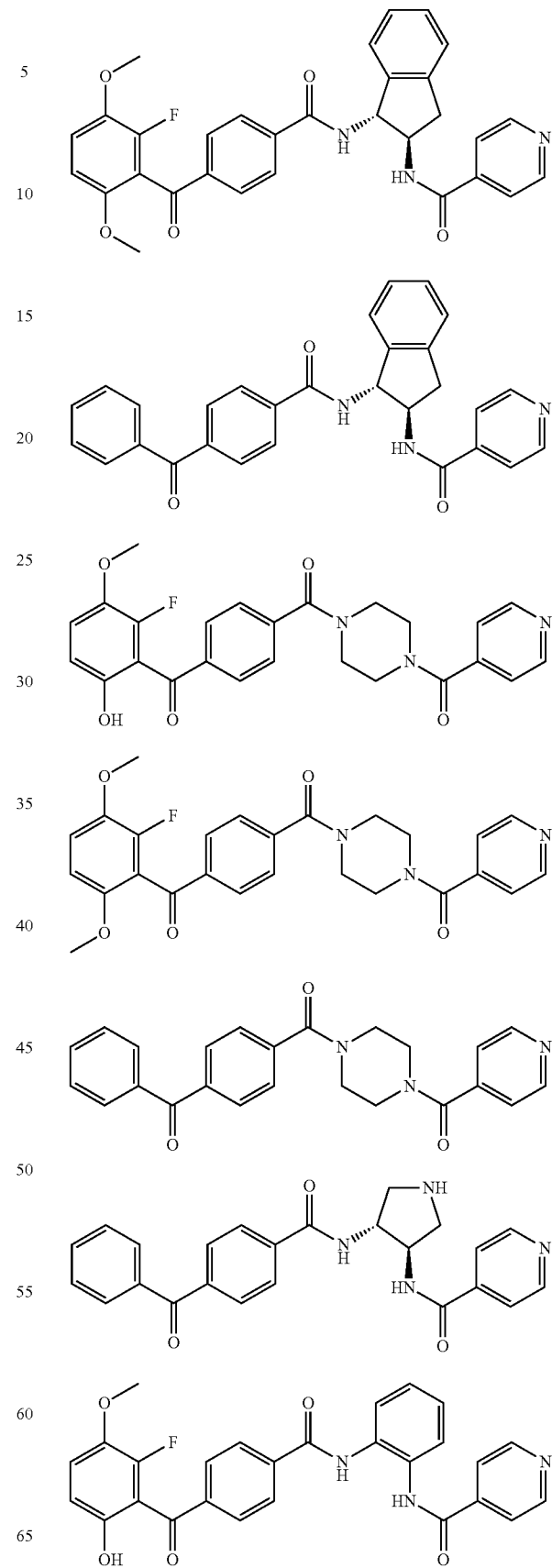

TABLE C-continued

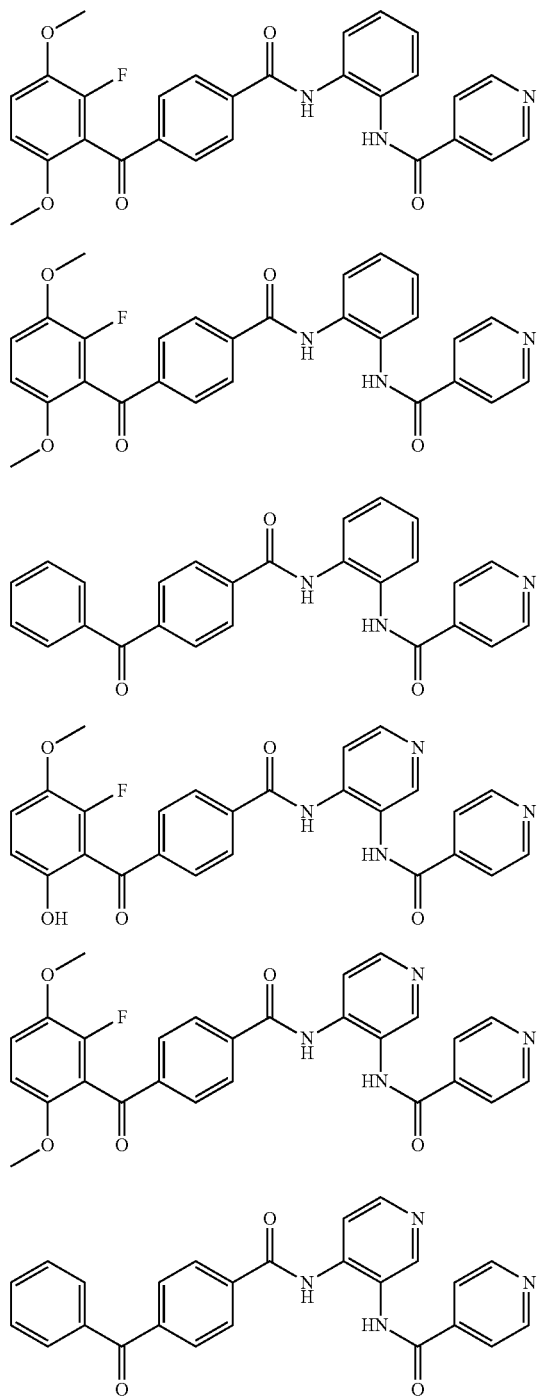

The compounds disclosed herein can be as a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Synthesis of Compounds

Compounds disclosed herein can be synthesized by any means available to the synthetic organic chemist. Guidance for the synthesis of compounds are shown in the Examples.

For example, a compound of Formula (I) can be prepared by selection of the appropriate starting materials and reagents in line with the below synthetic scheme:

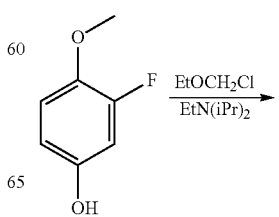

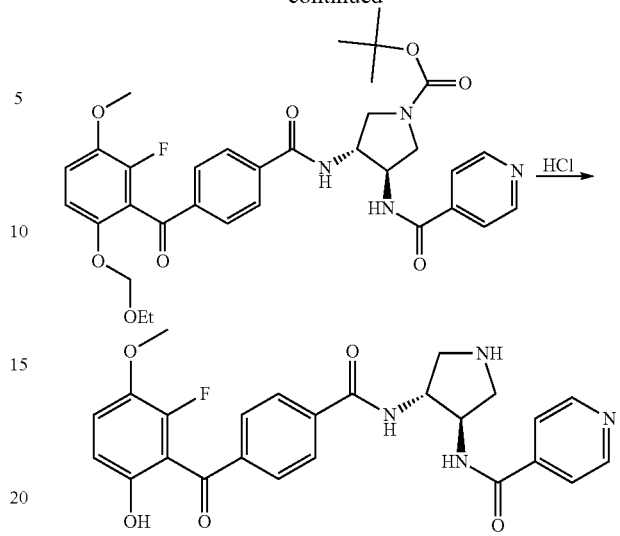
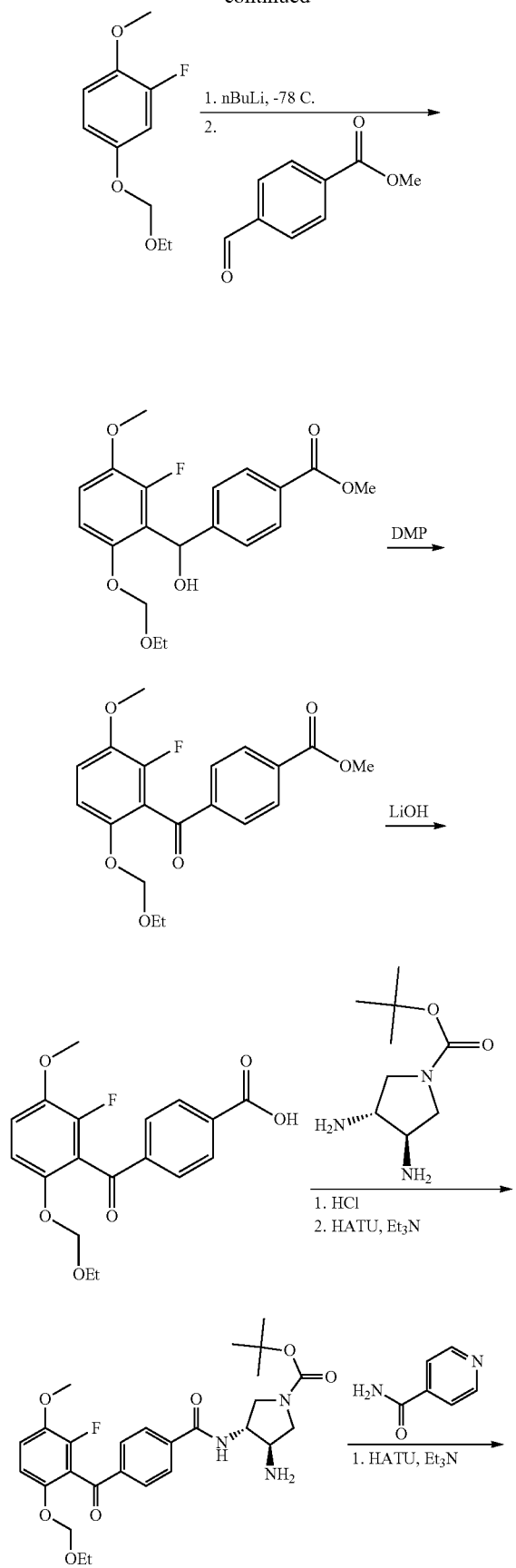

Pharmaceutical Formulations, Dosing, and Routes of Administration

Further provided are pharmaceutical formulations comprising a compound as described herein (e.g., compounds of Formula (I), or pharmaceutically acceptable salts thereof) and a pharmaceutically acceptable excipient.

The compounds described herein can be administered to a subject in a therapeutically effective amount (e.g., in an amount sufficient to inhibit ROCK, S6K, and/or PKC). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more subdoses administered separately at appropriate intervals throughout the day, optionally, in unit dosage forms. The treatment period will depend on the particular condition and type of pain, and may last one day to several months.

Suitable methods of administering a physiologically-acceptable composition, such as a pharmaceutical composition comprising the compounds disclosed herein (e.g., compounds of Formula (I)), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (i.e., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

When appropriate, the compound is administered in combination with other substances (e.g., therapeutics) and/or other therapeutic modalities to achieve an additional (or augmented) biological effect. These other therapeutics/co-treatments include, for example, surgery, radiation treatment, chemotherapy, anti-angiogenic factors (for instance, soluble growth factor receptors (e.g., sflt), growth factor antagonists (e.g., angiotensin), etc.), antibiotics, hormone therapy, anti-inflammatory agents (e.g., Non-Steroidal Anti-Inflammatory Drugs (NSAIDs) or steroidal anti-inflammatory substances), antiviral agents, anti-bacterial agents, cough suppressant, decongestant, or expectorant, pain relievers, and the like. Optionally, the compound is administered in combination with an agent that facilitates transport across the blood-brain barrier and/or an agent that blocks efflux from the brain. Additional combination therapies not specifically listed herein are also within the scope of the present disclosure.

The disclosure thus includes administering to a subject the compound in combination with one or more additionally suitable substances(s), each being administered according to a regimen suitable for that medicament. This aspect includes concurrent administration (i.e., substantially simultaneous administration) and non-concurrent administration (i.e., administration at different times, in any order, whether overlapping or not) of the agent and one or more additionally suitable agents(s). It will be appreciated that different components are, in certain aspects, administered in the same or in separate compositions, and by the same or different routes of administration.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds disclosed herein can inhibit one or more of ROCK, S6K, and PKC. In some cases, the compound inhibits ROCK, PKC, and S6K. In some cases, the compound inhibits each of ROCK, S6K, and PKC.

The co-inhibition of ROCK and S6K synergistically promotes neurite outgrowth in primary neurons. This synergy is likely due to the simultaneous modulation of mechanisms that mediate both extrinsic and intrinsic suppression of neurite outgrowth.

The inhibitory activity of a compound disclosed herein can be assessed using an assay as described in the examples. In some cases, the $IC_{50}$ of the compound against ROCK is 0.1 to 3000 nM, 0.1 to 1000 nM, 0.1 to 500 nM, 0.1 to 100 nM, 0.1 to 50 nM, 0.1 to 25 nM, 0.1 to 10 nM, 0.1 to 5 nM, 0.1 to 1 nM, 0.1 to 0.5 nM, 1000 to 2000 nM, 100 to 1000 nM, 10 or 100 nM, 5 to 50 nM, or 1 to 10 nM. In some cases, the $IC_{50}$ of the compound against S6K is 0.1 to 3000 nM, 0.1 to 1000 nM, 0.1 to 500 nM, 0.1 to 100 nM, 0.1 to 50 nM, 0.1 to 25 nM, 0.1 to 10 nM, 0.1 to 5 nM, 0.1 to 1 nM, 0.1 to 0.5 nM, 1000 to 2000 nM, 100 to 1000 nM, 10 or 100 nM, 5 to 50 nM, or 1 to 10 nM. In some cases, the $IC_{50}$ of the compound against PKC is 0.1 to 3000 nM, 0.1 to 1000 nM, 0.1 to 500 nM, 0.1 to 100 nM, 0.1 to 50 nM, 0.1 to 25 nM, 0.1 to 10 nM, 0.1 to 5 nM, 0.1 to 1 nM, 0.1 to 0.5 nM, 1000 to 2000 nM, 100 to 1000 nM, 10 or 100 nM, 5 to 50 nM, or 1 to 10 nM.

The compounds disclosed herein can induce neurite outgrowth. In some cases, the compounds disclosed herein can treat a CNS disorder associated with neuronal and/or axonal damage. For example, the compounds disclosed herein can treat a CNS disorder such as paralysis, spinal cord injury, optic nerve injury, glaucoma, multiple sclerosis, traumatic brain injury, diffuse axonal injury, stroke, or a degenerative disease (such as Parkinson's disease).

In some cases, the compounds disclosed herein can treat a peripheral nervous system (PNS) disorder associated with neuronal and/or axonal damage. In some cases, the PNS disorder is peripheral nerve trauma, repetitive stress, amyotropic lateral sclerosis (ALS), erectile dysfunction, a disorder associated with an organ transplant, neurofibromatosis, blood vessel disease, diabetes, an autoimmune disorder, a disorder associated with chemical toxicity, or kidney disease.

In some cases, the compounds disclosed herein can treat nerve degeneration in a subject undergoing cancer therapy.

The compounds disclosed herein can be useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) memory loss, and (v) psychiatric disorders.

Examples of neurodegenerative diseases and conditions that can be prevented or treated by promoting neurite outgrowth according to the invention include amyotrophic lateral sclerosis (ALS), trigeminal neuralgia, glossopharyngeal neuralgia, Bell's palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson-plus syndromes (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dementail complex (also known as HIV dementia, HIV encephalopathy, and HIV-associated dementia).

Certain diseases and conditions having primary effects outside of the nervous system can lead to damage to the nervous system, which can be treated using compounds as disclosed herein. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the compounds disclosed herein can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The compounds disclosed herein can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), chemical trauma (e.g., due to chemotherapy as a cancer treatment) as well as damage to the central nervous system due to, for example, stroke or intracranial hemorrhage (such as cerebral hemorrhage).

Further, the compounds disclosed herein can be used in the prevention or treatment of memory loss such as, for example, age-related memory loss. Types of memory that can be affected by loss include episodic memory, semantic memory, short-term memory, and long-term memory. Examples of diseases and conditions associated with memory loss include mild cognitive impairment, Alzheimer's disease, Parkinson's disease, Huntington's disease, chemotherapy, stress, stroke, and traumatic brain injury (e.g., concussion).

The compounds disclosed herein can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

EXAMPLES

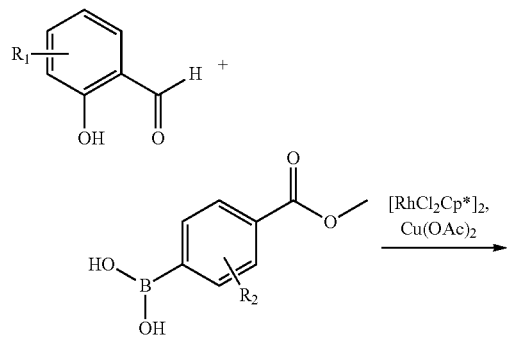

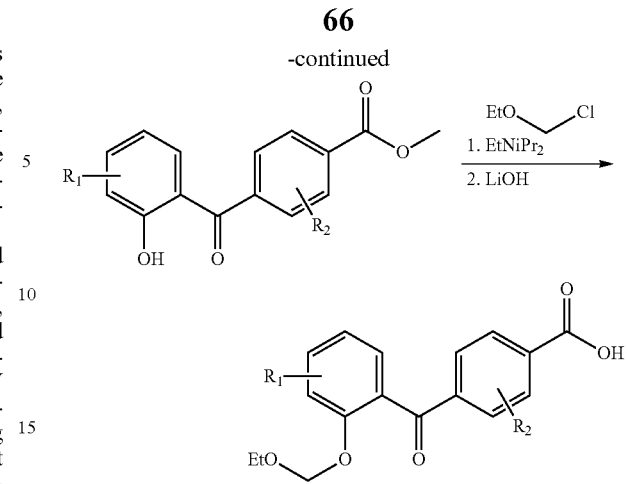

General Procedure 1: A vial was charged with a salicylaldehyde (1.0 equiv) and DMF (0.25 M) at room temperature. (4-(methoxycarbonyl) phenyl)boronic acid (1.2 equiv) was then added, followed by [RhCl$_2$Cp*]$_2$ (0.04 equiv) and Cu(OAc)$_2$ (1.2 equiv). The resulting suspension was warmed to 80° C. for 3-4 h. The mixture was cooled to room temperature and filtered to remove the insoluble salts. The solution was then diluted with EtOAc and washed twice with water. The organic portion was concentrated to give the crude intermediate methyl 4-(2-hydroxybenzoyl)benzoate which could be used without further purification. This solid was dissolved in CH$_2$Cl$_2$ (0.5 M) and treated with diisoproplyethylamine (1.5 equiv) and (chloromethoxy)ethane (1.5 equiv). This solution was stirred at room temperature until protection of the phenol was complete by LCMS. The reaction was then diluted with CH$_2$Cl$_2$ and thrice washed with water. Concentration of the organic portion and purification on silica gel (hexane/EtOAc gradient) gave the methyl 4-(2-(ethoxymethoxy)benzoyl)benzoate derivatives. This ester (1.0 equiv) was dissolved in THF (0.25 M) and H$_2$O (0.5 M) and treated with LiOH (4.0 equiv). The mixture was stirred at room temperature until saponification was complete, then was diluted with EtOAc and washed with a 10% citric acid solution and then water. Concentration of the organic portion gave the 4-(2-(ethoxymethoxy)benzoyl)benzoic acid derivatives.

-continued

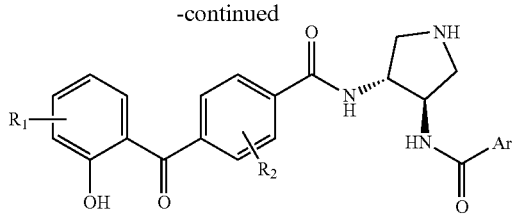

General Procedure 2: A vial was charged with a 4-(2-(ethoxymethoxy)benzoyl)benzoic acid (1 equiv), Et₃N (1 equiv) and DMF (0.5 M) at room temperature. To this solution was then added HATU (1 equiv) and the mixture was stirred for 5 min. This solution was then added to a second vial containing a freshly prepared mixture of tert-butyl (3R,4S)-3,4-diaminopyrrolidine-1-carboxylate (1 equiv) and HCl (4.0 M dioxane solution, 2 equiv) in DMF (0.5 M). The resulting solution was stirred at room temperature for 18 h to give a tert-butyl (3R,4R)-3-amino-4-(4-(2-(ethoxymethoxy)benzoyl)benzamido)pyrrolidine-1-carboxylate analog which could be directly used in situ. To this solution was added heteroarylcarboxylic acid (1 equiv), Et₃N (2 equiv) and HATU (1 equiv). The mixture was stirred at room temperature for 1 h, then quenched with water and extracted with EtOAc. The organic portion was concentrated in vacuo and then redissolved in THF (0.2 M) and aqueous 1N HCl (0.1 M). The solution was warmed to 65° C. and stirred until the carbamate and acetal protecting groups were fully removed by LCMS. The solution was then purified via HPLC to give the final product as a formate salt.

Example 1: 1 4-(2-(ethoxymethoxy)benzoyl)benzoic acid

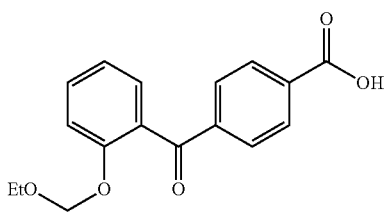

Prepared according to the general procedure 1. ¹H NMR (500 MHz, Chloroform-d) δ 8.15 (d, J=7.8 Hz, 2H), 7.88 (d, J=7.4 Hz, 2H), 7.49 (t, J=8.1 Hz, 1H), 7.43 (d, J=7.6 Hz, 1H), 7.13 (t, J=7.4 Hz, 1H), 5.07 (s, 2H), 3.49 (m, 2H), 1.12 (t, J=7.1 Hz, 3H).

Example 2:
4-(5-chloro-2-(ethoxymethoxy)benzoyl)benzoic acid

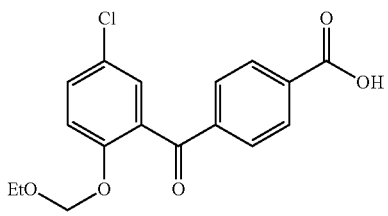 [SMILES: CCOCOc1ccc(Cl)cc1C(=O)c1ccc(C(=O)O)cc1]

Prepared according to the general procedure 1. ¹H NMR (500 MHz, Chloroform-d) δ 8.16 (d, J=8.9 Hz, 2H), 7.87 (d, J=8.0 Hz, 2H), 7.44 (dd, J=8.9, 2.7 Hz, 1H), 7.39 (d, J=2.8 Hz, 1H), 7.22 (d, J=8.9 Hz, 1H), 5.04 (s, 2H), 3.48 (q, J=6.9 Hz, 2H), 1.12 (t, J=7.0 Hz, 3H).

Example 3:
4-(2-(ethoxymethoxy)-5-methylbenzoyl)benzoic acid

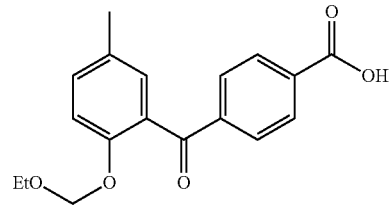 [SMILES: CCOCOc1ccc(C)cc1C(=O)c1ccc(C(=O)O)cc1]

Prepared according to the general procedure 1. ¹H NMR (500 MHz, Chloroform-d) δ 8.15 (d, J=8.5 Hz, 2H), 7.88 (d, J=8.4 Hz, 2H), 7.28 (dd, J=8.6, 2.4 Hz, 1H), 7.23 (d, J=2.3 Hz, 1H), 7.14 (d, J=8.5 Hz, 1H), 5.02 (s, 2H), 3.47 (q, J=7.1 Hz, 2H), 2.34 (s, 3H), 1.11 (t, J=7.1 Hz, 3H).

Example 4:
4-(2-(ethoxymethoxy)-5-methoxybenzoyl)benzoic acid

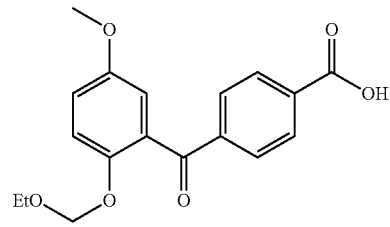 [SMILES: CCOCOc1ccc(OC)cc1C(=O)c1ccc(C(=O)O)cc1]

Prepared according to the general procedure 1. ¹H NMR (500 MHz, Chloroform-d) δ 8.16 (d, J=8.4 Hz, 2H), 7.89 (d, J=8.2 Hz, 2H), 7.19 (d, J=9.0 Hz, 1H), 7.03 (dd, J=9.1, 3.1 Hz, 1H), 6.96 (d, J=3.1 Hz, 1H), 4.97 (s, 2H), 3.81 (s, 3H), 3.48 (q, J=7.0 Hz, 2H), 1.12 (t, J=7.1 Hz, 3H).

Example 5:
4-(2-(ethoxymethoxy)-4-methylbenzoyl)benzoic acid

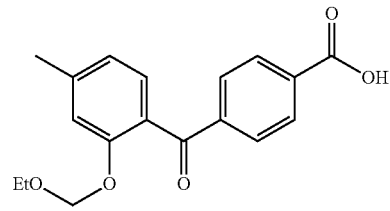 [SMILES: CCOCOc1cc(C)ccc1C(=O)c1ccc(C(=O)O)cc1]

Prepared according to the general procedure 1. ¹H NMR (500 MHz, Chloroform-d) δ 8.14 (d, J=8.1 Hz, 2H), 7.86 (d, J=8.1 Hz, 2H), 7.36 (d, J=7.7 Hz, 1H), 7.05 (s, 1H), 6.93 (d, J=7.8 Hz, 1H), 5.04 (s, 2H), 3.49 (q, J=7.0 Hz, 2H), 2.42 (s, 3H), 1.13 (t, J=7.1 Hz, 3H).

Example 6:
4-(4-chloro-2-(ethoxymethoxy)benzoyl)benzoic acid

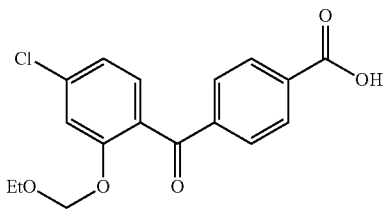 [SMILES: CCOCOc1cc(Cl)ccc1C(=O)c1ccc(C(=O)O)cc1]

Prepared according to the general procedure 1. $^1$H NMR (500 MHz, Chloroform-d) δ 8.09 (d, J=8.4 Hz, 2H), 7.82 (d, J=8.3 Hz, 2H), 7.36 (d, J=8.2 Hz, 1H), 7.27 (d, J=1.8 Hz, 1H), 7.10 (dd, J=8.1, 1.8 Hz, 1H), 5.04 (s, 2H), 3.94 (s, 3H), 3.48 (q, J=7.1 Hz, 2H), 1.13 (t, J=7.1 Hz, 3H).

Example 7:
4-(2-(ethoxymethoxy)-4-methoxybenzoyl)benzoic acid

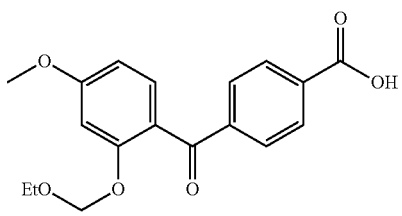 [SMILES: CCOCOc1cc(OC)ccc1C(=O)c1ccc(C(=O)O)cc1]

Prepared according to the general procedure 1. $^1$H NMR (500 MHz, Chloroform-d) δ 8.14 (d, J=8.4 Hz, 2H), 7.83 (d, J=8.3 Hz, 2H), 7.49 (d, J=8.5 Hz, 1H), 6.79 (d, J=2.2 Hz, 1H), 6.65 (dd, J=8.6, 2.3 Hz, 1H), 5.03 (s, 2H), 3.87 (s, 3H), 3.49 (q, J=7.1 Hz, 2H), 1.13 (t, J=7.1 Hz, 3H).

Example 8:
4-(2-(ethoxymethoxy)-3-methylbenzoyl)benzoic acid

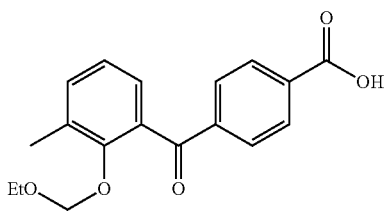 [SMILES: CCOCOc1c(C)cccc1C(=O)c1ccc(C(=O)O)cc1]

Prepared according to the general procedure 1. $^1$H NMR (500 MHz, Chloroform-d) δ 8.16 (d, J=8.0 Hz, 2H), 7.91 (d, J=8.2 Hz, 2H), 7.39 (d, J=7.5 Hz, 1H), 7.23 (d, J=7.4 Hz, 1H), 7.14 (t, J=7.5 Hz, 1H), 4.87 (s, 2H), 3.46 (q, J=7.0 Hz, 2H), 2.37 (s, 3H), 1.01 (t, J=7.0 Hz, 3H).

Example 9:
4-(3-chloro-2-(ethoxymethoxy)benzoyl)benzoic acid

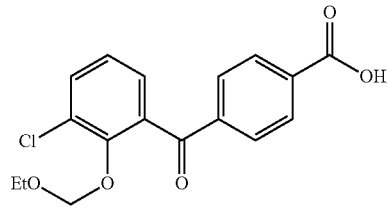 [SMILES: CCOCOc1c(Cl)cccc1C(=O)c1ccc(C(=O)O)cc1]

Prepared according to the general procedure 1. $^1$H NMR (500 MHz, Chloroform-d) δ 8.17 (d, J=8.1 Hz, 2H), 7.91 (d, J=8.1 Hz, 2H), 7.60 (d, J=7.9 Hz, 1H), 7.31 (d, J=7.7 Hz, 1H), 7.20 (t, J=7.9 Hz, 1H), 5.01 (s, 2H), 3.44 (q, J=7.0 Hz, 2H), 1.05-0.93 (m, 3H).

Example 10:
4-(2-(ethoxymethoxy)-3-methoxybenzoyl)benzoic acid

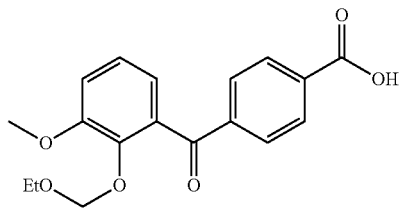 [SMILES: CCOCOc1c(OC)cccc1C(=O)c1ccc(C(=O)O)cc1]

Prepared according to the general procedure 1. $^1$H NMR (500 MHz, Chloroform-d) δ 8.15 (d, J=8.3 Hz, 2H), 7.93 (d, J=8.3 Hz, 2H), 7.19 (t, J=7.9 Hz, 1H), 7.10 (dd, J=8.4, 1.4 Hz, 1H), 6.98 (dd, J=7.7, 1.5 Hz, 1H), 5.01 (s, 2H), 3.91 (s, 3H), 3.38 (q, J=7.1 Hz, 2H), 0.98 (t, J=7.0 Hz, 3H).

Example 11:
2-chloro-4-(2-(ethoxymethoxy)benzoyl)benzoic acid

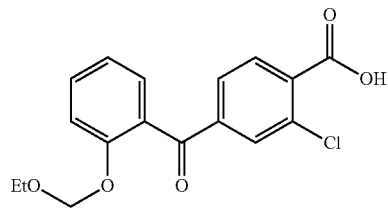 [SMILES: CCOCOc1ccccc1C(=O)c1ccc(C(=O)O)c(Cl)c1]

Prepared according to the general procedure 1. $^1$H NMR (500 MHz, Chloroform-d) δ 8.02 (d, J=8.1 Hz, 1H), 7.87 (d, J=1.5 Hz, 1H), 7.77-7.72 (m, 1H), 7.51 (t, J=7.7 Hz, 1H), 7.45 (d, J=7.6 Hz, 1H), 7.28 (m, 1H), 7.14 (t, J=7.6 Hz, 1H), 5.08 (s, 2H), 3.52 (q, J=7.1 Hz, 2H), 1.15 (t, J=7.1 Hz, 3H).

Example 12: 4-(2-(ethoxymethoxy)benzoyl)-2-methoxybenzoic acid

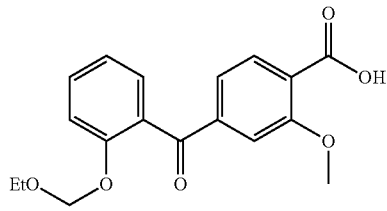

Prepared according to the general procedure 1. $^1$H NMR (500 MHz, Chloroform-d) δ 8.21 (d, J=8.0 Hz, 1H), 7.66 (d, J=1.3 Hz, 1H), 7.53-7.48 (m, 1H), 7.42 (dd, J=7.5, 1.7 Hz, 1H), 7.39-7.35 (m, 1H), 7.28 (m, 1H), 7.13 (dd, J=8.0, 6.9 Hz, 1H), 5.08 (s, 2H), 4.15 (s, 3H), 3.51 (q, J=7.1 Hz, 2H), 1.14 (t, J=7.1 Hz, 3H).

Example 13: 3-chloro-4-(2-(ethoxymethoxy)benzoyl)benzoic acid

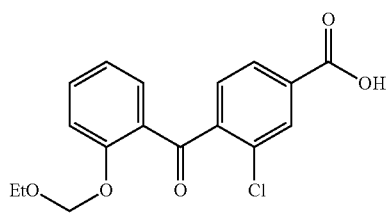

Prepared according to the general procedure 1. LCMS indicated some loss of chlorine.

Example 14: 4-(2-(ethoxymethoxy)benzoyl)-3-methylbenzoic acid

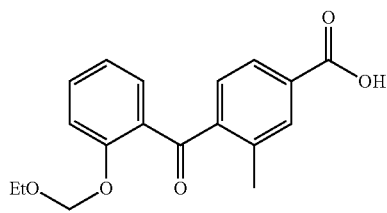

Prepared according to the general procedure 1 with pinacol boronate in place of boronic acid. This compound contained impurities and was used without further purification. $^1$H NMR (500 MHz, Chloroform-d) δ 8.00 (s, 1H), 7.91 (d, J=8.2 Hz, 1H), 7.61 (dd, J=7.6, 1.6 Hz, 1H), 7.52-7.46 (m, 1H), 7.38 (d, J=8.0 Hz, 1H), 7.18 (d, J=8.4 Hz, 1H), 7.10 (t, J=7.6 Hz, 1H), 4.98 (s, 2H), 3.39 (q, J=7.0 Hz, 2H), 2.48 (s, 3H), 1.09 (t, J=7.1 Hz, 3H).

Example 15: N-((3R,4R)-4-(4-(2-hydroxybenzoyl)benzamido)pyrrolidin-3-yl)isonicotinamide

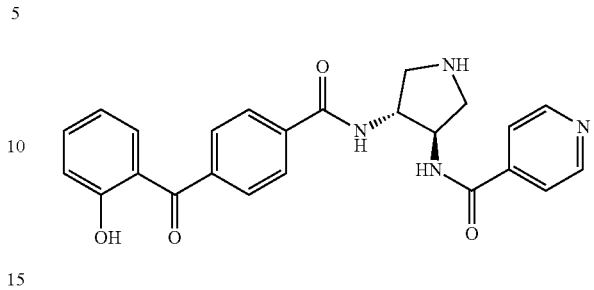

Prepared according to the general procedure 2. $^1$H NMR (400 MHz, Methanol-d$_4$) δ 8.76-8.66 (m, 2H), 8.37 (s, 2H), 8.00 (d, J=8.0 Hz, 2H), 7.85-7.77 (m, 4H), 7.61-7.47 (m, 2H), 7.04 (d, J=8.4 Hz, 1H), 6.94 (t, J=7.8 Hz, 1H), 4.75 (m, 2H), 3.85 (m, 2H), 3.47 (m, 2H). LCMS (ESI+) for $C_{24}H_{22}N_4O_4$ [M+H] expected=431.17, found=431.53.

Example 16: N-((3R,4R)-4-(4-(5-chloro-2-hydroxybenzoyl)benzamido)pyrrolidin-3-yl)isonicotinamide

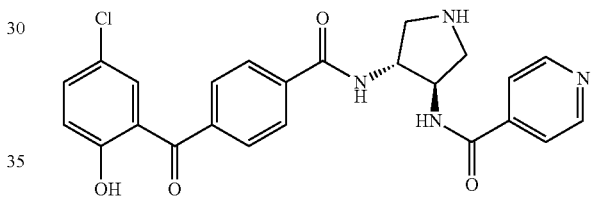

Prepared according to the general procedure 2. $^1$H NMR (500 MHz, Methanol-d$_4$) δ 8.72 (s, 2H), 8.37 (d, J=4.1 Hz, 2H), 8.00 (t, J=5.7 Hz, 2H), 7.82 (t, J=5.3 Hz, 4H), 7.50 (dt, J=8.4, 2.8 Hz, 1H), 7.42 (t, J=2.8 Hz, 1H), 7.03 (dd, J=8.9, 4.5 Hz, 1H), 4.74 (s, 2H), 3.90-3.81 (m, 2H), 3.50-3.41 (m, 2H). LCMS (ESI+) for $C_{24}H_{21}ClN_4O_4$ [M+H] expected=465.13, found=465.52.

Example 17: 2-amino-N-((3R,4R)-4-(4-(5-chloro-2-hydroxybenzoyl)benzamido)pyrrolidin-3-yl)pyrimidine-4-carboxamide

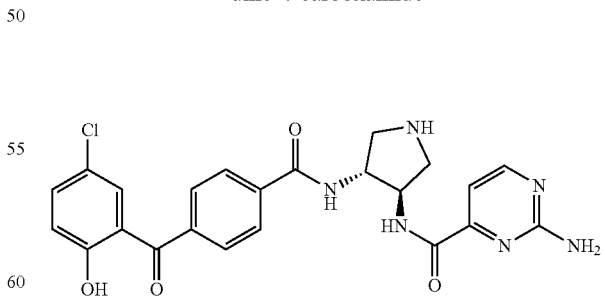

Prepared according to the general procedure 2. $^1$H NMR (500 MHz, Methanol-d$_4$) δ 7.99 (m, 2H), 7.82 (s, 2H), 7.50 (m, 1H), 7.43 (m, 1H), 7.21 (s, 1H), 7.04 (m, 1H), 4.67 (m, 2H), 3.76 (m, 2H), 3.35 (m, 2H). LCMS (ESI+) for $C_{23}H_{21}ClN_6O_4$ [M+H] expected=481.13, found=481.57.

Example 18: N-((3R,4R)-4-(4-(2-hydroxy-4-methoxybenzoyl)benzamido)pyrrolidin-3-yl)isonicotinamide

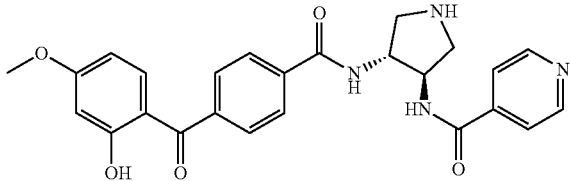 [SMILES: COc1ccc(C(=O)c2ccc(C(=O)N[C@@H]3CNC[C@H]3NC(=O)c3ccncc3)cc2)c(O)c1]

Prepared according to the general procedure 2. $^1$H NMR (500 MHz, Methanol-$d_4$) δ 8.71 (d, J=5.2 Hz, 2H), 8.48 (s, 1H), 7.99 (d, J=8.0 Hz, 2H), 7.84-7.78 (m, 2H), 7.73 (d, J=7.9 Hz, 2H), 7.46 (d, J=9.0 Hz, 1H), 6.56 (d, J=2.4 Hz, 1H), 6.49 (dd, J=9.0, 2.5 Hz, 1H), 4.67 (m, 2H), 3.88 (s, 3H), 3.77-3.68 (m, 2H). LCMS (ESI+) for $C_{25}H_{24}N_4O_5$ [M+H] expected=461.18, found=461.55.

Example 19: 2-amino-N-((3R,4R)-4-(4-(2-hydroxy-4-methoxybenzoyl)benzamido)pyrrolidin-3-yl)pyrimidine-4-carboxamide

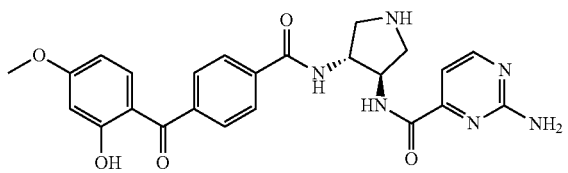 [SMILES: COc1ccc(C(=O)c2ccc(C(=O)N[C@@H]3CNC[C@H]3NC(=O)c3ccnc(N)n3)cc2)c(O)c1]

Prepared according to the general procedure 2. $^1$H NMR (500 MHz, Methanol-$d_4$) δ 8.49 (s, 1H), 8.46 (d, J=5.0 Hz, 1H), 7.98 (d, J=8.4 Hz, 2H), 7.73 (d, J=8.0 Hz, 2H), 7.46 (d, J=9.0 Hz, 1H), 7.21 (d, J=5.0 Hz, 1H), 6.56 (d, J=2.4 Hz, 1H), 6.49 (dd, J=9.0, 2.5 Hz, 1H), 4.64 (m, 2H), 3.88 (s, 3H), 3.76-3.64 (m, 2H), 3.26 (m, 2H). LCMS (ESI+) for $C_{24}H_{24}N_6O_5$ [M+H] expected=477.18, found=477.58.

Example 20: N-((3R,4R)-4-(4-(2-hydroxy-4-methylbenzoyl)benzamido)pyrrolidin-3-yl)isonicotinamide

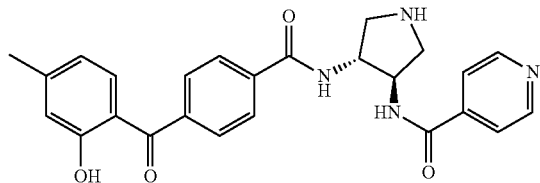 [SMILES: Cc1ccc(C(=O)c2ccc(C(=O)N[C@@H]3CNC[C@H]3NC(=O)c3ccncc3)cc2)c(O)c1]

Prepared according to the general procedure 2. $^1$H NMR (500 MHz, Methanol-$d_4$) δ 8.72 (d, J=6.1 Hz, 2H), 8.44 (s, 1H), 7.99 (d, J=8.1 Hz, 2H), 7.81 (d, J=6.1 Hz, 2H), 7.76 (d, J=8.0 Hz, 2H), 7.41 (d, J=8.2 Hz, 1H), 6.88 (s, 1H), 6.77 (d, J=8.2 Hz, 1H), 4.73-4.66 (m, 2H), 3.74 (dd, J=12.1, 6.9 Hz, 2H), 2.38 (s, 3H). LCMS (ESI+) for $C_{25}H_{24}N_4O_4$ [M+H] expected=445.18, found=445.55.

Example 21: 2-amino-N-((3R,4R)-4-(4-(2-hydroxy-4-methylbenzoyl)benzamido)pyrrolidin-3-yl)pyrimidine-4-carboxamide

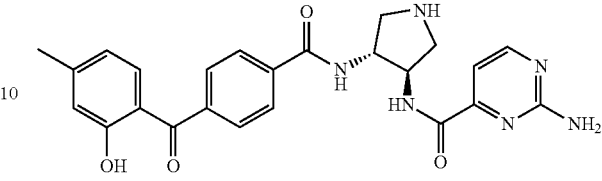

Prepared according to the general procedure 2. $^1$H NMR (500 MHz, Methanol-$d_4$) δ 8.46 (d, J=4.9 Hz, 1H), 8.40 (s, 4H), 7.99 (d, J=8.3 Hz, 2H), 7.76 (d, J=8.2 Hz, 2H), 7.40 (d, J=8.2 Hz, 1H), 7.22 (d, J=4.9 Hz, 1H), 6.88 (s, 1H), 6.78-6.75 (m, 1H), 4.72 (m, 2H), 3.84 (dd, J=11.8, 7.5 Hz, 2H), 3.49-3.41 (m, 2H), 2.37 (s, 3H). LCMS (ESI+) for $C_{24}H_{24}N_6O_4$ [M+H] expected=461.19, found=461.78.

Example 22: N-((3R,4R)-4-(4-(4-chloro-2-hydroxybenzoyl)benzamido)pyrrolidin-3-yl)isonicotinamide

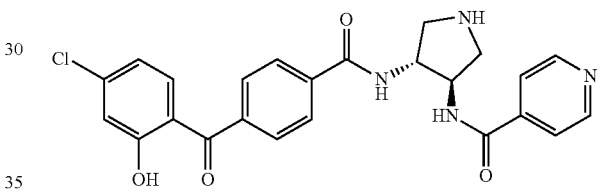

Prepared according to the general procedure 2. $^1$H NMR (500 MHz, Methanol-$d_4$) δ 8.76-8.67 (m, 2H), 8.50 (s, 1H), 7.99 (d, J=8.1 Hz, 2H), 7.83-7.78 (m, 4H), 7.50 (d, J=8.5 Hz, 1H), 7.08 (d, J=2.0 Hz, 1H), 6.96 (dd, J=8.5, 2.1 Hz, 1H), 4.74-4.68 (m, 2H), 3.74 (dd, J=12.0, 7.0 Hz, 2H), 3.33 (m, 2H). LCMS (ESI+) for $C_{24}H_{21}ClN_4O_4$ [M+H] expected=465.13, found=465.52.

Example 23: N-((3R,4R)-4-(4-(2-hydroxy-5-methylbenzoyl)benzamido)pyrrolidin-3-yl)isonicotinamide

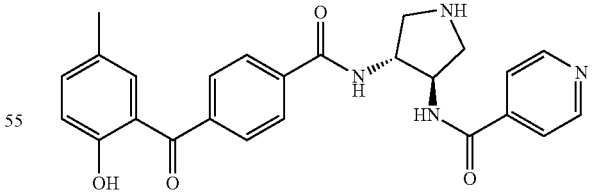 [SMILES: O=C(N[C@@H]1CNC[C@H]1NC(=O)c1ccc(C(=O)c2ccc(Cl)cc2O)cc1)c1ccncc1]

Prepared according to the general procedure 2. $^1$H NMR (500 MHz, Methanol-$d_4$) δ 8.72 (d, J=6.0 Hz, 2H), 8.37 (s, 3H), 8.00 (d, J=8.1 Hz, 2H), 7.82 (d, J=6.1 Hz, 2H), 7.78 (d, J=8.1 Hz, 2H), 7.38 (dd, J=8.5, 2.2 Hz, 1H), 7.27 (d, J=2.1 Hz, 1H), 6.94 (d, J=8.5 Hz, 1H), 4.72 (d, J=7.4 Hz, 2H), 3.84 (dd, J=12.0, 6.8 Hz, 2H), 3.48-3.40 (m, 2H), 2.24 (s, 3H). LCMS (ESI+) for $C_{25}H_{24}N_4O_4$ [M+H] expected=445.18, found=445.55.

Example 24: N-((3R,4R)-4-(4-(2-hydroxy-5-methoxybenzoyl)benzamido)pyrrolidin-3-yl)isonicotinamide

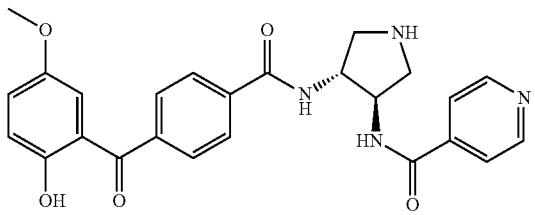 [SMILES: COc1ccc(O)c(C(=O)c2ccc(C(=O)N[C@@H]3CNC[C@H]3NC(=O)c3ccncc3)cc2)c1]

Prepared according to the general procedure 2. $^1$H NMR (500 MHz, Methanol-$d_4$) δ 8.76-8.69 (m, 2H), 8.45 (s, 1H), 8.00 (d, J=8.1 Hz, 2H), 7.87-7.77 (m, 4H), 7.19 (dd, J=9.0, 3.1 Hz, 1H), 6.99 (s, 1H), 6.98-6.95 (m, 1H), 4.73-4.66 (m, 2H), 3.75 (dd, J=12.1, 7.1 Hz, 2H), 3.70 (s, 3H). LCMS (ESI+) for $C_{25}H_{24}N_4O_5$ [M+H] expected=461.18, found=461.45.

Example 25: 2-amino-N-((3R,4R)-4-(4-(2-hydroxy-5-methoxybenzoyl)benzamido)pyrrolidin-3-yl)pyrimidine-4-carboxamide

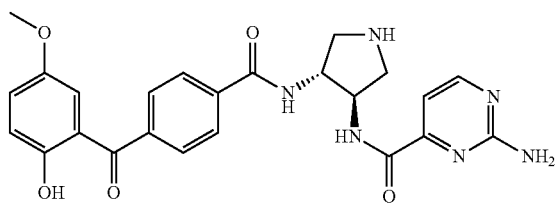 [SMILES: COc1ccc(O)c(C(=O)c2ccc(C(=O)N[C@@H]3CNC[C@H]3NC(=O)c3ccnc(N)n3)cc2)c1]

Prepared according to the general procedure 2. $^1$H NMR (500 MHz, Methanol-$d_4$) δ 8.48-8.43 (m, 1H), 7.99 (d, J=8.1 Hz, 2H), 7.82 (d, J=8.1 Hz, 2H), 7.22 (d, J=4.9 Hz, 1H), 7.19 (dd, J=9.1, 3.1 Hz, 1H), 7.01-6.95 (m, 2H), 4.67 (dq, J=19.9, 6.9 Hz, 2H), 3.81-3.73 (m, 2H), 3.69 (s, 3H), 3.39-3.33 (m, 2H). LCMS (ESI+) for $C_{24}H_{24}N_6O_5$ [M+H] expected=477.18, found=477.44.

Example 26: N-((3R,4R)-4-(4-(2-hydroxy-3-methylbenzoyl)benzamido)pyrrolidin-3-yl)isonicotinamide

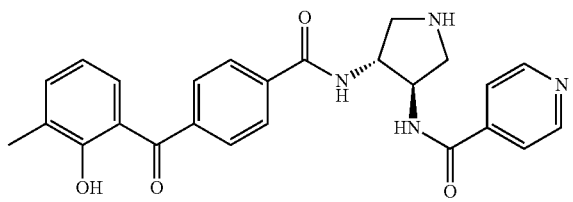 [SMILES: Cc1cccc(C(=O)c2ccc(C(=O)N[C@@H]3CNC[C@H]3NC(=O)c3ccncc3)cc2)c1O]

Prepared according to the general procedure 2. $^1$H NMR (500 MHz, Methanol-$d_4$) δ 8.75-8.68 (m, 2H), 8.46 (s, 1H), 8.00 (d, J=7.9 Hz, 2H), 7.85-7.79 (m, 2H), 7.77 (d, J=8.0 Hz, 2H), 7.46 (d, J=7.3 Hz, 1H), 7.37 (d, J=8.1 Hz, 1H), 6.83 (t, J=7.7 Hz, 1H), 4.73-4.65 (m, 2H), 3.73 (dd, J=12.0, 7.0 Hz, 2H), 3.29 (s, 2H), 2.30 (s, 3H). LCMS (ESI+) for $C_{25}H_{24}N_4O_4$ [M+H] expected=445.18, found=445.44.

Example 27: 2-amino-N-((3R,4R)-4-(4-(2-hydroxy-3-methylbenzoyl)benzamido)pyrrolidin-3-yl)pyrimidine-4-carboxamide

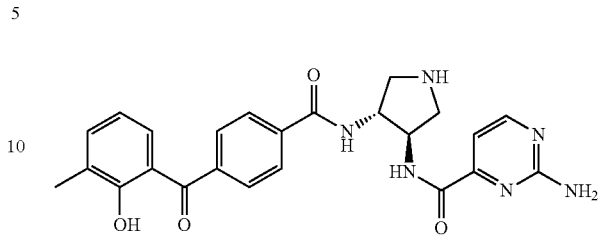

Prepared according to the general procedure 2. $^1$H NMR (500 MHz, Methanol-$d_4$) δ 8.49 (s, 2H), 8.46 (d, J=4.9 Hz, 1H), 7.99 (d, J=8.0 Hz, 2H), 7.76 (d, J=7.9 Hz, 2H), 7.45 (d, J=7.3 Hz, 1H), 7.37 (d, J=8.0 Hz, 1H), 7.22 (d, J=4.9 Hz, 1H), 6.83 (t, J=7.7 Hz, 1H), 4.66 (dq, J=22.0, 7.0 Hz, 2H), 3.78-3.67 (m, 2H), 3.27 (m, 2H), 2.30 (s, 3H). LCMS (ESI+) for $C_{24}H_{24}N_6O_4$ [M+H] expected=461.19, found=461.42.

Example 28: N-((3R,4R)-4-(4-(2-hydroxy-3-methoxybenzoyl)benzamido)pyrrolidin-3-yl)isonicotinamide

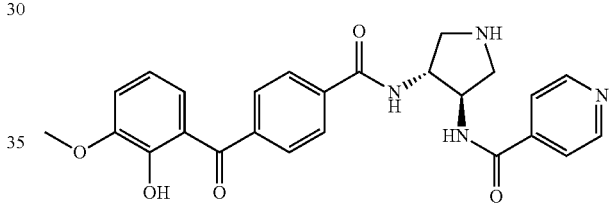

Prepared according to the general procedure 2. $^1$H NMR (500 MHz, Methanol-$d_4$) δ 8.75-8.68 (m, 2H), 8.45 (s, 1H), 7.97 (d, J=7.9 Hz, 2H), 7.85-7.77 (m, 4H), 7.22 (d, J=8.0 Hz, 1H), 7.05 (d, J=8.0 Hz, 1H), 6.90 (t, J=8.0 Hz, 1H), 4.67 (s, 2H), 3.91 (s, 3H), 3.73 (s, 2H). LCMS (ESI+) for $C_{25}H_{24}N_4O_5$ [M+H] expected=461.18, found=461.55.

Example 29: 2-amino-N-((3R,4R)-4-(4-(2-hydroxy-3-methoxybenzoyl)benzamido)pyrrolidin-3-yl)pyrimidine-4-carboxamide

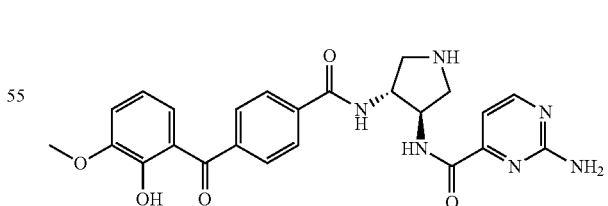

Prepared according to the general procedure 2. $^1$H NMR (500 MHz, Methanol-$d_4$) δ 8.48 (s, 2H), 8.46 (d, J=5.0 Hz, 1H), 7.96 (d, J=7.9 Hz, 2H), 7.81 (d, J=7.9 Hz, 2H), 7.22 (m, 2H), 7.06 (d, J=8.0 Hz, 1H), 6.91 (t, J=8.0 Hz, 1H), 4.67 (s, 2H), 3.92 (s, 3H), 3.71 (s, 2H), 3.27 (s, 1H). LCMS (ESI+) for $C_{24}H_{24}N_6O_5$ [M+H] expected=477.18, found=477.58.

Example 30: N-((3R,4R)-4-(4-(3-chloro-2-hydroxybenzoyl)benzamido)pyrrolidin-3-yl)isonicotinamide

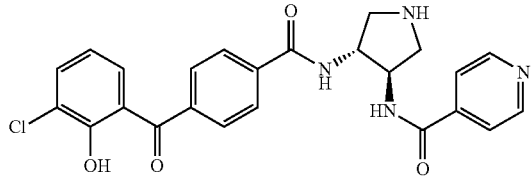 [SMILES: O=C(N[C@@H]1CNC[C@H]1NC(=O)c1ccc(C(=O)c2cccc(Cl)c2O)cc1)c1ccncc1]

Prepared according to the general procedure 2. $^1$H NMR (500 MHz, Methanol-$d_4$) δ 8.74-8.69 (m, 2H), 8.47 (s, 1H), 8.01 (dd, J=8.3, 1.6 Hz, 2H), 7.85-7.79 (m, 4H), 7.67 (d, J=7.8 Hz, 1H), 7.49 (d, J=7.9 Hz, 1H), 6.95 (dd, J=8.7, 7.2 Hz, 1H), 4.71 (d, J=6.4 Hz, 2H), 3.76 (dd, J=12.0, 6.8 Hz, 2H), 3.35 (d, J=6.3 Hz, 2H). LCMS (ESI+) for $C_{24}H_{21}ClN_4O_4$ [M+H] expected=465.13, found=465.52.

Example 31: 2-amino-N-((3R,4R)-4-(4-(3-chloro-2-hydroxybenzoyl)benzamido)pyrrolidin-3-yl)pyrimidine-4-carboxamide

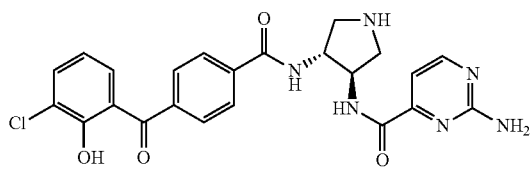 [SMILES: Nc1nccc(C(=O)N[C@@H]2CNC[C@H]2NC(=O)c2ccc(C(=O)c3cccc(Cl)c3O)cc2)n1]

Prepared according to the general procedure 2. $^1$H NMR (500 MHz, Methanol-$d_4$) δ 8.48 (s, 1H), 8.46 (d, J=4.9 Hz, 1H), 7.99 (d, J=7.9 Hz, 2H), 7.81 (d, J=7.9 Hz, 2H), 7.71-7.64 (m, 1H), 7.49 (dd, J=7.9, 1.5 Hz, 1H), 7.21 (d, J=5.0 Hz, 1H), 6.95 (t, J=8.0 Hz, 1H), 4.63 (m, 2H), 3.69 (s, 2H), 3.25 (m, 2H). LCMS (ESI+) for $C_{23}H_{21}ClN_6O_4$ [M+H] expected=481.13, found=481.51.

Example 32: N-((3R,4R)-4-(4-(2-hydroxybenzoyl)-2-methoxybenzamido)pyrrolidin-3-yl)isonicotinamide

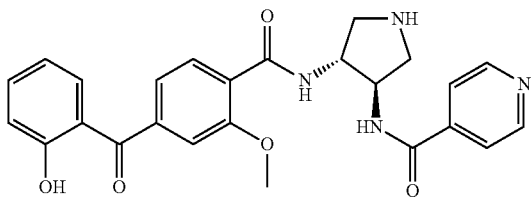 [SMILES: COc1cc(C(=O)c2ccccc2O)ccc1C(=O)N[C@@H]1CNC[C@H]1NC(=O)c1ccncc1]

Prepared according to the general procedure 2. $^1$H NMR (500 MHz, Methanol-$d_4$) δ 8.76-8.69 (m, 2H), 8.51 (s, 1H), 7.96 (d, J=7.8 Hz, 1H), 7.86-7.79 (m, 2H), 7.55 (dd, J=8.9, 7.4 Hz, 2H), 7.43 (d, J=1.4 Hz, 1H), 7.33 (d, J=7.9 Hz, 1H), 7.04 (d, J=8.4 Hz, 1H), 6.94 (t, J=7.6 Hz, 1H), 4.69 (q, J=7.3 Hz, 1H), 4.60 (q, J=7.2 Hz, 1H), 4.01 (s, 3H), 3.71 (dd, J=11.8, 7.8 Hz, 1H), 3.65 (dd, J=11.9, 7.8 Hz, 1H), 3.22 (td, J=8.0, 3.8 Hz, 2H). LCMS (ESI+) for $C_{25}H_{24}N_4O_5$ [M+H] expected=461.18, found=461.60.

Example 33: 2-amino-N-((3R,4R)-4-(4-(2-hydroxybenzoyl)-2-methoxybenzamido)pyrrolidin-3-yl)pyrimidine-4-carboxamide

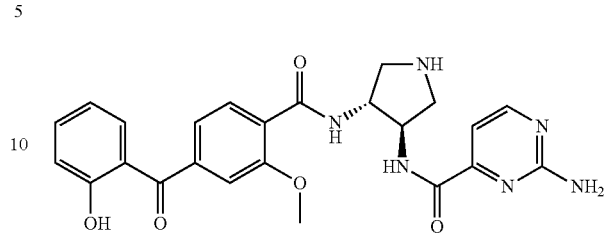

Prepared according to the general procedure 2. $^1$H NMR (500 MHz, Methanol-$d_4$) δ 8.48 (s, 1H), 8.47 (d, J=5.0 Hz, 1H), 7.97 (d, J=7.9 Hz, 1H), 7.55 (t, J=8.1 Hz, 2H), 7.43 (s, 1H), 7.33 (d, J=8.1 Hz, 1H), 7.23 (d, J=5.1 Hz, 1H), 7.04 (d, J=8.2 Hz, 1H), 6.94 (t, J=7.6 Hz, 1H), 4.64 (dt, J=22.6, 7.3 Hz, 2H), 4.01 (s, 3H), 3.73 (ddd, J=31.3, 11.9, 7.8 Hz, 2H), 3.26 (m, 2H). LCMS (ESI+) for $C_{24}H_{24}N_6O_5$ [M+H] expected=477.18, found=477.61.

Example 34: N-((3R,4R)-4-(3-chloro-4-(2-hydroxybenzoyl)benzamido)pyrrolidin-3-yl)isonicotinamide

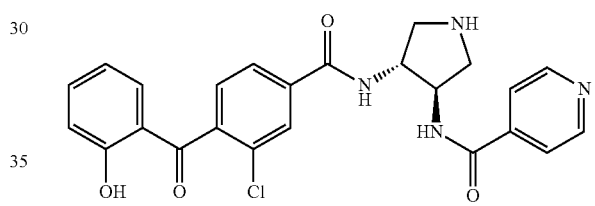

Prepared according to the general procedure 2. $^1$H NMR (500 MHz, Methanol-$d_4$) δ 8.75-8.69 (m, 2H), 8.48 (s, 1H), 8.04 (d, J=1.6 Hz, 1H), 7.94 (d, J=7.8 Hz, 1H), 7.83-7.79 (m, 2H), 7.63-7.53 (m, 2H), 7.22 (d, J=7.9 Hz, 1H), 7.05 (d, J=8.4 Hz, 1H), 6.89 (t, J=7.6 Hz, 1H), 4.66 (t, J=5.7 Hz, 2H), 3.68 (dd, J=12.4, 6.4 Hz, 2H), 3.28-3.21 (m, 2H). LCMS (ESI+) for $C_{24}H_{21}ClN_4O_4$ [M+H] expected=465.13, found=465.52.

Example 35: 2-amino-N-((3R,4R)-4-(3-chloro-4-(2-hydroxybenzoyl)benzamido)pyrrolidin-3-yl)pyrimidine-4-carboxamide

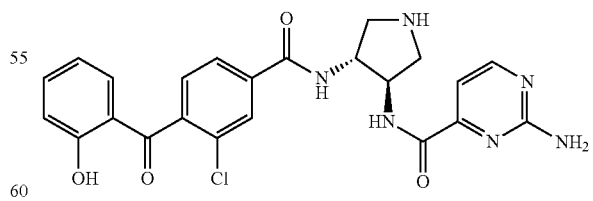

Prepared according to the general procedure 2. $^1$H NMR (500 MHz, Methanol-$d_4$) δ 8.49 (s, 1H), 8.46 (d, J=4.8 Hz, 1H), 8.04 (s, 1H), 7.93 (d, J=8.0 Hz, 1H), 7.63-7.54 (m, 2H), 7.22 (d, J=5.9 Hz, 2H), 7.05 (d, J=8.4 Hz, 1H), 6.89 (t, J=7.6 Hz, 1H), 4.68-4.60 (m, 2H), 3.67 (m, 2H), 3.25 (m, 2H). LCMS (ESI+) for $C_{23}H_{21}ClN_6O_4$ [M+H] expected=481.13, found=481.54. LCMS (ESI+) for C$_{25}$H$_{24}$N$_4$O$_4$ [M+H] expected=445.18, found=445.55.

Example 36: N-((3R,4R)-4-(2-chloro-4-(2-hydroxybenzoyl)benzamido)pyrrolidin-3-yl)isonicotinamide

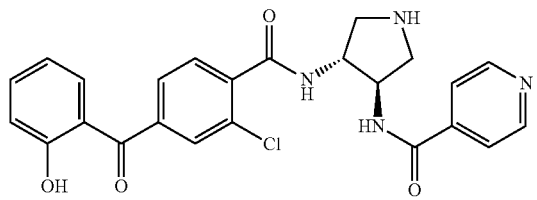 [SMILES: O=C(N[C@@H]1CNC[C@H]1NC(=O)c1ccc(C(=O)c2ccccc2O)cc1Cl)c1ccncc1]

Prepared according to the general procedure 2. $^1$H NMR (500 MHz, Methanol-d$_4$) δ 8.74-8.69 (m, 2H), 8.46 (s, 1H), 7.86-7.79 (m, 2H), 7.78 (d, J=1.4 Hz, 1H), 7.69 (d, J=7.7 Hz, 1H), 7.63 (d, J=7.9 Hz, 1H), 7.55 (dd, J=8.6, 6.9 Hz, 1H), 7.49 (d, J=8.0 Hz, 1H), 7.03 (d, J=8.4 Hz, 1H), 6.96 (t, J=7.6 Hz, 1H), 4.66 (dq, J=25.7, 7.2 Hz, 2H), 3.65 (ddd, J=30.6, 11.9, 7.4 Hz, 2H), 3.23-3.15 (m, 2H). LCMS (ESI+) for C$_{24}$H$_{21}$ClN$_4$O$_4$ [M+H] expected=465.13, found=465.52.

Example 37: N-((3R,4R)-4-(4-(2-hydroxybenzoyl)-3-methylbenzamido)pyrrolidin-3-yl)isonicotinamide

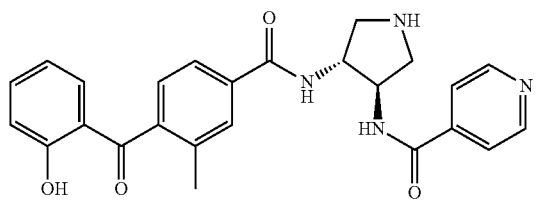 [SMILES: Cc1cc(C(=O)N[C@@H]2CNC[C@H]2NC(=O)c2ccncc2)ccc1C(=O)c1ccccc1O]

Prepared according to the general procedure 2. $^1$H NMR (500 MHz, Methanol-d$_4$) δ 8.72 (d, J=5.2 Hz, 2H), 8.48 (s, 1H), 7.86-7.76 (m, 4H), 7.57 (t, J=7.7 Hz, 1H), 7.41 (d, J=7.9 Hz, 1H), 7.23 (d, J=8.1 Hz, 1H), 7.05 (d, J=8.4 Hz, 1H), 6.87 (t, J=7.5 Hz, 1H), 4.65 (d, J=7.5 Hz, 2H), 3.68 (dd, J=12.6, 6.7 Hz, 2H), 3.26-3.20 (m, 2H), 2.33 (s, 3H).

Example 38: 4-(ethoxymethoxy)-2-fluoro-1-methoxybenzene

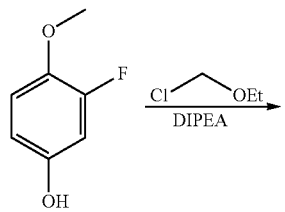

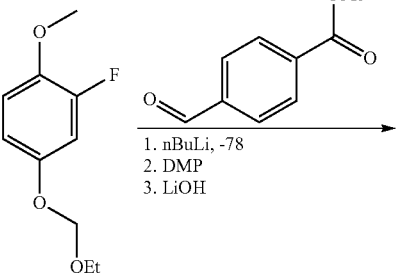

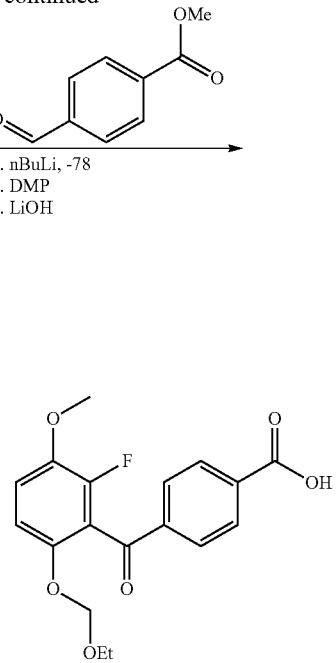

A round bottom flask was charged with 3-fluoro-4-methoxyphenol (5.0 g, 0.035 mol) and CH$_2$Cl$_2$ (50 mL) at room temperature. This solution was cooled to 0° C. and then diisopropylethylamine (12.2 mL, 0.070 mol) was added followed by (chloromethoxy)ethane (6.52 mL, 0.070 mol). The resulting solution was warmed to room temperature and monitored by LC-MS. After 24 h, the solution was sequentially washed with water and NaHCO$_3$. The organic portion was concentrated and purified on silica gel (40 g, hexane/EtOAc gradient 0%-20%) to give 4-(ethoxymethoxy)-2-fluoro-1-methoxybenzene which was used without further purification. $^1$H NMR (500 MHz, Chloroform-d) δ 6.93-6.81 (m, 2H), 6.80-6.72 (m, 1H), 5.14 (s, 2H), 3.85 (s, 3H), 3.72 (q, J=7.1 Hz, 2H), 1.23 (t, J=7.1 Hz, 3H).

methyl 4-((6-(ethoxymethoxy)-2-fluoro-3-methoxyphenyl)(hydroxy)methyl)benzoate

A flame-dried round bottom flask was charged with 4-(ethoxymethoxy)-2-fluoro-1-methoxybenzene (1.5 g, 7.49 mmol) and anhydrous THF (25 mL) under an atmosphere of N$_2$. The solution was cooled in a dry ice/acetone bath and then treated slowly with nBuLi (4.48 mL of a 2.5 M hexane solution, 11.2 mmol). After two hours of stirring cold, the solution was slowly treated with a solution of methyl 4-formylbenzoate (1.85 mL, 11.2 mmol) in anhydrous THF (5 mL). The resulting mixture was allowed to warm to room temperature slowly and monitored by LC-MS. Upon completion, the solution was diluted with ethyl acetate and sequentially washed with water and brine. Concentration gave 3.36 g of a yellow oil, which was then purified on silica gel (40 g, hexane/EtOAc gradient 12%-100%) to give methyl 4-((6-(ethoxymethoxy)-2-fluoro-3-methoxyphenyl)(hydroxy)methyl)benzoate. $^1$H NMR (500 MHz, Chloroform-d) δ 7.97 (d, J=8.5 Hz, 2H), 7.43 (d, J=8.1 Hz, 2H), 6.86 (m, 2H), 6.25 (d, J=11.2 Hz, 1H), 5.08 (d, J=6.9 Hz, 1H), 4.98 (d, J=6.9 Hz, 1H), 3.89 (s, 3H), 3.87 (s, 3H), 3.53-3.29 (m, 2H), 1.09 (t, J=7.0 Hz, 3H).

methyl 4-(6-(ethoxymethoxy)-2-fluoro-3-methoxy-benzoyl)benzoate

A round bottom flask was charged with methyl 4-((6-(ethoxymethoxy)-2-fluoro-3-methoxyphenyl)(hydroxy)methyl)benzoate (2.13 g, 5.85 mmol) and $CH_2Cl_2$ (40 mL) at room temperature. Dess-Martin Periodinane (3.72 g, 8.77 mmol) was then added and the resulting pale yellow suspension was stirred for 30 min. The solution was diluted with dichloromethane and washed with $NaHCO_3$. Concentration and purification on silica gel (40 g, hexane/EtOAc gradient 6%-50%) gave methyl 4-(6-(ethoxymethoxy)-2-fluoro-3-methoxybenzoyl)benzoate. $^1H$ NMR (500 MHz, Chloroform-d) δ 8.11 (d, J=8.5 Hz, 2H), 7.91 (d, J=8.5 Hz, 2H), 7.07-6.95 (m, 2H), 5.05 (s, 2H), 3.95 (s, 3H), 3.89 (s, 3H), 3.51 (q, J=7.1 Hz, 2H), 1.11 (t, J=7.1 Hz, 3H).

4-(6-(ethoxymethoxy)-2-fluoro-3-methoxybenzoyl)benzoic acid

A vial was charged with methyl 4-(6-(ethoxymethoxy)-2-fluoro-3-methoxybenzoyl)benzoate (1.0 g, 2.76 mmol), THF (9 mL), and water (3 mL). LiOH (264 mg, 11.0 mmol) was added and the resulting mixture was stirred at 60° C. for 30 min. The solution was then diluted with ethyl acetate and washed with a 10% citric acid solution. Concentration of the organic portion resulted in 4-(6-(ethoxymethoxy)-2-fluoro-3-methoxybenzoyl)benzoic acid. $^1H$ NMR (500 MHz, DMSO-$d_6$) δ 8.10 (d, J=8.4 Hz, 2H), 7.88 (d, J=8.3 Hz, 2H), 7.32 (t, J=9.5 Hz, 1H), 7.08 (dd, J=9.2, 1.4 Hz, 1H), 5.11 (s, 2H), 3.86 (s, 3H), 3.36 (obscured by solvent, m, 2H), 0.98 (t, J=7.1 Hz, 3H).

Example 39: N-(2-(4-(2-fluoro-6-hydroxy-3-methoxybenzoyl)benzamido)ethyl)isonicotinamide

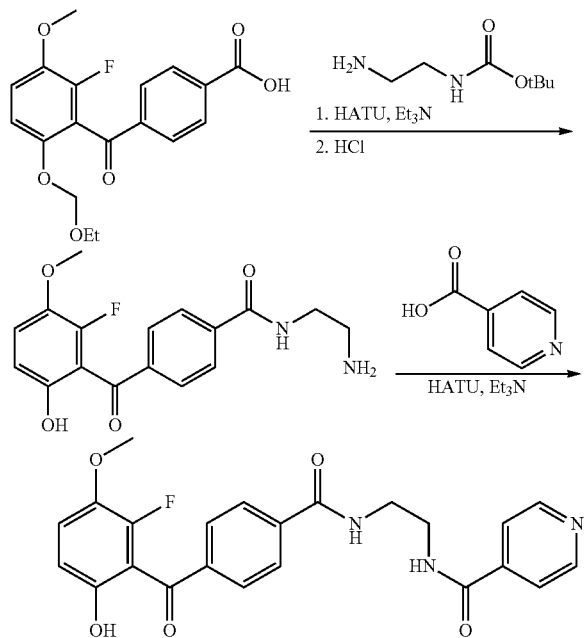

A reaction vial was charged with 4-(6-(ethoxymethoxy)-2-fluoro-3-methoxybenzoyl)benzoic acid (75 mg, 0.215 mmol) and MeCN (2 mL) at room temperature. To this solution was sequentially added triethylamine (60 μL, 0.430 mmol), tert-butyl (2-aminoethyl)carbamate (35 mg, 0.215 mmol), and HATU (82 mg, 0.215 mmol). Upon completion by LCMS, the solution was diluted with water and twice extracted with EtOAc. The solution was concentrated in vacuo, and then dissolved in THF (3 mL). This solution was then treated with 1 N HCl (3 mL) and warmed to 65° C. Upon completion by LCMS, the solution was cooled to room temperature and diluted with EtOAc. The organic portion was then washed with water, $NaHCO_3$ and brine solutions. The EtOAc solution was dried over sodium sulfate and concentrated to give 131 mg of N-(2-aminoethyl)-4-(2-fluoro-6-hydroxy-3-methoxybenzoyl)benzamide as an oil which was used directly without further purification. This oil was dissolved in DMF (2 mL) and treated with triethylamine (90 μL, 0.645 mmol) at room temperature. Isonicotinic acid (32 mg, 0.258 mmol), followed by HATU (98 mg, 0.258 mmol) were added and stirred for 15 min. LCMS indicated some acylation of the phenol, so LiOH (20 mg in 1 mL $H_2O$) was added and stirred for 2 h. The aqueous solution was purified directly on HPLC to give N-(2-(4-(2-fluoro-6-hydroxy-3-methoxybenzoyl)benzamido)ethyl)isonicotinamide. $^1H$ NMR (500 MHz, Methanol-$d_4$) δ 8.98 (s, 1H), 8.81 (s, 1H), 8.72 (d, J=6.3 Hz, 2H), 7.90 (m, 4H), 7.85-7.80 (m, 2H), 7.13 (t, J=9.3 Hz, 1H), 6.68 (dd, J=9.0, 1.7 Hz, 1H), 3.84 (s, 3H), 3.68-3.63 (m, 4H). LCMS (ESI+) for $C_{23}H_{20}FN_3O_5$ [M+H] expected=438.14, found=438.36.

Example 40: N-(2-(4-(2-fluoro-3,6-dimethoxybenzoyl)benzamido)ethyl)isonicotinamide

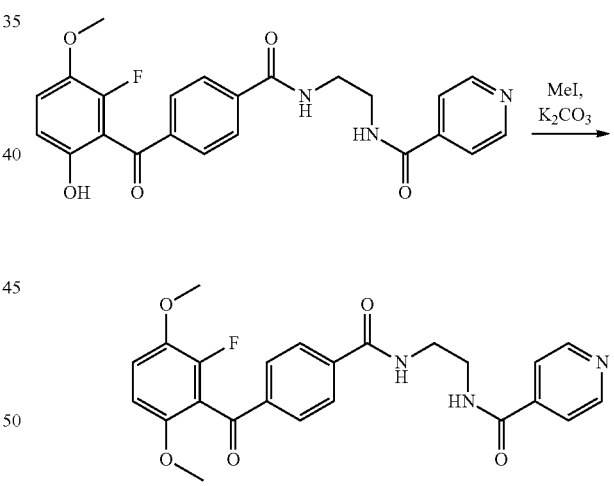

A vial was charged with N-(2-(4-(2-fluoro-6-hydroxy-3-methoxybenzoyl)benzamido)ethyl)isonicotinamide (4.4 mg) and DMF (1 mL) at room temperature. The solution was treated with iodomethane (0.64, added as a DMF solution) and excess potassium carbonate. The solution was stirred for 18 h, quenched with water and purified directly on HPLC to give N-(2-(4-(2-fluoro-3,6-dimethoxybenzoyl)benzamido)ethyl)isonicotinamide. $^1H$ NMR (500 MHz, Chloroform-d) δ 8.75 (d, J=5.1 Hz, 2H), 7.92 (d, J=8.2 Hz, 2H), 7.86 (d, J=8.3 Hz, 2H), 7.68 (d, J=5.1 Hz, 2H), 7.54 (s, 1H), 7.08-7.00 (m, 2H), 6.69 (dd, J=9.1, 1.5 Hz, 1H), 3.88 (s, 3H), 3.80-3.71 (m, 4H), 3.68 (s, 3H). LCMS (ESI+) for $C_{24}H_{22}FN_3O_5$ [M+H] expected=452.16, found=452.39.

Example 41: N-((1R,2R)-2-(4-(2-fluoro-6-hydroxy-3-methoxybenzoyl)benzamido)cycloheptyl)isonicotinamide

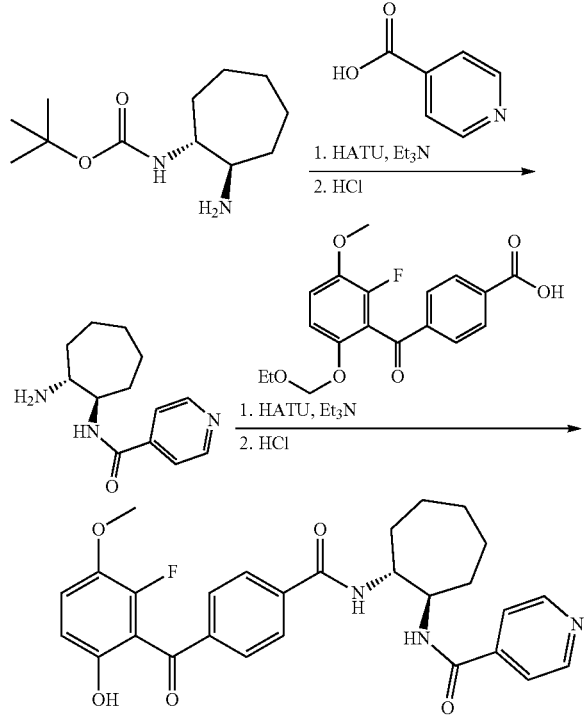

HATU (114 mg, 0.300 mmol) was added to a room temperature solution of tert-butyl ((1R,2R)-2-aminocycloheptyl)carbamate (69 mg, 0.300 mmol), isonicotinic acid (37 mg, 0.300 mmol), and triethyl amine (84 µL, 0.600 mmol) in acetonitrile (1.5 mL). After 5 min, the solution was quenched with water and extracted with EtOAc. The organic extract was thrice washed with water and concentrated in vacuo. The residue was then dissolved in 4 N HCl in dioxane (2 mL) which formed a precipitate. Concentration gave a solid which was used without further purification. The N-((1R,2R)-2-aminocycloheptyl)isonicotinamide (0.200 mmol) thus formed was dissolved in a mixture of acetonitrile (1.5 mL) and DMF (1.0 mL). Triethylamine (167⎵, 1.2 mmol) was added, followed by 4-(6-(ethoxymethoxy)-2-fluoro-3-methoxybenzoyl)benzoic acid (70 mg, 0.200 mmol) and HATU (76 mg, 0.200 mmol). The resulting solution was stirred at room temperature for 30 min and then quenched with water. The solution was twice extracted with EtOAc and then concentrated in vacuo. Dissolution in THF (1 mL) and 1N HCl (1 mL) was followed by warming to 55° C. for 3 h. The solution was then cooled to room temperature and partitioned between aqueous NaHCO₃ and EtOAc. The organic portion was concentrated and purified on silica gel (12 g, hexane/EtOAc gradient 25%-100%) to give N-((1R,2R)-2-(4-(2-fluoro-6-hydroxy-3-methoxybenzoyl)benzamido)cycloheptyl)isonicotinamide. $^1$H NMR (500 MHz, Chloroform-d) δ 10.23 (s, 1H), 8.70 (d, J=5.5 Hz, 2H), 7.76 (d, J=8.2 Hz, 2H), 7.71 (dd, J=8.5, 2.3 Hz, 2H), 7.67 (s, 2H), 7.21 (t, J=9.2 Hz, 1H), 6.83 (dd, J=9.2, 1.8 Hz, 1H), 6.66 (s, 1H), 4.18 (m, 2H), 3.84 (s, 3H), 2.06 (m, 2H), 1.88-1.72 (m, 4H), 1.60 (m, 4H). LCMS (ESI+) for $C_{28}H_{28}FN_3O_5$ [M+H] expected=506.20, found=506.42.

Example 42: N-((1R,2R)-2-(4-(2-fluoro-3,6-dimethoxybenzoyl)benzamido)cycloheptyl)isonicotinamide

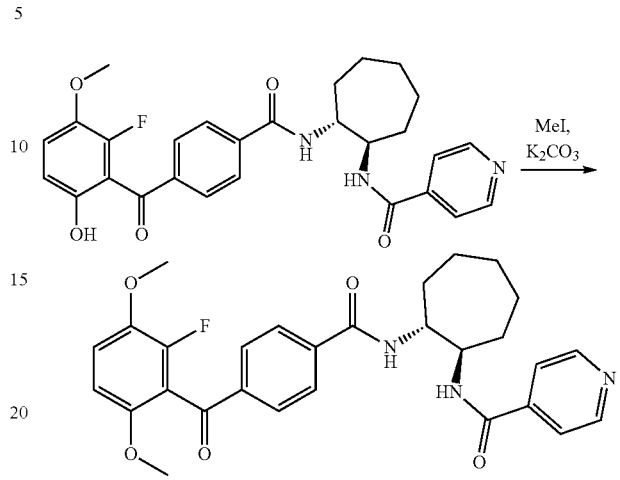

A vial was charged with N-((1R,2R)-2-(4-(2-fluoro-6-hydroxy-3-methoxybenzoyl)benzamido)cycloheptyl) isonicotinamide (5.0 mg) and DMF (0.5 mL) at room temperature. The solution was treated with iodomethane (0.6 µL, added as a DMF solution) and excess potassium carbonate. The solution was stirred for 2 h, quenched with water and purified directly on HPLC to give N-((1R,2R)-2-(4-(2-fluoro-3,6-dimethoxybenzoyl)benzamido)cycloheptyl) isonicotinamide. $^1$H NMR (500 MHz, Chloroform-d) δ 8.73-8.65 (m, 2H), 7.86 (d, J=8.4 Hz, 2H), 7.75 (d, J=8.4 Hz, 2H), 7.61 (d, J=5.5 Hz, 2H), 7.21 (d, J=7.6 Hz, 1H), 7.02 (t, J=9.2 Hz, 1H), 6.71 (d, J=8.2 Hz, 1H), 6.68 (dd, J=9.0, 1.6 Hz, 1H), 4.25-4.06 (m, 2H), 3.88 (s, 3H), 3.66 (s, 3H), 2.03 (m, 2H), 1.75 (m, 8H). LCMS (ESI+) for $C_{29}H_{30}FN_3O_5$ [M+H] expected=520.22, found=520.47.

Example 43: N-((1R,2R)-2-(4-benzoylbenzamido)cycloheptyl)isonicotinamide

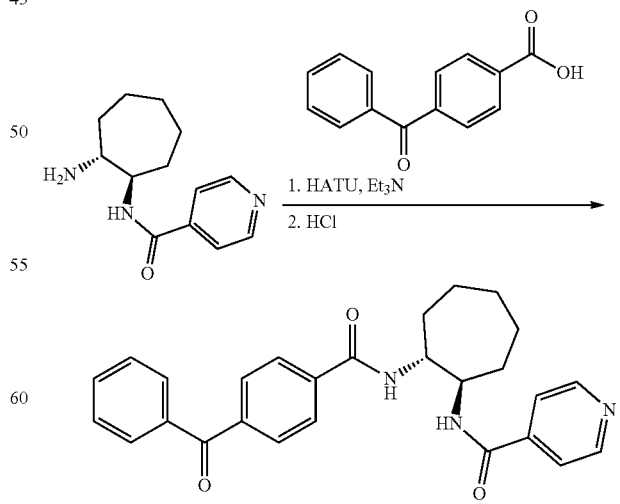

The N-((1R,2R)-2-aminocycloheptyl) isonicotinamide (0.100 mmol) thus formed was dissolved in a mixture of acetonitrile (1.0 mL) and DMF (1.0 mL). Triethylamine (84 μL, 0.6 mmol) was added, followed by 4-(benzoyl)benzoic acid (23 mg, 0.100 mmol) and HATU (38 mg, 0.100 mmol). The resulting solution was stirred at room temperature for 120 min and then quenched with water. The solution was purified directly on HPLC to give N-((1R,2R)-2-(4-benzoylbenzamido)cycloheptyl)isonicotinamide. ¹H NMR (500 MHz, Chloroform-d) δ 8.69 (d, J=6.1 Hz, 2H), 7.80 (q, J=8.4 Hz, 4H), 7.77-7.73 (m, 2H), 7.65-7.56 (m, 3H), 7.48 (t, J=7.8 Hz, 2H), 7.32 (d, J=7.6 Hz, 1H), 6.95 (d, J=8.0 Hz, 1H), 4.24-4.06 (m, 2H), 2.11-1.98 (m, 2H), 1.86-1.66 (m, 4H), 1.62 (m, 4H). LCMS (ESI+) for $C_{27}H_{27}N_3O_3$ [M+H] expected=442.21, found=442.46.

Example 44: N-((1R,2R)-2-(4-(2-fluoro-6-hydroxy-3-methoxybenzoyl)benzamido)cyclohexyl)isonicotinamide

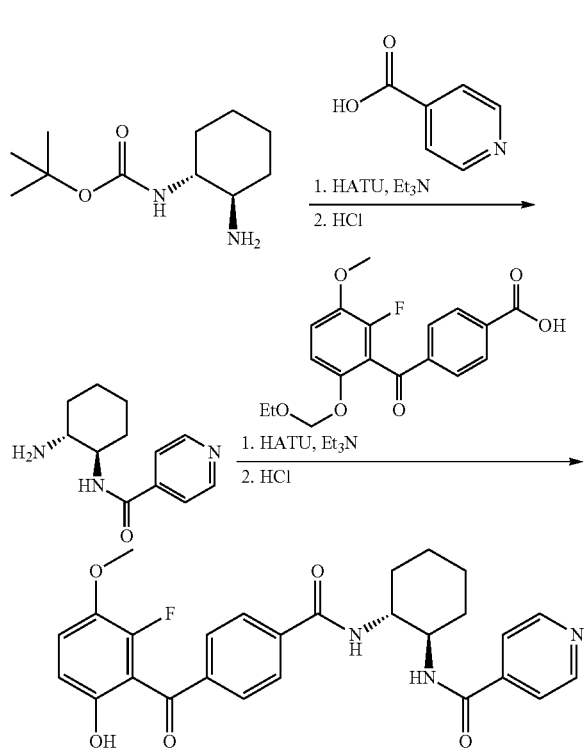

HATU (114 mg, 0.300 mmol) was added to a room temperature solution of tert-butyl ((1R,2R)-2-aminocyclohexyl)carbamate (64 mg, 0.300 mmol), isonicotinic acid (37 mg, 0.300 mmol), and triethyl amine (84 μL, 0.600 mmol) in acetonitrile (1.5 mL). After 5 min, the solution was quenched with water and extracted with EtOAc. The organic extract was thrice washed with water and concentrated in vacuo. The residue was then dissolved in 4 N HCl in dioxane (4 mL) and stirred for 20 min. Concentration gave a white solid (152 mg) which was used without further purification. The N-((1R,2R)-2-aminocyclohexyl)isonicotinamide (0.150 mmol) thus formed was dissolved in DMF (1.5 mL). Triethylamine (84 μL, 0.60 mmol) was added, followed by 4-(6-(ethoxymethoxy)-2-fluoro-3-methoxybenzoyl)benzoic acid (52 mg, 0.150 mmol) and HATU (57 mg, 0.150 mmol). The resulting solution was stirred at room temperature for 30 min and then quenched with water. The solution was twice extracted with EtOAc and then concentrated in vacuo. Dissolution in THF (2 mL) and 1N HCl (2 mL) was followed by warming to 55° C. for 2 h. The solution was then cooled to room temperature and partitioned between aqueous NaHCO₃ and EtOAc. The organic portion was concentrated and purified on reverse phase HPLC to give N-((1R,2R)-2-(4-(2-fluoro-6-hydroxy-3-methoxybenzoyl)benzamido)cyclohexyl)isonicotinamide. ¹H NMR (500 MHz, Chloroform-d) δ 10.25 (s, 1H), 8.71 (d, J=5.2 Hz, 2H), 7.79 (d, J=8.3 Hz, 2H), 7.76-7.71 (m, 2H), 7.67 (s, 2H), 7.21 (t, J=9.1 Hz, 1H), 6.83 (dd, J=9.2, 1.9 Hz, 1H), 6.57 (s, 1H), 4.01 (m, 2H), 3.84 (s, 3H), 2.31 (m, 1H), 2.21 (m, 1H), 1.89 (m, 2H), 1.48 (m, 4H). LCMS (ESI+) for $C_{27}H_{26}FN_3O_5$ [M+H] expected=492.19, found=492.43.

Example 45: N-((1R,2R)-2-(4-(2-fluoro-3,6-dimethoxybenzoyl)benzamido)cyclohexyl)isonicotinamide

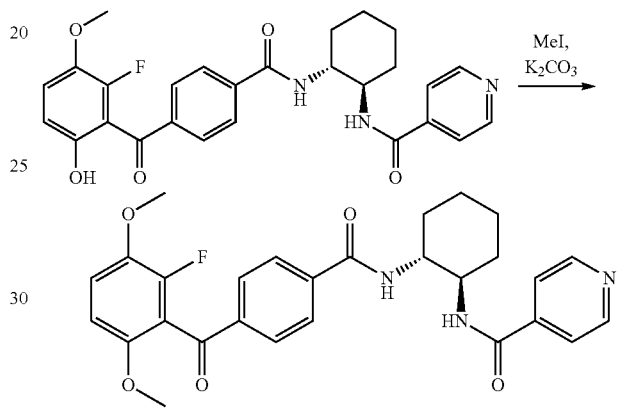

A vial was charged with N-((1R,2R)-2-(4-(2-fluoro-6-hydroxy-3-methoxybenzoyl)benzamido)cyclohexyl) isonicotinamide (4.5 mg) and DMF (0.5 mL) at room temperature. The solution was treated with iodomethane (1 eq added as a DMF solution) and excess potassium carbonate. The solution was stirred for 18 h, quenched with water and purified directly on HPLC to give N-((1R,2R)-2-(4-(2-fluoro-3,6-dimethoxybenzoyl)benzamido)cyclohexyl)isonicotinamide. ¹H NMR (500 MHz, Chloroform-d) δ 8.70 (s, 2H), 7.87 (d, J=8.3 Hz, 2H), 7.76 (d, J=8.4 Hz, 2H), 7.60 (s, 2H), 7.11 (d, J=7.5 Hz, 1H), 7.02 (t, J=9.2 Hz, 1H), 6.68 (dd, J=9.1, 1.6 Hz, 1H), 6.60 (d, J=8.0 Hz, 1H), 4.00 (m, 2H), 3.88 (s, 3H), 3.66 (s, 3H), 2.32-2.15 (m, 2H), 1.87 (m, 2H), 1.44 (m, 4H). LCMS (ESI+) for $C_{28}H_{28}FN_3O_5$ [M+H] expected=506.20, found=506.45.

Example 46: N-((1R,2R)-2-(4-benzoylbenzamido)cyclohexyl)isonicotinamide

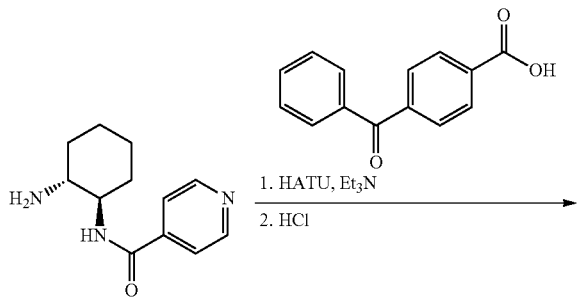

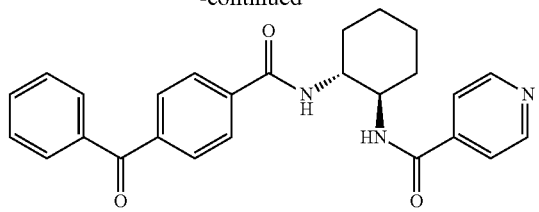

The N-((1R,2R)-2-aminocyclohexyl) isonicotinamide (0.150 mmol) was dissolved in DMF (1.5 mL). Triethylamine (844, 0.60 mmol) was added, followed by 4-(benzoyl)benzoic acid (34 mg, 0.150 mmol) and HATU (57 mg, 0.150 mmol). The resulting solution was stirred at room temperature for 15 min and then quenched with water. Extraction with EtOAc (twice) followed by concentration gave a residue which was purified on silica gel (12 g hexane/EtOAc gradient 15%-100%) to yield N-((1R,2R)-2-(4-benzoylbenzamido)cyclohexyl)isonicotinamide. $^1$H NMR (500 MHz, Chloroform-d) δ 8.72 (d, J=6.1 Hz, 2H), 7.81 (s, 4H), 7.79-7.73 (m, 2H), 7.67 (d, J=5.2 Hz, 2H), 7.61 (t, J=7.5 Hz, 1H), 7.48 (t, J=7.7 Hz, 2H), 7.19 (d, J=7.4 Hz, 1H), 6.60 (d, J=8.0 Hz, 1H), 4.11-3.92 (m, 2H), 2.38-2.18 (m, 2H), 1.89 (m, 2H), 1.47 (m, 4H). LCMS (ESI+) for $C_{26}H_{25}N_3O_3$ [M+H] expected=428.19, found=428.43.

Example 47: N-((1R,2R)-2-(4-(2-fluoro-6-hydroxy-3-methoxybenzoyl)benzamido)cyclopentyl)isonicotinamide was quenched with water and extracted with EtOAc. The organic extract was thrice washed with water and concentrated in vacuo. The residue was then dissolved in 4 N HCl in dioxane (2 mL) and stirred for 18 h. Concentration in vacuo gave a solid which was used without further purification. The N-((1R,2R)-2-aminocyclopentyl)isonicotinamide (0.200 mmol) thus formed was dissolved in DMF (1.5 mL). Triethylamine (111 µL, 0.80 mmol) was added, followed by 4-(6-(ethoxymethoxy)-2-fluoro-3-methoxybenzoyl)benzoic acid (70 mg, 0.200 mmol) and HATU (76 mg, 0.200 mmol). The resulting solution was stirred at room temperature for 3 h and then quenched with water. The solution was twice extracted with EtOAc and then concentrated in vacuo. Dissolution in THF (1 mL) and 1N HCl (2 mL) was followed by warming to 60° C. for 2 h. The solution was then cooled to room temperature and partitioned between aqueous $NaHCO_3$ and EtOAc. The organic portion was concentrated and purified on silica gel (12 g, hexane/EtOAc gradient 25%-100%) to give N-((1R,2R)-2-(4-(2-fluoro-6-hydroxy-3-methoxybenzoyl)benzamido)cyclopentyl)isonicotinamide. $^1$H NMR (500 MHz, Chloroform-d) δ 10.26 (s, 1H), 8.74 (d, J=6.2 Hz, 2H), 7.87 (d, J=8.5 Hz, 2H), 7.76 (dd, J=8.4, 2.4 Hz, 2H), 7.73-7.68 (m, 2H), 7.62 (d, J=5.6 Hz, 1H), 7.21 (t, J=9.2 Hz, 1H), 6.93 (d, J=6.5 Hz, 1H), 6.83 (dd, J=9.2, 1.9 Hz, 1H), 4.41-4.29 (m, 1H), 4.18 (m, 1H), 3.83 (s, 3H), 2.42 (ddq, J=58.7, 13.5, 6.8 Hz, 2H), 1.92 (m, 2H), 1.72-1.59 (m, 2H). LCMS (ESI+) for $C_{26}H_{24}FN_3O_5$ [M+H] expected=478.17, found=478.44.

Example 48: N-((1R,2R)-2-(4-(2-fluoro-3,6-dimethoxybenzoyl)benzamido)cyclopentyl)isonicotinamide

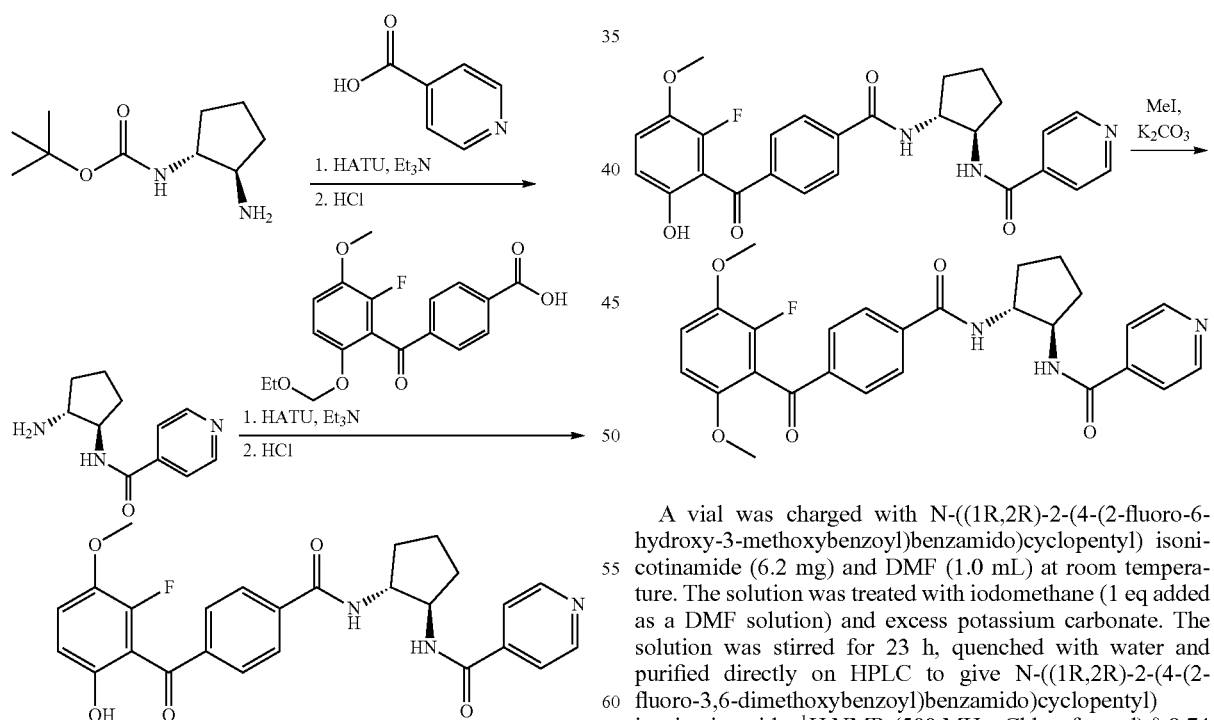

HATU (114 mg, 0.300 mmol) was added to a room temperature solution of tert-butyl ((1R,2R)-2-aminocyclopentyl)carbamate (60 mg, 0.300 mmol), isonicotinic acid (37 mg, 0.300 mmol), and triethyl amine (84 µL, 0.600 mmol) in acetonitrile (1.5 mL). After 30 min, the solution A vial was charged with N-((1R,2R)-2-(4-(2-fluoro-6-hydroxy-3-methoxybenzoyl)benzamido)cyclopentyl) isonicotinamide (6.2 mg) and DMF (1.0 mL) at room temperature. The solution was treated with iodomethane (1 eq added as a DMF solution) and excess potassium carbonate. The solution was stirred for 23 h, quenched with water and purified directly on HPLC to give N-((1R,2R)-2-(4-(2-fluoro-3,6-dimethoxybenzoyl)benzamido)cyclopentyl) isonicotinamide. $^1$H NMR (500 MHz, Chloroform-d) δ 8.74 (d, J=6.1 Hz, 2H), 7.91 (d, J=8.4 Hz, 2H), 7.85 (d, J=8.4 Hz, 2H), 7.65 (d, J=6.1 Hz, 2H), 7.51 (d, J=5.7 Hz, 1H), 7.03 (t, J=9.2 Hz, 1H), 6.93 (d, J=6.4 Hz, 1H), 6.68 (dd, J=9.0, 1.7 Hz, 1H), 4.32 (ddd, J=17.5, 10.4, 7.3 Hz, 1H), 4.23-4.12 (m, 1H), 3.88 (s, 3H), 3.67 (s, 3H), 2.46 (dq, J=13.3, 6.8 Hz, 1H), 2.35 (dq, J=13.4, 6.8 Hz, 1H), 1.97-1.86 (m, 2H), 1.74-1.55 (m, 4H). LCMS (ESI+) for $C_{27}H_{26}FN_3O_5$ [M+H] expected=492.19, found=492.45.

Example 49: N-((1R,2R)-2-(4-benzoylbenzamido)cyclopentyl)isonicotinamide

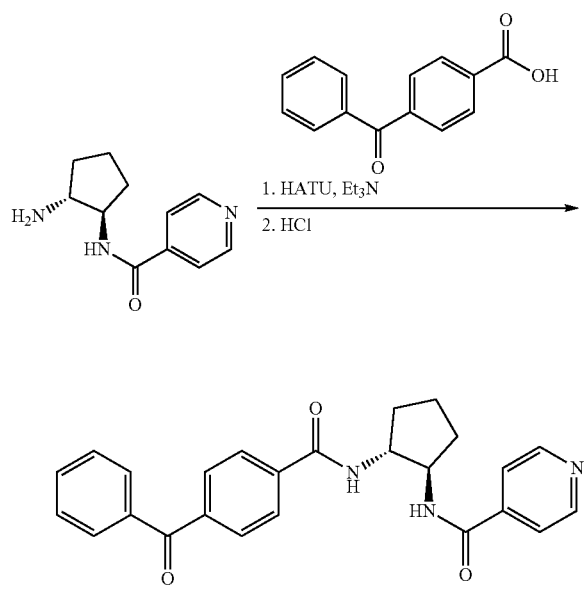

The N-((1R,2R)-2-aminocyclopentyl) isonicotinamide (0.100 mmol) was dissolved in DMF (1.5 mL). Triethylamine (844, 0.60 mmol) was added, followed by 4-(benzoyl)benzoic acid (23 mg, 0.100 mmol) and HATU (38 mg, 0.100 mmol). The resulting solution was stirred at room temperature for 70 min and then quenched with water. Extraction with EtOAc (twice) followed by concentration gave a residue which was purified on silica gel (12 g hexane/EtOAc gradient 25%-80%) to yield N-((1R,2R)-2-(4-benzoylbenzamido)cyclopentyl) isonicotinamide. ¹H NMR (500 MHz, Chloroform-d) δ 8.75 (d, J=5.1 Hz, 2H), 7.89 (d, J=8.4 Hz, 2H), 7.84 (d, J=8.4 Hz, 2H), 7.81-7.75 (m, 2H), 7.75-7.67 (m, 2H), 7.65-7.57 (m, 2H), 7.49 (t, J=7.7 Hz, 2H), 6.96 (d, J=6.5 Hz, 1H), 4.36 (m, 1H), 4.25-4.12 (m, 1H), 2.47 (dq, J=13.3, 6.8 Hz, 1H), 2.37 (dq, J=13.4, 6.8 Hz, 1H), 1.91 (m, 2H), 1.67 (m, 2H). LCMS (ESI+) for $C_{25}H_{23}N_3O_3$ [M+H] expected=414.18, found=414.40.

Example 50: N-((1R,2R)-1-(4-(2-fluoro-6-hydroxy-3-methoxybenzoyl)benzamido)-2,3-dihydro-1H-inden-2-yl)isonicotinamide

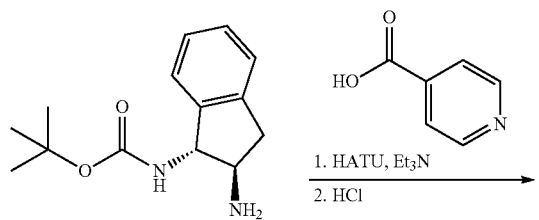

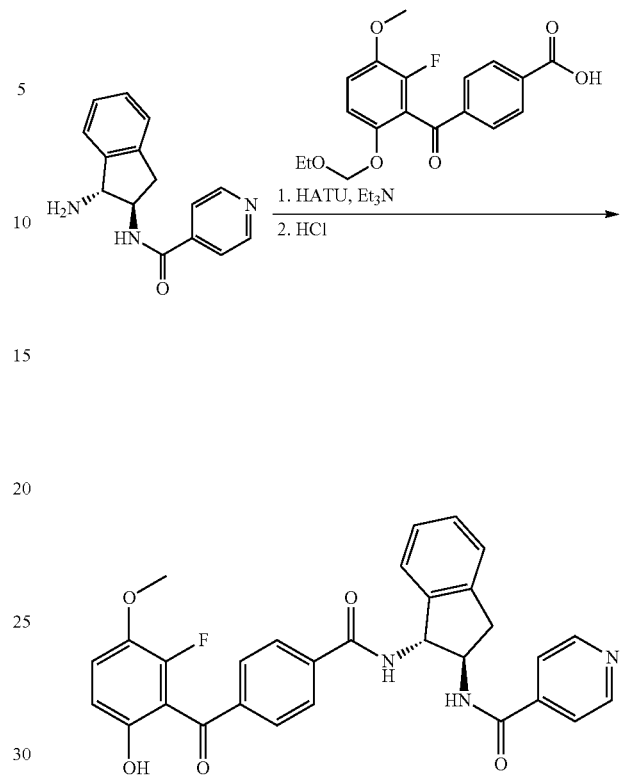

HATU (114 mg, 0.300 mmol) was added to a room temperature solution of tert-butyl ((1R,2R)-2-amino-2,3-dihydro-1H-inden-1-yl)carbamate (75 mg, 0.300 mmol), isonicotinic acid (37 mg, 0.300 mmol), and triethyl amine (84 μL, 0.600 mmol) in acetonitrile (1.5 mL). After 30 min, the solution was quenched with water and extracted with EtOAc. The organic extract was thrice washed with water and concentrated in vacuo. The residue was then dissolved in 4 N HCl in dioxane (2 mL) and stirred for 18 h. Concentration in vacuo gave a solid which was used without further purification. The N-((1R,2R)-1-amino-2,3-dihydro-1H-inden-2-yl)isonicotinamide (0.200 mmol) thus formed was dissolved in MeCN (2.0 mL) and DMF (1.5 mL). Triethylamine (111 μL, 0.80 mmol) was added, followed by 4-(6-(ethoxymethoxy)-2-fluoro-3-methoxybenzoyl)benzoic acid (70 mg, 0.200 mmol) and HATU (76 mg, 0.200 mmol). The resulting solution was stirred at room temperature for 3 h and then quenched with water. The solution was twice extracted with EtOAc and then concentrated in vacuo. Dissolution in THF (1 mL) and 1N HCl (2 mL) was followed by warming to 60° C. for 2 h. The solution was then cooled to room temperature and partitioned between aqueous $NaHCO_3$ and EtOAc. The organic portion was concentrated and purified on silica gel (5 g, hexane/EtOAc gradient 20%-100%) to give N-((1R,2R)-1-(4-(2-fluoro-6-hydroxy-3-methoxybenzoyl)benzamido)-2,3-dihydro-1H-inden-2-yl)isonicotinamide. ¹H NMR (500 MHz, Chloroform-d) δ 10.30 (s, 1H), 8.85-8.74 (m, 2H), 8.13 (s, 1H), 7.94 (d, J=8.3 Hz, 2H), 7.88-7.75 (m, 4H), 7.34 (m, 4H), 7.22 (t, J=9.1 Hz, 1H), 6.90-6.82 (m, 2H), 5.76 (t, J=8.5 Hz, 1H), 4.48 (q, J=9.5, 6.7 Hz, 1H), 3.84 (s, 3H), 3.79 (dd, J=15.3, 7.7 Hz, 1H), 2.99-2.86 (m, 1H). LCMS (ESI+) for $C_{30}H_{24}FN_3O_5$ [M+H] expected=526.17, found=526.45.

Example 51: N-((1R,2R)-1-(4-(2-fluoro-3,6-dimethoxybenzoyl)benzamido)-2,3-dihydro-1H-inden-2-yl)isonicotinamide

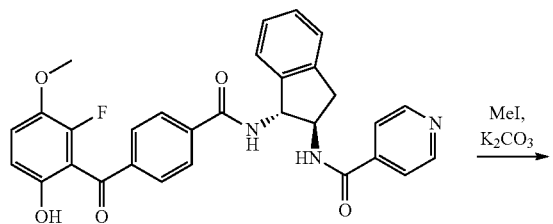

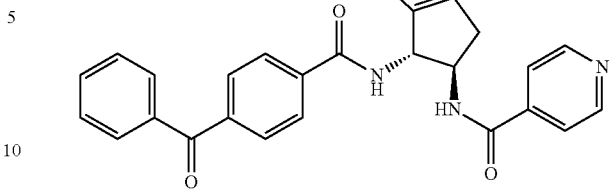

A vial was charged with N-((1R,2R)-1-(4-(2-fluoro-6-hydroxy-3-methoxybenzoyl)benzamido)-2,3-dihydro-1H-inden-2-yl)isonicotinamide (5.0 mg) and DMF (1.0 mL) at room temperature. The solution was treated with iodomethane (1 eq added as a DMF solution) and excess potassium carbonate. The solution was stirred for 2 h, quenched with water and purified directly on HPLC to give N-((1R,2R)-2-(4-(2-fluoro-3,6-dimethoxybenzoyl)benzamido)cyclopentyl)isonicotinamide. $^1$H NMR (500 MHz, Chloroform-d) δ 8.78 (d, J=5.6 Hz, 2H), 8.09 (s, 1H), 7.95 (d, J=8.3 Hz, 2H), 7.92 (d, J=8.4 Hz, 2H), 7.80 (d, J=5.1 Hz, 2H), 7.39-7.29 (m, 4H), 7.04 (t, J=9.2 Hz, 1H), 6.85 (d, J=7.7 Hz, 1H), 6.69 (dd, J=9.1, 1.6 Hz, 1H), 5.74 (t, J=8.5 Hz, 1H), 4.53-4.43 (m, 1H), 3.89 (s, 3H), 3.78 (dd, J=15.5, 7.6 Hz, 1H), 3.68 (s, 3H), 2.91 (dd, J=15.5, 9.9 Hz, 1H). LCMS (ESI+) for $O_{31}H_{26}FN_3O_5$ [M+H] expected=540.19, found=540.48.

Example 52: N-((1R,2R)-1-(4-benzoylbenzamido)-2,3-dihydro-1H-inden-2-yl)isonicotinamide

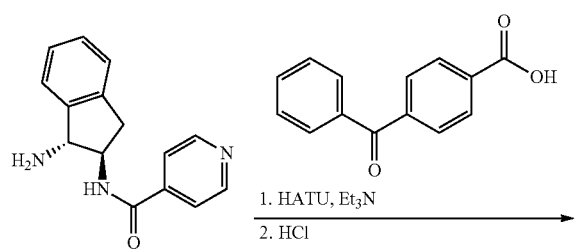

The N-((1R,2R)-1-amino-2,3-dihydro-1H-inden-2-yl)isonicotinamide (0.100 mmol) was dissolved in DMF (1.5 mL). Triethylamine (844, 0.60 mmol) was added, followed by 4-(benzoyl)benzoic acid (23 mg, 0.100 mmol) and HATU (38 mg, 0.100 mmol). The resulting solution was stirred at room temperature for 60 min and then quenched with water. Extraction with EtOAc (twice) followed by concentration gave a residue which was purified on silica gel (5 g hexane/EtOAc gradient 25%-100%) to yield N-((1R,2R)-1-(4-benzoylbenzamido)-2,3-dihydro-1H-inden-2-yl)isonicotinamide. $^1$H NMR (500 MHz, Chloroform-d) δ 8.71 (d, J=6.1 Hz, 2H), 8.12 (d, J=5.3 Hz, 1H), 7.96 (d, J=8.3 Hz, 2H), 7.81 (d, J=8.3 Hz, 2H), 7.79-7.75 (m, 2H), 7.71-7.67 (m, 2H), 7.65-7.59 (m, 1H), 7.49 (t, J=7.8 Hz, 2H), 7.36 (d, J=7.9 Hz, 1H), 7.31 (t, J=6.6 Hz, 1H), 7.29-7.27 (m, 1H), 7.24 (d, J=7.2 Hz, 1H), 5.75 (t, J=8.6 Hz, 1H), 4.48 (tdd, J=9.6, 7.6, 5.3 Hz, 1H), 3.62 (dd, J=15.4, 7.6 Hz, 1H), 2.88 (dd, J=15.4, 9.9 Hz, 1H). LCMS (ESI+) for $C_{29}H_{23}N_3O_3$ [M+H] expected=462.18, found=462.43.

Example 53: (4-(4-(2-fluoro-6-hydroxy-3-methoxybenzoyl)benzoyl)piperazin-1-yl)(pyridin-4-yl)methanone

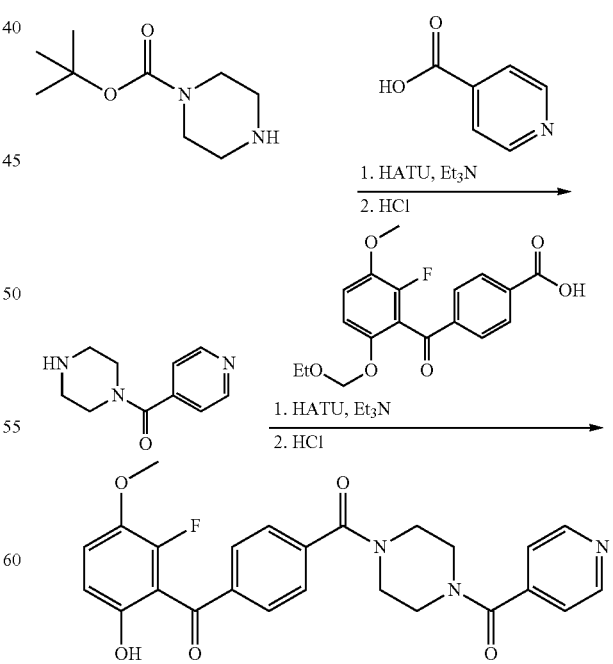

HATU (114 mg, 0.300 mmol) was added to a room temperature solution of tert-butyl piperazine-1-carboxylate (56 mg, 0.300 mmol), isonicotinic acid (37 mg, 0.300 mmol), and triethyl amine (84 μL, 0.600 mmol) in acetonitrile (1.5 mL). After 30 min, the solution was quenched with water and extracted with EtOAc. The organic extract was thrice washed with water and concentrated in vacuo. The residue was then dissolved in 4 N HCl in dioxane (1 mL) and stirred for 30 min. Concentration in vacuo gave a solid which was used without further purification. The piperazin-1-yl(pyridin-4-yl)methanone (0.200 mmol) thus formed was dissolved in MeCN (2.0 mL) and DMF (1.0 mL). Triethylamine (111 μL, 0.80 mmol) was added, followed by 4-(6-(ethoxymethoxy)-2-fluoro-3-methoxybenzoyl)benzoic acid (70 mg, 0.200 mmol) and HATU (76 mg, 0.200 mmol). The resulting solution was stirred at room temperature for 18 h and then quenched with water. The solution was twice extracted with EtOAc and then concentrated in vacuo. Dissolution in THF (1 mL) and 1N HCl (2 mL) was followed by warming to 60° C. for 0.5 h. The solution was then cooled to room temperature and partitioned between aqueous NaHCO$_3$ and EtOAc. The organic portion was concentrated and purified on silica gel (5 g, EtOAc/MeOH gradient 0%-20%) to give (4-(4-(2-fluoro-6-hydroxy-3-methoxybenzoyl)benzoyl)piperazin-1-yl)(pyridin-4-yl)methanone. $^1$H NMR (500 MHz, Chloroform-d) δ 10.23 (s, 1H), 8.73 (s, 2H), 7.77 (s, 2H), 7.50 (d, J=7.8 Hz, 2H), 7.30 (d, J=5.0 Hz, 2H), 7.22 (t, J=9.2 Hz, 1H), 6.84 (dd, J=9.2, 1.8 Hz, 1H), 3.85 (s, 3H), 3.84 (br, 4H), 3.48 (br, 4H). LCMS (ESI+) for C$_{25}$H$_{22}$FN$_3$O$_5$ [M+H] expected=464.16, found=464.39.

Example 54: (4-(4-(2-fluoro-3,6-dimethoxybenzoyl)benzoyl)piperazin-1-yl)(pyridin-4-yl)methanone

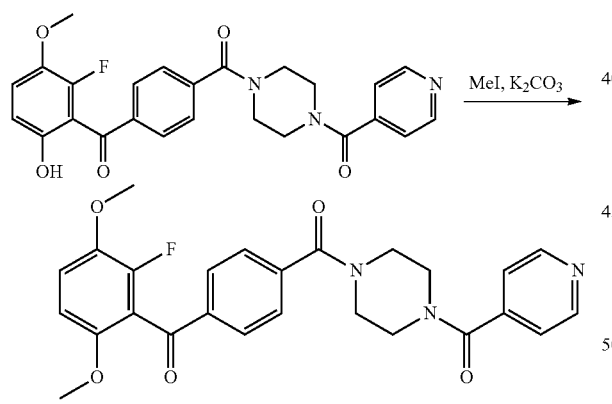

A vial was charged with (4-(4-(2-fluoro-6-hydroxy-3-methoxybenzoyl)benzoyl)piperazin-1-yl)(pyridin-4-yl)methanone (5.0 mg) and DMF (1.0 mL) at room temperature. The solution was treated with iodomethane (1 eq added as a DMF solution) and excess potassium carbonate. The solution was stirred for 2 h, quenched with water and purified directly on HPLC to give (4-(4-(2-fluoro-3,6-dimethoxybenzoyl)benzoyl)piperazin-1-yl)(pyridin-4-yl)methanone. $^1$H NMR (500 MHz, Chloroform-d) δ 8.73 (s, 2H), 7.91 (s, 2H), 7.48 (d, J=7.6 Hz, 2H), 7.30 (s, 2H), 7.03 (t, J=9.2 Hz, 1H), 6.69 (d, J=8.8 Hz, 1H), 3.88 (s, 3H), 3.75 (br, 4H), 3.70 (s, 3H), 3.49 (br, 4H). LCMS (ESI+) for C$_{26}$H$_{24}$FN$_3$O$_5$ [M+H] expected=478.17, found=478.41.

Example 55: (4-(4-benzoylbenzoyl)piperazin-1-yl)(pyridin-4-yl)methanone

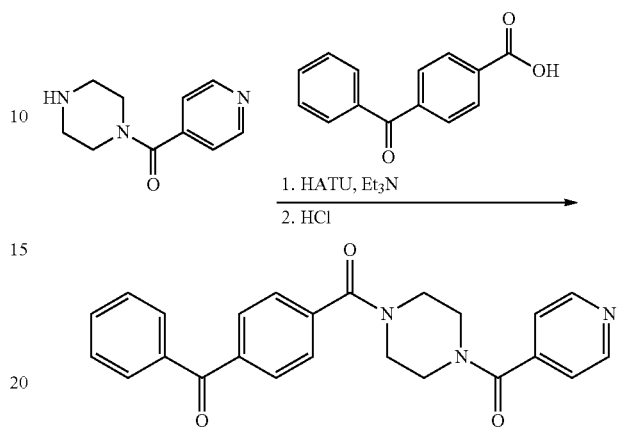

The piperazin-1-yl(pyridin-4-yl) methanone (0.100 mmol) was dissolved in DMF (1.5 mL). Triethylamine (84 μL, 0.60 mmol) was added, followed by 4-(benzoyl)benzoic acid (23 mg, 0.100 mmol) and HATU (38 mg, 0.100 mmol). The resulting solution was stirred at room temperature for 85 min and then quenched with water. Extraction with EtOAc (twice) followed by concentration gave a residue which was purified on reverse phase to yield (4-(4-benzoylbenzoyl)piperazin-1-yl)(pyridin-4-yl)methanone. $^1$H NMR (500 MHz, Chloroform-d) δ 8.74 (s, 2H), 7.85 (s, 2H), 7.80 (d, J=7.6 Hz, 2H), 7.62 (t, J=7.4 Hz, 1H), 7.51 (m, 4H), 7.34 (d, J=4.8 Hz, 2H), 3.79 (br, 4H), 3.49 (br, 4H). LCMS (ESI+) for C$_{24}$H$_{21}$N$_3$O$_3$ [M+H] expected=400.16, found=400.38.

Example 56: N-((3R,4R)-4-(4-benzoylbenzamido)pyrrolidin-3-yl)isonicotinamide

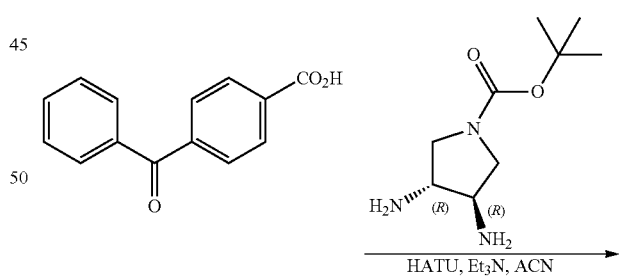

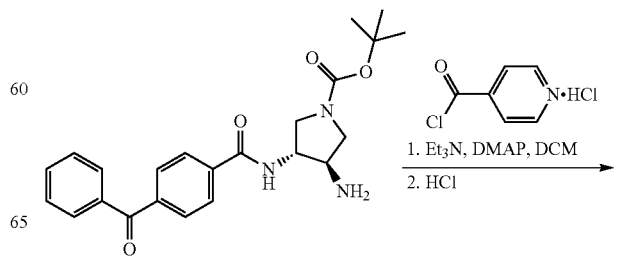

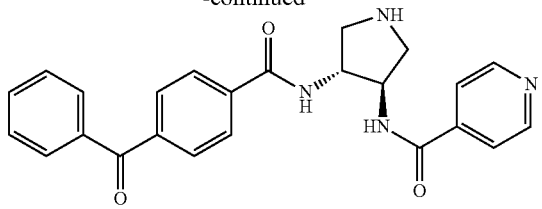

4-benzoylbenzoic acid and HATU were weighed in a 20 mL vial and 2 ml dry MeCN was added followed by triethylamine and the mixture was stirred at 23° C. for 10 min. A solution of tert-butyl (3R,4R)-3,4-diaminopyrrolidine-1-carboxylate in 2 ml dry MeCN was added and the mixture allowed to stir at 23° C. for 1 h. LCMS analysis of an aliquot showed complete conversion of starting acid and mono and bis-acylation products. The reaction mixture was diluted with ethyl acetate and extracted with sat. sodium bicarbonate solution and brine. The organic layer was concentrated and the residue was purified by prep. TLC and elution with methanol/ethyl acetate (0-20%) to obtain amine, tert-butyl (3R,4R)-3-amino-4-(4-benzoylbenzamido)pyrrolidine-1-carboxylate (25 mg, 28%). $^1$H NMR (400 MHz, Methanol-$d_4$) δ 8.68 (d, J=6.1 Hz, 2H), 8.27 (s, 1H), 7.94 (d, J=8.4 Hz, 2H), 7.82 (d, J=8.4 Hz, 2H), 7.79-7.75 (m, 4H), 7.69-7.62 (m, 1H), 7.53 (t, J=7.7 Hz, 2H), 4.80-4.68 (m, 2H), 3.98-3.86 (m, 2H), 3.42-3.33 (m, 2H). To tert-butyl (3R,4R)-3-amino-4-(4-benzoylbenzamido)pyrrolidine-1-carboxylate (25 mg, 61.06 μmol) in 2 ml dry dichloromethane, triethylamine, DMAP, and isonicotinoyl chloride hydrochloride (16.3 mg, 91.6 μmol) were added and the mixture was stirred at 23° C. for 2 h. The reaction mixture was diluted with 2 ml dichloromethane and washed thrice with sat. sodium bicarbonate. The organic layers were combined and evaporated and the residue was purified by RP-HPLC to obtain product tert-butyl (3R,4R)-3-(4-benzoylbenzamido)-4-(isonicotinamido)pyrrolidine-1-carboxylate as a colorless oil (7 mg, 22%). To tert-butyl (3R,4R)-3-(4-benzoylbenzamido)-4-(isonicotinamido)pyrrolidine-1-carboxylate, was added 1 ml 0.5 M HCl and the mixture was heated at 70° C. for 1 h. The solvent was evaporated and 0.5 mL methanol added and evaporated (2×) and the hydrochloride salt of the product N-((3R,4R)-4-(4-benzoylbenzamido)pyrrolidin-3-yl)isonicotinamide was obtained as a white solid (6 mg, 98%) after drying under vacuum; $^1$H NMR (500 MHz, Methanol-$d_4$) δ 8.92 (d, J=6.6 Hz, 2H), 8.62 (d, J=6.7 Hz, 2H), 8.06 (d, J=8.3 Hz, 2H), 7.81 (d, J=8.4 Hz, 2H), 7.74 (d, J=6.9 Hz, 2H), 7.62-7.58 (m, 2H), 7.47 (t, J=7.8 Hz, 2H), 4.91-4.81 (m, 2H), 3.94 (ddd, J=12.6, 7.2, 1.8 Hz, 2H), 3.65 (dt, J=12.4, 4.3 Hz, 2H); LCMS (ESI+) calculated for $C_{24}H_{22}N_4O_3$ [M+H]=415.17, found=415.44.

Example 57: N-(2-(4-(2-fluoro-6-hydroxy-3-methoxybenzoyl)benzamido)phenyl)isonicotinamide

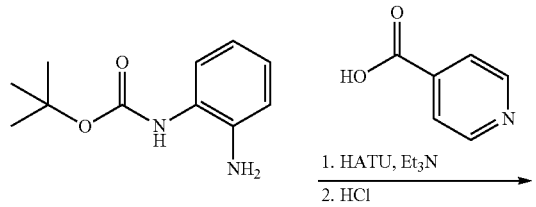

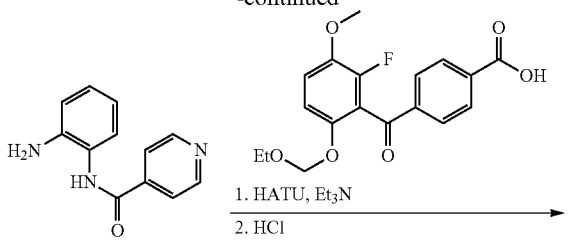

Isonicotinic acid (48 mg, 0.39 mmol) was charged with 2 mL acetonitrile, 0.11 mL (0.78 mmol) triethylamine, 177 mg (0.47 mmol) HATU, and then 81 mg (0.39 mmol) 2-BOC-aminoaniline (CAS #146551-75-4). After 1.5 h, LCMS suggested good conversion and the mixture was concentrated. The residue was treated with 1 mL dichloromethane and 1 mL trifluoroacetic acid. After 15 minutes, LCMS suggested good conversion and the mixture was concentrated to an orange liquid. This sample was divided into two halves, one of which was used in the synthesis of N-(2-(4-benzoylbenzamido)phenyl)isonicotinamide described below. The remaining portion (ca. 0.2 mmol) was combined with 1 mL acetonitrile, 0.27 mL (2 mmol) triethylamine, 91 mg (0.24 mmol) HATU, and 70 mg (0.2 mmol) 4-(6-(ethoxymethoxy)-2-fluoro-3-methoxybenzoyl)benzoic acid. After stirring 18 h, the mixture was diluted with 5 mL water and extracted with three 2 mL portions of ethyl acetate. The organics were passed through a plug of magnesium sulfate and concentrated to a brown oil (332 mg) which was partially purified by flash chromatography (25 mL silica gel, 50% ethyl acetate/hexane, ethyl acetate, 5% methanol/ethyl acetate) to return 128 mg of a yellow film. This sample was dissolved in 2 mL tetrahydrofuran and treated with 1 mL 1N HCl. After stirring 17 h, LCMS suggested 50% conversion so the temperature was increased to 60° C. After 6.5 h, the mixture was diluted with 8 mL water and the pH adjusted to ~8 with 3.75 N NaOH. The resulting white solid in yellow solution was concentrated and extracted with three 2 mL portions of 20% methanol/chloroform. The organics were filtered and the yellow filtrate concentrated to a yellow solid, 127 mg. This sample was purified by reverse phase preparative HPLC to give the desired compound, 20.8 mg. $^1$H NMR (500 MHz, Methanol-$d_4$) δ 8.79-8.65 (m, 2H), 8.04 (d, J=8.1 Hz, 2H), 7.92 (d, J=8.3 Hz, 2H), 7.89-7.79 (m, 2H), 7.67 (ddd, J=22.5, 6.2, 3.7 Hz, 2H), 7.38 (dd, J=6.1, 3.5 Hz, 2H), 7.13 (t, J=9.3 Hz, 1H), 6.68 (dd, J=9.0, 1.7 Hz, 1H), 3.84 (s, 3H). LCMS (ESI+) for $C_{27}H_{20}FN_3O_5$ [M+H] expected=486.14, found=486.39.

Example 58: N-(2-(4-(2-fluoro-3,6-dimethoxybenzoyl)benzamido)phenyl)isonicotinamide

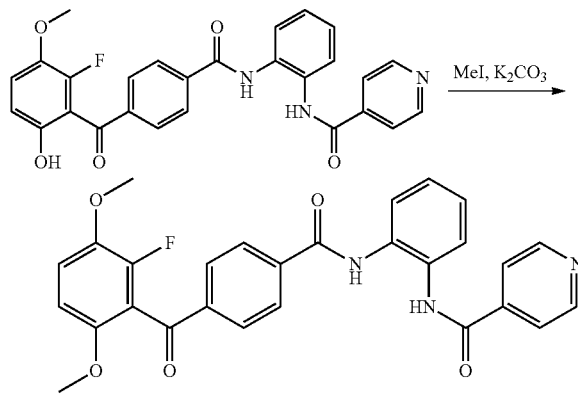

A stock solution was prepared from 0.20 mL iodomethane and 20 mL of N,N-dimethylformamide. A portion of N-(2-(4-(2-fluoro-6-hydroxy-3-methoxybenzoyl)benzamido)phenyl)isonicotinamide (11.9 mg, 0.025 mmol, synthesis described above) was charged with potassium carbonate (10.4 mg, 0.075 mmol), 0.8 mL DMF, and 0.2 mL of the stock solution to deliver 2 μL of iodomethane (0.032 mmol). After 3 days, the mixture was diluted with 8 mL water and extracted with 2, 1, and 1 mL portions of 20% methanol/chloroform. The organics were filtered through a plug of magnesium sulfate and concentrated to 70 mg of orange oil. This sample was purified by reverse phase preparative HPLC to give the desired compound as the formate salt, a white film, 2.3 mg. $^1$H NMR (500 MHz, Methanol-$d_4$) δ 8.77-8.65 (m, 2H), 8.49 (s, 1H), 8.10-7.98 (m, 2H), 7.96-7.79 (m, 4H), 7.68 (dd, J=6.1, 3.5 Hz, 1H), 7.64 (dt, J=7.4, 3.7 Hz, 1H), 7.38 (dd, J=6.0, 3.6 Hz, 2H), 7.22 (t, J=9.4 Hz, 1H), 6.88 (dd, J=9.1, 1.6 Hz, 1H), 3.88 (s, 3H), 3.67 (s, 3H). LCMS (ESI+) for $C_{28}H_{22}FN_3O_5$ [M+H] expected=500.15, found=500.43.

Example 59: N-(2-(4-benzoylbenzamido)phenyl)isonicotinamide

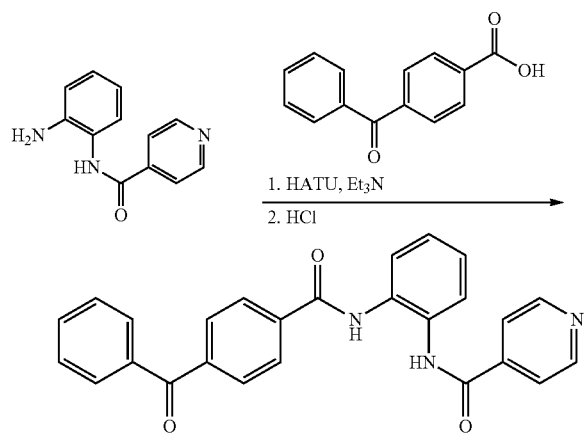

The remaining portion (ca. 0.2 mmol) of the intermediate derived from isonicotinic acid in the synthesis of N-(2-(4-(2-fluoro-6-hydroxy-3-methoxybenzoyl)benzamido)phenyl)isonicotinamide was combined with 1 mL acetonitrile, 0.27 mL (2 mmol) trimethylamine, 91 mg (0.24 mmol) HATU, and 45 mg (0.2 mmol) of 4-(benzoyl)benzoic acid. LCMS suggested completion after 1 h; thus, after 1.3 h the mixture was charged with 4 mL water. After stirring overnight, a yellow solid (81 mg) was collected and purified by reverse phase preparative HPLC to give 13.4 mg of the desired compound. $^1$H NMR (500 MHz, Methanol-$d_4$) δ 8.16 (d, J=8.1 Hz, 4H), 7.81 (dd, J=19.6, 7.9 Hz, 8H), 7.70 (t, J=7.4 Hz, 2H), 7.57 (t, J=7.7 Hz, 4H). LCMS (ESI+) for $C_{26}H_{19}N_3O_3$ [M+H] expected=422.14, found=422.38.

Example 60: N-(4-(4-(2-fluoro-6-hydroxy-3-methoxybenzoyl)benzamido)pyridin-3-yl)isonicotinamide

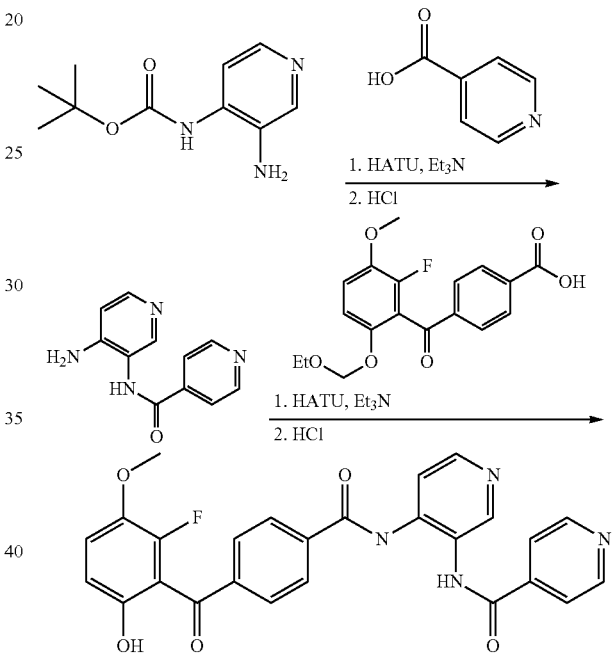

Isonicotinic acid (49 mg, 0.40 mmol) was charged with 2 mL acetonitrile, 0.11 mL (0.80 mmol) triethylamine, 183 mg (0.48 mmol) HATU, and then 84.1 mg (0.40 mmol) 3-amino-4-BOC-aminopyridine (CAS #183311-28-6). After 30 minutes, LCMS suggested ca. 75% conversion and the mixture was concentrated after 1 h. The residue was treated with 1 mL dichloromethane and 1 mL trifluoroacetic acid. After 17 h, LCMS suggested good conversion and the mixture was concentrated to an orange suspension, 1 gram. This sample was divided into two halves, one of which was used in the synthesis of N-(2-(4-N-(4-(4-benzoylbenzamido)pyridin-3-yl)isonicotinamide described below. The remaining portion (ca. 0.2 mmol) was combined with 1 mL acetonitrile, 0.28 mL (2 mmol) triethylamine, 91 mg (0.24 mmol) HATU, and 70 mg (0.2 mmol) 4-(6-(ethoxymethoxy)-2-fluoro-3-methoxybenzoyl)benzoic acid. LCMS after 4 and 24 h suggested the reaction stalled at around 50% conversion, so another 0.28 mL of trimethylamine and 91 mg of HATU were added. After 4 additional hours, LCMS indicated good conversion, and the mixture was diluted with 10 mL water and extracted with three 2 mL portions of ethyl acetate. The organics were passed through a plug of magnesium sulfate and concentrated to an orange oil (294 mg) which was partially purified by flash chromatography (25 mL silica gel, 2% to 5% methanol/chloroform) to return 73 mg of a yellow oil. This sample was dissolved in 1 mL tetrahydrofuran and treated with 1 mL 1N HCl. After stirring at 60° C. for 1.25 h, the mixture was diluted with 8 mL water and the pH adjusted to ~7 with ca. 0.3 mL 3.75 N NaOH. The resulting yellow solid was collected, 122 mg, and purified by reverse phase preparative HPLC to give the desired compound, 49.2 mg yellow film, as the diformate salt. $^1$H NMR (400 MHz, Methanol-d$_4$) δ 8.82-8.65 (m, 3H), 8.46 (d, J=5.6 Hz, 1H), 8.21 (s, 2H), 8.14-7.99 (m, 3H), 7.99-7.84 (m, 4H), 7.13 (t, J=9.3 Hz, 1H), 6.68 (dd, J=8.9, 1.7 Hz, 1H), 3.84 (s, 3H). LCMS (ESI+) for C$_{26}$H$_{19}$FN$_4$O$_5$ [M+H] expected=487.13, found=487.36.

Example 61: N-(4-(4-(2-fluoro-3,6-dimethoxybenzoyl)benzamido)pyridin-3-yl)isonicotinamide

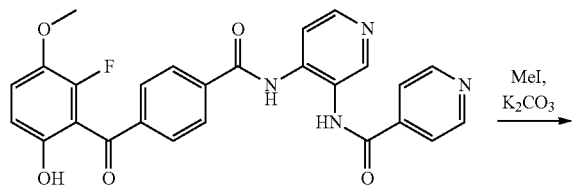

A stock solution was prepared from 0.20 mL iodomethane and 20 mL of N,N-dimethylformamide. A portion of N-(4-(4-(2-fluoro-6-hydroxy-3-methoxybenzoyl)benzamido)pyridin-3-yl)isonicotinamide (21.1 mg, 0.0434 mmol, synthesis described above) was charged with potassium carbonate (18 mg, 0.13 mmol), 0.8 mL DMF, and 0.27 mL of the stock solution to deliver 2.7 µL of iodomethane (0.043 mmol). After 3 days, the mixture was diluted with 8 mL water and extracted with 2, 1, and 1 mL portions of 20% methanol/chloroform. The organics were filtered through a plug of magnesium sulfate and concentrated to 110 mg of yellow oil. This sample was purified by reverse phase preparative HPLC to give the desired compound as the diformate salt, a yellow solid, 10.2 mg. $^1$H NMR (500 MHz, Methanol-d$_4$) δ 9.24 (d, J=1.8 Hz, 1H), 8.81-8.63 (m, 3H), 8.40 (dd, J=7.0, 1.8 Hz, 1H), 8.24 (s, 2H), 8.12 (d, J=8.5 Hz, 2H), 8.02-7.83 (m, 4H), 7.13 (t, J=9.3 Hz, 1H), 6.69 (dd, J=9.0, 1.6 Hz, 1H), 4.24 (s, 3H), 3.84 (s, 3H). LCMS (ESI+) for C$_{27}$H$_{21}$FN$_4$O$_5$ [M+H] expected=501.15, found=501.40.

Example 62: N-(4-(4-benzoylbenzamido)pyridin-3-yl)isonicotinamide

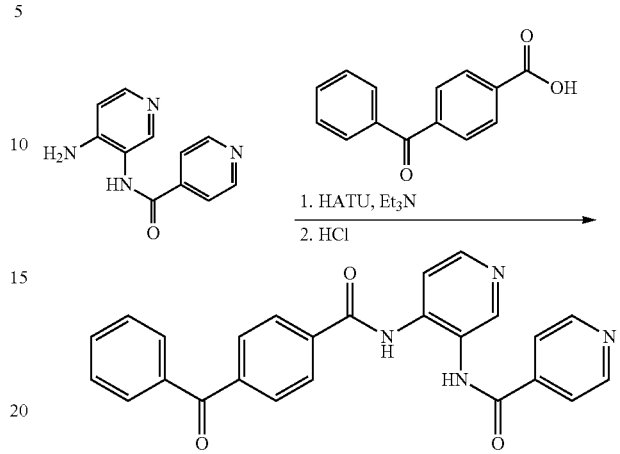

The remaining portion (ca. 0.2 mmol) of the intermediate derived from isonicotinic acid in the synthesis of N-(4-(4-(2-fluoro-6-hydroxy-3-methoxybenzoyl)benzamido)pyridin-3-yl)isonicotinamide described above was combined with 1 mL acetonitrile, 0.28 mL (2 mmol) trimethylamine, 91 mg (0.24 mmol) HATU, and 45 mg (0.2 mmol) of 4-(benzoyl)benzoic acid. LCMS suggested completion after 3.5 h. The mixture was charged with 8 mL water and extracted with 2, 1, and 1 mL portions of ethyl acetate. The organics were filtered through a plug of magnesium sulfate and concentrated to a yellow oil, 254 mg, which was purified by reverse phase preparative HPLC to deliver the desired compound as the formate salt, 26.8 mg of white solid. $^1$H NMR (500 MHz, Methanol-d$_4$) δ 8.84-8.67 (m, 3H), 8.48 (d, J=5.6 Hz, 1H), 8.13 (d, J=5.6 Hz, 1H), 8.08 (d, J=8.7 Hz, 3H), 8.02-7.92 (m, 2H), 7.92-7.84 (m, 2H), 7.86-7.74 (m, 2H), 7.73-7.62 (m, 1H), 7.55 (t, J=7.8 Hz, 2H). LCMS (ESI+) for C$_{25}$H$_{18}$N$_4$O$_3$ [M+H] expected=423.14, found=423.34.

Example 63: N-((3R,4R)-4-(4-(2-fluoro-6-hydroxy-3-methoxybenzoyl)benzamido)pyrrolidin-3-yl)-1H-pyrazole-4-carboxamide

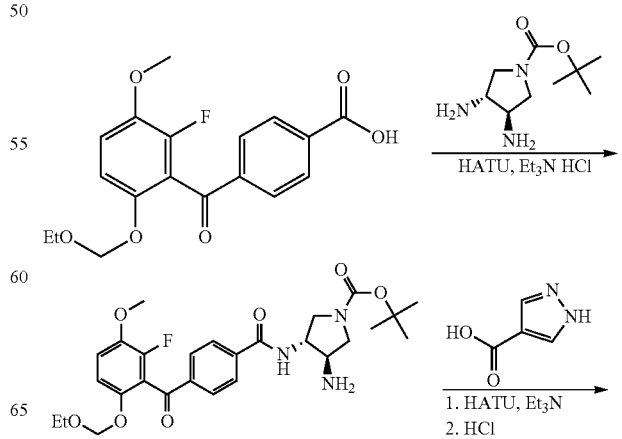

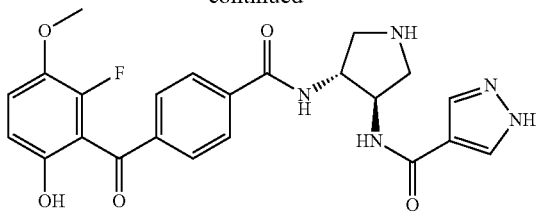

A vial was charged with 4-(6-(ethoxymethoxy)-2-fluoro-3-methoxybenzoyl)benzoic acid (138 mg, 0.397 mmol), Et₃N (55 μL, 0.397 mmol) and DMF (2.0 mL) at room temperature. To this solution was then added HATU (151 mg, 0.397 mmol) and the mixture was stirred for 5 min. This solution was then added to a second vial containing a freshly prepared mixture of tert-butyl (3R,4R)-3,4-diaminopyrrolidine-1-carboxylate (80 mg, 0.397 mmol) and HCl (4.0 M dioxane solution, 200 μL) in DMF (2.0 mL). The resulting solution was stirred at room temperature for 18 h to give tert-butyl (3R,4R)-3-amino-4-(4-(6-(ethoxymethoxy)-2-fluoro-3-methoxybenzoyl)benzamido)pyrrolidine-1-carboxylate which could be isolated or directly used in situ.

A vial was charged with tert-butyl (3R,4R)-3-amino-4-(4-(6-(ethoxymethoxy)-2-fluoro-3-methoxybenzoyl)benzamido)pyrrolidine-1-carboxylate (30 mg, 0.056 mmol), 1H-pyrazole-4-carboxylic acid (6.3 mg, 0.056 mmol), Et₃N (16 μL, 0.112 mmol) and DMF (500 μL). HATU (22 mg, 0.056 mmol) was added and the mixture was stirred at room temperature for 1 h. The solution was quenched with water and extracted with EtOAc. The organic portion was concentrated in vacuo and then redissolved in THF (1 mL) and aqueous HCl (1.0 M, 1 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-pyrazole-4-carboxamide. ¹H NMR (500 MHz, Methanol-d₄) δ 8.53 (s, 1H), 8.09 (s, 2H), 7.97 (d, J=8.4 Hz, 2H), 7.92 (d, J=8.2 Hz, 2H), 7.15 (t, J=9.3 Hz, 1H), 6.70 (dd, J=9.0, 1.7 Hz, 1H), 4.66 (h, J=6.4 Hz, 2H), 3.86 (s, 3H), 3.76 (td, J=11.8, 7.4 Hz, 2H) formate salt. LCMS (ESI+) for C₂₃H₂₂FN₅O₅ [M+H] expected=468.16, found=468.45.

Example 64: N-((3R,4R)-4-(4-(2-fluoro-6-hydroxy-3-methoxybenzoyl)benzamido)pyrrolidin-3-yl)-1H-indazole-5-carboxamide

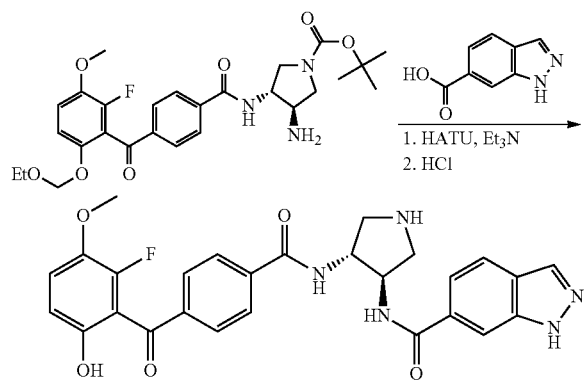

A vial was charged with tert-butyl (3R,4R)-3-amino-4-(4-(6-(ethoxymethoxy)-2-fluoro-3-methoxybenzoyl)benzamido)pyrrolidine-1-carboxylate (30 mg, 0.056 mmol), 1H-indazole-6-carboxylic acid (9.0 mg, 0.056 mmol), Et₃N (32 μL, 0.22 mmol) and DMF (500 μL). HATU (22 mg, 0.056 mmol) was added and the mixture was stirred at room temperature for 1 h. The solution was quenched with water and extracted with EtOAc. The organic portion was concentrated in vacuo and then redissolved in THF (0.5 mL) and aqueous HCl (1.0 M, 0.5 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-indazole-5-carboxamide as a formate salt. ¹H NMR (500 MHz, Methanol-d₄) δ 8.37 (s, 1H), 8.18 (s, 1H), 7.97 (d, J=8.2 Hz, 2H), 7.94-7.88 (m, 3H), 7.60 (d, J=8.9 Hz, 1H), 7.13 (t, J=9.2 Hz, 1H), 6.68 (dd, J=9.0, 1.7 Hz, 1H), 4.71 (m, 2H), 3.84 (s, 3H), 3.79 (m, 2H), 3.35 (m, 2H). LCMS (ESI+) for C₂₇H₂₄FN₅O₅ [M+H] expected=518.18, found=518.46.

Example 65: N-((3R,4R)-4-(4-(2-fluoro-6-hydroxy-3-methoxybenzoyl)benzamido)pyrrolidin-3-yl)pyrimidine-4-carboxamide

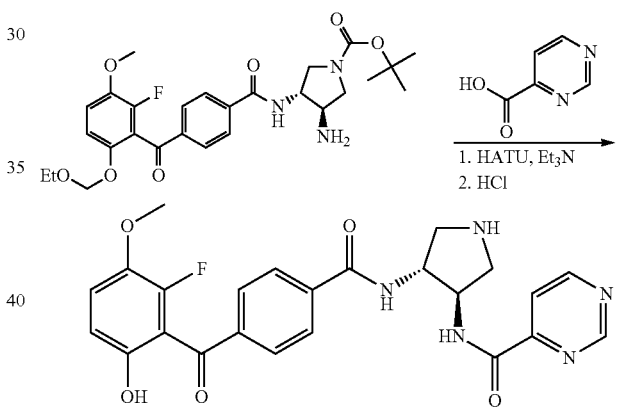

A vial was charged with tert-butyl (3R,4R)-3-amino-4-(4-(6-(ethoxymethoxy)-2-fluoro-3-methoxybenzoyl)benzamido)pyrrolidine-1-carboxylate (30 mg, 0.056 mmol), pyrimidine-4-carboxylic acid (7.0 mg, 0.056 mmol), Et₃N (32 μL, 0.22 mmol) and DMF (500 μL). HATU (22 mg, 0.056 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)pyrimidine-4-carboxamide as a formate salt. ¹H NMR (500 MHz, Methanol-d₄) δ 9.29 (s, 1H), 9.03 (d, J=5.1 Hz, 1H), 8.09 (d, J=5.0 Hz, 1H), 7.95 (d, J=8.2 Hz, 2H), 7.89 (d, J=8.3 Hz, 2H), 7.13 (t, J=9.3 Hz, 1H), 6.69 (d, J=8.9 Hz, 1H), 4.77 (m, 2H), 3.84 (m, 5H), 3.47 (ddd, J=16.6, 12.1, 6.7 Hz, 2H). LCMS (ESI+) for C₂₄H₂₂FN₅O₅ [M+H] expected=480.16, found=480.42.

Example 66: N-((3R,4R)-4-(4-(2-fluoro-6-hydroxy-3-methoxybenzoyl)benzamido)pyrrolidin-3-yl)-2-hydroxyisonicotinamide

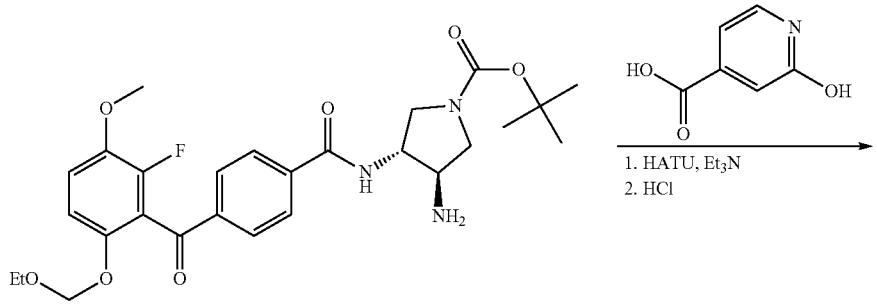

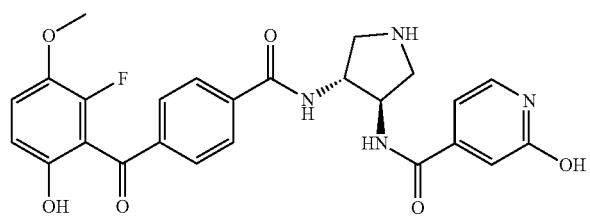

A vial was charged with tert-butyl (3R,4R)-3-amino-4-(4-(6-(ethoxymethoxy)-2-fluoro-3-methoxybenzoyl)benzamido)pyrrolidine-1-carboxylate (30 mg, 0.056 mmol), 2-hydroxyisonicotinic acid (7.8 mg, 0.056 mmol), Et$_3$N (32 µL, 0.22 mmol) and DMF (500 µL). HATU (22 mg, 0.056 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-2-hydroxyisonicotinamide as a formate salt. $^1$H NMR (500 MHz, Methanol-d$_4$) δ 7.95 (d, J=8.3 Hz, 2H), 7.90 (d, J=8.1 Hz, 2H), 7.53 (d, J=6.8 Hz, 1H), 7.14 (t, J=9.3 Hz, 1H), 6.90 (s, 1H), 6.73-6.65 (m, 2H), 4.67-4.63 (m, 2H), 3.84 (s, 3H), 3.75 (m, 2H), 3.38-3.33 (m, 2H). LCMS (ESI+) for C$_{25}$H$_{23}$FN$_4$O$_6$ [M+H] expected=495.16, found=495.42.

Example 67: N-((3R,4R)-4-(4-(2-fluoro-6-hydroxy-3-methoxybenzoyl)benzamido)pyrrolidin-3-yl)-6-hydroxynicotinamide

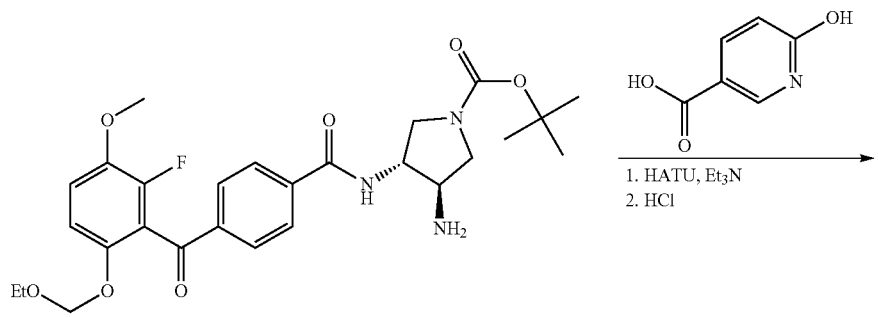

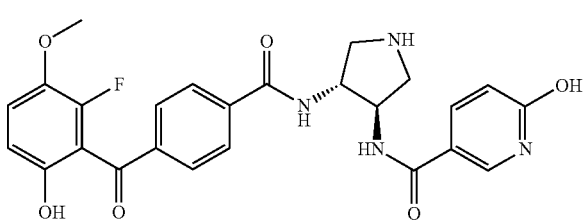

A vial was charged with tert-butyl (3R,4R)-3-amino-4-(4-(6-(ethoxymethoxy)-2-fluoro-3-methoxybenzoyl)benzamido)pyrrolidine-1-carboxylate (30 mg, 0.056 mmol), 6-hydroxynicotinic acid (7.8 mg, 0.056 mmol), Et$_3$N (32 µL, 0.22 mmol) and DMF (500 µL). HATU (22 mg, 0.056 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-6-hydroxynicotinamide as a formate salt. $^1$H NMR (500 MHz, Methanol-d$_4$) δ 8.10 (d, J=2.6 Hz, 1H), 7.99 (dd, J=9.6, 2.7 Hz, 1H), 7.96 (d, J=8.3 Hz, 2H), 7.90 (d, J=8.2 Hz, 2H), 7.13 (t, J=9.3 Hz, 1H), 6.69 (d, J=9.0 Hz, 1H), 6.54 (d, J=9.6 Hz, 1H), 4.70-4.66 (m, 2H), 3.84 (s, 3H), 3.82 (m, 2H), 3.42 (td, J=11.8, 6.3 Hz, 2H). LCMS (ESI+) for C$_{25}$H$_{23}$FN$_4$O$_6$ [M+H] expected=495.16, found=495.45.

Example 68: N-((3R,4R)-4-(4-(2-fluoro-6-hydroxy-3-methoxybenzoyl)benzamido)pyrrolidin-3-yl)nicotinamide

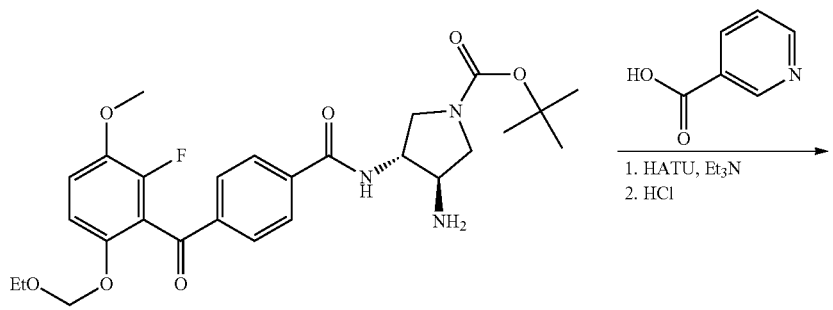

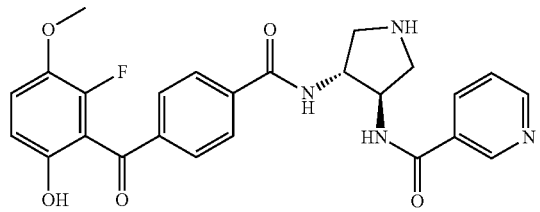

A vial was charged with tert-butyl (3R,4R)-3-amino-4-(4-(6-(ethoxymethoxy)-2-fluoro-3-methoxybenzoyl)benzamido)pyrrolidine-1-carboxylate (20 mg, 0.038 mmol), nicotinic acid (4.6 mg, 0.038 mmol), Et$_3$N (21 µL, 0.15 mmol) and DMF (500 µL). HATU (15 mg, 0.038 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)nicotinamide as a formate salt. $^1$H NMR (500 MHz, Methanol-d$_4$) δ 9.00 (s, 1H), 8.71 (d, J=4.9 Hz, 1H), 8.28 (d, J=8.0 Hz, 1H), 7.96 (d, J=8.2 Hz, 2H), 7.90 (d, J=8.3 Hz, 2H), 7.57 (dd, J=8.0, 4.9 Hz, 1H), 7.14 (t, J=9.3 Hz, 1H), 6.69 (d, J=9.0 Hz, 1H), 4.76-4.72 (m, 2H), 3.93-3.81 (m, 5H), 3.46 (dd, J=13.3, 5.9 Hz, 2H). LCMS (ESI+) for C$_{25}$H$_{23}$FN$_4$O$_5$ [M+H] expected=479.17, found=479.41.

Example 69: 4-(2-fluoro-6-hydroxy-3-methoxybenzoyl)-N-((3R,4R)-4-(4-hydroxybenzamido)pyrrolidin-3-yl)benzamide

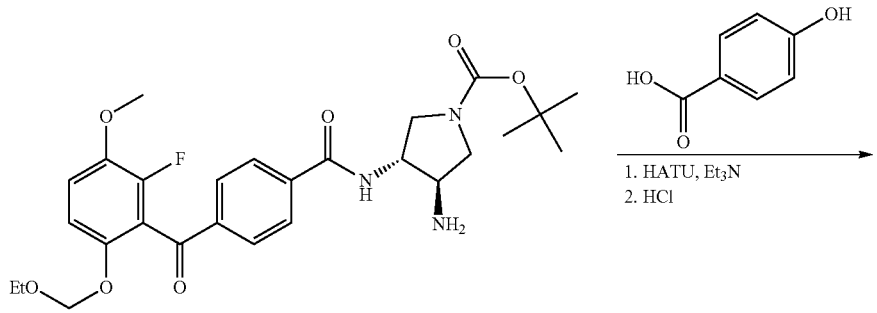

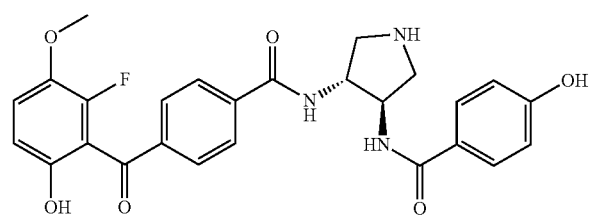

A vial was charged with tert-butyl (3R,4R)-3-amino-4-(4-(6-(ethoxymethoxy)-2-fluoro-3-methoxybenzoyl)benzamido)pyrrolidine-1-carboxylate (20 mg, 0.038 mmol), 4-hydroxybenzoic acid (5.2 mg, 0.038 mmol), Et$_3$N (21 µL, 0.15 mmol) and DMF (500 µL). HATU (15 mg, 0.038 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give 4-(2-fluoro-6-hydroxy-3-methoxybenzoyl)-N-((3R,4R)-4-(4-hydroxybenzamido)pyrrolidin-3-yl)benzamide as a formate salt. $^1$H NMR (500 MHz, Methanol-d$_4$) δ 7.95 (d, J=8.3 Hz, 2H), 7.90 (d, J=8.4 Hz, 2H), 7.73 (d, J=8.7 Hz, 2H), 7.13 (t, J=9.3 Hz, 1H), 6.83 (d, J=8.7 Hz, 2H), 6.68 (dd, J=8.9, 1.7 Hz, 1H), 4.59 (d, J=6.2 Hz, 2H), 3.84 (s, 3H), 3.63 (m, 2H), 3.22-3.16 (m, 2H). LCMS (ESI+) for C$_{26}$H$_{24}$FN$_3$O$_6$ [M+H] expected=494.17, found=494.44.

Example 70: 2-amino-N-((3R,4R)-4-(4-(2-fluoro-6-hydroxy-3-methoxybenzoyl)benzamido)pyrrolidin-3-yl)pyrimidine-4-carboxamide

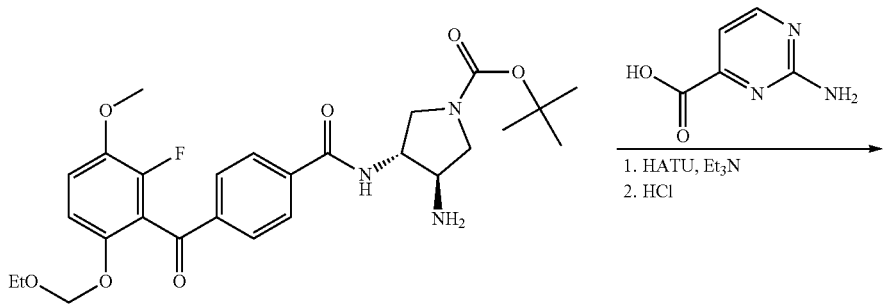

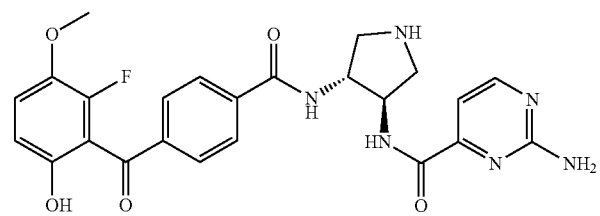

A vial was charged with tert-butyl (3R,4R)-3-amino-4-(4-(6-(ethoxymethoxy)-2-fluoro-3-methoxybenzoyl)benzamido)pyrrolidine-1-carboxylate (20 mg, 0.038 mmol), 2-aminopyrimidine-4-carboxylic acid (5.3 mg, 0.038 mmol), Et₃N (21 µL, 0.15 mmol) and DMF (500 µL). HATU (15 mg, 0.038 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 50° C. and stirred until the carbamate and acetal protecting groups were fully removed by LCMS. The solution was then purified via HPLC to give 2-amino-N-((3R,4R)-4-(4-(2-fluoro-6-hydroxy-3-methoxybenzoyl)benzamido)pyrrolidin-3-yl)pyrimidine-4-carboxamide as a formate salt. $^1$H NMR (500 MHz, Methanol-d₄) δ 8.45 (d, J=5.0 Hz, 1H), 7.94 (d, J=8.5 Hz, 2H), 7.90 (d, J=8.2 Hz, 2H), 7.20 (d, J=5.0 Hz, 1H), 7.13 (t, J=9.3 Hz, 1H), 6.68 (dd, J=9.0, 1.7 Hz, 1H), 4.63 (dq, J=24.7, 6.9 Hz, 2H), 3.84 (s, 3H), 3.70 (dd, J=12.0, 7.8 Hz, 2H), 3.27 (m, 2H). LCMS (ESI+) for $C_{24}H_{23}FN_6O_5$ [M+H] expected=495.17, found=495.42.

Example 71: N-((3R,4R)-4-(4-(2-fluoro-6-hydroxy-3-methoxybenzoyl)benzamido)pyrrolidin-3-yl)-2-oxoindoline-5-carboxamide

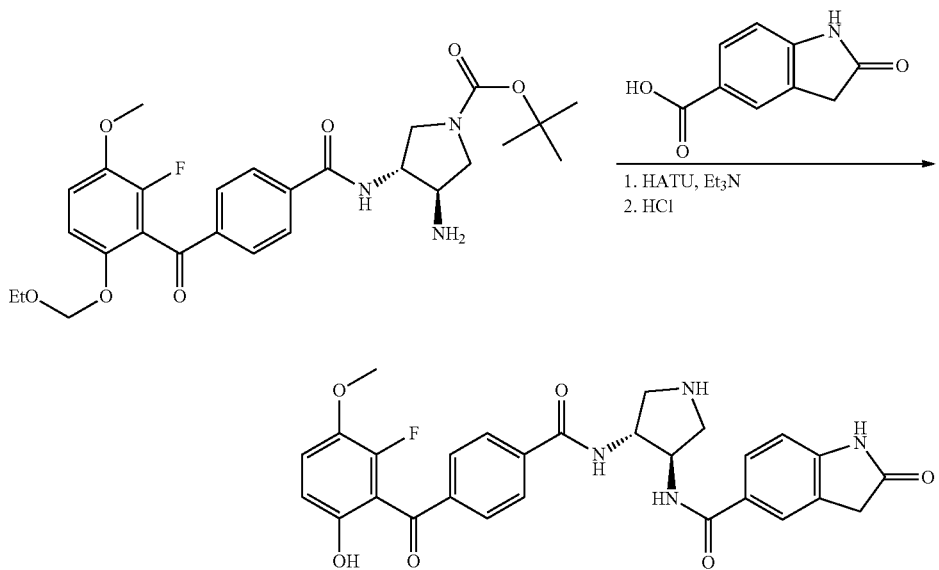

A vial was charged with tert-butyl (3R,4R)-3-amino-4-(4-(6-(ethoxymethoxy)-2-fluoro-3-methoxybenzoyl)benzamido)pyrrolidine-1-carboxylate (20 mg, 0.038 mmol), 2-oxoindoline-5-carboxylic acid (6.7 mg, 0.038 mmol), Et₃N (21 µL, 0.15 mmol) and DMF (500 µL). HATU (15 mg, 0.038 mmol) was added and the mixture was stirred at room temperature for 1 h. The solution was quenched with water and extracted with EtOAc. The organic portion was concentrated in vacuo and then redissolved in THF (0.75 mL) and aqueous HCl (1.0 M, 0.75 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-2-oxoindoline-5-carboxamide as a formate salt. $^1$H NMR (500 MHz, Methanol-d₄) δ 7.95 (d, J=8.5 Hz, 2H), 7.90 (d, J=8.4 Hz, 2H), 7.78-7.73 (m, 2H), 7.13 (t, J=9.3 Hz, 1H), 6.95 (d, J=8.1 Hz, 1H), 6.68 (dd, J=9.0, 1.7 Hz, 1H), 4.69-4.60 (m, 2H), 3.84 (s, 3H), 3.74 (dt, J=11.8, 7.0 Hz, 2H), 3.57 (d, J=10.7 Hz, 1H). LCMS (ESI+) for $C_{28}H_{25}FN_4O_6$ [M+H] expected=533.18, found=533.45.

Example 72: N-((3S,4S)-4-(4-(2-fluoro-6-hydroxy-3-methoxybenzoyl)benzamido)pyrrolidin-3-yl)isonicotinamide

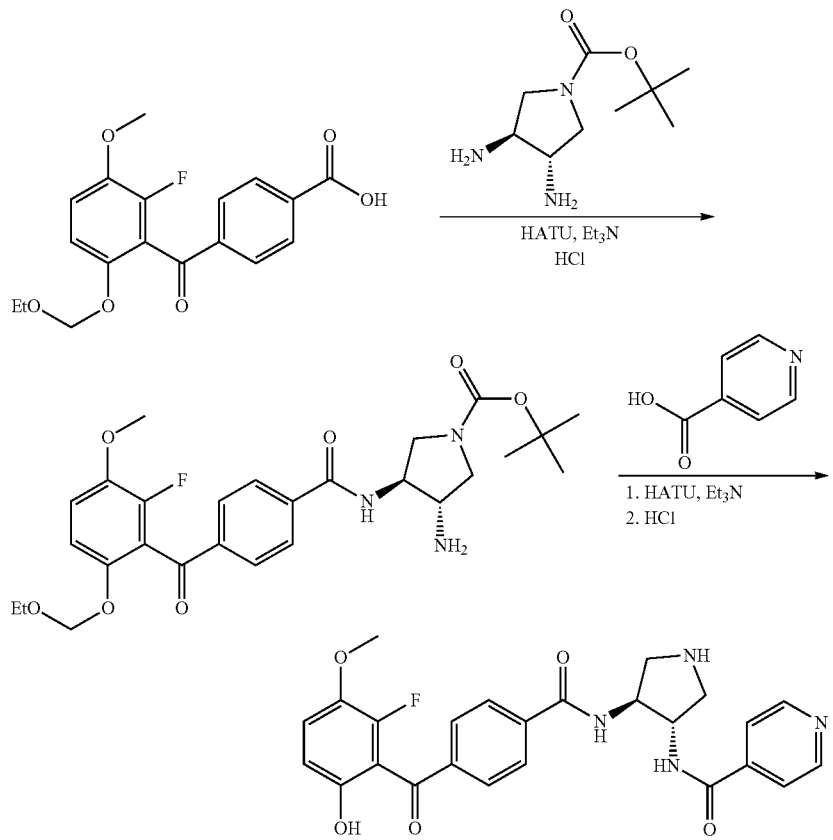

A vial was charged with 4-(6-(ethoxymethoxy)-2-fluoro-3-methoxybenzoyl)benzoic acid (86 mg, 0.248 mmol), Et$_3$N (35 µL, 0.248 mmol) and DMF (2.0 mL) at room temperature. To this solution was then added HATU (94 mg, 0.248 mmol) and the mixture was stirred for 5 min. This solution was then added to a second vial containing a freshly prepared mixture of tert-butyl (3S,4S)-3,4-diaminopyrrolidine-1-carboxylate (50 mg, 0.248 mmol) and HCl (4.0 M dioxane solution, 124 µL) in DMF (2.0 mL). The resulting solution was stirred at room temperature for 18 h, then partitioned between EtOAc and NaHCO$_3$. The organic portion was washed with water and concentrated. Purification on silica gel (5 g, CH$_2$Cl$_2$/MeOH gradient) gave tert-butyl (3S,4S)-3-amino-4-(4-(6-(ethoxymethoxy)-2-fluoro-3-methoxybenzoyl)benzamido)pyrrolidine-1-carboxylate (81 mg). This material was then dissolved in DMF (2.0 mL) and sequentially treated with Et$_3$N (84 µL, 0.60 mmol) and isonicotinic acid (18 mg, 0.15 mmol) at room temperature. After 20 min, the solution was diluted with EtOAc and twice washed with water. The organic portion was concentrated in vacuo and then redissolved in THF (1.0 mL) and aqueous HCl (1.0 M, 1.0 mL). The solution was warmed to 65° C. and stirred until the carbamate and acetal protecting groups were fully removed by LCMS. The solution was then purified via HPLC to give N-((3S,4S)-4-(4-(2-fluoro-6-hydroxy-3-methoxybenzoyl)benzamido)pyrrolidin-3-yl)isonicotinamide as a formate salt. $^1$H NMR (500 MHz, Methanol-d$_4$) δ 8.71 (d, J=5.8 Hz, 2H), 7.96 (d, J=8.2 Hz, 2H), 7.90 (d, J=8.3 Hz, 2H), 7.81 (d, J=5.8 Hz, 2H), 7.14 (t, J=9.3 Hz, 1H), 6.69 (d, J=8.9 Hz, 1H), 4.73-4.70 (m, 2H), 3.84 (s, 3H), 3.80 (dd, J=12.8, 6.9 Hz, 2H), 3.39 (dd, J=12.2, 6.6 Hz, 2H). LCMS (ESI+) for C$_{25}$H$_{23}$FN$_4$O$_5$ [M+H] expected=479.17, found=479.41.

Example 73: N-((3R,4R)-4-(4-(2-fluoro-3,6-dimethoxybenzoyl)benzamido)-1-methylpyrrolidin-3-yl)isonicotinamide

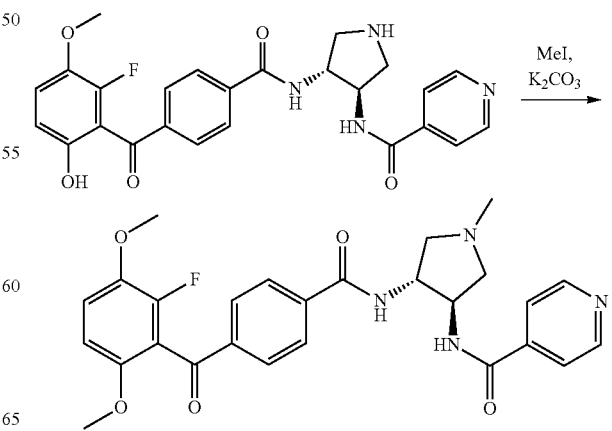

A vial was charged with N-((3R,4R)-4-(4-(2-fluoro-6-hydroxy-3-methoxybenzoyl)benzamido)pyrrolidin-3-yl)isonicotinamide (16.0 mg, 0.033 mmol) and DMF (1 mL) at room temperature. The solution was treated with iodomethane (10 μL, 0.16 mmol) and excess potassium carbonate. The solution was stirred for 18 h, quenched with water and purified directly on HPLC to give N-((3R,4R)-4-(4-(2-fluoro-3,6-dimethoxybenzoyl)benzamido)-1-methylpyrrolidin-3-yl)isonicotinamide as a formate salt. $^1$H NMR (500 MHz, Methanol-$d_4$) δ 8.72 (s, 2H), 7.96 (s, 2H), 7.91 (d, J=8.2 Hz, 2H), 7.81 (s, 2H), 7.13 (t, J=9.3 Hz, 1H), 6.68 (d, J=9.1 Hz, 1H), 5.10 (m, 2H), 4.22 (m, 2H), 3.84 (m, 5H), 3.45 (br, 3H). Peak missing, possibly obscured by MeOD. LCMS (ESI+) for $C_{27}H_{27}FN_4O_5$ [M+H] expected=507.20, found=507.50.

Example 74: N-((cis)-4-(4-(2-fluoro-6-hydroxy-3-methoxybenzoyl)benzamido)pyrrolidin-3-yl)isonicotinamide pyrrolidine-1-carboxylate (50 mg, 0.248 mmol) and HCl (4.0 M dioxane solution, 124 μL) in DMF (2.0 mL). The resulting solution was stirred at room temperature for 18 h to give tert-butyl (3R,4S)-3-amino-4-(4-(6-(ethoxymethoxy)-2-fluoro-3-methoxybenzoyl)benzamido)pyrrolidine-1-carboxylate which could be directly used in situ. To this solution was added isonicotinic acid (31 mg, 0.248 mmol), Et$_3$N (139 μL, 0.992 mmol) and HATU (94 mg, 0.248 mmol). The mixture was stirred at room temperature for 1 h, diluted with water and then purified on HPLC to give tert-butyl (3S,4R)-3-(4-(6-(ethoxymethoxy)-2-fluoro-3-methoxybenzoyl)benzamido)-4-(isonicotinamido)pyrrolidine-1-carboxylate (50 mg). This material was then dissolved in THF (1 mL) and aqueous HCl (1.0 M, 0.5 mL). The solution was warmed to 65° C. and stirred until the carbamate and acetal protecting groups were fully removed by LCMS. The solution was then purified via HPLC to give N-((3R,4S)-4-(4-(2-fluoro-6-hydroxy-3-methoxybenzoyl)

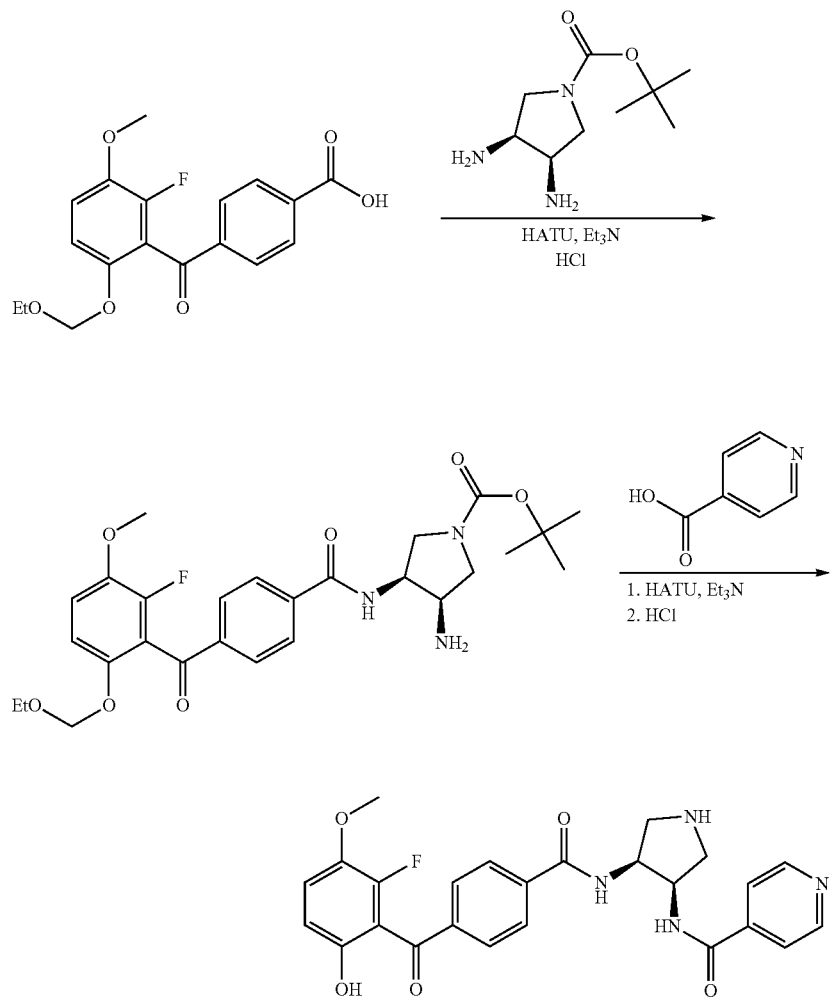

A vial was charged with 4-(6-(ethoxymethoxy)-2-fluoro-3-methoxybenzoyl)benzoic acid (86 mg, 0.248 mmol), Et$_3$N (35 μL, 0.248 mmol) and DMF (2.0 mL) at room temperature. To this solution was then added HATU (94 mg, 0.248 mmol) and the mixture was stirred for 5 min. This solution was then added to a second vial containing a freshly prepared mixture of tert-butyl tert-butyl (3R,4S)-3,4-diamino-benzamido)pyrrolidin-3-yl)isonicotinamide as a formate salt. $^1$H NMR (500 MHz, Methanol-$d_4$) δ 8.62 (d, J=6.2 Hz, 2H), 7.91-7.80 (m, 4H), 7.71-7.62 (m, 2H), 7.13 (t, J=9.3 Hz, 1H), 6.67 (dd, J=8.9, 1.7 Hz, 1H), 4.83 (s, 2H), 3.84 (s, 3H), 3.66 (m, 2H), 3.59 (m, 2H). LCMS (ESI+) for $C_{25}H_{23}FN_4O_5$ [M+H] expected=479.17, found=479.46.

Example 75: (3R,4R)-3-(isonicotinamido)piperidin-4-yl 4-(2-fluoro-6-hydroxy-3-methoxybenzoyl)benzoate

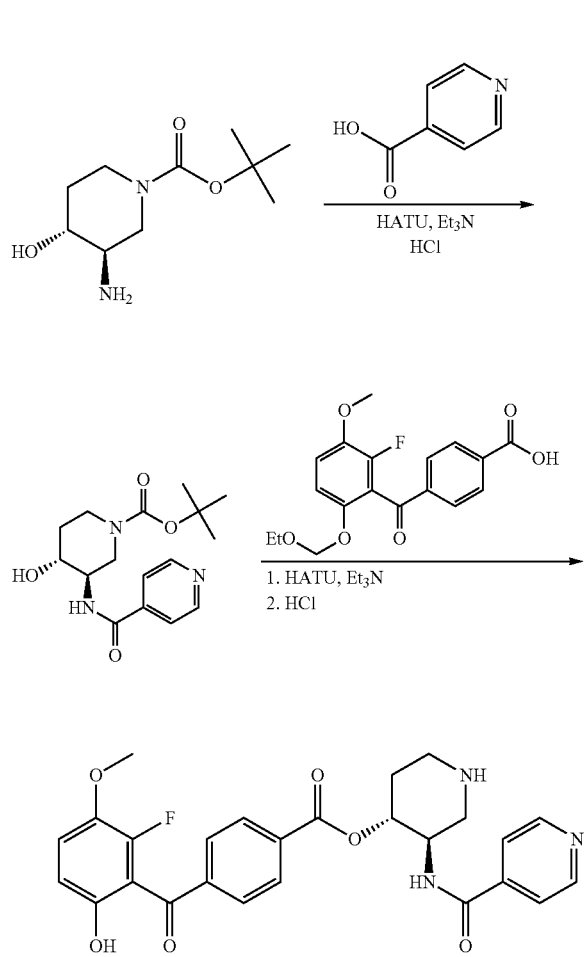

A vial was charged with tert-butyl (3R,4R)-3-amino-4-hydroxypiperidine-1-carboxylate (50 mg, 0.23 mmol), isonicotinic acid (28 mg, 0.23 mmol), Et₃N (644, 0.46 mmol) and DMF (1.5 mL). HATU (87 mg, 0.23 mmol) was then added and stirred at room temperature for 45 min to give tert-butyl (3R,4R)-4-hydroxy-3-(isonicotinamido)piperidine-1-carboxylate. To this solution was then added Et₃N (644, 0.46 mmol), 4-(6-(ethoxymethoxy)-2-fluoro-3-methoxybenzoyl)benzoic acid (80 mg, 0.23 mmol) and lastly HATU (87 mg, 0.23 mmol). The solution was stirred at room temperature for 18 h, then diluted with EtOAc and twice washed with water. The organic portion was concentrated and then redissolved in THF (1.0 mL) and HCl (1.0 N, 1.0 mL) and warmed to 65° C. for 1 h. The solution was then purified via HPLC to give (3R,4R)-3-(isonicotinamido)piperidin-4-yl 4-(2-fluoro-6-hydroxy-3-methoxybenzoyl)benzoate as a formate salt. $^1$H NMR (500 MHz, Methanol-d$_4$) δ 8.67-8.60 (m, 2H), 8.09 (d, J=8.4 Hz, 2H), 7.87 (d, J=8.3 Hz, 2H), 7.71-7.60 (m, 2H), 7.13 (t, J=9.3 Hz, 1H), 6.67 (dd, J=9.0, 1.7 Hz, 1H), 5.30 (td, J=10.3, 4.6 Hz, 1H), 4.56 (td, J=10.8, 4.7 Hz, 1H), 3.84 (s, 3H), 3.56 (dd, J=12.9, 4.6 Hz, 1H), 3.50-3.41 (m, 1H), 3.20-3.01 (m, 2H), 2.47 (m, 1H), 2.00 (m, 1H). LCMS (ESI+) for C$_{26}$H$_{24}$FN$_3$O$_6$ [M+H] expected=494.17, found=494.47.

Example 76: (3R,4R)-3-(isonicotinamido)-1-methylpiperidin-4-yl 4-(2-fluoro-3,6-dimethoxybenzoyl)benzoate

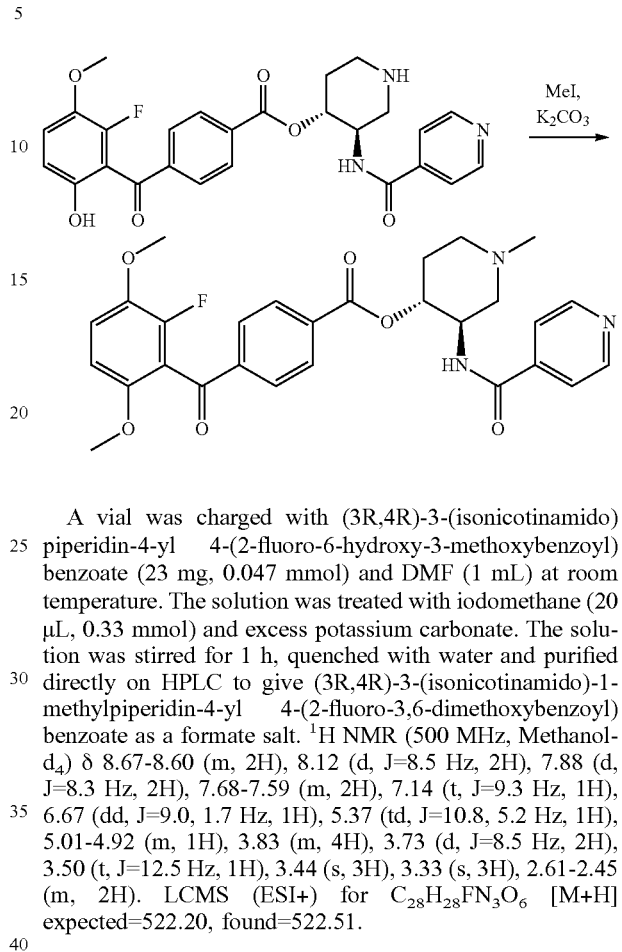

A vial was charged with (3R,4R)-3-(isonicotinamido)piperidin-4-yl 4-(2-fluoro-6-hydroxy-3-methoxybenzoyl)benzoate (23 mg, 0.047 mmol) and DMF (1 mL) at room temperature. The solution was treated with iodomethane (20 μL, 0.33 mmol) and excess potassium carbonate. The solution was stirred for 1 h, quenched with water and purified directly on HPLC to give (3R,4R)-3-(isonicotinamido)-1-methylpiperidin-4-yl 4-(2-fluoro-3,6-dimethoxybenzoyl)benzoate as a formate salt. $^1$H NMR (500 MHz, Methanol-d$_4$) δ 8.67-8.60 (m, 2H), 8.12 (d, J=8.5 Hz, 2H), 7.88 (d, J=8.3 Hz, 2H), 7.68-7.59 (m, 2H), 7.14 (t, J=9.3 Hz, 1H), 6.67 (dd, J=9.0, 1.7 Hz, 1H), 5.37 (td, J=10.8, 5.2 Hz, 1H), 5.01-4.92 (m, 1H), 3.83 (m, 4H), 3.73 (d, J=8.5 Hz, 2H), 3.50 (t, J=12.5 Hz, 1H), 3.44 (s, 3H), 3.33 (s, 3H), 2.61-2.45 (m, 2H). LCMS (ESI+) for C$_{28}$H$_{28}$FN$_3$O$_6$ [M+H] expected=522.20, found=522.51.

Example 77: (3R,4R)-4-(isonicotinamido)pyrrolidin-3-yl 4-(2-fluoro-6-hydroxy-3-methoxybenzoyl)benzoate

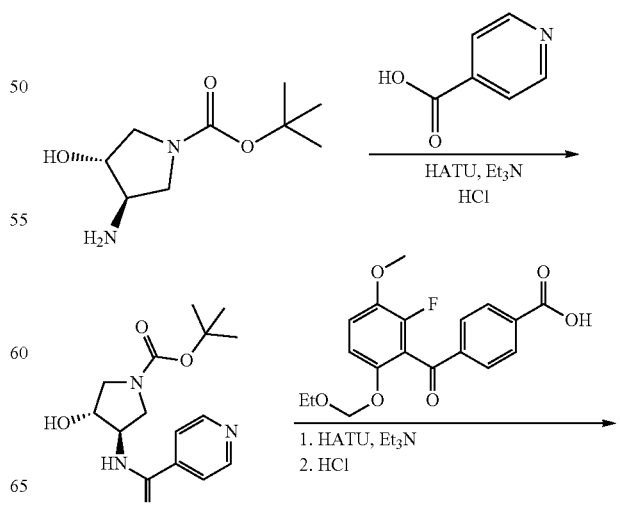

117

-continued

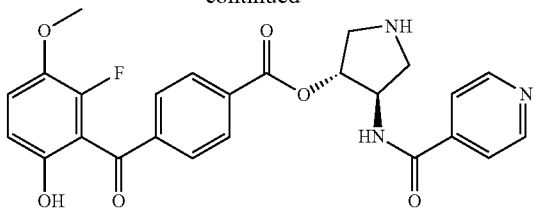

A vial was charged with tert-butyl (3R,4R)-3-amino-4-hydroxypyrrolidine-1-carboxylate (50 mg, 0.247 mmol), isonicotinic acid (30 mg, 0.247 mmol), Et$_3$N (138 µL, 0.988 mmol) and MeCN (1.5 mL). HATU (94 mg, 0.247 mmol) was then added and stirred at room temperature for 20 min to give tert-butyl (3R,4R)-3-hydroxy-4-(isonicotinamido)pyrrolidine-1-carboxylate. To this solution was then added 4-(6-(ethoxymethoxy)-2-fluoro-3-methoxybenzoyl)benzoic acid (86 mg, 0.247 mmol) and HATU (94 mg, 0.247 mmol). The solution was stirred at room temperature for 18 h, then diluted with EtOAc and twice washed with water. The organic portion was concentrated and then redissolved in THF (1.0 mL) and HCl (1.0 N, 1.0 mL) and warmed to 65° C. for 4 h. The solution was then purified via HPLC to give (3R,4R)-4-(isonicotinamido)pyrrolidin-3-yl 4-(2-fluoro-6-hydroxy-3-methoxybenzoyl)benzoate as a formate salt. $^1$H NMR (500 MHz, Methanol-d$_4$) δ 8.73-8.68 (m, 2H), 8.18 (d, J=8.4 Hz, 2H), 7.92 (d, J=8.2 Hz, 2H), 7.84-7.77 (m, 2H), 7.14 (t, J=9.2 Hz, 1H), 6.68 (d, J=9.0 Hz, 1H), 5.49 (m, 1H), 4.60 (m, 1H), 3.84 (s, 3H), 3.52 (m, 1H), 3.48-3.40 (m, 1H), 3.35 (s, 3H), 3.17 (m, 1H), 2.96 (m, 1H). LCMS (ESI+) for C$_{25}$H$_{22}$FN$_3$O$_6$ [M+H] expected=480.15, found=480.43.

Example 78: (3R,4R)-4-(isonicotinamido)-1-methylpyrrolidin-3-yl 4-(2-fluoro-3,6-dimethoxybenzoyl)benzoate

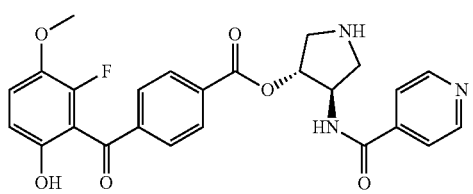

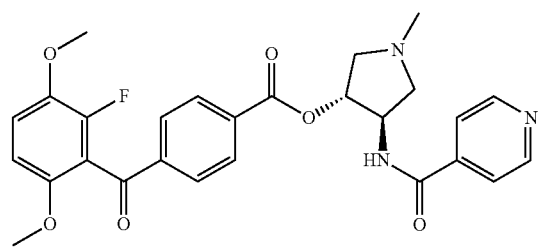

118

A vial was charged with (3R,4R)-4-(isonicotinamido)pyrrolidin-3-yl 4-(2-fluoro-6-hydroxy-3-methoxybenzoyl)benzoate (13 mg) and DMF (1 mL) at room temperature. The solution was treated with iodomethane (20 µL) and excess potassium carbonate. The solution was stirred for 1 h, quenched with water and purified directly on HPLC to give (3R,4R)-4-(isonicotinamido)-1-methylpyrrolidin-3-yl 4-(2-fluoro-3,6-dimethoxybenzoyl)benzoate as a formate salt. $^1$H NMR (500 MHz, Methanol-d$_4$) δ 8.74 (d, J=5.0 Hz, 2H), 8.21 (d, J=8.2 Hz, 2H), 7.94 (d, J=8.1 Hz, 2H), 7.84 (d, J=5.0 Hz, 2H), 7.15 (t, J=9.3 Hz, 1H), 6.69 (dd, J=9.0, 1.7 Hz, 1H), 5.95 (s, 1H), 5.01 (m, 1H), 4.38 (m, 1H), 4.28 (m, 1H), 4.16 (m, 1H), 3.90 (s, 1H), 3.84 (s, 3H), 3.45 (s, 3H), 3.43 (s, 3H). LCMS (ESI+) for C$_{27}$H$_{26}$FN$_3$O$_6$ [M+H] expected=508.18, found=508.47.

Example 79: N-((3R,4R)-4-(4-((2-fluoro-6-hydroxy-3-methoxyphenyl)(hydroxy)methyl)benzamido)pyrrolidin-3-yl)isonicotinamide

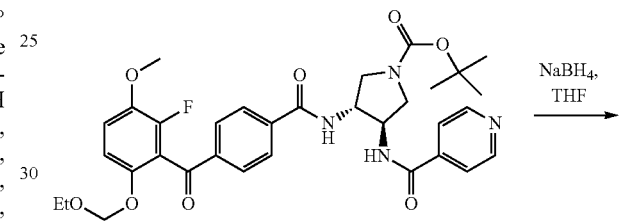

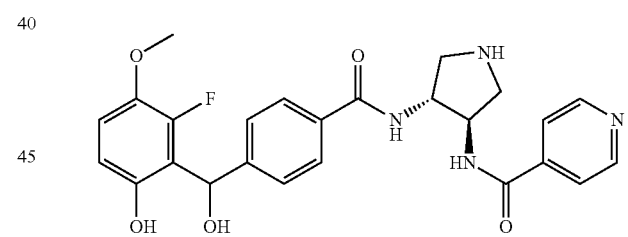

A vial was charged with tert-butyl (3R,4R)-3-(4-(6-(ethoxymethoxy)-2-fluoro-3-methoxybenzoyl)benzamido)-4-(isonicotinamido)pyrrolidine-1-carboxylate (20 mg, 0.031 mmol) and CH$_2$Cl$_2$ (1.0 mL) at room temperature. To this solution was then added NaBH$_4$ (4 mg, 0.11 mmol) followed by trifluoroactic acid (0.5 mL), which turned the colorless solution a red color which faded over 10 min. After 4 h the solution was concentrated and purified on HPLC to give N-((3R,4R)-4-(4-((2-fluoro-6-hydroxy-3-methoxyphenyl)(hydroxy)methyl)benzamido)pyrrolidin-3-yl)isonicotinamide as a formate salt. $^1$H NMR (500 MHz, Methanol-d$_4$) δ 8.70 (d, J=6.2 Hz, 2H), 8.32 (s, 1H), 7.84-7.77 (m, 4H), 7.52 (d, J=8.2 Hz, 2H), 6.88 (t, J=9.2 Hz, 1H), 6.55 (dd, J=9.0, 1.7 Hz, 1H), 6.29 (s, 1H), 4.69 (q, J=6.9 Hz, 2H), 3.84 (dt, J=14.3, 7.5 Hz, 2H), 3.76 (s, 3H), 3.49-3.40 (m, 2H). LCMS (ESI+) for C$_{25}$H$_{25}$FN$_4$O$_5$ [M+H] expected=481.18, found=481.27.

Example 80: N-((3R,4R)-4-(4-(2-fluoro-6-hydroxy-3-methoxybenzoyl)benzamido)pyrrolidin-3-yl)-1H-benzo[d][1,2,3]triazole-5-carboxamide

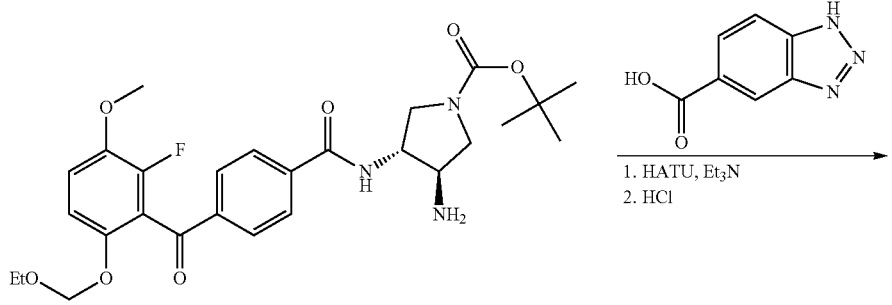

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 1H-benzo[d][1,2,3]triazole-5-carboxylic acid (16 mg, 0.099 mmol), HATU (38 mg, 0.099 mmol) and DMF (1 mL). Et₃N (404, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 1.0 mL). The solution was warmed to 60° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-benzo[d][1,2,3]triazole-5-carboxamide as a formate salt. $^1$H NMR (500 MHz, Methanol-d₄) δ 8.56-8.47 (m, 3H), 7.99 (d, J=8.3 Hz, 3H), 7.93 (dd, J=8.5, 3.3 Hz, 3H), 7.15 (t, J=9.3 Hz, 1H), 6.70 (d, J=8.9 Hz, 1H), 4.74 (s, 2H), 3.86 (s, 3H), 3.84-3.76 (m, 2H), 3.40 (d, J=7.7 Hz, 2H). LCMS (ESI+) for $C_{26}H_{23}FN_6O_5$ [M+H] expected=519.17, found=519.28.

Example 81: N-((3R,4R)-4-(4-(2-fluoro-6-hydroxy-3-methoxybenzoyl)benzamido)pyrrolidin-3-yl)-1H-indazole-6-carboxamide

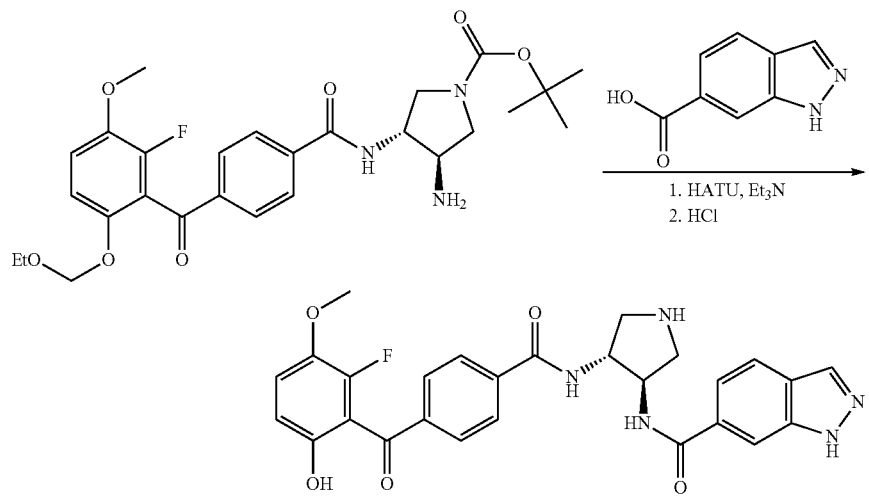

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 1H-indazole-6-carboxylic acid (16 mg, 0.099 mmol), HATU (38 mg, 0.099 mmol) and DMF (1 mL). Et₃N (40 μL, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 1.0 mL). The solution was warmed to 60° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-indazole-6-carboxamide as a formate salt. ¹H NMR (500 MHz, Methanol-d₄) δ 8.15-8.10 (m, 3H), 7.99 (d, J=8.0 Hz, 2H), 7.92 (d, J=8.1 Hz, 2H), 7.91-7.78 (m, 2H), 7.63 (d, J=8.5 Hz, 1H), 7.15 (t, J=9.2 Hz, 1H), 6.70 (d, J=9.0 Hz, 1H), 3.91 (m, 2H), 3.86 (s, 3H), 3.52 (s, 1H), 2.75-2.70 (m, 1H). LCMS (ESI+) for C₂₇H₂₄FN₅O₅ [M+H] expected=518.18, found=518.30.

Example 82: N-((3R,4R)-4-(4-(2-fluoro-6-hydroxy-3-methoxybenzoyl)benzamido)pyrrolidin-3-yl)-1H-pyrrolo[2,3-b]pyridine-4-carboxamide

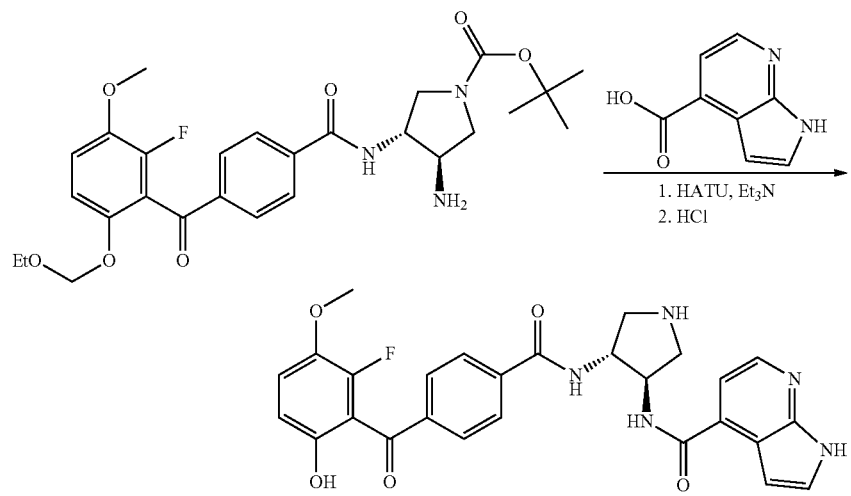

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 1H-pyrrolo[2,3-b]pyridine-4-carboxylic acid (16 mg, 0.099 mmol), HATU (38 mg, 0.099 mmol) and DMF (1 mL). Et₃N (40 μL, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 1.0 mL). The solution was warmed to 60° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-pyrrolo[2,3-b]pyridine-4-carboxamide as a formate salt. ¹H NMR (500 MHz, Methanol-d₄) δ 8.32 (s, 1H), 7.99 (s, 2H), 7.93 (d, J=8.0 Hz, 2H), 7.55 (s, 1H), 7.43 (s, 1H), 7.15 (t, J=9.3 Hz, 1H), 6.88 (d, J=16.4 Hz, 1H), 6.70 (d, J=9.0 Hz, 1H), 3.93 (m, 2H), 3.86 (s, 3H), 3.55 (m, 2H), 3.22 (d, J=7.8 Hz, 2H). LCMS (ESI+) for C₂₇H₂₄FN₅O₅ [M+H] expected=518.18, found=518.25.

Example 83: N-((3R,4R)-4-(4-(2-fluoro-6-hydroxy-3-methoxybenzyl)benzamido)pyrrolidin-3-yl)isonicotinamide

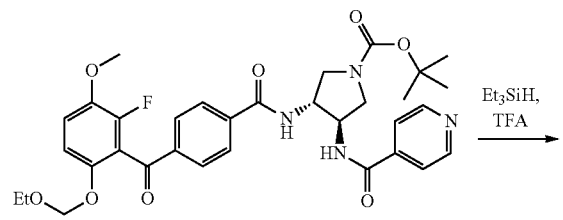

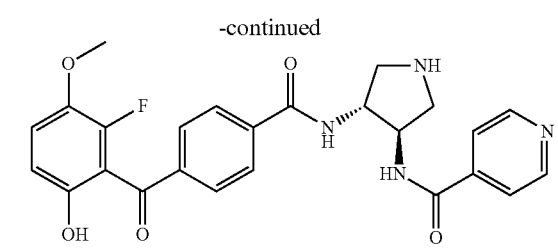

-continued

A vial was charged with tert-butyl (3R,4R)-3-(4-(6-(ethoxymethoxy)-2-fluoro-3-methoxybenzoyl)benzamido)-4-(isonicotinamido)pyrrolidine-1-carboxylate (20 mg, 0.031 mmol) and CH₂Cl₂ (1.0 mL) at room temperature. To this solution was then added trifluoroactic acid (0.5 mL) followed by Et₃SiH (148 μL, 10 equiv). After 20 h the solution was concentrated and purified on HPLC to give N-((3R,4R)-4-(4-(2-fluoro-6-hydroxy-3-methoxybenzyl)benzamido)pyrrolidin-3-yl)isonicotinamide as a formate salt. ¹H NMR (500 MHz, Methanol-$d_4$) δ 8.72 (d, J=4.5 Hz, 2H), 8.44 (s, 2H), 7.85-7.78 (m, 2H), 7.75 (d, J=7.7 Hz, 2H), 7.37 (d, J=7.9 Hz, 2H), 6.85-6.79 (m, 1H), 6.57 (d, J=8.8 Hz, 1H), 4.70 (q, J=6.7 Hz, 2H), 4.04 (s, 2H), 3.84 (d, J=9.8 Hz, 2H), 3.79 (d, J=2.1 Hz, 3H), 3.46 (d, J=14.8 Hz, 2H). LCMS (ESI+) for $C_{25}H_{25}FN_4O_4$ [M+H] expected=465.19, found=465.27.

Example 84: 2-amino-N-((3R,4R)-4-(4-(2-fluoro-6-hydroxy-3-methoxybenzoyl)benzamido)pyrrolidin-3-yl)isonicotinamide

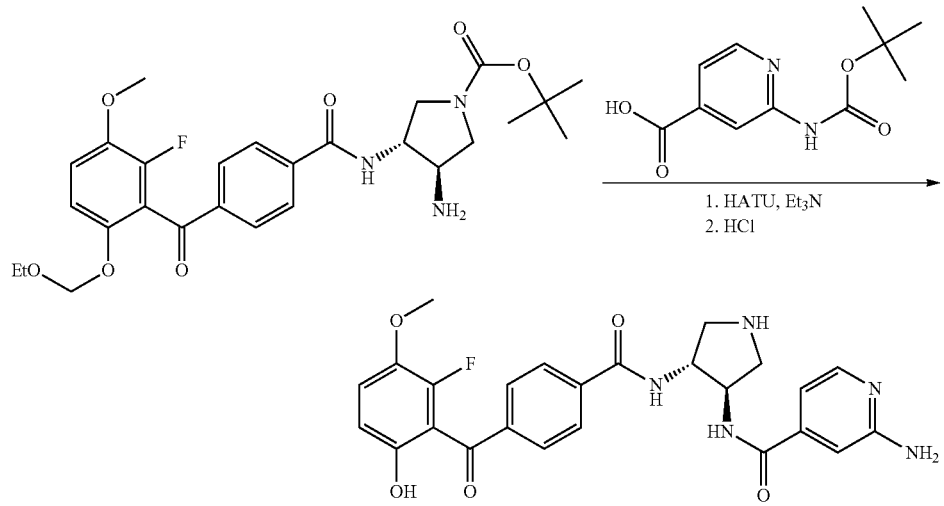

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 2-((tert-butoxycarbonyl)amino)isonicotinic acid (24 mg, 0.099 mmol), HATU (38 mg, 0.099 mmol) and DMF (1 mL). Et$_3$N (40 µL, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give 2-amino-N-((3R,4R)-4-(4-(2-fluoro-6-hydroxy-3-methoxybenzoyl)benzamido)pyrrolidin-3-yl)isonicotinamide as a formate salt. $^1$H NMR (500 MHz, Methanol-$d_4$) δ 8.05-7.89 (m, 5H), 7.20-7.13 (m, 1H), 7.01-6.91 (m, 2H), 6.71 (d, J=9.0 Hz, 1H), 4.72 (t, J=5.4 Hz, 2H), 3.94-3.79 (m, 5H), 3.53-3.39 (m, 2H). LCMS (ESI+) for $C_{25}H_{24}FN_5O_5$ [M+H] expected=494.18, found=494.26.

Example 85: N-((3R,4R)-4-(4-(2-fluoro-6-hydroxy-3-methoxybenzoyl)benzamido)pyrrolidin-3-yl)-1-methyl-1H-indazole-5-carboxamide

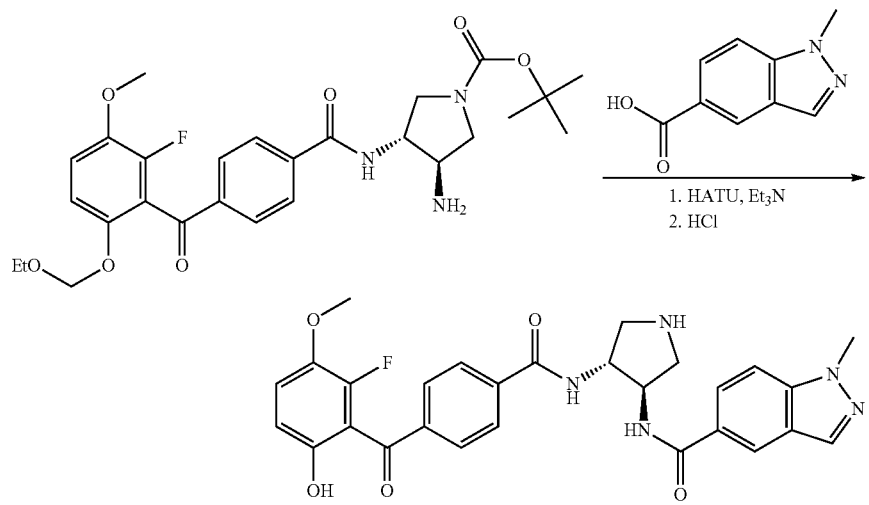

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 1-methyl-1H-indazole-5-carboxylic acid (18 mg, 0.099 mmol), HATU (38 mg, 0.099 mmol) and DMF (1 mL). Et$_3$N (40 µL, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1-methyl-1H-indazole-5-carboxamide as a formate salt. $^1$H NMR (500 MHz, Methanol-d$_4$) δ 8.45 (s, 3H), 8.37 (s, 1H), 8.15 (s, 1H), 8.03-7.89 (m, 5H), 7.70-7.61 (m, 1H), 7.15 (t, J=9.3 Hz, 1H), 6.70 (d, J=9.1 Hz, 1H), 4.75 (d, J=5.0 Hz, 2H), 4.12 (d, J=3.4 Hz, 3H), 3.86 (d, J=3.1 Hz, 5H), 3.47 (s, 2H). LCMS (ESI+) for C$_{28}$H$_{26}$FN$_5$O$_5$ [M+H] expected=532.20, found=532.34.

Example 86: N-((3R,4R)-4-(4-(2-fluoro-6-hydroxy-3-methoxybenzoyl)benzamido)pyrrolidin-3-yl)-1H-benzo[d]imidazole-5-carboxamide

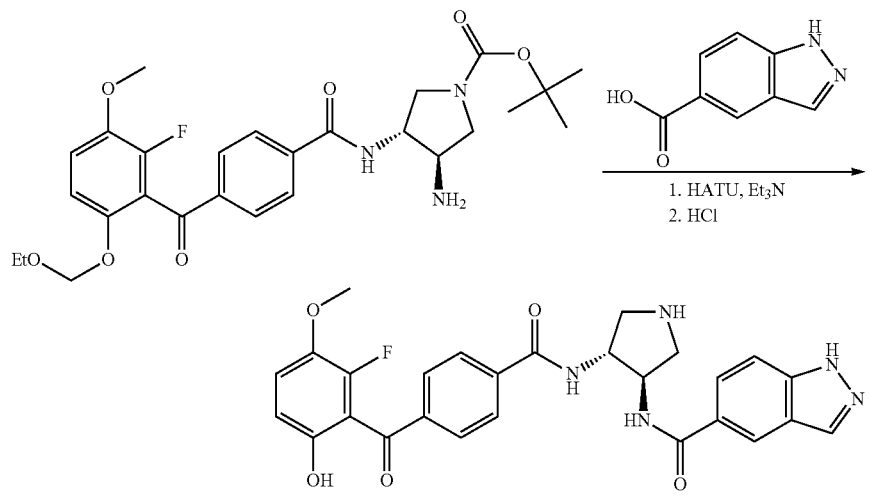

A vial was charged with tert-butyl (3R,4R)-3-amino-4-(4-(6-(ethoxymethoxy)-2-fluoro-3-methoxybenzoyl)benzamido)pyrrolidine-1-carboxylate (52 mg, 0.099 mmol), 1H-benzo[d]imidazole-5-carboxylic acid (16 mg, 0.099 mmol), HATU (38 mg, 0.099 mmol) and DMF (1 mL). Et$_3$N (40 µL, 0.29 mmol) was added and the mixture was stirred at room temperature for 1 h. The solution was quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-1H-benzo[d]imidazole-5-carboxamide as a formate salt. $^1$H NMR (500 MHz, Methanol-d$_4$) δ 8.52 (s, 1H), 8.33 (d, J=3.5 Hz, 1H), 8.21 (s, 1H), 7.99 (d, J=7.3 Hz, 2H), 7.93 (d, J=7.5 Hz, 2H), 7.83 (d, J=8.3 Hz, 1H), 7.70 (t, J=5.7 Hz, 1H), 7.15 (t, J=9.4 Hz, 1H), 6.70 (d, J=9.1 Hz, 1H), 4.77-4.69 (m, 2H), 3.86 (d, J=3.3 Hz, 3H), 3.84-3.75 (m, 2H), 3.39 (dd, J=11.6, 5.7 Hz, 2H). LCMS (ESI+) for C$_{27}$H$_{24}$FN$_5$O$_5$ [M+H] expected=518.18, found=518.29.

Example 87: 4-(2-(ethoxymethoxy)-6-fluorobenzoyl)benzoic acid

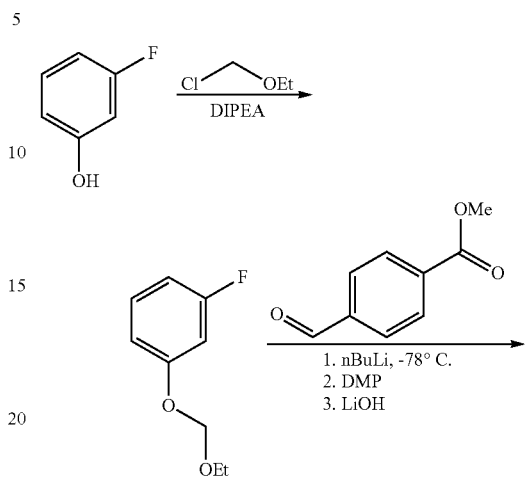

-continued

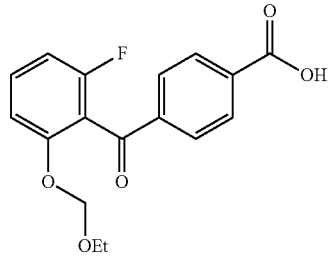

A round bottom flask was charged with 3-fluorophenol (1.0 g, 8.92 mmol) and CH$_2$Cl$_2$ (10 mL) at room temperature. To this solution was then added diisopropylethylamine (3.10 mL, 17.8 mmol) followed by (chloromethoxy)ethane (1.65 mL, 17.8 mmol). The resulting solution was stirred at room temperature until complete by LC-MS (18 h). The solution was washed twice with water, and the organic portion was concentrated and purified on silica gel (20 g, hexane/EtOAc gradient 2%-25%) to give 1-(ethoxymethoxy)-3-fluorobenzene. ¹H NMR (500 MHz, Chloroform-d) δ 7.26-7.18 (m, 1H), 6.82 (dd, J=8.3, 2.2 Hz, 1H), 6.79 (dd, J=10.8, 2.3 Hz, 1H), 6.74-6.65 (m, 1H), 5.21 (d, J=1.8 Hz, 2H), 3.73 (qd, J=7.1, 1.8 Hz, 2H), 1.23 (t, J=7.1 Hz, 3H).

A flame-dried round bottom flask was charged with 1-(ethoxymethoxy)-3-fluorobenzene (1.08 g, 6.35 mmol) and anhydrous THF (20 mL) under an atmosphere of N₂. The solution was cooled in a dry ice/acetone bath and then treated slowly with nBuLi (3.80 mL of a 2.5 M hexane solution, 9.51 mmol). After two hours of stirring cold, the solution was slowly treated with a solution of methyl 4-formylbenzoate (1.56 mL, 9.51 mmol) in anhydrous THF (4 mL). The resulting mixture was allowed to warm to room temperature slowly and monitored by LC-MS. Upon completion, the solution was diluted with ethyl acetate and sequentially washed with water and brine. Concentration gave an oil, which was then purified on silica gel (20 g, hexane/EtOAc gradient 10%-100%) to give methyl 4-((2-(ethoxymethoxy)-6-fluorophenyl)(hydroxy)methyl)benzoate. ¹H NMR (500 MHz, Chloroform-d) δ 8.01-7.94 (m, 2H), 7.43 (d, J=7.9 Hz, 2H), 7.25-7.19 (m, 1H), 6.93 (d, J=8.5 Hz, 1H), 6.81 (t, J=9.1 Hz, 1H), 6.26 (d, J=11.0 Hz, 1H), 5.21-5.14 (m, 1H), 5.14-5.04 (m, 1H), 3.90 (s, 3H), 3.72 (dd, J=11.1, 2.3 Hz, 1H), 3.46 (m, 1H), 3.41-3.29 (m, 1H), 1.08 (td, J=7.1, 2.0 Hz, 3H).

A round bottom flask was charged with methyl 4-((2-(ethoxymethoxy)-6-fluorophenyl)(hydroxy)methyl)benzoate (1.93 g, 5.77 mmol) and CH₂Cl₂ (40 mL) at room temperature. Dess-Martin Periodinane (3.67 g, 8.66 mmol) was then added and the resulting pale yellow suspension was stirred for 30 min. The solution was diluted with dichloromethane and washed with NaHCO₃. Concentration and purification on silica gel (20 g, hexane/EtOAc gradient 5%-40%) gave methyl 4-(2-(ethoxymethoxy)-6-fluorobenzoyl)benzoate. ¹H NMR (500 MHz, Chloroform-d) δ 8.11 (d, J=6.8 Hz, 2H), 7.91 (d, J=7.49 Hz, 2H), 7.40 (q, J=8.8, 8.2 Hz, 1H), 7.06 (d, J=8.6, 1H), 6.88-6.80 (m, 1H), 5.12 (s, 2H), 3.95 (s, 3H), 3.57-3.47 (m, 2H), 1.16-1.07 (t, J=7.3, 3H).

A vial was charged with methyl 4-(6-(ethoxymethoxy)-2-fluoro-3-methoxybenzoyl)benzoate (300 mg, 0.903 mmol), THF (3 mL), and water (1 mL). LiOH (86 mg, 3.6 mmol) was added and the resulting mixture was stirred at room temperature for 2 h. The solution was then diluted with ethyl acetate and washed with a 10% citric acid solution. Concentration of the organic portion resulted in 4-(2-(ethoxymethoxy)-6-fluorobenzoyl)benzoic acid. ¹H NMR (500 MHz, Chloroform-d) δ 8.23-8.14 (d, J=7.7 Hz, 2H), 7.95 (d, J=7.5 Hz, 2H), 7.44-7.37 (m, 1H), 7.06 (dd, J=8.7, 2.9 Hz, 1H), 6.85 (t, J=8.6 Hz, 1H), 5.13 (s, 1H), 3.52 (q, J=6.9, 5.1 Hz, 2H), 1.16-1.08 (m, 3H).

Example 88: N-((3R,4R)-4-(4-(2-fluoro-6-hydroxybenzoyl)benzamido)pyrrolidin-3-yl)isonicotinamide

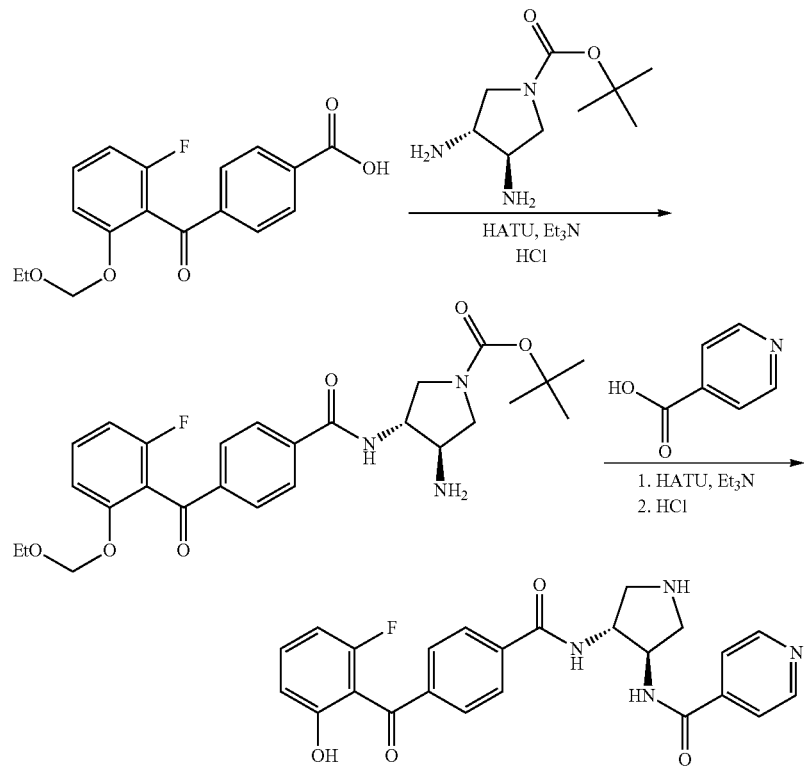

A vial was charged with 4-(2-(ethoxymethoxy)-6-fluorobenzoyl)benzoic acid (32 mg, 0.099 mmol), Et₃N (14 μL, 0.099 mmol) and DMF (1.0 mL) at room temperature. To this solution was then added HATU (38 mg, 0.099 mmol) and the mixture was stirred for 5 min. This solution was then added to a second vial containing a freshly prepared mixture of tert-butyl (3R,4S)-3,4-diaminopyrrolidine-1-carboxylate (20 mg, 0.099 mmol) and HCl (4.0 M dioxane solution, 50 μL) in DMF (0.5 mL). The resulting solution was stirred at room temperature for 18 h to give tert-butyl (3R,4R)-3-amino-4-(4-(2-(ethoxymethoxy)-6-fluorobenzoyl)benzamido)pyrrolidine-1-carboxylate which could be directly used in situ. To this solution was added isonicotinic acid (12 mg, 0.099 mmol), Et₃N (42 µL, 0.298 mmol) and HATU (38 mg, 0.099 mmol). The mixture was stirred at room temperature for 1 h, then quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxybenzoyl)benzamido)pyrrolidin-3-yl)isonicotinamide as a formate salt. ¹H NMR (500 MHz, Methanol-d₄) δ 8.78-8.69 (m, 2H), 8.50 (s, 1H), 7.97 (d, J=7.3 Hz, 2H), 7.91 (d, J=7.8 Hz, 2H), 7.82 (d, J=4.5 Hz, 2H), 7.39 (d, J=8.0 Hz, 1H), 6.82-6.76 (m, 1H), 6.72 (t, J=9.0 Hz, 1H), 4.73-4.65 (m, 2H), 3.75 (d, J=11.1 Hz, 2H), 3.32 (s, 2H). LCMS (ESI+) for C₂₄H₂₁FN₄O₄ [M+H] expected=449.16, found=449.26.

Example 89: 2-amino-N-((3R,4R)-4-(4-(2-fluoro-6-hydroxybenzoyl)benzamido)pyrrolidin-3-yl)pyrimidine-4-carboxamide added to a second vial containing a freshly prepared mixture of tert-butyl (3R,4S)-3,4-diaminopyrrolidine-1-carboxylate (20 mg, 0.099 mmol) and HCl (4.0 M dioxane solution, 50 µL) in DMF (0.5 mL). The resulting solution was stirred at room temperature for 18 h to give tert-butyl (3R,4R)-3-amino-4-(4-(2-(ethoxymethoxy)-6-fluorobenzoyl)benzamido)pyrrolidine-1-carboxylate which could be directly used in situ. To this solution was added 2-aminopyrimidine-4-carboxylic acid (14 mg, 0.099 mmol), Et₃N (42 µL, 0.298 mmol) and HATU (38 mg, 0.099 mmol). The mixture was stirred at room temperature for 1 h, then quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give 2-amino-N-((3R,4R)-4-(4-(2-fluoro-6-hydroxybenzoyl)benzamido)pyrrolidin-3-yl)pyrimidine-4-carboxamide as a formate salt. ¹H NMR (500 MHz, Methanol-d₄) δ 8.51 (s, 1H), 8.47 (d, J=5.2 Hz, 1H), 7.96 (s, 2H), 7.91 (d, J=8.9 Hz, 2H), 7.39 (d, J=8.1 Hz, 1H),

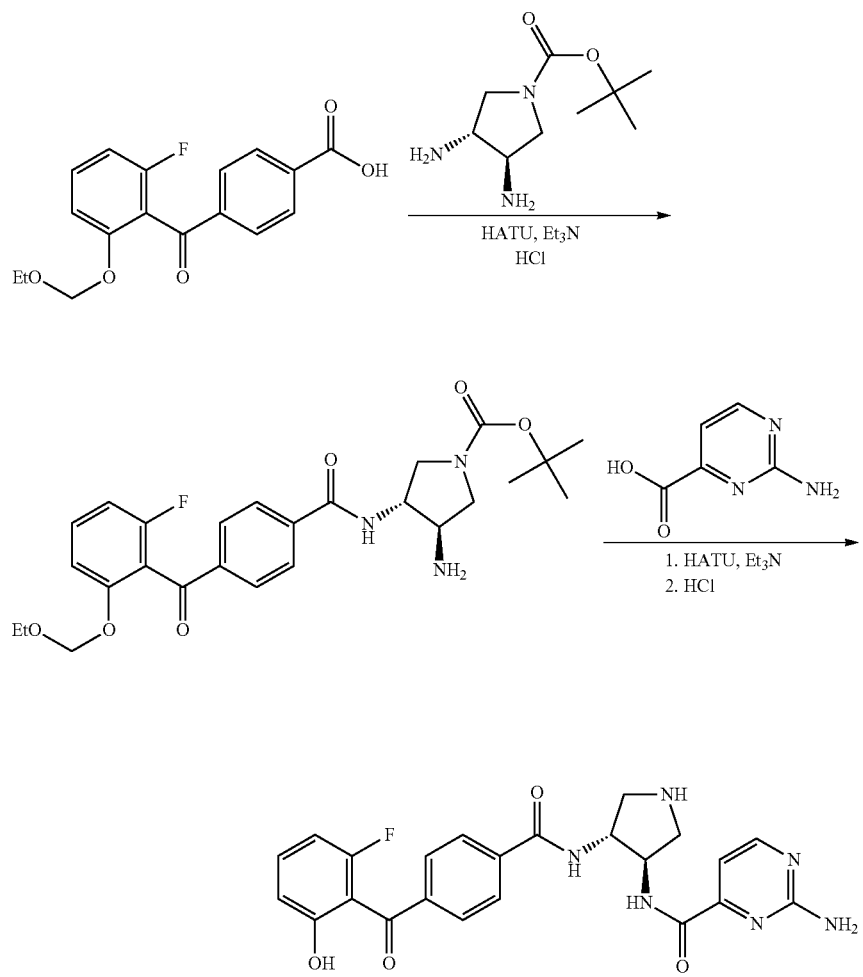

A vial was charged with 4-(2-(ethoxymethoxy)-6-fluorobenzoyl)benzoic acid (32 mg, 0.099 mmol), Et₃N (14 µL, 0.099 mmol) and DMF (1.0 mL) at room temperature. To this solution was then added HATU (38 mg, 0.099 mmol) and the mixture was stirred for 5 min. This solution was then 7.22 (d, J=5.3 Hz, 1H), 6.78 (d, J=8.6 Hz, 1H), 6.73 (d, J=9.4 Hz, 1H), 4.66 (d, J=24.8 Hz, 3H), 3.73 (t, J=10.0 Hz, 2H). LCMS (ESI+) for C₂₃H₂₁FN₆O₄ [M+H] expected=465.16, found=465.25.

Example 90: N-((3R,4R)-4-(4-(2-fluoro-6-hydroxy-benzoyl)benzamido)pyrrolidin-3-yl)-1H-indazole-5-carboxamide

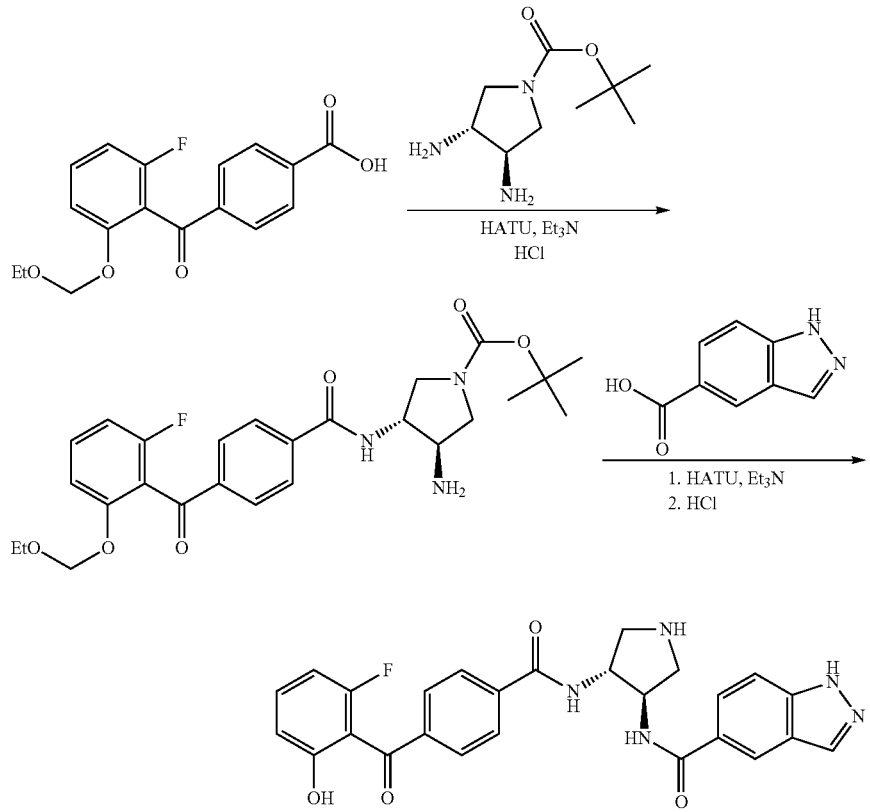

A vial was charged with 4-(2-(ethoxymethoxy)-6-fluorobenzoyl)benzoic acid (32 mg, 0.099 mmol), Et₃N (14 μL, 0.099 mmol) and DMF (1.0 mL) at room temperature. To this solution was then added HATU (38 mg, 0.099 mmol) and the mixture was stirred for 5 min. This solution was then added to a second vial containing a freshly prepared mixture of tert-butyl (3R,4S)-3,4-diaminopyrrolidine-1-carboxylate (20 mg, 0.099 mmol) and HCl (4.0 M dioxane solution, 50 μL) in DMF (0.5 mL). The resulting solution was stirred at room temperature for 18 h to give tert-butyl (3R,4R)-3-amino-4-(4-(2-(ethoxymethoxy)-6-fluorobenzoyl)benzamido)pyrrolidine-1-carboxylate which could be directly used in situ. To this solution was added 1H-indazole-5-carboxylic acid (16 mg, 0.099 mmol), Et₃N (42 μL, 0.298 mmol) and HATU (38 mg, 0.099 mmol). The mixture was stirred at room temperature for 1 h, then quenched with water and extracted with EtOAc. The organic portion was concentrated in vacuo and then redissolved in THF (1.0 mL) and aqueous HCl (1.0 M, 0.5 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxybenzoyl)benzamido)pyrrolidin-3-yl)-1H-indazole-5-carboxamide as a formate salt. $^1$H NMR (500 MHz, Methanol-$d_4$) δ 8.54 (s, 1H), 8.38 (s, 1H), 8.20 (s, 1H), 8.03-7.95 (m, 2H), 7.91 (d, J=8.7 Hz, 3H), 7.62 (d, J=8.5 Hz, 1H), 7.39 (s, 1H), 6.78 (d, J=7.9 Hz, 1H), 6.71 (d, J=12.3 Hz, 1H), 4.68 (s, 2H), 3.69 (d, J=9.0 Hz, 2H), 3.25 (s, 2H). LCMS (ESI+) for $C_{26}H_{22}FN_5O_4$ [M+H] expected=488.17, found=488.27.

Example 91: N-((3R,4R)-4-(4-(2-fluoro-6-hydroxy-3-methoxybenzoyl)benzamido)pyrrolidin-3-yl)-3H-imidazo[4,5-b]pyridine-7-carboxamide

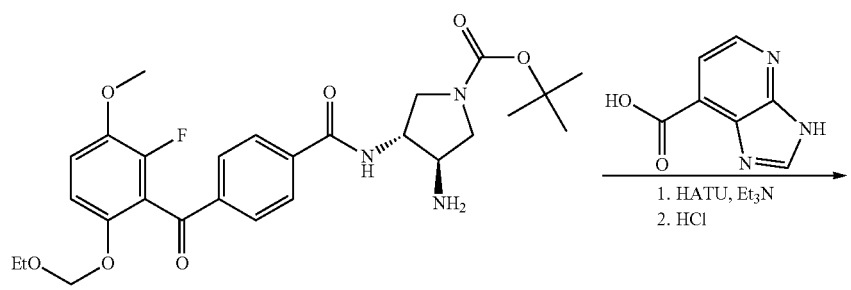

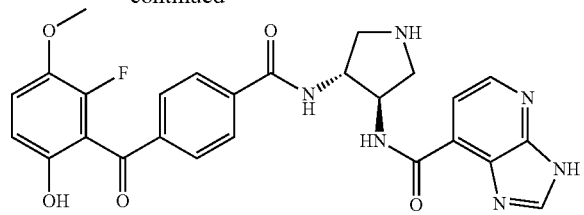

A vial was charged with tert-butyl (3R,4R)-3-amino-4-(4-(6-(ethoxymethoxy)-2-fluoro-3-methoxybenzoyl)benzamido)pyrrolidine-1-carboxylate (66 mg, 0.124 mmol), 3H-imidazo[4,5-b]pyridine-7-carboxylic acid (20 mg, 0.124 mmol), HATU (47 mg, 0.124 mmol) and DMF (1 mL). Et$_3$N (524, 0.372 mmol) was added and the mixture was stirred at room temperature for 2 h. The solution was quenched with water and extracted with EtOAc. The organic portion was concentrated in vacuo and then redissolved in THF (1.0 mL) and aqueous HCl (1.0 M, 0.3 mL). The solution was warmed to 65° C. and stirred until the carbamate and acetal protecting groups were fully removed by LCMS. The solution was then purified via HPLC to give N-((3R,4R)-4-(4-(2-fluoro-6-hydroxy-3-methoxybenzoyl)benzamido)pyrrolidin-3-yl)-3H-imidazo[4,5-b]pyridine-7-carboxamide as a formate salt. $^1$H NMR (500 MHz, Methanol-d$_4$) δ 8.55 (d, J=5.1 Hz, 1H), 8.53 (s, 1H), 8.50 (s, 2H), 7.98 (d, J=8.2 Hz, 2H), 7.92 (d, J=8.2 Hz, 2H), 7.81 (d, J=5.1 Hz, 1H), 7.15 (t, J=9.3 Hz, 1H), 6.70 (dd, J=9.0, 1.6 Hz, 1H), 4.84-4.71 (m, 2H), 3.92-3.81 (m, 5H), 3.48 (dd, J=12.3, 6.3 Hz, 1H), 3.41 (dd, J=12.1, 6.6 Hz, 1H). LCMS (ESI+) for C$_{26}$H$_{23}$FN$_6$O$_5$ [M+H] expected=519.17, found=519.32.

Example 92: N-((3R,4R)-4-(2-(1H-pyrazol-4-yl)acetamido)pyrrolidin-3-yl)-4-(2-fluoro-6-hydroxy-3-methoxybenzoyl) benzamide A vial was charged with tert-butyl (3R,4R)-3-amino-4-(4-(6-(ethoxymethoxy)-2-fluoro-3-methoxybenzoyl)benzamido)pyrrolidine-1-carboxylate (66 mg, 0.124 mmol), 2-(1H-pyrazol-4-yl)acetic acid (16 mg, 0.124 mmol), HATU (47 mg, 0.124 mmol) and DMF (1 mL). Et$_3$N (52 µL, 0.372 mmol) was added and the mixture was stirred at room temperature for 2 h. The solution was quenched with water and extracted with EtOAc. The organic portion was concentrated in vacuo and then redissolved in THF (1.0 mL) and aqueous HCl (1.0 M, 0.3 mL). The solution was warmed to 65° C. and stirred until the carbamate and acetal protecting groups were fully removed by LCMS. The solution was then purified via HPLC to give N-((3R,4R)-4-(2-(1H-pyrazol-4-yl)acetamido)pyrrolidin-3-yl)-4-(2-fluoro-6-hydroxy-3-methoxybenzoyl)benzamide as a formate salt. $^1$H NMR (400 MHz, Methanol-d$_4$) δ 8.39 (d, J=1.6 Hz, 2H), 7.92 (s, 4H), 7.55 (s, 1H), 7.15 (t, J=9.3 Hz, 1H), 6.70 (d, J=9.0 Hz, 1H), 4.53 (dq, J=27.9, 7.2 Hz, 2H), 3.86 (d, J=1.6 Hz, 3H), 3.82-3.69 (m, 2H), 3.47 (s, 2H), 3.30-3.21 (m, 2H). LCMS (ESI+) for C$_{24}$H$_{24}$FN$_5$O$_5$ [M+H] expected=482.18, found=482.30.

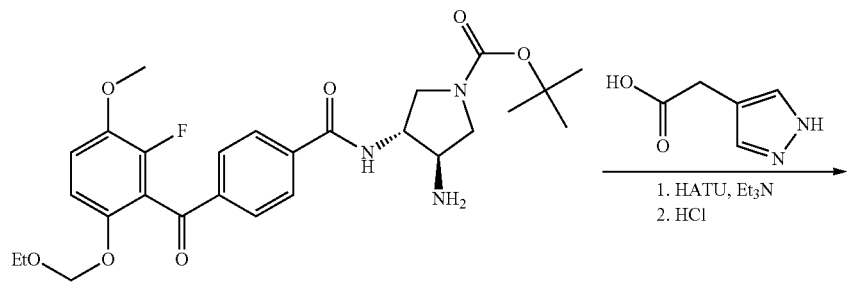

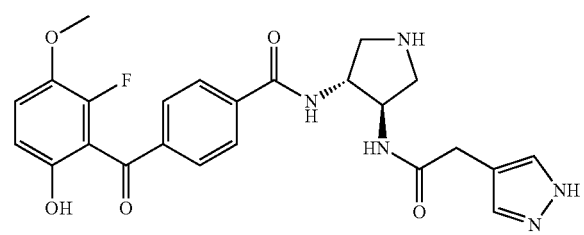

Example 93: 4-(2-fluoro-6-hydroxy-3-methoxybenzoyl)-N-((3R,4R)-4-(2-(pyridin-3-yl)acetamido)pyrrolidin-3-yl)benzamide

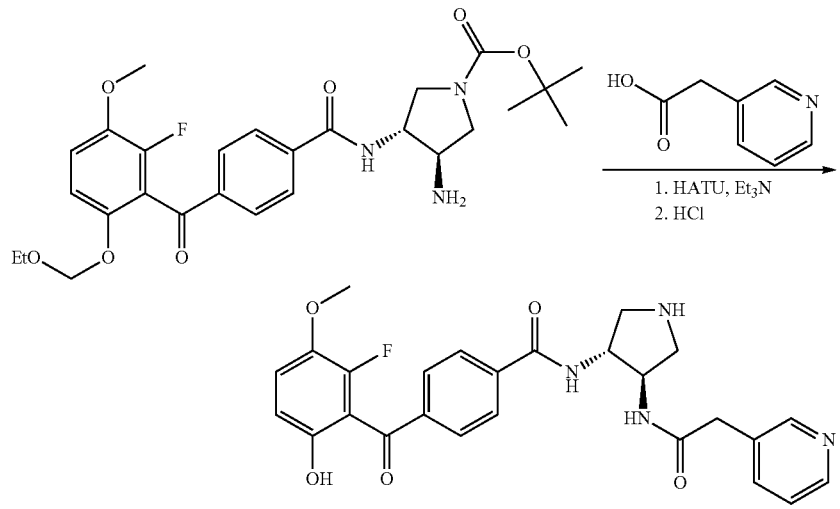

A vial was charged with tert-butyl (3R,4R)-3-amino-4-(4-(6-(ethoxymethoxy)-2-fluoro-3-methoxybenzoyl)benzamido)pyrrolidine-1-carboxylate (66 mg, 0.124 mmol), 2-(pyridin-3-yl)acetic acid (17 mg, 0.124 mmol), HATU (47 mg, 0.124 mmol) and DMF (1 mL). Et$_3$N (52 µL, 0.372 mmol) was added and the mixture was stirred at room temperature for 2 h. The solution was quenched with water and extracted with EtOAc. The organic portion was concentrated in vacuo and then redissolved in THF (1.0 mL) and aqueous HCl (1.0 M, 0.3 mL). The solution was warmed to 65° C. and stirred until the carbamate and acetal protecting groups were fully removed by LCMS. The solution was then purified via HPLC to give 4-(2-fluoro-6-hydroxy-3-methoxybenzoyl)-N-((3R,4R)-4-(2-(pyridin-3-yl)acetamido)pyrrolidin-3-yl)benzamide as a formate salt. $^1$H NMR (500 MHz, Methanol-d$_4$) δ 8.48 (d, J=2.2 Hz, 1H), 8.41 (dd, J=5.0, 1.5 Hz, 1H), 8.38 (s, 2H), 7.90 (s, 3H), 7.80-7.76 (m, 1H), 7.35 (dd, J=7.9, 4.9 Hz, 1H), 7.16 (t, J=9.3 Hz, 1H), 6.71 (dd, J=9.0, 1.6 Hz, 1H), 4.56 (dq, J=37.2, 7.3 Hz, 2H), 3.87 (s, 3H), 3.75 (ddd, J=12.0, 10.1, 7.8 Hz, 2H), 3.63 (s, 2H), 3.28 (dd, J=12.1, 7.5 Hz, 1H). LCMS (ESI+) for C$_{26}$H$_{25}$FN$_4$O$_5$ [M+H] expected=493.18, found=493.28.

Example 94: 2-amino-N-((3R,4R)-4-(4-(2-fluoro-6-hydroxy-3-methoxybenzyl)benzamido)pyrrolidin-3-yl)pyrimidine-4-carboxamide

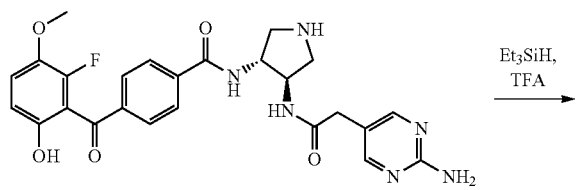

Et$_3$SiH, TFA

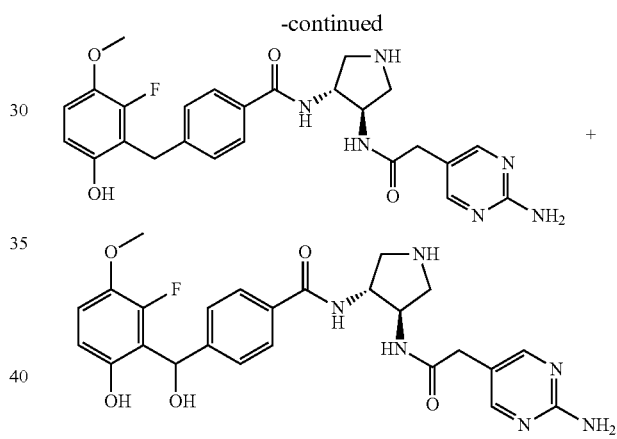

A vial was charged with 2-amino-N-((3R,4R)-4-(4-(2-fluoro-6-hydroxy-3-methoxybenzoyl)benzamido)pyrrolidin-3-yl)pyrimidine-4-carboxamide (8 mg, 0.016 mmol) and CH$_2$Cl$_2$ (1.0 mL) at room temperature. To this solution was then added trifluoroactic acid (0.5 mL) followed by Et$_3$SiH (30 µL). After 20 h the solution was concentrated and purified on HPLC to give both the partially reduced carbinol and the fully reduced methylene compounds. 2-amino-N-((3R,4R)-4-(4-(2-fluoro-6-hydroxy-3-methoxybenzyl)benzamido)pyrrolidin-3-yl)pyrimidine-4-carboxamide: $^1$H NMR (500 MHz, Methanol-d$_4$) δ 8.50 (s, 2H), 8.47 (d, J=5.1 Hz, 1H), 7.74 (d, J=7.9 Hz, 2H), 7.37 (d, J=7.9 Hz, 2H), 7.22 (d, J=5.0 Hz, 1H), 6.82 (t, J=9.2 Hz, 1H), 6.57 (d, J=8.9 Hz, 1H), 4.65 (dq, J=31.2, 7.2 Hz, 2H), 4.04 (s, 2H), 3.79 (s, 5H), 3.38 (s, 2H). LCMS (ESI+) for C$_{24}$H$_{25}$FN$_6$O$_4$ [M+H] expected=481.20, found=481.29. 2-amino-N-((3R,4R)-4-(4-((2-fluoro-6-hydroxy-3-methoxyphenyl)(hydroxy)methyl)benzamido) pyrrolidin-3-yl)pyrimidine-4-carboxamide: $^1$H NMR (500 MHz, Methanol-d$_4$) δ 8.47 (d, J=5.0 Hz, 1H), 8.39 (s, 8H), 7.81 (d, J=8.1 Hz, 2H), 7.53 (d, J=8.0 Hz, 2H), 7.22 (d, J=4.9 Hz, 1H), 6.90 (t, J=9.2 Hz, 1H), 6.57 (d, J=8.7 Hz, 1H), 6.30 (s, 1H), 4.68 (dd, J=24.2, 7.0 Hz, 2H), 3.85 (q, J=8.9 Hz, 2H), 3.78 (s, 3H), 3.45 (d, J=11.6 Hz, 2H). LCMS (ESI+) for $C_{24}H_{25}FN_6O_5$ [M+H] expected=497.19, found=497.27.

Other disclosed compounds for which a synthesis is not explicitly shown can be prepared by analogous methods to those shown in the above examples.

Example 95: Cell Preparation and Culture

PRE-COATING CULTURE PLATES: On the day before the experiment, 96-well plates were pre-coated by plating 50 µl of Poly-D-lysine solution (PDL, 0.5 mg/mL) in each well. The next morning, the plates were washed four or five times with HBSS or PBS (150 µl/rinse), then left in buffer until cell plating PREPARING THE CELLS: A timed pregnant rat carrying E18 embryos was euthanized using an IACUC approved method. In a laminar flow hood, the embryos were removed and placed in a petri dish containing Hank's Balanced Salt Solution (HBSS) with 20 mM HEPES, pH 7.3. Pup brains were dissected (see Meberg et al., 2003) and hippocampi were collected in 15 mL a conical tube containing Hibernate E with SM1 (2% v/v).

Dissociation media was prepared by combining 4.5 mL of Hibernate E (without SM1) with 0.5 mL of trypsin and 100 µl of DNAse solution. The medium over the hippocampi was carefully removed and replaced with dissociation solution, then incubated at 37° C. for 15-20 minutes, occasionally swirling the tube.

Using flame polished cotton plugged Pasteur pipettes, the dissociation media was removed, and then 5 mL of Hibernate E containing SM1 were added. The tube was swirled to thoroughly wash the tissue. The tissue was allowed to settle to the bottom of the tube, and the rinse solution was carefully removed. This step was repeated 5 times to dilute out trypsin and DNAse and remove any debris from lysed cells.

The final rinse media was removed from the tube and 1 pipette-full (1-2 mL) of Hibernate E with SM1 was added. Using the flame-polished Pasteur pipette (pre-wetted with rinse media), the tube was triturated until all cells had dissociated and no visible chunks of tissue remained. Fewer than ten triturations were typically performed. The volume was adjusted to 8-12 mL using Hibernate E containing SM1, the well was mixed and cell concentration was determined.

PLATING: The cells were diluted in culture media (NbActiv4 Cell-culture media) to a final concentration of 10,000 cells/mL. The HBSS was aspirated from PDL coated plates, and 150 µL of cell solution was loaded in the middle 48 wells at 1500 cells per well. Water was loaded in the outer wells to decrease evaporation from edge wells. Cells were allowed to adhere for 2 hours in tissue culture incubator prior to treatment.

TREATMENT: Compounds were diluted to various concentrations to provide 9 dose response concentrations of 20 µM, 10 µM, 5, µM, 2.5 µM, 1.25 µM, 0.625 µM, 0.3125 µM, 0.15625 µM, and 0.078125 µM. The plates were cultured for 48 hours, exposed to the compound at the various dose response concentrations.

FIXING THE CULTURES: The culture medium was removed from the plates and immediately replaced with 100-200 µl of warm (37° C.) 4% paraformaldehyde (PFA) solution in phosphate-buffered saline (PBS). The cells were fixed for 15-20 minutes at room temperature, and then rinsed with PBS (200 µl/well×3).

STAINING AND IMAGING: The PBS was removed and replaced with 100 µl of blocking/permeabilization buffer (PBS, 0.2% fish gelatin, 0.03% Triton X-100, 0.02% $NaN_3$), then incubated overnight at 4° C. To this was added 100 µl of primary antibody solution (mouse anti-Beta III tubulin in blocking buffer) and incubate overnight at 4° C. The wells were rinsed with PBS (200 µl×3), which was then removed and replaced with 100 µl of secondary antibody solution (Goat anti-mouse Alexa 488, 10 µg/ml Hoechst 33342, 0.2% fish gelatin, 0.02% azide, in PBS). The plate was shaken gently on a rotating shaker for 2 hours, then rinsed with PBS (200 µl×5).

The plate was imaged using a Cellomics ArrayScan VTI in 2 different channels for nuclear staining (Hoechst) and cell body/neurite staining (βIII-tubulin). Typically, nine fields per well were imaged with a 5× objective and automatically traced by the Neuronal Profiling Bioapplication. To get reproducible results, at least 200-300 valid neurons were measured per condition.

The data for each compound as assessed in the above assay are presented in Table 1, below, showing the neurite growth length (% NTL) upon exposure to the compound at each concentration.

TABLE 1

|  | 20 µM % NTL | 10 µM % NTL | 5 µM % NTL | 2.5 µM % NTL | 1.25 µM % NTL | 625 nM % NTL | 312 nM % NTL | 156 nM % NTL | 78 nM % NTL |
|---|---|---|---|---|---|---|---|---|---|
| A1 | 84.59 | 86.99 | 92.91 | 85.81 | 93.47 | 90.99 | 89.64 | 88.96 | 89.92 |
| A2 | 100.38 | 93.37 | 94.12 | 91.10 | 88.92 | 93.05 | 84.59 | 96.16 | 93.76 |
| A3 | 96.62 | 92.90 | 93.64 | 95.07 | 96.65 | 92.57 | 96.28 | 99.86 | 98.31 |
| A4 | 160.62 | 132.08 | 113.83 | 114.28 | 105.00 | 93.21 | 110.09 | 98.98 | 101.99 |
| A5 | 131.55 | 123.89 | 116.01 | 113.00 | 101.74 | 102.12 | 97.21 | 102.00 | 97.83 |
| A6 | 121.20 | 107.24 | 105.41 | 92.86 | 94.12 | 95.38 | 83.05 | 105.56 | 94.65 |
| A7 | 91.80 | 86.42 | 91.99 | 88.34 | 90.82 | 91.24 | 95.70 | 94.76 | 97.03 |
| A8 | 81.61 | 93.23 | 93.82 | 94.37 | 92.86 | 98.98 | 96.40 | 98.70 | 99.15 |
| A9 | 89.14 | 89.62 | 98.35 | 98.89 | 88.00 | 96.63 | 90.69 | 91.54 | 94.49 |
| A10 | 92.60 | 86.03 | 85.88 | 82.94 | 83.65 | 88.19 | 87.46 | 91.19 | 91.73 |
| A11 | 110.10 | 109.70 | 94.60 | 98.47 | 91.67 | 93.85 | 87.41 | 102.21 | 103.85 |
| A12 | 119.02 | 98.61 | 105.72 | 90.99 | 90.64 | 93.14 | 91.17 | 90.73 | 96.59 |
| A13 | 147.40 | 129.01 | 120.42 | 113.46 | 106.05 | 102.90 | 97.66 | 101.26 | 99.51 |
| A14 | 174.99 | 153.54 | 140.04 | 125.97 | 126.71 | 118.56 | 117.90 | 110.84 | 105.26 |
| A15 | 136.04 | 121.85 | 109.99 | 107.46 | 109.99 | 114.21 | 111.29 | 105.50 | 98.50 |
| A16 | 660.88 | 573.73 | 403.74 | 228.24 | 167.31 | 144.99 | 125.17 | 117.55 | 117.21 |
| A17 | 119.03 | 120.74 | 111.62 | 113.43 | 103.19 | 99.84 | 103.50 | 100.18 | 99.73 |
| A18 | 140.11 | 130.60 | 130.17 | 133.32 | 121.01 | 120.24 | 119.39 | 115.01 | 112.57 |
| A19 | 91.20 | 87.39 | 79.44 | 78.45 | 75.70 | 74.96 | 68.74 | 93.71 | 90.07 |
| A20 | 103.31 | 93.83 | 90.74 | 90.24 | 88.40 | 86.06 | 77.66 | 81.49 | 86.16 |
| A21 | 107.94 | 106.78 | 102.39 | 91.52 | 86.78 | 81.75 | 79.75 | 83.27 | 84.72 |
| A22 | 94.65 | 91.08 | 88.74 | 85.47 | 85.50 | 86.23 | 92.28 | 91.77 | 89.30 |

TABLE 1-continued

| | 20 μM % NTL | 10 μM % NTL | 5 μM % NTL | 2.5 μM % NTL | 1.25 μM % NTL | 625 nM % NTL | 312 nM % NTL | 156 nM % NTL | 78 nM % NTL |
|---|---|---|---|---|---|---|---|---|---|
| A23 | 144.40 | 116.62 | 104.71 | 100.79 | 96.98 | 93.58 | 95.61 | 101.78 | 98.34 |
| A24 | 168.53 | 130.98 | 113.84 | 101.49 | 91.75 | 96.90 | 93.41 | 96.83 | 96.27 |
| A25 | 163.32 | 146.22 | 134.45 | 121.94 | 120.29 | 111.16 | 109.64 | 97.54 | 98.93 |
| A26 | 117.38 | 97.77 | 102.47 | 99.91 | 93.51 | 99.28 | 94.24 | 99.25 | 93.29 |
| A27 | 150.50 | 141.32 | 117.42 | 105.14 | 110.42 | 118.35 | 107.37 | 101.33 | 103.27 |
| A28 | 139.00 | 137.19 | 132.96 | 118.22 | 102.88 | 83.66 | 102.99 | 113.43 | 97.76 |
| A29 | 269.49 | 226.69 | 172.95 | 151.95 | 123.67 | 121.54 | 119.66 | 117.83 | 123.24 |
| A30 | 117.38 | 107.23 | 103.00 | 94.79 | 93.78 | 83.52 | 90.55 | 89.72 | 93.11 |
| A31 | 137.38 | 142.13 | 150.97 | 140.22 | 135.94 | 114.65 | 118.44 | 120.15 | 122.27 |
| A32 | 86.59 | 82.90 | 88.24 | 90.59 | 81.36 | 84.61 | 88.20 | 86.89 | 98.72 |
| A33 | 207.05 | 159.35 | 141.98 | 129.36 | 114.66 | 106.63 | 99.34 | 106.08 | 107.83 |
| A34 | 130.91 | 118.29 | 110.06 | 105.94 | 95.84 | 92.27 | 92.06 | 102.77 | 102.90 |
| A35 | 106.81 | 96.69 | 97.19 | 95.04 | 86.88 | 89.26 | 86.33 | 90.06 | 91.75 |
| A36 | 470.23 | 480.45 | 516.37 | 358.08 | 238.96 | 149.25 | 130.71 | 126.39 | 115.57 |
| A37 | 211.85 | 154.55 | 132.14 | 123.52 | 113.19 | 107.07 | 113.37 | 109.29 | 99.97 |
| A38 | 87.68 | 100.44 | 106.01 | 99.97 | 100.40 | 96.60 | 103.22 | 101.57 | 107.67 |
| A39 | 100.58 | 98.87 | 98.03 | 87.33 | 82.95 | 80.49 | 85.55 | 92.99 | 96.28 |
| A40 | 121.39 | 106.33 | 100.73 | 107.86 | 94.11 | 86.22 | 86.15 | 91.18 | 86.29 |
| A41 | 190.30 | 152.00 | 124.40 | 102.24 | 95.91 | 86.95 | 86.20 | 88.45 | 91.35 |
| A42 | 368.85 | 431.35 | 402.61 | 255.45 | 169.05 | 117.86 | 126.44 | 109.72 | 115.00 |
| A43 | 173.26 | 154.98 | 143.76 | 135.87 | 123.55 | 113.63 | 115.41 | 117.86 | 117.56 |
| A44 | 105.09 | 102.87 | 103.74 | 96.16 | 99.37 | 76.36 | 78.84 | 87.12 | 94.04 |
| A45 | 111.39 | 97.19 | 89.06 | 93.34 | 84.84 | 86.95 | 83.72 | 90.16 | 96.49 |
| A46 | 90.20 | 100.33 | 88.09 | 86.76 | 93.08 | 77.54 | 90.83 | 94.95 | 95.62 |
| A47 | 161.73 | 128.27 | 121.79 | 111.68 | 104.25 | 96.82 | 99.67 | 99.28 | 100.42 |
| A48 | 421.47 | 460.51 | 331.77 | 219.41 | 144.30 | 120.02 | 116.40 | 117.05 | 108.76 |
| A49 | 206.59 | 321.91 | 298.34 | 200.44 | 138.61 | 111.70 | 101.33 | 99.50 | 106.71 |
| A50 | 457.37 | 561.20 | 431.11 | 285.18 | 193.50 | 135.55 | 118.09 | 113.45 | 112.84 |
| A51 | 420.94 | 506.09 | 361.80 | 260.12 | 191.35 | 157.66 | 134.95 | 128.52 | 129.32 |
| A52 | 100.15 | 115.27 | 120.18 | 112.62 | 93.31 | 101.62 | 99.51 | 99.93 | 104.15 |
| A53 | 70.00 | 91.90 | 90.14 | 88.53 | 85.81 | 76.28 | 79.27 | 82.49 | 90.02 |
| A54 | 227.71 | 151.47 | 120.06 | 105.05 | 94.72 | 84.11 | 84.31 | 79.92 | 83.12 |
| A55 | 96.04 | 98.77 | 93.58 | 90.13 | 81.96 | 76.79 | 80.06 | 77.96 | 85.02 |
| A56 | 488.07 | 374.82 | 267.31 | 196.25 | 165.48 | 132.68 | 130.54 | 136.70 | 127.78 |
| A57 | 111.06 | 107.49 | 105.35 | 93.54 | 97.27 | 93.92 | 95.07 | 97.82 | 92.24 |
| A58 | 88.58 | 89.45 | 85.34 | 84.80 | 76.29 | 75.71 | 79.27 | 87.57 | 88.35 |
| A59 | 105.80 | 110.70 | 95.38 | 91.20 | 76.68 | 82.32 | 73.56 | 82.81 | 91.90 |
| A60 | 91.78 | 100.82 | 88.88 | 98.45 | 84.35 | 69.75 | 80.81 | 79.69 | 88.95 |
| A61 | 152.19 | 108.17 | 97.02 | 91.67 | 95.68 | 91.52 | 92.77 | 91.78 | 94.56 |
| A62 | 133.49 | 96.18 | 93.93 | 93.64 | 92.12 | 94.16 | 92.63 | 90.36 | 88.98 |
| A63 | 223.87 | 143.60 | 117.99 | 104.27 | 91.93 | 103.77 | 96.44 | 96.30 | 100.17 |
| A64 | 126.26 | 120.74 | 124.31 | 129.41 | 116.10 | 105.44 | 106.93 | 99.78 | 91.33 |
| A65 | 160.83 | 149.93 | 127.75 | 128.51 | 126.01 | 112.65 | 122.60 | 116.94 | 108.46 |
| A66 | 161.12 | 144.82 | 129.09 | 128.72 | 121.97 | 111.17 | 122.31 | 107.02 | 112.95 |
| A67 | 128.29 | 119.57 | 108.09 | 106.24 | 112.46 | 104.43 | 103.63 | 97.87 | 94.15 |
| A68 | 94.26 | 102.28 | 96.78 | 101.06 | 101.75 | 91.25 | 94.76 | 95.73 | 101.04 |
| A69 | 117.28 | 119.25 | 111.98 | 111.87 | 109.93 | 106.76 | 96.04 | 96.20 | 94.29 |
| A70 | 144.96 | 135.12 | 121.56 | 117.33 | 123.15 | 121.97 | 115.07 | 106.96 | 102.89 |
| A71 | 123.56 | 116.78 | 118.60 | 109.30 | 102.26 | 109.02 | 104.56 | 98.98 | 94.77 |
| A72 | 156.98 | 126.65 | 113.38 | 104.86 | 106.49 | 107.88 | 97.65 | 94.01 | 96.38 |
| A73 | 158.80 | 135.55 | 120.66 | 117.34 | 125.11 | 104.94 | 101.50 | 109.85 | 96.70 |
| A74 | NA | 137.17 | 121.40 | 118.91 | 105.43 | 105.75 | 102.97 | 102.69 | 101.11 |
| A75 | 140.29 | 146.47 | 119.26 | 119.03 | 116.01 | 106.00 | 105.30 | 93.67 | 97.09 |
| A76 | 691.89 | 557.77 | 317.48 | 207.35 | 168.56 | 155.84 | 139.87 | 120.88 | 130.68 |
| A77 | 653.37 | 469.06 | 263.06 | 186.81 | 158.86 | 144.33 | 132.84 | 125.06 | 117.77 |
| A78 | 502.56 | 409.68 | 255.55 | 175.58 | 152.11 | 143.39 | 133.21 | 120.99 | 121.64 |
| A79 | 94.65 | 106.94 | 111.85 | 115.71 | 111.13 | 117.86 | 117.37 | 109.21 | 115.72 |
| A80 | 155.49 | 159.73 | 202.94 | 220.71 | 178.49 | 157.67 | 141.08 | 124.09 | 124.98 |
| A81 | 116.43 | 112.57 | 129.67 | 125.18 | 128.34 | 128.45 | 126.73 | 120.48 | 123.64 |
| A82 | 116.60 | 130.66 | 119.93 | 120.02 | 122.06 | 123.85 | 116.69 | 115.44 | 106.90 |
| A83 | 117.46 | 123.49 | 126.83 | 127.43 | 123.58 | 118.28 | 109.99 | 104.76 | 105.67 |
| A84 | 564.48 | 492.48 | 269.85 | 164.51 | 152.70 | 139.22 | 124.79 | 117.61 | 114.61 |
| A85 | 426.16 | 533.51 | 376.48 | 218.99 | 176.87 | 152.65 | 140.15 | 144.13 | 133.69 |
| A86 | 379.35 | 270.94 | 184.87 | 157.50 | 136.32 | 133.66 | 125.73 | 135.37 | 123.89 |

Example 96: In Vivo Axon Growth Determination

Figure 3A:
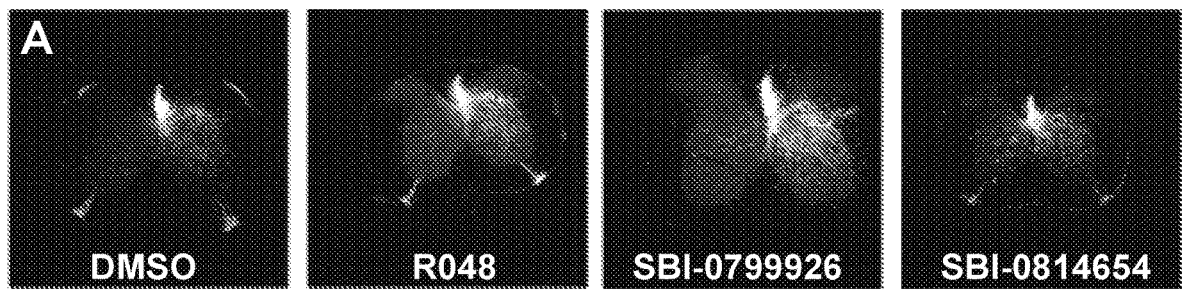
FIG. 3 shows that treatment with kinase inhibitor compounds RO48 (A92), SBI-0799926 (A-16) and SBI-0814654 (A88) promotes CST axon sprouting in the spinal cord. A) Transverse sections of cervical spinal cord 5 weeks after unilateral right pyramidotomy and coinjection of AAV8-GFP and compounds into motor cortex show more GFP+ axons sprouting into the denervated grey matter in animals treated with RO48 (A92), SBI-0799926 (A-16) and SBI-0814654 (A88). B) Graph represents averages of sprouting axon index across two animals treated with indicated compounds. Error bars indicate range of data points. N=2 animals (mice).
Figure 3B:
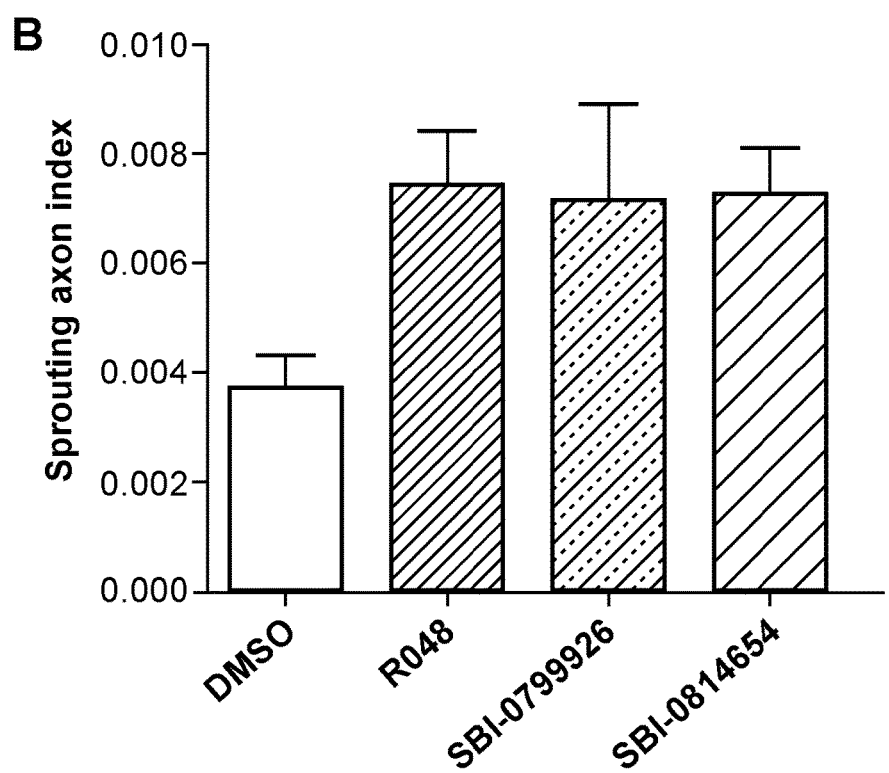

To assess the role of the compounds described herein in axon growth in vivo, the unilateral pyramidotomy model was employed, in which the pyramid in the ventral brainstem was severed unilaterally, rostral to the decussation of corticospinal tract (CST) axons. The animals then received bilateral cortical injections of a compound described herein (or DMSO) mixed 1:1 with AAV8-UbC-GFP or AAV8-UbC-TdTomato ($5\times10^{13}$ GC/mL) for a final concentration of 2 mM (2 animals (mice) for each condition). Five injections (500 nl each) were made into the sensorimotor cortex on each hemisphere at a depth of 0.5 mm and at the following coordinates: 2 mm/±1.5 mm, 1.25 mm/±1.5 mm, 0.5 mm/±1.5 mm, −0.25 mm/±1 mm, and −1 mm/±1 mm (anteroposterior/mediolateral to bregma). Axon growth in the cervical spinal cord was assessed after 5 weeks. Cervical sections of the spinal cord were stained with antibodies against PKCγ (to assess completeness of lesion), and GFP (to amplify the signal from the virus). For analyses, GFP+ axons sprouting into the denervated gray matter were counted at 0, 500, 1000 μm lateral to the central canal, and normalized to the number of GFP+ fibers at the level of the brainstem (sprouting axon index). In animals treated with RO48 (A92) or its derivatives (SBI-0799926-Compound A16, and SBI-0814654-Compound A88), there was nearly a two-fold increase in sprouting, measured by the sprouting axon index graph (FIG. 3). These results confirm that RO48 can promote CST axon growth following a single administration of the compound (Al-Ali et al., *ACS Chem Biol.* 2015; 10(8):1939-512015), and indicate that the derivative compounds are also able to promote axon growth in an in vivo setting.

Example 97: Neurite Outgrowth Determination

To assess the ability of the compounds to promote neurite outgrowth, an HCS assay was performed using the protocol as described in Al-Ali, et al., "High Content Screening with Primary Neurons" in *Assay Guidance Manual* [Internet], Sittampalam et al., eds., Bethesda (Md.): Eli Lilly & Company and the National Center for Advancing Translational Sciences; 2004. 2013 Oct. 15 [updated 2014 Oct. 1]. The results of this assay are presented in Table 2, below.

TABLE 2

| COMPOUND NO. | EC50 (μM) |
|---|---|
| A1 | 9.34 |
| A2 | 1.81 |
| A3 | 0.7985 |
| A4 | 9.64 |
| A5 | 10.44 |
| A6 | 1.67 |
| A7 | 1.665 |
| A8 | — |
| A9 | 4.9205 |
| A10 | 0.93 |
| A11 | 5.58 |
| A12 | — |
| A13 | 4.96 |
| A14 | — |
| A15 | 7.84 |
| A16 | 5.505 |
| A17 | 1.83 |
| A18 | 6.6085 |
| A19 | 2.2355 |
| A20 | 9.49 |
| A21 | 2.915 |
| A22 | 2.612 |
| A23 | 16.8 |
| A24 | 16.1 |
| A25 | — |
| A26 | — |
| A27 | 7.895 |
| A28 | 4.72 |
| A29 | 5.21 |
| A30 | 4.92 |
| A31 | 1.1505 |
| A32 | — |
| A33 | — |
| A34 | 13.025 |
| A35 | 0.163 |
| A36 | 1.835 |
| A37 | — |
| A38 | 3.15 |
| A39 | 3.76 |
| A40 | 9.62 |
| A41 | 11.045 |
| A42 | 2.45 |
| A43 | 3.11 |
| A44 | 2.05 |
| A45 | — |
| A46 | 1.646 |
| A47 | 7.43 |
| A48 | 6.075 |
| A49 | 2.46 |
| A50 | 3.605 |
| A51 | 4.9 |
| A52 | 2.06 |
| A53 | 0.814 |
| A54 | — |
| A55 | 4.74 |
| A56 | 8.54 |
| A57 | — |
| A58 | 5.27 |
| A59 | 7.13 |
| A60 | 1.25 |
| A61 | — |
| A62 | 16 |
| A63 | — |
| A64 | 0.593 |
| A65 | 7.11 |
| A66 | 2.33 |
| A67 | — |
| A68 | 1.24 |
| A69 | 0.401 |
| A70 | — |
| A71 | 2.15 |
| A72 | — |
| A73 | — |
| A74 | 4.5 |
| A75 | 6.565 |
| A76 | 8.37 |
| A77 | 10.42 |
| A78 | 7.765 |
| A79 | — |
| A80 | 0.534 |
| A81 | 5.22 |
| A82 | 0.154 |
| A83 | 0.486 |
| A84 | 6.86 |
| A85 | 3.82 |
| A86 | 11.9 |
| A87 | 13.1 |
| A88 | 1.165 |
| A89 | 8.08 |
| A90 | 1.795 |
| A91 | 3.41 |
| A92 | 0.711 |
| A93 | 13.35 |
| A94 | 0.813 |
| A95 | 9.7735 |
| A96 | 1.4475 |
| A97 | 11.3 |
| A98 | 9.975 |
| A99 | 2.36 |

"—" indicates activity of >20

What is claimed:

1. A compound, or pharmaceutically acceptable salt thereof, having a structure of Formula (1):

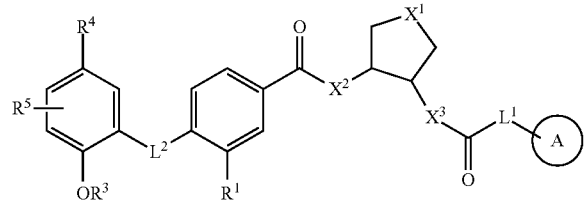

(I)

wherein
ring A is an unsubstituted or substituted 5-6-membered monocyclic heteroaryl ring or a 8-11-membered bicyclic heteroaryl ring having 1, 2, or 3 nitrogen ring atoms;
$L^1$ is null or $C_{1-2}$alkylene;
$X^1$ is —NH—, —CH$_2$NH—, or —NHCH$_2$—;
$X^2$ is —NR$^2$—;
$X^3$ is —NR$^2$—;
$L^2$ is —C(O)—, —O—, —CH—, or —CH(OH)—;
$R^1$ is H or halo;
each $R^2$ is independently H or $C_{1-3}$alkyl;
$R^3$ is H, $C_{1-3}$alky, $C_{3-6}$cycloalkyl, aryl, C(O)$C_{1-3}$alkyl, C(O)$C_{3-6}$cycloalkyl, or C(O)aryl;
$R^4$ is OH, halo, $C_{1-4}$alkyl, or $C_{1-4}$alkoxy; and
$R^5$ is H.

2. The compound or salt of claim 1, wherein ring A is pyrrolyl, pyrazolyl, imidazolyl, triazolyl, pyridyl, pyrazinyl, pyrimidinyl, indolyl, indazolyl, benzotriazolyl, benzoimidazolyl, pyrrolopyridinyl, or imidazopyridinyl.

3. The compound or salt of claim 1, wherein ring A is

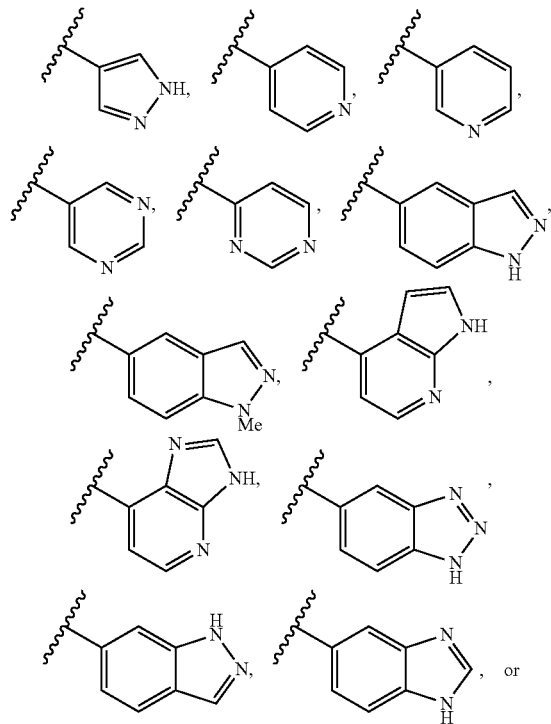

or

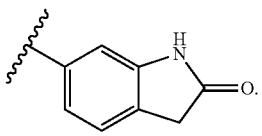

4. The compound of claim 1, wherein ring A is substituted with one or two groups selected from NH$_2$, OH, and $C_{1-3}$alkyl.

5. The compound of claim 1, wherein ring A is unsubstituted.

6. The compound or salt of claim 1, wherein $L^1$ is null or —CH$_2$—.

7. The compound or salt of claim 1, wherein $X^2$ is —NH— or —NMe-.

8. The compound or salt of claim 1, wherein $X^3$ is —NH— or —NMe-.

9. The compound or salt of claim 1, wherein $R^1$ is H or fluoro.

10. The compound or salt of claim 1, wherein $L^2$ is:
(i) —C(O)—; or
(ii) —O— or —CH(OH)—.

11. The compound or salt of claim 1, wherein $R^3$ is H or Me.

12. The compound or salt of claim 1, wherein $R^4$ is OMe, OH, F, Cl, or Me.

13. The compound of claim 1, wherein $R^5$ is ortho to $R^4$.

14. A compound selected from the group consisting of:

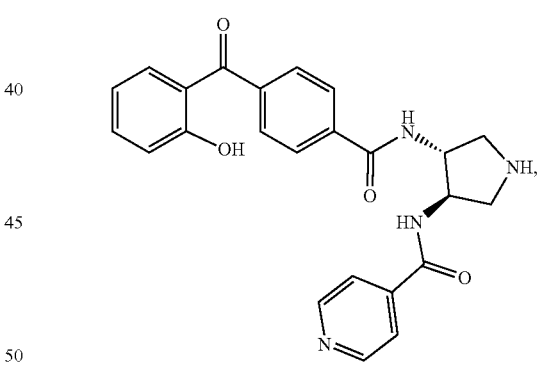

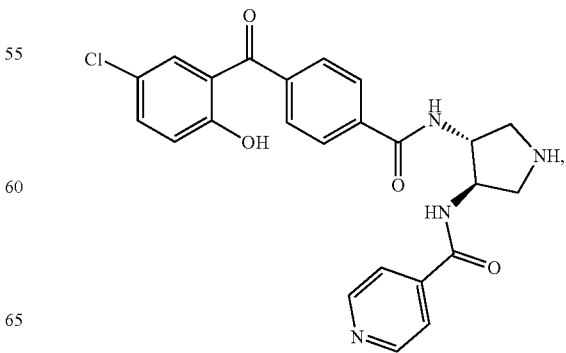

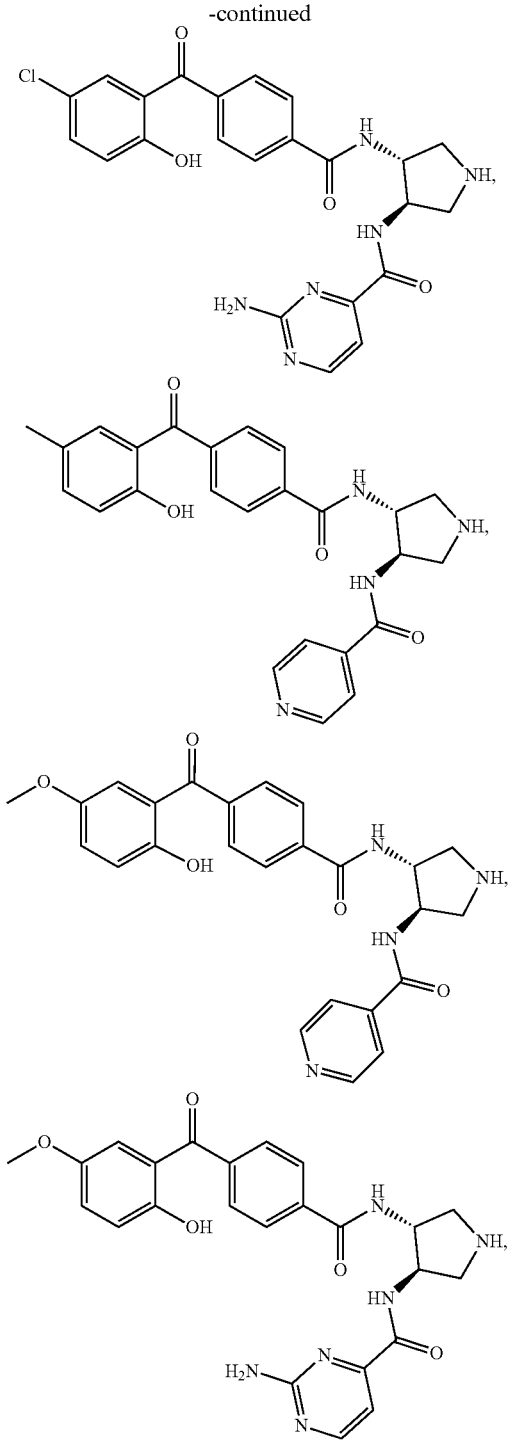
or a pharmaceutically acceptable salt thereof.
15. A composition comprising the compound or salt of claim 1 and a pharmaceutically acceptable excipient.

UNITED STATES PATENT AND TRADEMARK OFFICE
CERTIFICATE OF CORRECTION

PATENT NO. : 11,926,613 B2
APPLICATION NO. : 16/760365
DATED : March 12, 2024
INVENTOR(S) : Hassan Al-Ali et al.

It is certified that error appears in the above-identified patent and that said Letters Patent is hereby corrected as shown below:

In the Claims

At Column 143, Line 26, "—CH—," should be -- —CH$_2$—, --.

Signed and Sealed this
Twelfth Day of November, 2024

Katherine Kelly Vidal
*Director of the United States Patent and Trademark Office*